US012441810B2

(12) United States Patent
Panicker et al.

(10) Patent No.: US 12,441,810 B2
(45) Date of Patent: Oct. 14, 2025

(54) PROTEIN S ANTIBODIES, METHODS OF MAKING AND USES THEREOF

(71) Applicant: Vega Therapeutics, Inc., South San Francisco, CA (US)

(72) Inventors: Sandip Panicker, South San Francisco, CA (US); Adam David Rosenthal, South San Francisco, CA (US); Tony Sang Young Byun, South San Francisco, CA (US); Quehuong Thi Dong, South San Francisco, CA (US)

(73) Assignee: Vega Therapeutics, Inc., South San Francisco, CA (US)

( * ) Notice: Subject to any disclaimer, the term of this patent is extended or adjusted under 35 U.S.C. 154(b) by 116 days.

(21) Appl. No.: 17/923,503

(22) PCT Filed: May 5, 2021

(86) PCT No.: PCT/US2021/030900

§ 371 (c)(1),
(2) Date: Nov. 4, 2022

(87) PCT Pub. No.: WO2021/226243

PCT Pub. Date: Nov. 11, 2021

(65) Prior Publication Data

US 2023/0083243 A1 Mar. 16, 2023

Related U.S. Application Data

(60) Provisional application No. 63/169,755, filed on Apr. 1, 2021, provisional application No. 63/020,505, filed on May 5, 2020.

(51) Int. Cl.

| | |
|---|---|
| ***C07K 16/36*** | (2006.01) |
| ***A61K 47/68*** | (2017.01) |
| ***A61P 7/04*** | (2006.01) |
| *A61K 39/00* | (2006.01) |

(52) U.S. Cl.

CPC .......... *C07K 16/36* (2013.01); *A61K 47/6843* (2017.08); *A61P 7/04* (2018.01); *A61K 2039/505* (2013.01); *A61K 2039/54* (2013.01); *A61K 2039/545* (2013.01); *C07K 2317/21* (2013.01); *C07K 2317/24* (2013.01); *C07K 2317/32* (2013.01); *C07K 2317/34* (2013.01); *C07K 2317/52* (2013.01); *C07K 2317/565* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 5,147,638 | A | 9/1992 | Esmon et al. | |
| 5,187,067 | A | 2/1993 | Koike et al. | |
| 5,366,861 | A | 11/1994 | Hosoda et al. | |
| 6,180,370 | B1 * | 1/2001 | Queen | A61P 19/02 435/69.6 |
| 6,423,313 | B1 | 7/2002 | Esmon et al. | |
| RE38,202 | E | 7/2003 | Mertens et al. | |
| 7,041,458 | B2 | 5/2006 | Dahlbäck | |
| 8,669,263 | B2 | 3/2014 | Lemke et al. | |
| 9,233,144 | B2 | 1/2016 | Bernard-Pierrot et al. | |
| 9,447,147 | B2 | 9/2016 | Dockal et al. | |
| 12,145,999 | B2 | 11/2024 | Panicker et al. | |
| 2003/0124118 | A1 | 7/2003 | Rojkjaer | |
| 2003/0143759 | A1 | 7/2003 | Dahlback | |
| 2003/0165485 | A1 | 9/2003 | Bertilsson et al. | |
| 2004/0033561 | A1 * | 2/2004 | O'Keefe | C07K 16/2866 536/23.53 |
| 2007/0077603 | A1 | 4/2007 | Heeb et al. | |
| 2008/0057059 | A1 | 3/2008 | Rojkjaer | |
| 2015/0246947 | A1 | 9/2015 | Dockal et al. | |
| 2016/0297892 | A1 * | 10/2016 | Heibroch Petersen | C07K 16/36 |
| 2023/0174672 | A1 | 6/2023 | Panicker et al. | |
| 2024/0084038 | A1 | 3/2024 | Panicker et al. | |
| 2024/0425613 | A1 | 12/2024 | Panicker et al. | |

FOREIGN PATENT DOCUMENTS

| | | | | |
|---|---|---|---|---|
| EP | 0944837 | A1 | 9/1999 | |
| EP | 0944837 | B1 | 12/2004 | |
| EP | 0972781 | B1 | 1/2007 | |
| EP | 1780219 | A2 | 5/2007 | |
| WO | WO-9301209 | A1 * | 1/1993 | C07K 14/745 |
| WO | WO-9823963 | A1 | 6/1998 | |
| WO | WO-2007014749 | A2 | 2/2007 | |

(Continued)

OTHER PUBLICATIONS

Nath, Nidhi et al. "Antibody Labeling with Fluorescent Dyes Using Magnetic Protein A and Protein G Beads." Journal of visualized experiments : JoVE , 115 54545. Sep. 15, 2016, doi:10.3791/54545 (Year: 2016).*

Stryer, Biochemistry 4th, WH Freeman, New York. 1995 (Year: 1995).*

Colman, Research in Immunology 145.1 (1994): 33-36 (Year: 1994).*

Leong, Lilley, et al. "Pre-clinical characterization of VGA039, an anti-protein S monoclonal antibody being developed as a universal hemostatic agent for various bleeding disorders." Blood 140. Supplement 1 (2022): 1666-1667 (Year: 2022).*

(Continued)

*Primary Examiner* — Zachariah Lucas
*Assistant Examiner* — Lia E Taylor
(74) *Attorney, Agent, or Firm* — Cooley LLP

(57) ABSTRACT

Provided here are antibodies that bind Protein S, and methods of making and using such antibodies. In some embodiments, the Protein S antibodies provided herein are useful for treating a bleeding disorder or platelet disorder, or a condition characterized by reduced or impaired blood coagulation and/or clotting.

20 Claims, 53 Drawing Sheets

Specification includes a Sequence Listing.

(56) References Cited

FOREIGN PATENT DOCUMENTS

| | | | |
|---|---|---|---|
| WO | WO-2007018511 | A1 | 2/2007 |
| WO | WO-2021226243 | A1 | 11/2021 |
| WO | WO-2021226245 | A1 | 11/2021 |
| WO | WO-2022002880 | A1 | 1/2022 |
| WO | WO-2024124136 | A1 | 6/2024 |

OTHER PUBLICATIONS

Bolton-Maggs, Paula HB, D. J. Perry, and E. A. Chalmers. "The rare coagulation disorders." Treatment of hemophilia. World Federation of Hemophilia, Montreal 39 (2006): 1-2 (Year: 2006).*

Kirchmaier, Carl Maximilian, and Daniele Pillitteri. "Diagnosis and Management of Inherited Platelet Disorders." Transfusion medicine and hemotherapy : offizielles Organ der Deutschen Gesellschaft fur Transfusionsmedizin und Immunhamatologie vol. 37,5 (2010): 237-246. doi:10.1159/000320257 (Year: 2010).*

Chowdary, Pratima. "Nonfactor therapies: new approaches to prophylactic treatment of haemophilia." Hämostaseologie 41.04 (2021): 247-256 (Year: 2021).*

Panteli, M., I. Pountos, and P. V. Giannoudis. "Pharmacological adjuncts to stop bleeding: options and effectiveness." European Journal of Trauma and Emergency Surgery 42 (2016): 303-310 (Year: 2016).*

Kipriyanov, Sergey M., and Fabrice Le Gall. "Generation and production of engineered antibodies." Molecular biotechnology 26.1 (2004): 39-60. (Year: 2004).*

Janeway, Charles A. "Immunobiology: The Immune System in Health and Disease." 2001 (Year: 2001).*

Dahlbäck, B. (2022) "Calcium-dependent monoclonal antibody against Gla-domain of protein S efficiently inhibiting both protein C and TFPI anticoagulant pathways," International Society on Thrombosis and Haemostasis (ISTH) 2022 Congress, Jul. 9-13, London. 2022 Congress Abstracts [online], 2 pages. Retrieved from: https://abstracts.isth.org/abstract/calcium-dependent-monoclonal-antibody-against-gla-domain-of-protein-s-efficiently-inhibiting-both-protein-c-and-tfpi-anticoagulant-pathways/.

Dahlbäck, B. et al. (1990) "Characterization of Functionality Important Domains in Human Vitamin K-dependent Protein S Using Monoclonal Antibodies," J Biol Chem, 265(14):8127-8135.

Baroni, M., et al.; "Membrane binding and anticoagulant properties of protein S natural variants," Thromb Res. (2010); 125(2):e33-e39.

Bologna, L., et al.; "Blocking Protein S Improves Hemostasis in Hemophilia a and B," Blood (2016); 128(22):79, 3 pages.

Borgel, D., et al.; "Implication of protein S thrombin-sensitive region with membrane binding via conformational changes in the gamma-carboxyglutamic acid-rich domain," Biochem J. (2001); 360(Pt 2):499-506.

Bos, M.H.A., et al.; "Does activated protein C-resistant factor V contribute to thrombin generation in hemophilic plasma?" J Thromb Haemost. (2005); 3(3):522-530.

Colman, P.M. (1994) "Effects of amino acid sequence changes on antibody-antigen interactions" Research in Immunology, 145(1):33-36.

Janeway et al., "The interaction of the antibody molecule with specific antigen," Immunobiology: The Immune System in Health and Disease, 5th Edition, Garland Science, 2001, 5 pages.

Kaufman, R.J., et al.; "Molecular approaches for improved clotting factors for hemophilia," Blood (2013); 122(22):3568-3574.

Kipriyanov, S.M., et al.; "Generation and production of engineered antibodies," Mol Biotechnol.; 6(1):39-60 (2004).

Prince, R., et al.; "Targeting anticoagulant protein S to improve hemostasis in hemophilia," Blood (2018), 131(12):1360-1371.

Saller, F., et al.; "The protein S thrombin-sensitive region modulates phospholipid binding and the gamma-carboxyglutamic acid-rich (Gla) domain conformation in a non-specific manner," J Thromb Haemost (2006); 4(3):704-706.

Santa Cruz Biotechnology: Protein S Antibody (PS7): sc-52720, Product Sheet; [retrieved online May 30, 2024] URL: https://www.scbt.com/p/protein-s-antibody-ps7#citations, 3 pages.

Stryer, L., et al.; "Protein structure and function," Part 1, Chapter 2, Biochemistry (4th ed.) New York: W. H. Freeman and Company (1995), pp. 19-23.

Von Drygalski, A., et al.; "Superior in Vivo Hemostatic Properties of an Engineered Factor Va Variant for Hemophilia Mice," Blood (2012); 120(21):17, 2 pages.

Castoldi et al. (2009). "Hereditary and acquired protein S deficiencies are associated with low TFPI levels in plasma." Journal of Thrombosis and Haemostasis, 8: 294-300.

Hackeng T. M., et al., "Protein S Stimulates Inhibition of the Tissue Factor Pathway by Tissue Factor Pathway Inhibitor," Proceedings of the National Academy of Sciences of the United States of America, Feb. 2006, vol. 103(9), pp. 3106-3111.

International Preliminary Report on Patentability for International Application No. PCT/US2021/030900 dated Nov. 17, 2022, 8 pages.

International Preliminary Report on Patentability for International Application No. PCT/US2021/030902 dated Nov. 17, 2022, 8 pages.

International Search Report and Written Opinion for International Application No. PCT/US2021/030900, mailed Sep. 16, 2021, 12 pages.

International Search Report and Written Opinion for International Application No. PCT/US2021/030902, mailed Aug. 20, 2021, 16 pages.

Sakurai et al. (2018). "A microengineered vascularized bleeding model that integrates the principal components of hemostasis" Nature Communications. 9:509, pp. 1-9.

Clinicaltrials.gov, ID NCT05776069. Study of VGA039 in Healthy Volunteers and Patients With Von Willebrand Disease [online]. Version 1, dated Mar. 8, 2023 [retrieved on Nov. 30, 2023]. Retrieved from the Internet: https://clinicaltrials.gov/study/NCT05776069?term=NCT05776069&rank=1&tab=history&a=1; 7 printed pages.

ClinicalTrials.gov, ID NCT05776069. Study of VGA039 in Healthy Volunteers and Patients With Von Willebrand Disease [online]. Version 3, dated Apr. 4, 2023 [retrieved on Nov. 30, 2023]. Retrieved from the Internet: https://clinicaltrials.gov/study/NCT05776069?term=NCT05776069&rank=1&tab=history&a=3; 7 printed pages.

Co-pending U.S. Appl. No. 18/506,872, inventors Sandip Panicker; et al., filed Nov. 10, 2023.

Hackeng, T.M., et al.; "Human protein S inhibits prothrombinase complex activity on endothelial cells and platelets via direct interactions with factors Va and Xa," J Biol Chem., (1994); 269(33):21051-21058.

Arruda, V.R., et al.; "Emerging therapies for hemophilia: controversies and unanswered questions," F1000Res.; 7(F1000 Faculty Rev-489); pp. 1-14 (2018).

Bolton-Maggs, P.H.B.; "The rare coagulation disorders," Treatment of Hemophilia, World Federation of Hemophilia (WFH), Montreal; 39(Apr. 2006):1-2; pp. 1-20.

Chowdary, P.; "Nonfactor Therapies: New Approaches to Prophylactic Treatment of Haemophilia," Hamostaseologie; 41(4):247-256 (2021).

Leong, L., et al.; "Pre-Clinical Characterization of VGA039, an Anti-Protein S Monoclonal Antibody Being Developed as a Universal Hemostatic Agent for Various Bleeding Disorder," Blood; 140(Suppl. 1):1666-1667; doi: https://doi.org/10.1182/blood-2022-170245; 7 pages (2022).

Szanto, T., et al.; "Platelets compensate for poor thrombin generation in type 3 von Willebrand disease," Platelets; 31(1):103-111 (2020).

Hackeng, T.M., et al.; "Protein S binding to human endothelial cells is required for expression of cofactor activity for activated protein C," J Biol Chem.; 268(6):3993-4000 (Feb. 1993).

* cited by examiner

APC

TFPI

TFPI Cofactor Assay

APC Cofactor Assay

SEQUENCE LISTING

```
<160> NUMBER OF SEQ ID NOS: 218

<210> SEQ ID NO 1
<211> LENGTH: 6
<212> TYPE: PRT
<213> ORGANISM: Artificial Sequence
<220> FEATURE:
<223> OTHER INFORMATION: Protein S antibody CDR-L1 sequence

<400> SEQUENCE: 1

Lys Leu Gly Asp Lys Tyr
1               5


<210> SEQ ID NO 2
<211> LENGTH: 6
<212> TYPE: PRT
<213> ORGANISM: Artificial Sequence
<220> FEATURE:
<223> OTHER INFORMATION: Protein S antibody CDR-L1 sequence

<400> SEQUENCE: 2

Ser Leu Arg Asn Tyr Tyr
1               5


<210> SEQ ID NO 3
<211> LENGTH: 9
<212> TYPE: PRT
<213> ORGANISM: Artificial Sequence
<220> FEATURE:
<223> OTHER INFORMATION: Protein S antibody CDR-L1 sequence

<400> SEQUENCE: 3

Ser Ser Asp Val Gly Gly Tyr Glu Phe
1               5


<210> SEQ ID NO 4
<211> LENGTH: 6
<212> TYPE: PRT
<213> ORGANISM: Artificial Sequence
<220> FEATURE:
<223> OTHER INFORMATION: Protein S antibody CDR-L1 sequence

<400> SEQUENCE: 4

Gln Ser Val Ser Ile Tyr
1               5
```

<210> SEQ ID NO 5
<211> LENGTH: 6
<212> TYPE: PRT
<213> ORGANISM: Artificial Sequence
<220> FEATURE:
<223> OTHER INFORMATION: Protein S antibody CDR-L1 sequence

<400> SEQUENCE: 5

Gln Arg Ile Asn Ser Asn
1 5

<210> SEQ ID NO 6
<211> LENGTH: 11
<212> TYPE: PRT
<213> ORGANISM: Artificial Sequence
<220> FEATURE:
<223> OTHER INFORMATION: Protein S antibody CDR-L1 sequence

<400> SEQUENCE: 6

Gln Ser Leu Leu His Ser Asn Gly Tyr Asn Tyr
1 5 10

<210> SEQ ID NO 7

<400> SEQUENCE: 7

000

<210> SEQ ID NO 8

<400> SEQUENCE: 8

000

<210> SEQ ID NO 9
<211> LENGTH: 9
<212> TYPE: PRT
<213> ORGANISM: Artificial Sequence
<220> FEATURE:
<223> OTHER INFORMATION: Protein S antibody CDR-L1 sequence

<400> SEQUENCE: 9

Thr Gly Ala Val Thr Ala Ser Asn Tyr
1 5

<210> SEQ ID NO 10
<211> LENGTH: 6
<212> TYPE: PRT
<213> ORGANISM: Artificial Sequence
<220> FEATURE:
<223> OTHER INFORMATION: Protein S antibody CDR-L1 sequence

<400> SEQUENCE: 10

Gln Ser Val Thr Ser Asn
1 5

<210> SEQ ID NO 11
<211> LENGTH: 11
<212> TYPE: PRT
<213> ORGANISM: Artificial Sequence
<220> FEATURE:
<223> OTHER INFORMATION: Protein S antibody CDR-L1 sequence

<400> SEQUENCE: 11

Gln Ser Leu Val His Ser Asp Gly Asn Thr Tyr
1 5 10

<210> SEQ ID NO 12
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 12

Gln Asp Thr
1

<210> SEQ ID NO 13
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 13

Gly Lys Asn
1

<210> SEQ ID NO 14
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 14

Asp Val Ser
1

<210> SEQ ID NO 15
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 15

Gln Asn Ser
1

<210> SEQ ID NO 16
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 16

Asp Ala Ser
1

<210> SEQ ID NO 17
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 17

Gly Ala Ser
1

<210> SEQ ID NO 18
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 18

Leu Gly Ser
1

<210> SEQ ID NO 19
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 19

Ser Thr Asn
1

<210> SEQ ID NO 20
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 20

Lys Ile Ser
1

<210> SEQ ID NO 21
<211> LENGTH: 9
<212> TYPE: PRT
<213> ORGANISM: Artificial Sequence
<220> FEATURE:
<223> OTHER INFORMATION: Protein S antibody CDR-L3 sequence

<400> SEQUENCE: 21

Gln Ala Trp Asp Ser Asn Thr Val Val
1               5

<210> SEQ ID NO 22
<211> LENGTH: 11
<212> TYPE: PRT
<213> ORGANISM: Artificial Sequence
<220> FEATURE:
<223> OTHER INFORMATION: Protein S antibody CDR-L3 sequence

<400> SEQUENCE: 22

Asn Ser Arg Asp Ser Ser Gly Asn His Val Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Protein S antibody CDR-L3 sequence

<400> SEQUENCE: 23

Ser Ser Tyr Thr Arg Ser Ser Thr Val Val
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Protein S antibody CDR-L3 sequence

<400> SEQUENCE: 24

Gln Ala Trp Asp Ser Ser Thr Trp Val
1 5

<210> SEQ ID NO 25
<211> LENGTH: 9
<212> TYPE: PRT
<213> ORGANISM: Artificial Sequence
<220> FEATURE:
<223> OTHER INFORMATION: Protein S antibody CDR-L3 sequence

<400> SEQUENCE: 25

Gln Gln Arg Ser Asn Trp Pro Leu Thr
1 5

<210> SEQ ID NO 26
<211> LENGTH: 9
<212> TYPE: PRT
<213> ORGANISM: Artificial Sequence
<220> FEATURE:
<223> OTHER INFORMATION: Protein S antibody CDR-L3 sequence

<400> SEQUENCE: 26

Gln Gln Tyr Asp Asn Trp Pro Leu Thr
1 5

<210> SEQ ID NO 27
<211> LENGTH: 8
<212> TYPE: PRT
<213> ORGANISM: Artificial Sequence
<220> FEATURE:
<223> OTHER INFORMATION: Protein S antibody CDR-L3 sequence

<400> SEQUENCE: 27

Met Gln Ala Leu Gln Thr Phe Thr
1 5

<210> SEQ ID NO 28

<400> SEQUENCE: 28

000

<210> SEQ ID NO 29

<400> SEQUENCE: 29

000

<210> SEQ ID NO 30
<211> LENGTH: 9
<212> TYPE: PRT
<213> ORGANISM: Artificial Sequence
<220> FEATURE:
<223> OTHER INFORMATION: Protein S antibody CDR-L3 sequence

<400> SEQUENCE: 30

Ala Leu Trp Tyr Ser Asp His Phe Val
1 5

<210> SEQ ID NO 31
<211> LENGTH: 8
<212> TYPE: PRT
<213> ORGANISM: Artificial Sequence
<220> FEATURE:
<223> OTHER INFORMATION: Protein S antibody CDR-L3 sequence

<400> SEQUENCE: 31

Gln Gln Tyr Asn Asn Trp Pro Thr
1 5

<210> SEQ ID NO 32
<211> LENGTH: 10
<212> TYPE: PRT
<213> ORGANISM: Artificial Sequence
<220> FEATURE:
<223> OTHER INFORMATION: Protein S antibody CDR-L3 sequence

<400> SEQUENCE: 32

Met Gln Ala Thr Gln Phe Pro His Leu Thr
1 5 10

<210> SEQ ID NO 33
<211> LENGTH: 10
<212> TYPE: PRT
<213> ORGANISM: Artificial Sequence
<220> FEATURE:
<223> OTHER INFORMATION: Protein S antibody CDR-H1 sequence

<400> SEQUENCE: 33

Gly Gly Ser Ile Ser Ser Ser Ser Tyr Tyr
1 5 10

<210> SEQ ID NO 34
<211> LENGTH: 8
<212> TYPE: PRT
<213> ORGANISM: Artificial Sequence
<220> FEATURE:
<223> OTHER INFORMATION: Protein S antibody CDR-H1 sequence

<400> SEQUENCE: 34

Gly Gly Thr Phe Ser Ser Tyr Ser
1 5

<210> SEQ ID NO 35
<211> LENGTH: 10
<212> TYPE: PRT
<213> ORGANISM: Artificial Sequence
<220> FEATURE:
<223> OTHER INFORMATION: Protein S antibody CDR-H1 sequence

<400> SEQUENCE: 35

Gly Gly Ser Ile Thr Ser Asp Gly Tyr His
1 5 10

<210> SEQ ID NO 36
<211> LENGTH: 8
<212> TYPE: PRT
<213> ORGANISM: Artificial Sequence
<220> FEATURE:
<223> OTHER INFORMATION: Protein S antibody CDR-H1 sequence

<400> SEQUENCE: 36

Gly Phe Thr Phe Asp Asp Tyr Ala
1 5

<210> SEQ ID NO 37

<211> LENGTH: 8
<212> TYPE: PRT
<213> ORGANISM: Artificial Sequence
<220> FEATURE:
<223> OTHER INFORMATION: Protein S antibody CDR-H1 sequence

<400> SEQUENCE: 37

Gly Phe Thr Phe Ser Thr Tyr Gly
1 5

<210> SEQ ID NO 38
<211> LENGTH: 9
<212> TYPE: PRT
<213> ORGANISM: Artificial Sequence
<220> FEATURE:
<223> OTHER INFORMATION: Protein S antibody CDR-H1 sequence

<400> SEQUENCE: 38

Gly Tyr Ser Ile Ser Ser Gly Tyr Tyr
1 5

<210> SEQ ID NO 39
<211> LENGTH: 8
<212> TYPE: PRT
<213> ORGANISM: Artificial Sequence
<220> FEATURE:
<223> OTHER INFORMATION: Protein S antibody CDR-H1 sequence

<400> SEQUENCE: 39

Gly Asp Thr Phe Ser Asn His Ala
1 5

<210> SEQ ID NO 40

<400> SEQUENCE: 40

000

<210> SEQ ID NO 41

<400> SEQUENCE: 41

000

<210> SEQ ID NO 42
<211> LENGTH: 8
<212> TYPE: PRT
<213> ORGANISM: Artificial Sequence
<220> FEATURE:
<223> OTHER INFORMATION: Protein S antibody CDR-H1 sequence

<400> SEQUENCE: 42

Gly His Thr Phe Thr Gly Tyr Tyr
1 5

<210> SEQ ID NO 43
<211> LENGTH: 9
<212> TYPE: PRT
<213> ORGANISM: Artificial Sequence
<220> FEATURE:
<223> OTHER INFORMATION: Protein S antibody CDR-H1 sequence

<400> SEQUENCE: 43

Gly Gly Ser Ile Ser Ser Thr Asn Trp
1 5

<210> SEQ ID NO 44

<211> LENGTH: 8
<212> TYPE: PRT
<213> ORGANISM: Artificial Sequence
<220> FEATURE:
<223> OTHER INFORMATION: Protein S antibody CDR-H1 sequence

<400> SEQUENCE: 44

Gly Gly Ser Ile Ser Asn Tyr Tyr
1               5

<210> SEQ ID NO 45
<211> LENGTH: 7
<212> TYPE: PRT
<213> ORGANISM: Artificial Sequence
<220> FEATURE:
<223> OTHER INFORMATION: Protein S antibody CDR-H2 sequence

<400> SEQUENCE: 45

Ile Tyr Tyr Ser Gly Asn Thr
1               5

<210> SEQ ID NO 46
<211> LENGTH: 8
<212> TYPE: PRT
<213> ORGANISM: Artificial Sequence
<220> FEATURE:
<223> OTHER INFORMATION: Protein S antibody CDR-H2 sequence

<400> SEQUENCE: 46

Ile Ile Pro Ile Phe Gly Thr Thr
1               5

<210> SEQ ID NO 47
<211> LENGTH: 7
<212> TYPE: PRT
<213> ORGANISM: Artificial Sequence
<220> FEATURE:
<223> OTHER INFORMATION: Protein S antibody CDR-H2 sequence

<400> SEQUENCE: 47

Ile Tyr Tyr Thr Gly Asn Thr
1               5

<210> SEQ ID NO 48
<211> LENGTH: 8
<212> TYPE: PRT
<213> ORGANISM: Artificial Sequence
<220> FEATURE:
<223> OTHER INFORMATION: Protein S antibody CDR-H2 sequence

<400> SEQUENCE: 48

Ile Thr Trp Asn Ser Gly Asn Ile
1               5

<210> SEQ ID NO 49
<211> LENGTH: 8
<212> TYPE: PRT
<213> ORGANISM: Artificial Sequence
<220> FEATURE:
<223> OTHER INFORMATION: Protein S antibody CDR-H2 sequence

<400> SEQUENCE: 49

Ile Tyr Tyr Asp Gly Ile Asn Lys
1               5

<210> SEQ ID NO 50
<211> LENGTH: 7

<212> TYPE: PRT
<213> ORGANISM: Artificial Sequence
<220> FEATURE:
<223> OTHER INFORMATION: Protein S antibody CDR-H2 sequence

<400> SEQUENCE: 50

Ile Tyr Tyr Ser Gly Ser Thr
1 5

<210> SEQ ID NO 51
<211> LENGTH: 8
<212> TYPE: PRT
<213> ORGANISM: Artificial Sequence
<220> FEATURE:
<223> OTHER INFORMATION: Protein S antibody CDR-H2 sequence

<400> SEQUENCE: 51

Tyr Ile Pro Ile Phe Gly Thr Thr
1 5

<210> SEQ ID NO 52

<400> SEQUENCE: 52

000

<210> SEQ ID NO 53

<400> SEQUENCE: 53

000

<210> SEQ ID NO 54
<211> LENGTH: 8
<212> TYPE: PRT
<213> ORGANISM: Artificial Sequence
<220> FEATURE:
<223> OTHER INFORMATION: Protein S antibody CDR-H2 sequence

<400> SEQUENCE: 54

Ile Asn Pro Asn Ser Gly Asp Thr
1 5

<210> SEQ ID NO 55
<211> LENGTH: 7
<212> TYPE: PRT
<213> ORGANISM: Artificial Sequence
<220> FEATURE:
<223> OTHER INFORMATION: Protein S antibody CDR-H2 sequence

<400> SEQUENCE: 55

Ile Tyr Gln Thr Gly Ser Thr
1 5

<210> SEQ ID NO 56
<211> LENGTH: 7
<212> TYPE: PRT
<213> ORGANISM: Artificial Sequence
<220> FEATURE:
<223> OTHER INFORMATION: Protein S antibody CDR-H2 sequence

<400> SEQUENCE: 56

Ile Tyr Tyr Ile Gly Ile Thr
1 5

<210> SEQ ID NO 57
<211> LENGTH: 17

<212> TYPE: PRT
<213> ORGANISM: Artificial Sequence
<220> FEATURE:
<223> OTHER INFORMATION: Protein S antibody CDR-H3 sequence

<400> SEQUENCE: 57

Ala Arg Cys Ser Gly Tyr Gly Tyr Ser Ser Gly Arg Ser Tyr Phe Asp
1 5 10 15

Tyr

<210> SEQ ID NO 58
<211> LENGTH: 11
<212> TYPE: PRT
<213> ORGANISM: Artificial Sequence
<220> FEATURE:
<223> OTHER INFORMATION: Protein S antibody CDR-H3 sequence

<400> SEQUENCE: 58

Glu Gly Gly Arg Val Gly Ala Asp Phe Asp Tyr
1 5 10

<210> SEQ ID NO 59
<211> LENGTH: 12
<212> TYPE: PRT
<213> ORGANISM: Artificial Sequence
<220> FEATURE:
<223> OTHER INFORMATION: Protein S antibody CDR-H3 sequence

<400> SEQUENCE: 59

Ala Arg Arg Leu Ser Thr Gly Pro Tyr Phe Asp Tyr
1 5 10

<210> SEQ ID NO 60
<211> LENGTH: 12
<212> TYPE: PRT
<213> ORGANISM: Artificial Sequence
<220> FEATURE:
<223> OTHER INFORMATION: Protein S antibody CDR-H3 sequence

<400> SEQUENCE: 60

Ala Lys Gly Arg Ala Val Ser Asp Thr Phe Asp Ile
1 5 10

<210> SEQ ID NO 61
<211> LENGTH: 7
<212> TYPE: PRT
<213> ORGANISM: Artificial Sequence
<220> FEATURE:
<223> OTHER INFORMATION: Protein S antibody CDR-H3 sequence

<400> SEQUENCE: 61

Ala Glu Ser Asp Leu Asp Tyr
1 5

<210> SEQ ID NO 62
<211> LENGTH: 18
<212> TYPE: PRT
<213> ORGANISM: Artificial Sequence
<220> FEATURE:
<223> OTHER INFORMATION: Protein S antibody CDR-H3 sequence

<400> SEQUENCE: 62

Ala Thr Thr Tyr Ser Asp Ile Val Thr Gly Tyr Tyr Asn Asp Ala Phe
1 5 10 15

Asp Ile

<210> SEQ ID NO 63
<211> LENGTH: 20
<212> TYPE: PRT
<213> ORGANISM: Artificial Sequence
<220> FEATURE:
<223> OTHER INFORMATION: Protein S antibody CDR-H3 sequence

<400> SEQUENCE: 63

Ala Arg Gly Gly Leu Ala Gly Ser His Tyr Lys Asn Tyr Tyr Tyr Asp
1 5 10 15

Gly Met Asp Val
20

<210> SEQ ID NO 64

<400> SEQUENCE: 64

000

<210> SEQ ID NO 65

<400> SEQUENCE: 65

000

<210> SEQ ID NO 66
<211> LENGTH: 14
<212> TYPE: PRT
<213> ORGANISM: Artificial Sequence
<220> FEATURE:
<223> OTHER INFORMATION: Protein S antibody CDR-H3 sequence

<400> SEQUENCE: 66

Ala Arg Asp Ser Gln Ile Leu Trp Phe Gly Glu Leu Gly Tyr
1 5 10

<210> SEQ ID NO 67
<211> LENGTH: 9
<212> TYPE: PRT
<213> ORGANISM: Artificial Sequence
<220> FEATURE:
<223> OTHER INFORMATION: Protein S antibody CDR-H3 sequence

<400> SEQUENCE: 67

Ala Arg Arg Phe Gly Glu Leu Asp Tyr
1 5

<210> SEQ ID NO 68
<211> LENGTH: 11
<212> TYPE: PRT
<213> ORGANISM: Artificial Sequence
<220> FEATURE:
<223> OTHER INFORMATION: Protein S antibody CDR-H3 sequence

<400> SEQUENCE: 68

Ala Ala Leu Ser Gly Asp His Ala Phe Asp Ile
1 5 10

<210> SEQ ID NO 69
<211> LENGTH: 106
<212> TYPE: PRT
<213> ORGANISM: Artificial Sequence
<220> FEATURE:
<223> OTHER INFORMATION: Protein S monoclonal antibody variable light
chain sequence

<400> SEQUENCE: 69

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Thr Val Val
                85                  90                  95

Phe Gly Gly Gly Thr Lys Leu Thr Val Leu
            100                 105


<210> SEQ ID NO 70
<211> LENGTH: 125
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 70

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Met Thr Ala Ala Asp Thr Ala Val Tyr Tyr
                85                  90                  95

Cys Ala Arg Cys Ser Gly Tyr Gly Tyr Ser Ser Gly Arg Ser Tyr Phe
            100                 105                 110

Asp Tyr Trp Gly Gln Glu Thr Leu Val Thr Val Ser Ser
        115                 120                 125


<210> SEQ ID NO 71
<211> LENGTH: 108
<212> TYPE: PRT
<213> ORGANISM: Artificial Sequence
<220> FEATURE:
<223> OTHER INFORMATION: Protein S monoclonal antibody variable light
      chain sequence

<400> SEQUENCE: 71

Ser Ser Asp Leu Thr Gln Gly Pro Ala Val Ser Val Ala Leu Gly Gln
1               5                   10                  15

Thr Val Arg Ile Thr Cys Gln Gly Asp Ser Leu Arg Asn Tyr Tyr Ala
            20                  25                  30

Ser Trp Tyr Gln Gln Lys Pro Gly Gln Ala Pro Val Pro Val Ile Tyr
        35                  40                  45

Gly Lys Asn Asp Arg Pro Ser Gly Ile Pro Asp Arg Phe Ser Gly Ser
    50                  55                  60
```

```
Ile Ser Gly Asn Thr Ala Ser Leu Thr Ile Thr Gly Ala Gln Ala Glu
65                  70                  75                  80

Asp Glu Ala His Tyr Tyr Cys Asn Ser Arg Asp Ser Ser Gly Asn His
                85                  90                  95

Val Val Phe Gly Gly Gly Thr Lys Leu Thr Val Leu
            100                 105


<210> SEQ ID NO 72
<211> LENGTH: 118
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Val Ser Gly Gly Thr Phe Ser Ser Tyr
            20                  25                  30

Ser Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Asp Leu Ser Ser Leu Lys Ser Glu Asp Thr Ala Met Tyr Tyr Cys
                85                  90                  95

Glu Gly Gly Arg Val Gly Ala Asp Phe Asp Tyr Trp Gly Gln Gly Thr
            100                 105                 110

Leu Val Thr Val Ser Ser
        115


<210> SEQ ID NO 73
<211> LENGTH: 110
<212> TYPE: PRT
<213> ORGANISM: Artificial Sequence
<220> FEATURE:
<223> OTHER INFORMATION: Protein S monoclonal antibody variable light
      chain sequence

<400> SEQUENCE: 73

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Glu Phe Val Ser Trp Tyr Gln His His Pro Gly Lys Ala Pro Lys Leu
        35                  40                  45

Met Ile Tyr Asp Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Arg Ser
                85                  90                  95

Ser Thr Val Val Phe Gly Gly Gly Ala Arg Leu Thr Val Leu
            100                 105                 110


<210> SEQ ID NO 74
```

```
<211> LENGTH: 120
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 74

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Asp
            20                  25                  30

Gly Tyr His Trp Ser Trp Ile Arg Gln Tyr Pro Gly Lys Gly Leu Asp
        35                  40                  45

Trp Ile Gly Tyr Ile Tyr Tyr Thr Gly Asn Thr Tyr Tyr Asn Pro Ser
    50                  55                  60

Leu Lys Ser Arg Val Thr Ile Ser Val Gly Thr Ser Gln Asn Gln Phe
65                  70                  75                  80

Ser Leu Lys Leu Ile Ser Val Thr Ala Ala Asp Thr Ala Val Tyr Tyr
                85                  90                  95

Cys Ala Arg Arg Leu Ser Thr Gly Pro Tyr Phe Asp Tyr Trp Gly Gln
            100                 105                 110

Gly Thr Leu Val Thr Val Ser Ser
        115                 120


<210> SEQ ID NO 75
<211> LENGTH: 106
<212> TYPE: PRT
<213> ORGANISM: Artificial Sequence
<220> FEATURE:
<223> OTHER INFORMATION: Protein S monoclonal antibody variable light
      chain sequence

<400> SEQUENCE: 75

Ser Tyr Glu Leu Asn Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Gln Ser Pro Val Val Ala Ile Tyr
        35                  40                  45

Gln Asn Ser Lys Arg Pro Ser Gly Ile Pro Glu Arg Phe Ser Ala Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Ser Ser Thr Trp Val
                85                  90                  95

Phe Gly Gly Gly Thr Lys Leu Thr Val Leu
            100                 105


<210> SEQ ID NO 76
<211> LENGTH: 119
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 76

Glu Val Gln Leu Val Glu Ser Gly Gly Gly Leu Val Gln Pro Gly Arg
1               5                   10                  15
```

```
Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Gly Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu His Met Asn Ser Leu Arg Ile Glu Asp Thr Ala Phe Tyr Tyr Cys
                85                  90                  95

Ala Lys Gly Arg Ala Val Ser Asp Thr Phe Asp Ile Trp Gly Gln Gly
            100                 105                 110

Thr Met Val Thr Val Ser Ser
        115


<210> SEQ ID NO 77
<211> LENGTH: 107
<212> TYPE: PRT
<213> ORGANISM: Artificial Sequence
<220> FEATURE:
<223> OTHER INFORMATION: Protein S monoclonal antibody variable light
      chain sequence

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Pro Gly Thr Lys Val Asp Ile Lys
            100                 105


<210> SEQ ID NO 78
<211> LENGTH: 114
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 78

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Phe His Trp Val Arg Gln Pro Pro Gly Lys Gly Leu Glu Trp Val
        35                  40                  45

Ala Val Ile Tyr Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80
```

```
Leu Gln Met Asn Ser Leu Arg Ala Glu Asp Thr Ala Val Tyr Tyr Cys
                85                  90                  95

Ala Glu Ser Asp Leu Asp Tyr Trp Gly Gln Gly Thr Leu Val Thr Val
            100                 105                 110

Ser Ser


<210> SEQ ID NO 79
<211> LENGTH: 107
<212> TYPE: PRT
<213> ORGANISM: Artificial Sequence
<220> FEATURE:
<223> OTHER INFORMATION: Protein S monoclonal antibody variable light
      chain sequence

<400> SEQUENCE: 79

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Arg Ile Asn Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ala Tyr Tyr Cys Gln Gln Tyr Asp Asn Trp Pro Leu
                85                  90                  95

Thr Phe Gly Gly Gly Thr Lys Val Glu Ile Lys
            100                 105


<210> SEQ ID NO 80
<211> LENGTH: 125
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 80

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Asp Trp
        35                  40                  45

Ile Gly Ser Ile Tyr Tyr Ser Gly Ser Thr Tyr Tyr Asn Pro Ser Leu
    50                  55                  60

Lys Ser Arg Val Thr Ile Ser Val Asp Thr Ser Lys Asn Gln Ile Ser
65                  70                  75                  80

Leu Lys Leu Ser Ser Val Thr Ala Ala Asp Thr Ala Val Tyr Tyr Cys
                85                  90                  95

Ala Thr Thr Tyr Ser Asp Ile Val Thr Gly Tyr Tyr Asn Asp Ala Phe
            100                 105                 110

Asp Ile Trp Gly Gln Gly Thr Met Val Thr Val Ser Ser
        115                 120                 125


<210> SEQ ID NO 81
<211> LENGTH: 111
<212> TYPE: PRT
```

```
<213> ORGANISM: Artificial Sequence
<220> FEATURE:
<223> OTHER INFORMATION: Protein S monoclonal antibody variable light
      chain sequence

<400> SEQUENCE: 81

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Phe Thr Phe Gly Pro Gly Thr Lys Val Asp Ile Lys
            100                 105                 110


<210> SEQ ID NO 82
<211> LENGTH: 127
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 82

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Asn His
            20                  25                  30

Ala Ile Asn Trp Val Arg Gln Ala Pro Gly Gln Gly Leu Glu Trp Met
        35                  40                  45

Gly Gly Tyr Ile Pro Ile Phe Gly Thr Thr Asn Ser Ala Gln Lys Phe
    50                  55                  60

Arg Gly Arg Val Thr Ile Thr Ala Asp Lys Ser Thr Asn Thr Ala Tyr
65                  70                  75                  80

Met Ala Leu Ser Ser Leu Arg Ser Glu Asp Thr Ala Val Tyr Tyr Cys
                85                  90                  95

Ala Arg Gly Gly Leu Ala Gly Ser His Tyr Lys Asn Tyr Tyr Tyr Asp
            100                 105                 110

Gly Met Asp Val Trp Gly Gln Gly Thr Thr Val Thr Val Ser Ser
        115                 120                 125


<210> SEQ ID NO 83

<400> SEQUENCE: 83

000


<210> SEQ ID NO 84

<400> SEQUENCE: 84

000


<210> SEQ ID NO 85
```

<400> SEQUENCE: 85

000

<210> SEQ ID NO 86

<400> SEQUENCE: 86

000

<210> SEQ ID NO 87
<211> LENGTH: 109
<212> TYPE: PRT
<213> ORGANISM: Artificial Sequence
<220> FEATURE:
<223> OTHER INFORMATION: Protein S monoclonal antibody variable light chain sequence

<400> SEQUENCE: 87

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Ala Ser
            20                  25                  30

Asn Tyr Ala Asn Trp Val Gln Glu Lys Pro Asp His Leu Phe Thr Gly
        35                  40                  45

Leu Ile Gly Ser Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asp
                85                  90                  95

His Phe Val Phe Gly Gly Gly Thr Lys Leu Thr Val Leu
            100                 105
```

<210> SEQ ID NO 88
<211> LENGTH: 121
<212> TYPE: PRT
<213> ORGANISM: Artificial Sequence
<220> FEATURE:
<223> OTHER INFORMATION: Protein S monoclonal antibody variable heavy chain sequence

<400> SEQUENCE: 88

```
Gln Val Gln Leu Val Gln Ser Gly Ala Glu Val Lys Lys Pro Gly Ala
1               5                   10                  15

Ser Val Lys Val Ser Cys Lys Ser Ser Gly His Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Met Ser Arg Leu Arg Ser Asp Asp Thr Ala Val Tyr Tyr Cys
                85                  90                  95

Ala Arg Asp Ser Gln Ile Leu Trp Phe Gly Glu Leu Gly Tyr Trp Gly
            100                 105                 110

Gln Gly Thr Leu Val Thr Val Ser Ser
        115                 120
```

```
<210> SEQ ID NO 89
<211> LENGTH: 106
<212> TYPE: PRT
<213> ORGANISM: Artificial Sequence
<220> FEATURE:
<223> OTHER INFORMATION: Protein S monoclonal antibody variable light
      chain sequence

<400> SEQUENCE: 89

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Thr Ser Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Gln Tyr Asn Asn Trp Pro Thr
                85                  90                  95

Phe Gly Gln Gly Thr Arg Leu Glu Ile Lys
            100                 105


<210> SEQ ID NO 90
<211> LENGTH: 116
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 90

Gln Val Gln Leu Gln Glu Ser Gly Pro Gly Leu Val Lys Pro Ser Glu
1               5                   10                  15

Thr Leu Ser Leu Thr Cys Gly Val Ser Gly Gly Ser Ile Ser Ser Thr
            20                  25                  30

Asn Trp Trp Ser Trp Val Arg Gln Pro Pro Gly Lys Gly Leu Glu Trp
        35                  40                  45

Ile Gly Glu Ile Tyr Gln Thr Gly Ser Thr Asp Tyr Asp Pro Ser Leu
    50                  55                  60

Lys Ser Arg Val Thr Ile Ser Ile Asp Lys Ser Lys Asn Gln Phe Ser
65                  70                  75                  80

Leu Lys Leu Tyr Ser Val Thr Ala Ala Asp Thr Ala Val Tyr Tyr Cys
                85                  90                  95

Ala Arg Arg Phe Gly Glu Leu Asp Tyr Trp Gly Gln Gly Thr Leu Val
            100                 105                 110

Thr Val Ser Ser
        115


<210> SEQ ID NO 91
<211> LENGTH: 113
<212> TYPE: PRT
<213> ORGANISM: Artificial Sequence
<220> FEATURE:
<223> OTHER INFORMATION: Protein S monoclonal antibody variable light
      chain sequence

<400> SEQUENCE: 91

Asp Ile Val Met Thr Gln Thr Pro Leu Ser Ser Pro Val Thr Leu Gly
```

```
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro His Leu Thr Phe Gly Gly Gly Thr Lys Val Glu Ile
            100                 105                 110

Lys


<210> SEQ ID NO 92
<211> LENGTH: 117
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 92

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Asn Trp Ile Arg Gln Pro Pro Gly Lys Gly Leu Glu Trp Ile
        35                  40                  45

Gly Tyr Ile Tyr Tyr Ile Gly Ile Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Val Thr Ser Val Thr Ala Ala Asp Thr Ala Val Tyr Tyr Cys Ala
                85                  90                  95

Ala Leu Ser Gly Asp His Ala Phe Asp Ile Trp Gly Gln Gly Thr Leu
            100                 105                 110

Val Thr Val Ser Ser
        115


<210> SEQ ID NO 93
<211> LENGTH: 318
<212> TYPE: DNA
<213> ORGANISM: Artificial Sequence
<220> FEATURE:
<223> OTHER INFORMATION: Protein S monoclonal antibody variable light
      chain sequence

<400> SEQUENCE: 93

tcctatgagc tgactcagcc accctcagtg tccgtgtccc caggacagac agccagcatc      60

acctgctctg gagataaatt gggggataaa tatgcttgct ggtatcagca gaagccaggc     120

cagtcccctg tactggtcat ctatcaagat actaagcggc cctcagggat ccctgagcga     180

ttctctggct ccaactctgg gaacacagcc actctgacca tcagcgggac ccaggctatg     240

gatgaggctg actattactg tcaggcgtgg gacagcaaca ctgtggtctt cggcggaggg     300

accaagctga ccgtccta                                                   318
```

<210> SEQ ID NO 94
<211> LENGTH: 375
<212> TYPE: DNA
<213> ORGANISM: Artificial Sequence
<220> FEATURE:
<223> OTHER INFORMATION: Protein S monoclonal antibody variable heavy chain sequence

<400> SEQUENCE: 94
cagctgcagc tgcaggagtc gggcccagga ctggtgaagc cttcggagac cctgtccctc 60
acctgcactg tctctggtgg ctccatcagc agtagtagtt actactgggg ctggatccgc 120
cagcccccgg ggaagggact ggagtggatt gggaatatct attatagtgg gaacacctac 180
tacaacccgt ccctcaagag tcgagtcacc atatccgtag acacgtccaa gaaccagttc 240
tccctgaagc tgagctctat gaccgccgca gacacggctg tgtattactg tgcgagatgt 300
agtggctacg ggtatagcag tggccggtcc tactttgact actggggcca ggaaaccctg 360
gtcaccgtct cctca 375

<210> SEQ ID NO 95
<211> LENGTH: 324
<212> TYPE: DNA
<213> ORGANISM: Artificial Sequence
<220> FEATURE:
<223> OTHER INFORMATION: Protein S monoclonal antibody variable light chain sequence

<400> SEQUENCE: 95
tcctctgacc tgactcaggg ccctgctgtg tctgtggccc tgggacagac agtcaggatc 60
acatgccaag gagacagcct cagaaactat tatgcaagct ggtaccagca gaagccagga 120
caggcccctg tacctgtcat ctatggtaaa aacgaccggc cctcagggat cccagaccga 180
ttctctggct ccatctcagg aaacacagct tccttgacca tcactggggc tcaggcggaa 240
gatgaggctc actattactg taactcccgg gacagcagtg gtaaccatgt ggtattcggc 300
ggagggacca agctgaccgt cctg 324

<210> SEQ ID NO 96
<211> LENGTH: 354
<212> TYPE: DNA
<213> ORGANISM: Artificial Sequence
<220> FEATURE:
<223> OTHER INFORMATION: Protein S monoclonal antibody variable heavy chain sequence

<400> SEQUENCE: 96
caggtgcagc tggtgcagtc tggggctgag gtgaagaagc ctgggtcctc ggtgaaggtc 60
tcctgcaagg tttctggagg caccttcagc agctattcta tcagctgggt gcgacaggcc 120
cctggacaag ggcttgagtg gatgggaggg atcatcccta tatttggtac aacaaactac 180
gcacagaagt tccagggcag agtcacgatc accgcggacg aatccacgag cacagcctac 240
atggatctga gcagcctgaa atctgaggac acggccatgt attactgtga gggggggtaga 300 gtgggagcgg actttgacta ctggggccag ggaaccctgg tcaccgtctc ctca 354

<210> SEQ ID NO 97
<211> LENGTH: 330
<212> TYPE: DNA
<213> ORGANISM: Artificial Sequence
<220> FEATURE:
<223> OTHER INFORMATION: Protein S monoclonal antibody variable light chain sequence

<400> SEQUENCE: 97
cagtctgccc tgactcagcc tgcctccgtg tctgggtctc ctggacagtc gatcaccatc 60
tcctgcactg gaaccagcag tgacgttggt ggttatgaat ttgtctcctg gtaccaacat 120
cacccaggca aagcccccaa actcatgatt tatgatgtca gtagtcggcc ctcaggggtt 180
tctaatcgct tctctggctc caagtctggc aacacggcct ccctgaccat ctctgggctc 240
caggctgagg acgaggctga ttattactgc agctcatata cgcgcagcag cactgtggtg 300
ttcggcggcg gggccaggct gaccgtccta 330

<210> SEQ ID NO 98
<211> LENGTH: 360
<212> TYPE: DNA
<213> ORGANISM: Artificial Sequence
<220> FEATURE:
<223> OTHER INFORMATION: Protein S monoclonal antibody variable heavy
chain sequence

<400> SEQUENCE: 98
caggtgcagc tgcaggagtc gggcccagga ctggtgaagc cttcacagac cctgtccctc 60
acctgcactg tctctggtgg ctccatcacc agtgatggtt accactggag ctggatccgc 120
cagtacccag ggaagggcct ggactggatt ggatacatct attacactgg gaacacctac 180
tacaacccgt ccctcaagag tcgagtgacc atatcagtag gcacgtctca gaaccagttc 240
tccctgaagc tgatctctgt gactgccgcg gacacggccg tttattactg tgcgagaagg 300
ctgtcgactg ggccctactt tgactactgg ggccagggaa ccctggtcac cgtctcctcc 360

<210> SEQ ID NO 99
<211> LENGTH: 318
<212> TYPE: DNA
<213> ORGANISM: Artificial Sequence
<220> FEATURE:
<223> OTHER INFORMATION: Protein S monoclonal antibody variable light
chain sequence

<400> SEQUENCE: 99
tcctatgagc tgaatcagcc accctcagtg tccgtgtccc caggacagac agccagcatc 60
acctgctctg gagataaatt gggggataaa tatgcttcct ggtatcagca gaagccaggc 120
cagtcccctg tggtggccat ctatcaaaat agcaagcggc cctcagggat ccctgagcga 180
ttctctgcct ccaactctgg gaacacagcc actctgacca tcagcgggac ccaggctttg 240
gatgaggctg actattactg tcaggcgtgg gacagcagca cttgggtgtt cggcggaggg 300
accaagctga ccgtccta 318

<210> SEQ ID NO 100
<211> LENGTH: 357
<212> TYPE: DNA
<213> ORGANISM: Artificial Sequence
<220> FEATURE:
<223> OTHER INFORMATION: Protein S monoclonal antibody variable heavy
chain sequence

<400> SEQUENCE: 100
gaagtgcagc tggtggagtc tgggggaggc ttggtacagc ctggcaggtc cctgagactc 60
tcctgtgcag cctctggatt cacctttgat gattatgcca tgcactgggt ccggcaagct 120
ccagggaagg gcctggaatg ggtctcaggt attacttgga atagtggtaa cataggctat 180
gcggactctg tgaagggccg attcaccatc tccagagaca acgccaagaa ctccctgtat 240
ctgcacatga acagtctgag aattgaggac acggccttct attactgtgc aaaaggccga 300
gcagtgtctg atacttttga tatctggggc caagggacaa tggtcaccgt ctcttca 357

<210> SEQ ID NO 101
<211> LENGTH: 321
<212> TYPE: DNA
<213> ORGANISM: Artificial Sequence
<220> FEATURE:
<223> OTHER INFORMATION: Protein S monoclonal antibody variable light chain sequence

<400> SEQUENCE: 101
gaaattgtgt tgacacagtc tccagccacc ctgtctttgt ctccagggga aagagccacc 60
ctctcctgca gggccagtca gagtgttagt atctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag cgtagcaact ggcccctcac tttcggccct 300
gggaccaaag tggatatcaa a 321

<210> SEQ ID NO 102
<211> LENGTH: 342
<212> TYPE: DNA
<213> ORGANISM: Artificial Sequence
<220> FEATURE:
<223> OTHER INFORMATION: Protein S monoclonal antibody variable heavy chain sequence

<400> SEQUENCE: 102
caggtgcagt tggtggaatc tgggggaggc gtggtccagc ctgggaggtc cctgagactc 60
tcctgtgcag cgtctggatt caccttcagt acctatggct ttcactgggt ccgccagcct 120
ccaggcaagg gactggagtg ggtggcagtt atatattatg atggaattaa taaatattat 180
gcagactccg tgaagggccg attcaccatc tccagagaca attccaagaa cacgctgttt 240
cttcaaatga acagcctgag agccgaggac acggctgtgt attactgtgc ggagtccgac 300
ttggactact ggggccaggg aaccctggtc accgtctcct ca 342

<210> SEQ ID NO 103
<211> LENGTH: 321
<212> TYPE: DNA
<213> ORGANISM: Artificial Sequence
<220> FEATURE:
<223> OTHER INFORMATION: Protein S monoclonal antibody variable light chain sequence

<400> SEQUENCE: 103
gaaatagtga tgacgcagtc tccagccacc ctgtctgtgt ctccagggga aagagccacc 60
ctctcctgca gggccagtca gaggattaac agcaacttag cctggtacca gcagaaacct 120
ggccaggctc ccaggctcct catctatggt gcatccacca gggccactgg tatccccgcc 180
aggttcagtg gcagtgggtc tgggacagag ttcactctca ccatcagcag cctgcagtct 240
gaagattttg cagcttatta ctgtcagcag tatgataact ggccgctcac tttcggcgga 300
gggaccaagg tggagatcaa a 321

<210> SEQ ID NO 104
<211> LENGTH: 375
<212> TYPE: DNA

<213> ORGANISM: Artificial Sequence
<220> FEATURE:
<223> OTHER INFORMATION: Protein S monoclonal antibody variable heavy chain sequence

<400> SEQUENCE: 104
caggtgcagc tgcaggagtc gggcccagga ctggtgaagc cttcggagac cctgtccctc 60
acctgcgctg tctctggtta ttccatcagc agtggttact actggggctg gatccggcag 120
cccccaggga aggggctgga ctggattggg agtatctatt atagtgggag tacctactac 180
aacccgtccc tcaagagtcg agtcaccata tcagttgaca cgtccaagaa ccagatctcc 240
ctgaagctga gctctgtgac cgccgcagac acggccgtgt attactgtgc gaccacgtat 300
tccgatattg tgactggtta ttataatgat gcttttgata tctggggcca agggacaatg 360
gtcaccgtgt cttca 375

<210> SEQ ID NO 105
<211> LENGTH: 333
<212> TYPE: DNA
<213> ORGANISM: Artificial Sequence
<220> FEATURE:
<223> OTHER INFORMATION: Protein S monoclonal antibody variable light chain sequence

<400> SEQUENCE: 105
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattattgta tgcaagctct acaaactttc 300
actttcggcc ctgggaccaa agtggatatc aaa 333

<210> SEQ ID NO 106
<211> LENGTH: 381
<212> TYPE: DNA
<213> ORGANISM: Artificial Sequence
<220> FEATURE:
<223> OTHER INFORMATION: Protein S monoclonal antibody variable heavy chain sequence

<400> SEQUENCE: 106
caggtgcagc tggtgcagtc tggggctgag gtgaagaagc ctgggtcctc ggtgaaggtc 60
tcctgtaagg cttctggaga caccttcagc aaccatgcta tcaactgggt gcgacaggcc 120
cctggacaag ggcttgagtg gatgggaggg tacatcccta tctttggtac aacaaactcc 180
gcacagaagt tccggggcag agtcacgatt accgcggaca aatccacgaa cacagcctac 240
atggcgctga gcagcctgag atctgaggac acggccgttt attactgtgc gagaggggggg 300 ctcgcgggga gtcattataa gaactactac tatgacggta tggacgtctg gggccagggg 360
accacggtca ccgtctcctc a 381

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111
<211> LENGTH: 327
<212> TYPE: DNA
<213> ORGANISM: Artificial Sequence
<220> FEATURE:
<223> OTHER INFORMATION: Protein S monoclonal antibody variable light chain sequence

<400> SEQUENCE: 111
caggctgttg tgactcagga atctgcactc accacatcac ctggtgaaac agtcacactc 60
acttgtcgct caagtactgg ggctgttaca gctagtaact atgccaactg ggtccaagaa 120
aaaccagatc atttgttcac tggtctaata ggtagtacca ataaccgagc tccaggtgtt 180
cctgccagat tctcaggctc cctgattgga gacaaggctg ccctcaccat cacaggggca 240
cagactgagg atgaggcaat atatttctgt gctctatggt acagcgacca tttcgtgttc 300
ggtggaggaa ccaaactgac tgtccta 327

<210> SEQ ID NO 112
<211> LENGTH: 363
<212> TYPE: DNA
<213> ORGANISM: Artificial Sequence
<220> FEATURE:
<223> OTHER INFORMATION: Protein S monoclonal antibody variable heavy chain sequence

<400> SEQUENCE: 112
caggtgcaac tggtgcagtc tggggctgag gtgaagaagc ctggggcctc agtgaaggtc 60
tcctgcaagt cttctggcca caccttcacc ggctactata tgcactgggt gcgacaggcc 120
cctggacaag ggcttgagtg gatgggatgg atcaacccta acagtggtga cacaaactac 180
gcacagaagt ttcagggcag ggtcaccatg accagggaca cgtccatcag cacagcctac 240
atggagatga gcaggctgag atctgacgac acggccgtgt attactgtgc gagagactcc 300
caaatactat ggttcgggga gttaggctac tggggccagg gaaccctggt caccgtctcc 360
tcc 363

<210> SEQ ID NO 113
<211> LENGTH: 318
<212> TYPE: DNA
<213> ORGANISM: Artificial Sequence
<220> FEATURE:
<223> OTHER INFORMATION: Protein S monoclonal antibody variable light chain sequence

<400> SEQUENCE: 113
gaaatagtga tgacgcagtc tccagccacc ctgtctgtgt ctccagggga aagagccacc 60
ctctcctgca gggccagtca gagtgttacc agcaacttag cctggtacca gcagaaacct 120
ggccaggctc ccaggctcct catctatgat gcatccacca gggccactgg tatcccagcc 180
aggttcagtg gcagtgggtc tgggacagag ttcactctca ccatcagcag cctgcagtct 240
gaagattttg caatttatta ctgtcagcag tataataact ggcccacctt cggccaaggg 300
acacgactgg agattaaa 318

<210> SEQ ID NO 114
<211> LENGTH: 348
<212> TYPE: DNA
<213> ORGANISM: Artificial Sequence
<220> FEATURE:
<223> OTHER INFORMATION: Protein S monoclonal antibody variable heavy chain sequence

<400> SEQUENCE: 114
caggtgcagc tgcaggagtc gggcccagga ctggtgaagc cttcggagac cctgtccctc 60
acctgcggtg tctctggtgg ctccatcagc agtactaact ggtggagttg ggtccgccag 120
cccccaggga aggggctgga gtggattggg gaaatctatc aaactgggag taccgactac 180
gacccgtccc tcaagagtcg agtcaccata tcaatagaca agtccaagaa ccagttctcc 240
ctgaagctgt actctgtgac cgccgcggac acggccgtgt attactgtgc gagaaggttc 300
ggggagttag actactgggg ccagggaacc ctggtcaccg tctcctca 348

<210> SEQ ID NO 115
<211> LENGTH: 339
<212> TYPE: DNA
<213> ORGANISM: Artificial Sequence
<220> FEATURE:
<223> OTHER INFORMATION: Protein S monoclonal antibody variable light chain sequence

<400> SEQUENCE: 115
gatattgtga tgacccagac tccactctcc tcacctgtca cccttggaca gccggcctcc 60
atctcctgca ggtctagtca aagcctcgta cacagtgatg gaaacaccta cttgagttgg 120
cttcagcaga ggccaggcca gcctccaaga ctcctaattt ataagatttc taaccggttc 180
tctggggtcc cagacagatt cagtggcagt ggggcaggga cagatttcac actgaaaatc 240
agcagggtgg aagctgagga tgtcggggtt tattactgca tgcaagctac acaatttccc 300
catctcactt tcggcggagg gaccaaggtg gagatcaaa 339

<210> SEQ ID NO 116
<211> LENGTH: 351
<212> TYPE: DNA
<213> ORGANISM: Artificial Sequence
<220> FEATURE:
<223> OTHER INFORMATION: Protein S monoclonal antibody variable heavy chain sequence

<400> SEQUENCE: 116
caggtgcagc tgcaggagtc gggcccagga ctggtgaagc cttcggagac cctgtccctc 60
acctgcactg tctctggtgg ctccatcagt aattactact ggaactggat ccggcagccc 120
ccagggaagg gactggagtg gattgggtat atctattaca ttgggatcac cgactacaac 180
ccctccctca agagtcgagt caccatatca gtagacacgt ccaagaacca gttctccctg 240
aaggtgacct ctgtgaccgc tgcggacacg gccgtgtatt actgtgcggc tctaagtggg 300
gatcatgctt ttgacatctg gggccaaggg acactggtca ccgtctcttc a 351

<210> SEQ ID NO 117
<211> LENGTH: 6
<212> TYPE: PRT
<213> ORGANISM: Artificial Sequence
<220> FEATURE:
<223> OTHER INFORMATION: Protein S antibody CDR-L1 sequence

<400> SEQUENCE: 117

Gln Gly Ile Asn Asn Tyr
1 5

<210> SEQ ID NO 118
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 118

Ala Ala Ser
1

<210> SEQ ID NO 119
<211> LENGTH: 9
<212> TYPE: PRT
<213> ORGANISM: Artificial Sequence
<220> FEATURE:
<223> OTHER INFORMATION: Protein S antibody CDR-L3 sequence

<400> SEQUENCE: 119

Gln Gln Tyr Asn Ser Tyr Pro Arg Thr
1 5

<210> SEQ ID NO 120
<211> LENGTH: 10
<212> TYPE: PRT
<213> ORGANISM: Artificial Sequence
<220> FEATURE:
<223> OTHER INFORMATION: Protein S antibody CDR-H1 sequence

<400> SEQUENCE: 120

Gly Gly Ser Ile Thr Asn Ser Asn Tyr Tyr
1 5 10

<210> SEQ ID NO 121
<211> LENGTH: 7
<212> TYPE: PRT
<213> ORGANISM: Artificial Sequence
<220> FEATURE:
<223> OTHER INFORMATION: Protein S antibody CDR-H2 sequence

<400> SEQUENCE: 121

Val Tyr Tyr Ser Gly Thr Thr
1 5

<210> SEQ ID NO 122
<211> LENGTH: 14
<212> TYPE: PRT
<213> ORGANISM: Artificial Sequence
<220> FEATURE:
<223> OTHER INFORMATION: Protein S antibody CDR-H3 sequence

<400> SEQUENCE: 122

Val Arg Glu Ser Glu Ser Tyr Tyr Tyr Tyr Gly Ser Asp Val
1 5 10

<210> SEQ ID NO 123
<211> LENGTH: 9
<212> TYPE: PRT
<213> ORGANISM: Artificial Sequence
<220> FEATURE:
<223> OTHER INFORMATION: Protein S antibody CDR-L3 sequence

<400> SEQUENCE: 123

Gln Gln Tyr Asn Ser Tyr Pro Ile Thr
1 5

<210> SEQ ID NO 124
<211> LENGTH: 8
<212> TYPE: PRT
<213> ORGANISM: Artificial Sequence
<220> FEATURE:
<223> OTHER INFORMATION: Protein S antibody CDR-H1 sequence

<400> SEQUENCE: 124

Gly Phe Thr Phe Ser Ser Tyr Asn
1 5

<210> SEQ ID NO 125
<211> LENGTH: 8
<212> TYPE: PRT
<213> ORGANISM: Artificial Sequence
<220> FEATURE:
<223> OTHER INFORMATION: Protein S antibody CDR-H2 sequence

<400> SEQUENCE: 125

Ile Ser Ser Ser Ser Ser Tyr Ile
1 5

<210> SEQ ID NO 126
<211> LENGTH: 14
<212> TYPE: PRT
<213> ORGANISM: Artificial Sequence
<220> FEATURE:
<223> OTHER INFORMATION: Protein S antibody CDR-H3 sequence

<400> SEQUENCE: 126

Ala Arg Asp Glu Glu Trp Glu Leu Leu Thr Gly Phe Asp Tyr
1 5 10

<210> SEQ ID NO 127
<211> LENGTH: 6
<212> TYPE: PRT
<213> ORGANISM: Artificial Sequence
<220> FEATURE:
<223> OTHER INFORMATION: Protein S antibody CDR-L1 sequence

<400> SEQUENCE: 127

Gln Ser Ile Ser Thr Phe
1 5

<210> SEQ ID NO 128
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 128

Ala Thr Ser
1

<210> SEQ ID NO 129

<211> LENGTH: 9
<212> TYPE: PRT
<213> ORGANISM: Artificial Sequence
<220> FEATURE:
<223> OTHER INFORMATION: Protein S antibody CDR-L3 sequence

<400> SEQUENCE: 129

Gln Gln Ser Tyr Ser Thr Pro Arg Thr
1               5

<210> SEQ ID NO 130
<211> LENGTH: 8
<212> TYPE: PRT
<213> ORGANISM: Artificial Sequence
<220> FEATURE:
<223> OTHER INFORMATION: Protein S antibody CDR-H1 sequence

<400> SEQUENCE: 130

Gly Gly Ser Ile Ser Gly Asn Tyr
1               5

<210> SEQ ID NO 131
<211> LENGTH: 19
<212> TYPE: PRT
<213> ORGANISM: Artificial Sequence
<220> FEATURE:
<223> OTHER INFORMATION: Protein S antibody CDR-H3 sequence

<400> SEQUENCE: 131

Ala Arg Asp Leu Asp Tyr Phe Thr Trp Gly Ala Tyr Ser Asp Trp Tyr
1               5                   10                  15

Phe Asp Leu

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136
<211> LENGTH: 7
<212> TYPE: PRT
<213> ORGANISM: Artificial Sequence
<220> FEATURE:
<223> OTHER INFORMATION: Protein S antibody CDR-L1 sequence

<400> SEQUENCE: 136

Gln Ser Val Gly Ser Ser Tyr
1               5

<210> SEQ ID NO 137
<211> LENGTH: 9
<212> TYPE: PRT
<213> ORGANISM: Artificial Sequence
<220> FEATURE:
<223> OTHER INFORMATION: Protein S antibody CDR-L3 sequence

<400> SEQUENCE: 137

Gln Gln Tyr Gly Ser Ser Pro Tyr Thr
1               5

<210> SEQ ID NO 138
<211> LENGTH: 10
<212> TYPE: PRT
<213> ORGANISM: Artificial Sequence
<220> FEATURE:
<223> OTHER INFORMATION: Protein S antibody CDR-H1 sequence

<400> SEQUENCE: 138

Gly Asp Ser Val Ser Asn Asn Asn Ala Ala
1               5                   10

<210> SEQ ID NO 139
<211> LENGTH: 9
<212> TYPE: PRT
<213> ORGANISM: Artificial Sequence
<220> FEATURE:
<223> OTHER INFORMATION: Protein S antibody CDR-H2 sequence

<400> SEQUENCE: 139

Thr Tyr Tyr Arg Ser Lys Trp Tyr Asn
1               5

<210> SEQ ID NO 140
<211> LENGTH: 12
<212> TYPE: PRT
<213> ORGANISM: Artificial Sequence
<220> FEATURE:
<223> OTHER INFORMATION: Protein S antibody CDR-H3 sequence

<400> SEQUENCE: 140

Ala Arg Gly Ser Ser Trp Tyr Arg Phe Phe Asp Tyr
1               5                   10

<210> SEQ ID NO 141
<211> LENGTH: 6
<212> TYPE: PRT
<213> ORGANISM: Artificial Sequence
<220> FEATURE:
<223> OTHER INFORMATION: Protein S antibody CDR-L1 sequence

<400> SEQUENCE: 141

Gln Asn Ile His Met Trp
1               5

<210> SEQ ID NO 142
<211> LENGTH: 3
<212> TYPE: PRT
<213> ORGANISM: Artificial Sequence
<220> FEATURE:
<223> OTHER INFORMATION: Protein S antibody CDR-L2 sequence

<400> SEQUENCE: 142

Lys Thr Ser
1

<210> SEQ ID NO 143
<211> LENGTH: 9
<212> TYPE: PRT
<213> ORGANISM: Artificial Sequence
<220> FEATURE:
<223> OTHER INFORMATION: Protein S antibody CDR-L3 sequence

<400> SEQUENCE: 143

Leu Gln Gly Gln Ser Tyr Pro Phe Thr
1               5

<210> SEQ ID NO 144
<211> LENGTH: 8
<212> TYPE: PRT
<213> ORGANISM: Artificial Sequence
<220> FEATURE:
<223> OTHER INFORMATION: Protein S antibody CDR-H1 sequence

<400> SEQUENCE: 144

Gly Tyr Thr Phe Thr Asn His Trp
1               5

<210> SEQ ID NO 145
<211> LENGTH: 8
<212> TYPE: PRT
<213> ORGANISM: Artificial Sequence
<220> FEATURE:
<223> OTHER INFORMATION: Protein S antibody CDR-H2 sequence

<400> SEQUENCE: 145

Ile Tyr Pro Gly Gly Gly Tyr Thr
1               5

<210> SEQ ID NO 146
<211> LENGTH: 13
<212> TYPE: PRT
<213> ORGANISM: Artificial Sequence
<220> FEATURE:
<223> OTHER INFORMATION: Protein S antibody CDR-H3 sequence

<400> SEQUENCE: 146

Ser Arg Phe Gly Asp Gln Asn Trp Ala Trp Phe Ala Tyr
1               5                   10

<210> SEQ ID NO 147

<400> SEQUENCE: 147

000

<210> SEQ ID NO 148
<211> LENGTH: 107
<212> TYPE: PRT
<213> ORGANISM: Artificial Sequence
<220> FEATURE:
<223> OTHER INFORMATION: Protein S monoclonal antibody variable light
      chain sequence

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Ser Leu Ile
        35                  40                  45

```
Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105


<210> SEQ ID NO 149
<211> LENGTH: 122
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 149

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Asn Ser
            20                  25                  30

Asn Tyr Tyr Trp Gly Trp Ile Arg Gln Pro Pro Gly Lys Gly Leu Glu
        35                  40                  45

Trp Ile Gly Ser Val Tyr Tyr Ser Gly Thr Thr Tyr Tyr Asn Pro Ser
    50                  55                  60

Leu Lys Ser Arg Val Thr Ile Ser Val Asp Pro Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg Glu Ser Glu Ser Tyr Tyr Tyr Tyr Gly Ser Asp Val Trp
            100                 105                 110

Gly Gln Gly Thr Thr Val Thr Val Ser Ser
        115                 120


<210> SEQ ID NO 150
<211> LENGTH: 107
<212> TYPE: PRT
<213> ORGANISM: Artificial Sequence
<220> FEATURE:
<223> OTHER INFORMATION: Protein S monoclonal antibody variable light
      chain sequence

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Ser Leu Ile
        35                  40                  45

Tyr Ala Ala Ser Asn Leu Gln Ser Gly Val Pro Leu Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105
```

<210> SEQ ID NO 151
<211> LENGTH: 121
<212> TYPE: PRT
<213> ORGANISM: Artificial Sequence
<220> FEATURE:
<223> OTHER INFORMATION: Protein S monoclonal antibody variable heavy chain sequence

<400> SEQUENCE: 151

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asn Met Asn Trp Val Arg Gln Ala Pro Gly Arg Gly Leu Asp Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Ala Glu Asp Thr Ala Val Tyr Tyr Cys
                85                  90                  95

Ala Arg Asp Glu Glu Trp Glu Leu Leu Thr Gly Phe Asp Tyr Trp Gly
            100                 105                 110

Gln Gly Thr Leu Val Thr Val Ser Ser
        115                 120
```

<210> SEQ ID NO 152
<211> LENGTH: 107
<212> TYPE: PRT
<213> ORGANISM: Artificial Sequence
<220> FEATURE:
<223> OTHER INFORMATION: Protein S monoclonal antibody variable light chain sequence

<400> SEQUENCE: 152

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Phe
            20                  25                  30

Leu Asn Trp Tyr Gln Gln Lys Pro Gly Lys Ala Pro Lys Leu Leu Ile
        35                  40                  45

Tyr Ala Thr Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Ser Tyr Ser Thr Pro Arg
                85                  90                  95

Thr Phe Gly Gln Gly Thr Gln Val Glu Ile Lys
            100                 105
```

<210> SEQ ID NO 153
<211> LENGTH: 125
<212> TYPE: PRT
<213> ORGANISM: Artificial Sequence
<220> FEATURE:
<223> OTHER INFORMATION: Protein S monoclonal antibody variable heavy chain sequence

<400> SEQUENCE: 153

```
Gln Val Gln Leu Gln Glu Ser Gly Pro Gly Leu Val Lys Pro Ser Glu
```

```
1               5                   10                  15

Thr Leu Ser Leu Thr Cys Thr Val Ser Gly Gly Ser Ile Ser Gly Asn
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Leu Asp Tyr Phe Thr Trp Gly Ala Tyr Ser Asp Trp Tyr Phe
            100                 105                 110

Asp Leu Trp Gly Arg Gly Thr Leu Val Thr Val Ser Ser
        115                 120                 125


<210> SEQ ID NO 154

<400> SEQUENCE: 154

000


<210> SEQ ID NO 155

<400> SEQUENCE: 155

000


<210> SEQ ID NO 156
<211> LENGTH: 108
<212> TYPE: PRT
<213> ORGANISM: Artificial Sequence
<220> FEATURE:
<223> OTHER INFORMATION: Protein S monoclonal antibody variable light
      chain sequence

<400> SEQUENCE: 156

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Ser Gly Ala Ser Gly Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Thr Val Tyr Tyr Cys Gln Gln Tyr Gly Ser Ser Pro
                85                  90                  95

Tyr Thr Phe Gly Gln Gly Thr Lys Leu Glu Ile Lys
            100                 105


<210> SEQ ID NO 157
<211> LENGTH: 122
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 157
```

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Asn Asn
            20                  25                  30

Asn Ala Ala Trp Asn Trp Ile Arg Gln Ser Pro Ser Arg Gly Leu Glu
        35                  40                  45

Trp Leu Gly Gly Thr Tyr Tyr Arg Ser Lys Trp Tyr Asn Asp Tyr Ala
    50                  55                  60

Val Ser Val Lys Ser Arg Ile Ile Ile Asn Pro Val Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Ser Ser Trp Tyr Arg Phe Phe Asp Tyr Trp
            100                 105                 110

Gly Gln Gly Thr Leu Val Thr Val Ser Ser
        115                 120


<210> SEQ ID NO 158
<211> LENGTH: 107
<212> TYPE: PRT
<213> ORGANISM: Artificial Sequence
<220> FEATURE:
<223> OTHER INFORMATION: Protein S monoclonal antibody variable light
      chain sequence

<400> SEQUENCE: 158

Asp Ile Gln Met Asn Gln Ser Pro Ser Ser Leu Ser Ala Ser Leu Gly
1               5                   10                  15

Asp Thr Ile Thr Ile Thr Cys Arg Ala Ser Gln Asn Ile His Met Trp
            20                  25                  30

Leu Ser Trp Tyr Gln Gln Lys Pro Gly Asn Ile Pro Lys Leu Leu Ile
        35                  40                  45

Phe Lys Thr Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Gly Gln Ser Tyr Pro Phe
                85                  90                  95

Thr Phe Gly Gly Gly Thr Lys Leu Glu Ile Lys
            100                 105


<210> SEQ ID NO 159
<211> LENGTH: 120
<212> TYPE: PRT
<213> ORGANISM: Artificial Sequence
<220> FEATURE:
<223> OTHER INFORMATION: Protein S monoclonal antibody variable heavy
      chain sequence

<400> SEQUENCE: 159

Gln Val Gln Leu Gln Gln Ser Gly Thr Glu Leu Val Arg Pro Gly Thr
1               5                   10                  15

Ser Val Lys Met Ser Cys Lys Ala Ala Gly Tyr Thr Phe Thr Asn His
            20                  25                  30

Trp Ile Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60
```

```
Lys Gly Lys Ala Ser Leu Thr Ala Asp Thr Ser Ser Thr Thr Ala Tyr
65                  70                  75                  80

Met Gln Leu Ser Ser Leu Thr Ser Glu Asp Ser Ala Ile Tyr Tyr Cys
                85                  90                  95

Ser Arg Phe Gly Asp Gln Asn Trp Ala Trp Phe Ala Tyr Trp Gly Gln
            100                 105                 110

Gly Thr Leu Val Thr Val Ser Ala
        115                 120


<210> SEQ ID NO 160

<400> SEQUENCE: 160

000


<210> SEQ ID NO 161

<400> SEQUENCE: 161

000


<210> SEQ ID NO 162
<211> LENGTH: 321
<212> TYPE: DNA
<213> ORGANISM: Artificial Sequence
<220> FEATURE:
<223> OTHER INFORMATION: Protein S monoclonal antibody variable light
      chain sequence

<400> SEQUENCE: 162

gacatccaga tgacccagtc tccatcctca ctgtctgcat ctgtaggaga cagagtcacc     60

atcacttgtc gggcgagtca gggcattaac aattatttag cctggtttca gcagaaacca    120

gggaaagccc ctaagtccct gatctatgct gcatccagtt tgcaaagtgg ggtcccatca    180

aagttcagcg gcagtggatc tgggacagat ttcactctca ccatcagcag cctgcagcct    240

gaagattttg caacttatta ctgccaacag tataatagtt accctcggac gttcggccaa    300

gggaccaagg tggaaatcaa a                                              321


<210> SEQ ID NO 163
<211> LENGTH: 366
<212> TYPE: DNA
<213> ORGANISM: Artificial Sequence
<220> FEATURE:
<223> OTHER INFORMATION: Protein S monoclonal antibody variable heavy
      chain sequence

<400> SEQUENCE: 163

cagctgcagc tgcaggagtc gggcccagga ctggtgaagc cttcggagac cctgtccctc     60

acctgcactg tctctggtgg ctccatcacc aatagtaatt actactgggg ctggatccgc    120

cagcccccag ggaagggact ggagtggatt gggagtgtct attatagtgg gaccacctac    180

tacaacccgt ccctcaagag tcgagtcacc atatccgtag acccgtccaa gaaccagttc    240

tccctgaagc tgagctctgt gaccgccgca gacacggctg tgtattactg tgtgagagag    300

agtgagagct actactacta cggttcggac gtctggggcc aagggaccac ggtcaccgtc    360

tcctca                                                               366


<210> SEQ ID NO 164
<211> LENGTH: 321
<212> TYPE: DNA
```

<213> ORGANISM: Artificial Sequence
<220> FEATURE:
<223> OTHER INFORMATION: Protein S monoclonal antibody variable light
chain sequence

<400> SEQUENCE: 164
gacatccaga tgacccagtc tccatcctca ctgtctgcat ctgtaggaga cagagtcacc 60
atcacttgtc gggcgagtca gggcattaac aattatttag cctggtttca gcagaaacca 120
gggaaagccc ctaagtccct gatctatgct gcatccaatt tgcaaagtgg ggtcccatta 180
aagttcagcg gcagtggatc tgggacagat ttcactctca ccatcagcag cctgcagcct 240
gaagattttg caacttatta ctgccaacag tataatagtt acccgatcac cttcggccaa 300
gggacacgac tggagattaa a 321

<210> SEQ ID NO 165
<211> LENGTH: 363
<212> TYPE: DNA
<213> ORGANISM: Artificial Sequence
<220> FEATURE:
<223> OTHER INFORMATION: Protein S monoclonal antibody variable heavy
chain sequence

<400> SEQUENCE: 165
gaggtgcagc tggttgagtc tgggggaggc ctggtcaagc ctgggggtc cctgagactc 60 tcctgtgcag cctctggatt caccttcagt agctataaca tgaactgggt ccgccaggct 120
ccagggaggg ggctggactg ggtctcatcc attagtagta gtagtagtta catatactac 180
gcagactcag tgaagggccg attcaccatc tccagagaca acgccaagaa ctcactgtat 240
ctgcaaatga ataccctgag agccgaggac acggctgttt attactgtgc gagagatgag 300
gagtgggagc tactgacggg ctttgactac tggggccagg gaaccctggt caccgtctcc 360
tca 363

<210> SEQ ID NO 166
<211> LENGTH: 321
<212> TYPE: DNA
<213> ORGANISM: Artificial Sequence
<220> FEATURE:
<223> OTHER INFORMATION: Protein S monoclonal antibody variable light
chain sequence

<400> SEQUENCE: 166
gacatccaga tgacccagtc tccatcctcc ctgtctgcat ctgtaggaga cagagtcacc 60
atcacttgcc gggcaagtca gagcattagc acctttttaa attggtatca gcagaaacca 120
gggaaagccc ctaaactcct gatctatgct acatccagtt tgcgaagtgg ggtcccatca 180
aggttcagtg gcagtggatc tgggacagat ttcactctca ccatcagcag tctgcaacct 240
gaagattttg caatttatta ttgtcaacag agttacagta cccctcggac gttcggccaa 300
gggacccagg tggaaatcaa a 321

<210> SEQ ID NO 167
<211> LENGTH: 375
<212> TYPE: DNA
<213> ORGANISM: Artificial Sequence
<220> FEATURE:
<223> OTHER INFORMATION: Protein S monoclonal antibody variable heavy
chain sequence

<400> SEQUENCE: 167
caggtgcagc tgcaggagtc gggcccagga ctggtgaagc cttcggagac cctgtccctc 60
acctgcactg tctctggtgg ctccatcagt ggtaactact ggagctggat ccggcagccc 120
ccagggaagg gactggagtg gattgggtat atctattaca gtgggagcac caactacaat 180
ccctccctca agagtcgagt caccatatca gttgacacgt ccaagaacca gttctccctg 240
aagctgagct ctgtgaccgc tgcggatacg gccgtgtatt actgtgcgag agatcttgat 300
tactttactt ggggggctta ttctgactgg tacttcgatc tctggggccg tggcaccctg 360
gtcactgtct cctca 375

<210> SEQ ID NO 168

<400> SEQUENCE: 168

000

<210> SEQ ID NO 169

<400> SEQUENCE: 169

000

<210> SEQ ID NO 170
<211> LENGTH: 324
<212> TYPE: DNA
<213> ORGANISM: Artificial Sequence
<220> FEATURE:
<223> OTHER INFORMATION: Protein S monoclonal antibody variable light chain sequence

<400> SEQUENCE: 170
gaaattgtgt tgacgcagtc tccaggcacc ctgtctttgt ctccagggga aagagccacc 60
ctctcctgca gggccagtca gagtgttggc agcagctact tagcctggta ccagcagaaa 120
cctggccagg ctcccaggct cctcatctct ggtgcatccg gcagggccac tggcatccca 180
gacaggttca gtggcagtgg gtctgggaca gacttcactc tcaccatcag cagactggag 240
cctgaagatt ttacagtgta ttactgtcag cagtatggta gctcaccgta cacttttggc 300
caggggacca agctggagat caaa 324

<210> SEQ ID NO 171
<211> LENGTH: 366
<212> TYPE: DNA
<213> ORGANISM: Artificial Sequence
<220> FEATURE:
<223> OTHER INFORMATION: Protein S monoclonal antibody variable heavy chain sequence

<400> SEQUENCE: 171
caggtacagc tgcagcagtc aggtccagga ctggtgaagc cctcgcagac cctctcactc 60
acctgtgcca tctccgggga cagtgtctct aacaacaatg ctgcttggaa ctggatcagg 120
cagtccccat cgagaggcct tgagtggctg ggagggacat actacaggtc caagtggtat 180
aatgattatg cagtatctgt gaaaagtcga ataatcatca acccagtcac atccaagaac 240
cagttctccc tacagctgaa ctctgtgact cccgaggaca cggctgtgta ttactgtgca 300
agaggcagca gctggtacag gttttttgac tactggggcc agggaaccct ggtcaccgtc 360
tcctca 366

<210> SEQ ID NO 172
<211> LENGTH: 321
<212> TYPE: DNA

<213> ORGANISM: Artificial Sequence
<220> FEATURE:
<223> OTHER INFORMATION: Protein S monoclonal antibody variable light chain sequence

<400> SEQUENCE: 172
gacatccaga tgaaccagtc tccatccagt ctgtctgcat ccctcggaga cacaattacc 60
atcacttgcc gtgccagtca gaacattcat atgtggttaa gctggtacca gcagaaacca 120
ggaaatattc ctaaactatt gatctttaag acttccaatt tgcacacagg cgtcccatca 180
aggtttagtg gcagtggatc tggaacagat ttcacattaa ccatcagcag tctgcagcct 240
gaagacattg ccacttacta ctgtctacag ggtcaaagtt atccgttcac gttcggaggg 300
gggaccaagc tggaaataaa g 321

<210> SEQ ID NO 173
<211> LENGTH: 360
<212> TYPE: DNA
<213> ORGANISM: Artificial Sequence
<220> FEATURE:
<223> OTHER INFORMATION: Protein S monoclonal antibody variable heavy chain sequence

<400> SEQUENCE: 173
caggtccagc tgcagcagtc tggaactgag ctggtaaggc ctgggacttc agtgaagatg 60
tcctgtaagg ctgctggata caccttcact aaccactgga taggttgggt aaagcagagg 120
cctggacatg gccttgagtg gattggagat atttaccctg gaggtggtta tactaactac 180
aatgagaagt tcaagggcaa ggcctcactg actgcagaca catcctccac cacagcctac 240
atgcagctca gcagcctgac atctgaggac tctgccatct attactgttc aagattcggg 300
gatcaaaact gggcctggtt tgcttactgg ggccaaggga ctctggtcac tgtctctgca 360

<210> SEQ ID NO 174
<211> LENGTH: 6
<212> TYPE: PRT
<213> ORGANISM: Artificial Sequence
<220> FEATURE:
<223> OTHER INFORMATION: Hc-M1 VL CDR-1

<400> SEQUENCE: 174

Gln Ser Ile Ser Ser Tyr
1 5

<210> SEQ ID NO 175
<211> LENGTH: 3
<212> TYPE: PRT
<213> ORGANISM: Artificial Sequence
<220> FEATURE:
<223> OTHER INFORMATION: Hc-M1 VL CDR-2

<400> SEQUENCE: 175

Ala Ala Ser
1

<210> SEQ ID NO 176
<211> LENGTH: 8
<212> TYPE: PRT
<213> ORGANISM: Artificial Sequence
<220> FEATURE:
<223> OTHER INFORMATION: Hc-M1 VL CDR-3

<400> SEQUENCE: 176

Gln Gln Ser Tyr Ser Ser Leu Thr 1 5

<210> SEQ ID NO 177
<211> LENGTH: 106
<212> TYPE: PRT
<213> ORGANISM: Artificial Sequence
<220> FEATURE:
<223> OTHER INFORMATION: Hc-M1 VL V region

<400> SEQUENCE: 177

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Ser Leu Thr
85 90 95

Phe Gly Gln Gly Thr Arg Leu Glu Ile Lys
100 105

<210> SEQ ID NO 178
<211> LENGTH: 318
<212> TYPE: DNA
<213> ORGANISM: Artificial Sequence
<220> FEATURE:
<223> OTHER INFORMATION: Hc-M1 VL

<400> SEQUENCE: 178
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagtt ccctcacctt cggccaaggg 300
acacgactgg agattaaa 318

<210> SEQ ID NO 179
<211> LENGTH: 8
<212> TYPE: PRT
<213> ORGANISM: Artificial Sequence
<220> FEATURE:
<223> OTHER INFORMATION: Hc-M1 VH CDR-1

<400> SEQUENCE: 179

Gly Ile Ser Phe Ser Asn Ala Trp
1 5

<210> SEQ ID NO 180
<211> LENGTH: 10
<212> TYPE: PRT
<213> ORGANISM: Artificial Sequence
<220> FEATURE:
<223> OTHER INFORMATION: Hc-M1 VH CDR-2

<400> SEQUENCE: 180

Ile Lys Ala Asn Pro Asp Gly Gly Thr Thr 1 5 10

<210> SEQ ID NO 181
<211> LENGTH: 15
<212> TYPE: PRT
<213> ORGANISM: Artificial Sequence
<220> FEATURE:
<223> OTHER INFORMATION: Hc-M1 VH CDR-3

<400> SEQUENCE: 181

Thr Thr Glu Leu Asp Ile Leu Leu Trp Phe Thr Ser Phe Asp Tyr
1 5 10 15

<210> SEQ ID NO 182
<211> LENGTH: 124
<212> TYPE: PRT
<213> ORGANISM: Artificial Sequence
<220> FEATURE:
<223> OTHER INFORMATION: Hc-M1 VH V region

<400> SEQUENCE: 182

Glu Val Gln Leu Val Glu Ser Gly Gly Gly Leu Val Lys Pro Gly Gly
1 5 10 15

Ser Leu Arg Leu Ser Cys Ala Ala Ser Gly Ile Ser Phe Ser Asn Ala
20 25 30

Trp Met Ser Trp Val Arg Gln Ala Pro Gly Lys Gly Leu Glu Trp Val
35 40 45

Gly Arg Ile Lys Ala Asn Pro Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Thr Thr Glu Leu Asp Ile Leu Leu Trp Phe Thr Ser Phe Asp
100 105 110

Tyr Trp Gly Gln Gly Thr Leu Val Thr Val Ser Ser
115 120

<210> SEQ ID NO 183
<211> LENGTH: 372
<212> TYPE: DNA
<213> ORGANISM: Artificial Sequence
<220> FEATURE:
<223> OTHER INFORMATION: Hc-M1 VH

<400> SEQUENCE: 183
gaggtgcagc tggtggagtc tgggggaggc ttggtaaagc ctggggggtc ccttagactc 60
tcctgtgcag cctctggaat cagtttcagt aacgcctgga tgagctgggt ccgccaggct 120
ccagggaagg ggctggaatg ggttggccgt attaaagcca atcctgatgg tgggacaaca 180
gactacgctg cacccgtgaa aggcagattc accatctcaa gagatgattc aaaaaacacg 240
ctatatctgc aaatgaacag cctgaaaacc gaggacacag ccgtgtatta ctgtaccaca 300
gagttggaca ttttactatg gttcacctcc tttgactact ggggccaggg aaccctggtc 360
accgtctcct ca 372

<210> SEQ ID NO 184
<211> LENGTH: 6
<212> TYPE: PRT
<213> ORGANISM: Artificial Sequence
<220> FEATURE:

<223> OTHER INFORMATION: Od-M4 VL CDR-1

<400> SEQUENCE: 184

Asn Ile Gly Gly Lys Ser
1 5

<210> SEQ ID NO 185
<211> LENGTH: 3
<212> TYPE: PRT
<213> ORGANISM: Artificial Sequence
<220> FEATURE:
<223> OTHER INFORMATION: Od-M4 VL CDR-2

<400> SEQUENCE: 185

Asp Asp Ser
1

<210> SEQ ID NO 186
<211> LENGTH: 11
<212> TYPE: PRT
<213> ORGANISM: Artificial Sequence
<220> FEATURE:
<223> OTHER INFORMATION: Od-M4 VL CDR-3

<400> SEQUENCE: 186

Gln Val Trp Glu Ile Thr Ser Asp His Pro Ala
1 5 10

<210> SEQ ID NO 187
<211> LENGTH: 108
<212> TYPE: PRT
<213> ORGANISM: Artificial Sequence
<220> FEATURE:
<223> OTHER INFORMATION: Od-M4 VL V region

<400> SEQUENCE: 187

Ser Tyr Val Leu Thr Gln Pro Pro Ser Val Ser Val Ala Pro Gly Gln
1 5 10 15

Thr Ala Arg Ile Thr Cys Gly Gly Asp Asn Ile Gly Gly Lys Ser Val
20 25 30

His Trp Tyr Gln Gln Lys Pro Gly Gln Ala Pro Val Met Val Val Tyr
35 40 45

Asp Asp Ser Asp Arg Pro Ser Gly Ile Pro Glu Arg Phe Ala Gly Ser
50 55 60

Asn Ser Gly Asn Thr Ala Thr Leu Ala Ile Ser Arg Val Glu Ala Gly
65 70 75 80

Asp Glu Ala Asp Tyr Tyr Cys Gln Val Trp Glu Ile Thr Ser Asp His
85 90 95

Pro Ala Phe Gly Gly Gly Thr Arg Leu Thr Val Leu
100 105

<210> SEQ ID NO 188
<211> LENGTH: 324
<212> TYPE: DNA
<213> ORGANISM: Artificial Sequence
<220> FEATURE:
<223> OTHER INFORMATION: Od-M4 VL

<400> SEQUENCE: 188
tcctatgtgc tgactcagcc accctcggtg tcagtggccc caggacagac ggccaggatt 60
acctgtgggg gagacaacat tggaggtaaa agtgtgcact ggtaccagca gaagccaggc 120
caggcccctg tgatggtcgt ctatgatgat agcgaccggc cctcagggat ccctgagcga 180

```
ttcgctggct ccaattctgg gaacacggcc accctggcca tcagcagggt cgaagccggg    240

gatgaggccg actattactg tcaggtgtgg gagataacta gtgatcatcc ggcattcggc    300

ggagggacca ggctgaccgt ccta                                           324
```

<210> SEQ ID NO 189
<211> LENGTH: 8
<212> TYPE: PRT
<213> ORGANISM: Artificial Sequence
<220> FEATURE:
<223> OTHER INFORMATION: Od-M4 VH CDR-1

<400> SEQUENCE: 189

```
Gly Phe Thr Phe Ser Ser Tyr Ser
1               5
```

<210> SEQ ID NO 190
<211> LENGTH: 8
<212> TYPE: PRT
<213> ORGANISM: Artificial Sequence
<220> FEATURE:
<223> OTHER INFORMATION: Od-M4 VH CDR-2

<400> SEQUENCE: 190

```
Ile Ser Ser Ser Thr Arg Thr Ile
1               5
```

<210> SEQ ID NO 191
<211> LENGTH: 9
<212> TYPE: PRT
<213> ORGANISM: Artificial Sequence
<220> FEATURE:
<223> OTHER INFORMATION: Od-M4 VH CDR-3

<400> SEQUENCE: 191

```
Ala Arg Glu Arg Ser Ala Phe Asp Tyr
1               5
```

<210> SEQ ID NO 192
<211> LENGTH: 116
<212> TYPE: PRT
<213> ORGANISM: Artificial Sequence
<220> FEATURE:
<223> OTHER INFORMATION: Od-M4 VH V region

<400> SEQUENCE: 192

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Tyr Ile Ser Ser Ser Thr Arg Thr Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Phe Tyr Tyr Cys
                85                  90                  95

Ala Arg Glu Arg Ser Ala Phe Asp Tyr Trp Gly Gln Gly Thr Leu Val
            100                 105                 110

Thr Val Ser Ser
        115
```

<210> SEQ ID NO 193
<211> LENGTH: 348
<212> TYPE: DNA
<213> ORGANISM: Artificial Sequence
<220> FEATURE:
<223> OTHER INFORMATION: Od-M4 VH

<400> SEQUENCE: 193
gaggtgcagc tggtggagtc tgggggaggc ttggtacagc ctggggggtc cctgagactc 60
tcctgtgcag cctctggatt caccttcagt agctatagca tgaactgggt ccgccaggct 120
ccagggaagg ggctggagtg ggttgcatac attagtagta gtactcgtac catattctac 180
gcagactctg tgaagggccg attcaccatc tccagagaca atgccaagaa ctcactgtat 240
ctgcaaatga acagcctgag agacgaggac acggcttttt attattgtgc gagagaacgt 300
tcggcctttg actactgggg ccagggaacc ctggtcaccg tctcctca 348

<210> SEQ ID NO 194
<211> LENGTH: 6
<212> TYPE: PRT
<213> ORGANISM: Artificial Sequence
<220> FEATURE:
<223> OTHER INFORMATION: Od-M7 VL CDR-1

<400> SEQUENCE: 194

Lys Leu Gly Asp Lys Tyr
1 5

<210> SEQ ID NO 195
<211> LENGTH: 3
<212> TYPE: PRT
<213> ORGANISM: Artificial Sequence
<220> FEATURE:
<223> OTHER INFORMATION: Od-M7 VL CDR-2

<400> SEQUENCE: 195

Gln Asp Ser
1

<210> SEQ ID NO 196
<211> LENGTH: 9
<212> TYPE: PRT
<213> ORGANISM: Artificial Sequence
<220> FEATURE:
<223> OTHER INFORMATION: Od-M7 VL CDR-3

<400> SEQUENCE: 196

Gln Ala Trp Asp Ser Ser Thr Val Gly
1 5

<210> SEQ ID NO 197
<211> LENGTH: 106
<212> TYPE: PRT
<213> ORGANISM: Artificial Sequence
<220> FEATURE:
<223> OTHER INFORMATION: Od-M7 VL V region

<400> SEQUENCE: 197

Ser Tyr Glu Leu Thr Gln Pro Pro Ser Val Ser Val Ser Pro Gly Gln
1 5 10 15

Thr Ala Ser Ile Thr Cys Ser Gly Asp Lys Leu Gly Asp Lys Tyr Val
20 25 30

Phe Trp Tyr Gln Gln Lys Pro Gly Gln Ser Pro Val Leu Val Ile Tyr

```
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Thr Met
65                  70                  75                  80

Asp Glu Ala Asp Tyr Tyr Cys Gln Ala Trp Asp Ser Ser Thr Val Gly
                85                  90                  95

Phe Gly Gly Gly Thr Lys Leu Ala Val Leu
            100                 105


<210> SEQ ID NO 198
<211> LENGTH: 318
<212> TYPE: DNA
<213> ORGANISM: Artificial Sequence
<220> FEATURE:
<223> OTHER INFORMATION: Od-M7 VL

<400> SEQUENCE: 198

tcctatgagc tgactcagcc accctcagtg tccgtgtccc caggacagac agccagcatc      60

acctgctctg gagataaatt gggggataaa tatgttttct ggtatcagca gaagccaggc     120

cagtcccctg tgttggtcat ctatcaagat agcaagcggc cctcagggat ccctgagcga     180

ttctctggct ccaactctgg gaacacagcc actctgacca tcagcgggac ccagactatg     240

gatgaggctg actattactg tcaggcgtgg gacagcagca ctgtgggatt cggcggaggg     300

accaagctgg ccgtcctg                                                    318


<210> SEQ ID NO 199
<211> LENGTH: 8
<212> TYPE: PRT
<213> ORGANISM: Artificial Sequence
<220> FEATURE:
<223> OTHER INFORMATION: Od-M7 VH CDR-1

<400> SEQUENCE: 199

Gly Tyr Thr Phe Thr Asn Tyr Tyr
1               5


<210> SEQ ID NO 200
<211> LENGTH: 8
<212> TYPE: PRT
<213> ORGANISM: Artificial Sequence
<220> FEATURE:
<223> OTHER INFORMATION: Od-M7 VH CDR-2

<400> SEQUENCE: 200

Ile Thr Pro Ser Gly Gly Thr Thr
1               5


<210> SEQ ID NO 201
<211> LENGTH: 15
<212> TYPE: PRT
<213> ORGANISM: Artificial Sequence
<220> FEATURE:
<223> OTHER INFORMATION: Od-M7 VH CDR-3

<400> SEQUENCE: 201

Ala Arg Ala Gly Val Gln Leu Asp Arg Arg Gly Trp Phe Asp Pro
1               5                   10                  15


<210> SEQ ID NO 202
<211> LENGTH: 122
<212> TYPE: PRT
```

```
<213> ORGANISM: Artificial Sequence
<220> FEATURE:
<223> OTHER INFORMATION: Od-M7 VH V region

<400> SEQUENCE: 202

Gln Val Gln Leu Val Gln Ser Gly Ser Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Ile Ile Thr Pro Ser Gly Gly Thr Thr Ser Tyr Ala Gln Lys Phe
    50                  55                  60

Gln Gly Arg Val Thr Met Thr Arg Asp Thr Ser Thr Asn Thr Val Tyr
65                  70                  75                  80

Met Gly Leu Ser Ser Leu Arg Ser Glu Asp Thr Ala Met Tyr Tyr Cys
                85                  90                  95

Ala Arg Ala Gly Val Gln Leu Asp Arg Arg Gly Trp Phe Asp Pro Trp
            100                 105                 110

Gly Gln Gly Thr Leu Val Thr Val Ser Ser
        115                 120


<210> SEQ ID NO 203
<211> LENGTH: 366
<212> TYPE: DNA
<213> ORGANISM: Artificial Sequence
<220> FEATURE:
<223> OTHER INFORMATION: Od-M7 VH

<400> SEQUENCE: 203

caggtgcagc tggtgcagtc tgggtctgag gtgaagaagc ctggggcctc agtgaaggtt      60

tcctgcaagg catctggata caccttcacc aactactata tacactgggt gcggcaggcc     120

cctggacaag ggcttgagtg gatgggaata atcaccccta gtggtggtac cacaagctac     180

gcacagaagt tccagggcag agtcactatg accagggaca cgtccacgaa cacagtctac     240

atggggctga gcagcctgag atctgaggac acggccatgt attactgtgc gagagccggg     300

gtacaactgg atcgacgagg gtggttcgac ccctggggcc agggaaccct ggtcaccgtc     360

tcctca                                                                366


<210> SEQ ID NO 204
<211> LENGTH: 6
<212> TYPE: PRT
<213> ORGANISM: Artificial Sequence
<220> FEATURE:
<223> OTHER INFORMATION: Od-M67 VL CDR-1

<400> SEQUENCE: 204

Lys Leu Gly Asp Lys Tyr
1               5


<210> SEQ ID NO 205
<211> LENGTH: 3
<212> TYPE: PRT
<213> ORGANISM: Artificial Sequence
<220> FEATURE:
<223> OTHER INFORMATION: Od-M67 VL CDR-2

<400> SEQUENCE: 205

Gln Asp Asn
1
```

<210> SEQ ID NO 206
<211> LENGTH: 9
<212> TYPE: PRT
<213> ORGANISM: Artificial Sequence
<220> FEATURE:
<223> OTHER INFORMATION: Od-M67 VL CDR-3

<400> SEQUENCE: 206

Gln Ala Trp Asp Ser Ser Thr Ala Val
1               5

<210> SEQ ID NO 207
<211> LENGTH: 106
<212> TYPE: PRT
<213> ORGANISM: Artificial Sequence
<220> FEATURE:
<223> OTHER INFORMATION: Od-M67 VL V region

<400> SEQUENCE: 207

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Phe Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Val
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105

<210> SEQ ID NO 208
<211> LENGTH: 318
<212> TYPE: DNA
<213> ORGANISM: Artificial Sequence
<220> FEATURE:
<223> OTHER INFORMATION: Od-M67 VL

<400> SEQUENCE: 208
tcctatgagc tgactcagcc accctcagtg tccgtgtccc cgggacagac agccagcatc     60
acctgctctg gagataaatt gggggataaa tatgctttct ggtatcagca gaagccaggc    120
cagtcccctg tgctggtcat ctatcaagat aacaagcggc cctcagggat ccctgagcga    180
ttctctggct ccaactctgg gaacacagcc actctaacca tcagcgggac ccaggctgtg    240
gatgaggctg actattactg tcaggcgtgg gacagcagca ctgcggtatt cggcggaggg    300
accaagctga ccgtccta                                                  318

<210> SEQ ID NO 209
<211> LENGTH: 8
<212> TYPE: PRT
<213> ORGANISM: Artificial Sequence
<220> FEATURE:
<223> OTHER INFORMATION: Od-M67 VH CDR-1

<400> SEQUENCE: 209

Gly Tyr Thr Phe Thr Ser Tyr Tyr
1               5

<210> SEQ ID NO 210
<211> LENGTH: 8
<212> TYPE: PRT
<213> ORGANISM: Artificial Sequence
<220> FEATURE:
<223> OTHER INFORMATION: Od-M67 VH CDR-2

<400> SEQUENCE: 210

Thr Ser Pro Ser Gly Arg Ser Thr
1               5

<210> SEQ ID NO 211
<211> LENGTH: 17
<212> TYPE: PRT
<213> ORGANISM: Artificial Sequence
<220> FEATURE:
<223> OTHER INFORMATION: Od-M67 VH CDR-3

<400> SEQUENCE: 211

Ala Arg Gly Gly Val Thr Ile His Leu Glu Arg Arg Gly Tyr Phe Asp
1               5                   10                  15

Tyr

<210> SEQ ID NO 212
<211> LENGTH: 124
<212> TYPE: PRT
<213> ORGANISM: Artificial Sequence
<220> FEATURE:
<223> OTHER INFORMATION: Od-M67 VH V region

<400> SEQUENCE: 212

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Val Thr Ser Pro Ser Gly Arg Ser Thr Ser Phe Ala Gln Lys Phe
    50                  55                  60

Gln Gly Arg Val Thr Met Thr Arg Asp Thr Ser Thr Ser Ala Val Tyr
65                  70                  75                  80

Met Asp Leu Asp Ser Leu Arg Ser Glu Asp Thr Ala Val Tyr Tyr Cys
                85                  90                  95

Ala Arg Gly Gly Val Thr Ile His Leu Glu Arg Arg Gly Tyr Phe Asp
            100                 105                 110

Tyr Trp Gly Gln Gly Thr Leu Val Ile Val Ser Ser
        115                 120

<210> SEQ ID NO 213
<211> LENGTH: 372
<212> TYPE: DNA
<213> ORGANISM: Artificial Sequence
<220> FEATURE:
<223> OTHER INFORMATION: Od-M67 VH

<400> SEQUENCE: 213
caggtgcagc tggtgcagtc tggggctgag gtgaagaagc ctggggcctc agtgaaggtt 60
tcctgcaagg catctggata caccttcacc agctactata tacactgggt acgacaggcc 120
cctggacaag ggcttgagtg gatgggagta accagcccta gtggtcgtag cacaagcttc 180

```
gcacagaagt tccagggcag agtcaccatg accagggaca cgtccacgag cgcagtctat    240

atggacctgg acagcctgag atctgaggac acggccgtgt attactgtgc gagaggggga    300

gtgacgatac acctggaacg acggggctac tttgactact ggggccaggg aaccctggtc    360

attgtctcct ca                                                        372
```

```
<210> SEQ ID NO 214
<211> LENGTH: 107
<212> TYPE: PRT
<213> ORGANISM: Artificial Sequence
<220> FEATURE:
<223> OTHER INFORMATION: Kappa light chain

<400> SEQUENCE: 214

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 215
<211> LENGTH: 106
<212> TYPE: PRT
<213> ORGANISM: Artificial Sequence
<220> FEATURE:
<223> OTHER INFORMATION: Lambda light chain

<400> SEQUENCE: 215

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 216
<211> LENGTH: 676
<212> TYPE: PRT
<213> ORGANISM: Homo sapiens

<400> SEQUENCE: 216

Met Arg Val Leu Gly Gly Arg Cys Gly Ala Leu Leu Ala Cys Leu Leu
```

-continued

```
1               5                   10                  15

Leu Val Leu Pro Val Ser Glu Ala Asn Phe Leu Ser Lys Gln Gln Ala
            20                  25                  30

Ser Gln Val Leu Val Arg Lys Arg Arg Ala Asn Ser Leu Leu Glu Glu
        35                  40                  45

Thr Lys Gln Gly Asn Leu Glu Arg Glu Cys Ile Glu Glu Leu Cys Asn
    50                  55                  60

Lys Glu Glu Ala Arg Glu Val Phe Glu Asn Asp Pro Glu Thr Asp Tyr
65                  70                  75                  80

Phe Tyr Pro Lys Tyr Leu Val Cys Leu Arg Ser Phe Gln Thr Gly Leu
                85                  90                  95

Phe Thr Ala Ala Arg Gln Ser Thr Asn Ala Tyr Pro Asp Leu Arg Ser
            100                 105                 110

Cys Val Asn Ala Ile Pro Asp Gln Cys Ser Pro Leu Pro Cys Asn Glu
        115                 120                 125

Asp Gly Tyr Met Ser Cys Lys Asp Gly Lys Ala Ser Phe Thr Cys Thr
    130                 135                 140

Cys Lys Pro Gly Trp Gln Gly Glu Lys Cys Glu Phe Asp Ile Asn Glu
145                 150                 155                 160

Cys Lys Asp Pro Ser Asn Ile Asn Gly Gly Cys Ser Gln Ile Cys Asp
                165                 170                 175

Asn Thr Pro Gly Ser Tyr His Cys Ser Cys Lys Asn Gly Phe Val Met
            180                 185                 190

Leu Ser Asn Lys Lys Asp Cys Lys Asp Val Asp Glu Cys Ser Leu Lys
        195                 200                 205

Pro Ser Ile Cys Gly Thr Ala Val Cys Lys Asn Ile Pro Gly Asp Phe
    210                 215                 220

Glu Cys Glu Cys Pro Glu Gly Tyr Arg Tyr Asn Leu Lys Ser Lys Ser
225                 230                 235                 240

Cys Glu Asp Ile Asp Glu Cys Ser Glu Asn Met Cys Ala Gln Leu Cys
                245                 250                 255

Val Asn Tyr Pro Gly Gly Tyr Thr Cys Tyr Cys Asp Gly Lys Lys Gly
            260                 265                 270

Phe Lys Leu Ala Gln Asp Gln Lys Ser Cys Glu Val Val Ser Val Cys
        275                 280                 285

Leu Pro Leu Asn Leu Asp Thr Lys Tyr Glu Leu Leu Tyr Leu Ala Glu
    290                 295                 300

Gln Phe Ala Gly Val Val Leu Tyr Leu Lys Phe Arg Leu Pro Glu Ile
305                 310                 315                 320

Ser Arg Phe Ser Ala Glu Phe Asp Phe Arg Thr Tyr Asp Ser Glu Gly
                325                 330                 335

Val Ile Leu Tyr Ala Glu Ser Ile Asp His Ser Ala Trp Leu Leu Ile
            340                 345                 350

Ala Leu Arg Gly Gly Lys Ile Glu Val Gln Leu Lys Asn Glu His Thr
        355                 360                 365

Ser Lys Ile Thr Thr Gly Gly Asp Val Ile Asn Asn Gly Leu Trp Asn
    370                 375                 380

Met Val Ser Val Glu Glu Leu Glu His Ser Ile Ser Ile Lys Ile Ala
385                 390                 395                 400

Lys Glu Ala Val Met Asp Ile Asn Lys Pro Gly Pro Leu Phe Lys Pro
                405                 410                 415

Glu Asn Gly Leu Leu Glu Thr Lys Val Tyr Phe Ala Gly Phe Pro Arg
            420                 425                 430
```

```
Lys Val Glu Ser Glu Leu Ile Lys Pro Ile Asn Pro Arg Leu Asp Gly
        435                 440                 445

Cys Ile Arg Ser Trp Asn Leu Met Lys Gln Gly Ala Ser Gly Ile Lys
    450                 455                 460

Glu Ile Ile Gln Glu Lys Gln Asn Lys His Cys Leu Val Thr Val Glu
465                 470                 475                 480

Lys Gly Ser Tyr Tyr Pro Gly Ser Gly Ile Ala Gln Phe His Ile Asp
                485                 490                 495

Tyr Asn Asn Val Ser Ser Ala Glu Gly Trp His Val Asn Val Thr Leu
            500                 505                 510

Asn Ile Arg Pro Ser Thr Gly Thr Gly Val Met Leu Ala Leu Val Ser
        515                 520                 525

Gly Asn Asn Thr Val Pro Phe Ala Val Ser Leu Val Asp Ser Thr Ser
    530                 535                 540

Glu Lys Ser Gln Asp Ile Leu Leu Ser Val Glu Asn Thr Val Ile Tyr
545                 550                 555                 560

Arg Ile Gln Ala Leu Ser Leu Cys Ser Asp Gln Gln Ser His Leu Glu
                565                 570                 575

Phe Arg Val Asn Arg Asn Asn Leu Glu Leu Ser Thr Pro Leu Lys Ile
            580                 585                 590

Glu Thr Ile Ser His Glu Asp Leu Gln Arg Gln Leu Ala Val Leu Asp
        595                 600                 605

Lys Ala Met Lys Ala Lys Val Ala Thr Tyr Leu Gly Gly Leu Pro Asp
    610                 615                 620

Val Pro Phe Ser Ala Thr Pro Val Asn Ala Phe Tyr Asn Gly Cys Met
625                 630                 635                 640

Glu Val Asn Ile Asn Gly Val Gln Leu Asp Leu Asp Glu Ala Ile Ser
                645                 650                 655

Lys His Asn Asp Ile Arg Ala His Ser Cys Pro Ser Val Trp Lys Lys
            660                 665                 670

Thr Lys Asn Ser
        675


<210> SEQ ID NO 217
<211> LENGTH: 330
<212> TYPE: PRT
<213> ORGANISM: Homo sapiens

<400> SEQUENCE: 217

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 218
<211> LENGTH: 327
<212> TYPE: PRT
<213> ORGANISM: Homo sapiens

<400> SEQUENCE: 218

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

-continued

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

PROTEIN S ANTIBODIES, METHODS OF MAKING AND USES THEREOF

CROSS REFERENCE TO RELATED APPLICATIONS

This application is a U.S. National Stage Application under 35 U.S.C. § 371 of International Application No. PCT/US2021/030900, filed on May 5, 2021, which claims priority to U.S. Provisional Patent Application No. 63/020,505, filed on May 5, 2020 and to U.S. Provisional Patent Application No. 63/169,755 filed Apr. 1, 2021. The contents of each of the preceding applications are incorporated by reference herein in their entirety.

INCORPORATION OF SEQUENCE LISTING

The Sequence Listing associated with this application is provided electronically in TXT file format and is hereby incorporated by reference into the specification. The name of the TXT file containing the Sequence Listing is VEGA_001_02WO_SeqList_ST25. The TXT file is 103,674 bytes and was created on May 3, 2021.

BACKGROUND

Protein S (also known as ProS, ProS1) is a vitamin K-dependent plasma protein involved in the anti-coagulation cascade. The protein is multi-modular, comprising a γ-carboxy-glutamic acid domain (Gla domain), an epidermal growth factor-like domain (EGF domain), a thrombin-sensitive region (TSR), and a sex hormone binding globulin-like domain (SHBG-like domain). The protein is found in both a free form and as part of a complex with proteins such as C4 binding protein (C4BP) and tissue factor pathway inhibitor (TFPI). Among other functions, in its free form, Protein S is a cofactor in at least two pathways of the anti-coagulation cascade: (1) Protein S is a cofactor for plasma activated Protein C (APC), involved in the inactivation and degradation of coagulation factors Factor Va and Factor VIIIa; and (2) Protein S is also a cofactor for TFPI, also present in plasma, involved in the inactivation of coagulation factors Factor Xa and Factor VIIa.

Protein S is a potential therapeutic target for bleeding disorders, thus there is a need for agents that bind and modulate its activities within the coagulation pathway.

SUMMARY

Provided here are antibodies that bind Protein S, and methods of making and using such antibodies. In some embodiments, the Protein S antibodies provided herein are useful for treating a bleeding disorder, or a condition characterized by reduced or impaired blood coagulation and/or clotting.

Accordingly, in one aspect, provided herein are antibodies that bind Protein S, wherein the antibodies are inhibitors of the cofactor activity of Protein S for activated Protein C (APC), inhibitors of the cofactor activity of Protein S for tissue factor pathway inhibitor (TFPI), or inhibitors of the cofactor activity of Protein S for both APC and TFPI (dual inhibitor of cofactor activity), and wherein the antibody is human, humanized, or chimeric. In some preferred embodiments, the antibodies provided herein specifically bind Protein S.

In another aspect, provided herein are antibodies that bind Protein S, wherein the antibodies are capable of promoting coagulation and/or modulating a component in the coagulation cascade.

In another aspect, provided herein are exemplary Protein S antibodies comprising any one or more of the amino acid sequences of the complementarity determining region (CDR) sequences provided in Tables 1A, 1B, 1C, 2A, 2B, and 2C. In another aspect, the exemplary Protein S antibodies comprise any one of the CDR-L1 amino acid sequences of Table 1A; any one of the CDR-L2 amino acid sequences of Table 1B; any one of the CDR-L3 amino acid sequences of Table 1C; any one of the CDR-H1 amino acid sequences of Table 2A; any one of the CDR-H2 amino acid sequences of Table 2B; any one of the CDR-H3 amino acid sequences of Table 2B. In another aspect, provided herein are exemplary Protein S antibodies comprising the combinations of variable light chains and variable heavy chains presented in Table 4C. In another aspect, provided herein are the sequences of different antibodies as presented in Table 6. In another aspect, provided herein are nucleic acids encoding for any of the Protein S antibodies provided herein.

In another aspect, provided herein are pharmaceutical compositions comprising any one of the Protein S antibodies provided herein, and optionally a pharmaceutically acceptable excipient.

Provided herein are methods of using the exemplary Protein S antibodies described herein. Accordingly, in one aspect, provided herein is an in vitro method of promoting the coagulation of blood, comprising contacting any one of the Protein S antibodies provided herein with a blood sample.

In another aspect, provided herein is a method of promoting the coagulation of blood in a subject in need thereof, comprising administering to the subject any of the exemplary Protein S antibodies provided herein, or pharmaceutical compositions provided herein. In exemplary embodiments, the route of administration is subcutaneous.

In another aspect, provided herein is a method of promoting the generation of thrombin in a subject in need thereof, comprising administering to the subject any of the Protein S antibodies provided herein, or pharmaceutical compositions provided herein.

In another aspect, provided herein is a method of treating a condition in a subject in need thereof, comprising administering to the subject any of the Protein S antibodies provided herein, or pharmaceutical compositions provided herein, wherein the condition is selected from the group consisting of: bleeding disorders, platelet disorders, trauma, bleeding resulting from a surgery or a medical procedure, and combinations thereof.

In another aspect, provided herein is the use of any one of the Protein S antibodies or pharmaceutical compositions provided herein, for the treatment of a condition in a subject in need thereof. The condition may be selected from the group consisting of: bleeding disorders, platelet disorders, trauma, bleeding resulting from a surgery or a medical procedure, and combinations thereof.

In another aspect, any one of the Protein S antibodies or pharmaceutical compositions provided herein, may be used for the manufacture of a medicament for the treatment of a condition in a subject in need thereof. The condition may be selected from the group consisting of: bleeding disorders, platelet disorders, trauma, bleeding resulting from a surgery or a medical procedure, and combinations thereof.

BRIEF DESCRIPTION OF THE DRAWINGS

FIGS. 5, 6), an APC cofactor inhibitor (Antibody 21; FIGS. 7, 8), and a TFPI cofactor inhibitor (Antibody 23; FIGS. 9, 10) when using a TFPI cofactor assay and an APC cofactor assay.

DETAILED DESCRIPTION

Figure 1:
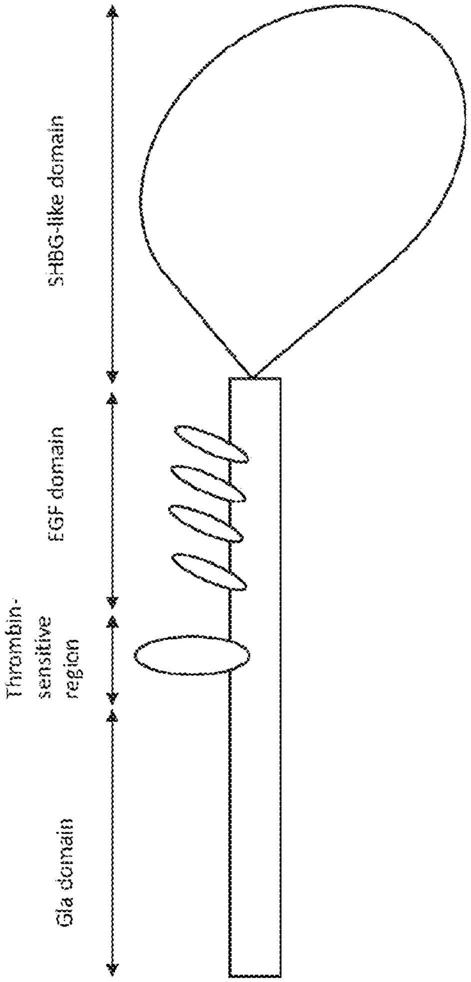
FIG. 1 depicts a schematic diagram of Protein S showing the modular domains of Protein S.

Provided herein are antibodies that bind Protein S, and methods of making and using such antibodies. In some embodiments, the Protein S antibodies provided herein specifically bind Protein S. For example, antibodies that bind to Protein S and inhibit its cofactor activity for TFPI and/or APC, may be useful in the treatment of bleeding disorders and other related diseases by promoting clot formation Where elements are presented in a list format (e.g., in a Markush group), it should be understood that each possible subgroup of the elements is also disclosed, and that any one or more elements can be removed from the list or group.

It should be understood that, unless clearly indicated, in any method described or disclosed herein that includes more than one act, the order of the acts is not necessarily limited to the order in which the acts of the method are recited, but the disclosure encompasses exemplary embodiments in which the order of the acts is so limited.

The terms used throughout the specification are defined as follows unless otherwise limited in specific instances. As used in the specification and the claims, the singular forms "a," "an," and "the" include plural referents unless the context clearly dictates otherwise. All technical and scientific terms, acronyms, and abbreviates used in the specification and claims have the same meaning as commonly understood by one of ordinary skill in the art to which the disclosure pertains, unless defined or stated otherwise. All numerical ranges are inclusive of the values defining the range as well as all integer values in between, unless indicated or defined otherwise.

The term "antibody" as used herein throughout is used in the broadest sense and may include a monoclonal antibody, polyclonal antibody, human antibody, humanized antibody, non-human antibody, chimeric antibody, a monovalent antibody, an antigen-binding fragment (e.g., a Fab fragment, a Fab'2 fragment, an scFv), and other antibody fragments that retain specificity for and binding of Protein S. In some embodiments, the antibodies are monoclonal antibodies. In some embodiments, the antibodies are monoclonal antibodies. In some embodiments, the antibodies are monoclonal human antibodies. In some embodiments, the antibodies are monoclonal humanized antibodies. In some embodiments, the antibodies are monoclonal chimeric antibodies.

Also provided herein are antibody-drug conjugates, bispecific antibodies, and multispecific antibodies that exhibit specificity for and binding of Protein S.

The terms "polynucleotide" and "nucleic acid" are used interchangeably herein, and refer to a polymeric form of nucleotides of any length, which may be ribonucleotides or deoxyribonucleotides. The terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms encompass nucleic acids containing known analogues of natural nucleotides and having similar binding properties, and are metabolized in a manner similar to naturally-occurring nucleotides, unless specifically limited or stated otherwise.

When a nucleic acid or amino acid sequence is said to have a certain percent "sequence identity" or "identity" or is a certain percent "identical" to another nucleic acid or amino acid sequence, that percentage of bases or amino acids are the same, and in the same relative position, when the sequences are aligned, when comparing the two sequences.

The term "subject," as used herein refers to any subject for whom treatment or therapy is provided. The subject may be a mammalian subject. Mammalian subjects include, e. g., humans, non-human primates (e.g., cynomolgus monkey), rodents, (e.g., rats, mice), lagomorphs (e.g., rabbits), ungulates (e.g., cows, sheep, pigs, horses, goats, and the like), etc. In some embodiments, the subject is a human. In some embodiments, the subject is a non-human primate, e.g. a cynomolgus monkey. In some embodiments, the subject is a companion animal (e.g. cats, dogs).

All publications, patents, and patent applications mentioned in this specification are herein incorporated by reference to the same extent as if each individual publication, patent, or patent application was specifically and individually indicated to be incorporated by reference.

I. ANTIBODIES THAT BIND AND MODULATE PROTEIN S ACTIVITY

A. Protein S Antibodies

Provided here are antibodies that bind to Protein S, and in some embodiments are specific for Protein S. The Protein S can be of any species, e.g. any mammalian species. In some embodiments, the Protein S antibody binds to human Protein S. In some embodiments, the Protein S antibody binds to the Protein S of non-human primates. In some embodiments, the non-human primate is cynomolgus monkey.

The amino acid sequence of human Protein S, targeted by antibodies of the disclosure, is shown below as SEQ ID. NO: 216.

```
                                   (SEQ ID. NO: 216)
        10         20         30         40
MRVLGGRCGA LLACLLLVLP VSEANFLSKQ QASQVLVRKR

        50         60         70         80
RANSLLEETK QGNLERECIE ELCNKEEARE VFENDPETDY

        90        100        110        120
FYPKYLVCLR SFQTGLFTAA RQSTNAYPDL RSCVNAIPDQ

       130        140        150        160
CSPLPCNEDG YMSCKDGKAS FTCTCKPGWQ GEKCEFDINE

       170        180        190        200
CKDPSNINGG CSQICDNTPG SYHCSCKNGF VMLSNKKDCK
```

-continued

```
       210        220        230        240
DVDECSLKPS ICGTAVCKNI PGDFECECPE GYRYNLKSKS

       250        260        270        280
CEDIDECSEN MCAQLCVNYP GGYTCYCDGK KGFKLAQDQK

       290        300        310        320
SCEVVSVCLP LNLDTKYELL YLAEQFAGVV LYLKFRLPEI

       330        340        350        360
SRFSAEFDFR TYDSEGVILY AESIDHSAWL LIALRGGKIE

       370        380        390        400
VQLKNEHTSK ITTGGDVINN GLWNMVSVEE LEHSISIKIA

       410        420        430        440
KEAVMDINKP GPLFKPENGL LETKVYFAGF PRKVESELIK

       450        460        470        480
PINPRLDGCI RSWNLMKQGA SGIKEIIQEK QNKHCLVTVE

       490        500        510        520
KGSYYPGSGI AQFHIDYNNV SSAEGWHVNV TLNIRPSTGT

       530        540        550        560
GVMLALVSGN NTVPFAVSLV DSTSEKSQDI LLSVENTVIY

       570        580        590        600
RIQALSLCSD QQSHLEFRVN RNNLELSTPL KIETISHEDL

       610        620        630        640
QRQLAVLDKA MKAKVATYLG GLPDVPFSAT PVNAFYNGCM

       650        660        670
EVNINGVQLD LDEAISKHND IRAHSCPSVW KKTKNS
```

In some embodiments, provided herein are Protein S antibodies comprising a binding affinity (KD) to Protein S of about 0.0005 nM or lower, 0.001 nM or lower, 0.005 nM or lower, 0.01 nM or lower, 0.05 nM or lower, about 0.1 nM or lower, about 0.5 nM or lower, about 1 nM or lower, about 5 nM or lower, about 10 nM or lower, about 50 nM or lower, about 100 nM or lower, about 500 nM or lower, or about 1 μM or lower.

The Protein S antibodies provided herein are capable of modulating one or more activities of Protein S, including, for example, modulating Protein S cofactor activity, as well as promoting coagulation and altering levels of markers associated with coagulation, and modulating a component in the coagulation cascade.

In some embodiments, the Protein S antibodies provided herein are capable of modulating the Protein S ability to act as a cofactor within pathways of the coagulation cascade.

Accordingly, in some embodiments, the Protein S antibodies provided herein are useful for reducing or inhibiting the cofactor activity of Protein S for activated Protein C ("APC").

In some embodiments, the Protein S antibodies provided herein are useful for reducing or inhibiting the cofactor activity of Protein S for tissue factor pathway inhibitor ("TFPI"). TFPI is an inhibitor of procoagulant activity and is produced as at least two alternatively spliced isoforms in humans, TFPIα, and TFPIβ, which differ in domain structure and mechanism for cell surface association. TFPIα, but not TFPIβ contains Kunitz domain 3, the domain which is believed to be involved in binding to Protein S. Without being held to any theory or mechanism, it is believed that the Protein S antibodies of the disclosure inhibit the cofactor activity of Protein S for at least TFPIα, as it contains Kunitz domain 3.

In some embodiments, the Protein S antibodies provided herein are useful for reducing or inhibiting the cofactor activity of Protein S for APC, but show negligible or no effect on cofactor activity of Protein S for TFPI (such antibodies are referred to interchangeably herein as "APC cofactor inhibitors", "APC cofactor specific inhibitors", or "APC pathway inhibitors").

In some embodiments, the Protein S antibodies provided herein are useful for reducing or inhibiting the cofactor activity of Protein S for TFPI, but show negligible or no effect on cofactor activity of Protein S for APC (such antibodies are referred to interchangeably herein as "TFPI cofactor inhibitors", "TFPI cofactor specific inhibitors", or "TFPI pathway inhibitors").

In some embodiments, the Protein S antibodies provided herein are useful for reducing or inhibiting the cofactor activity of Protein S for both APC and TFPI (such antibodies are referred to herein as "dual inhibitors"). The dual inhibitors of the disclosure may reduce the activities of APC and TFPI to different degrees.

In some embodiments, the Protein S antibodies provided herein are capable of causing a reduction in the activity of APC. For example, APC activity may be reduced by about 10%, about 20%, about 30%, about 40%, about 50%, about 60%, about 70%, about 80%, about 90%, or about 100% as compared to in the absence of the Protein S antibodies.

In some embodiments, the Protein S antibodies provided herein are capable of causing a reduction in the activity of TFPI. For example, TFPI activity may be reduced by about 10%, about 20%, about 30%, about 40%, about 50%, about 60%, about 70%, about 80%, about 90%, or about 100% as compared to in the absence of the Protein S antibodies.

In some embodiments, the Protein S antibodies provided herein are capable of causing a reduction in the activity of both APC and TFPI. For example, APC activity may be reduced by about 10%, about 20%, about 30%, about 40%, about 50%, about 60%, about 70%, about 80%, about 90%, or about 100%, and TFPI activity may also be reduced by about 10%, about 20%, about 30%, about 40%, about 50%, about 60%, about 70%, about 80%, about 90%, or about 100% as compared to in the absence of the Protein S antibodies. The reduction in APC activity and TFPI activity may be affected to different degrees by the same Protein S antibody.

In some embodiments, the Protein S antibodies provided herein are APC cofactor inhibitors, and the capability of the antibody for affecting the cofactor activity of Protein S for TFPI is negligible. In other embodiments, the Protein S antibodies provided herein are TFPI cofactor inhibitors, and the capability of the antibody for affecting the cofactor activity of Protein S for APC is negligible.

In some embodiments, the Protein S antibodies provided herein are capable of promoting coagulation and/or modulating a component in the coagulation cascade, e.g., in a subject in need thereof, or in a sample. In some embodiments, the Protein S antibodies provided herein are capable of promoting the clotting of blood. In some embodiments, the antibodies are capable of promoting clotting of blood by reducing the ability of Protein S to act as a cofactor for APC. For example, clotting of blood may be promoted by reducing APC activity by about 10%, about 20%, about 30%, about 40%, about 50%, about 60%, about 70%, about 80%, about 90%, or about 100%, as compared to in the absence of the Protein S antibodies.

In some embodiments, the antibodies are capable of promoting clotting of blood by reducing an ability of Protein S to act as a cofactor for TFPI. For example, clotting of blood may be promoted by reducing TFPI activity by about 10%, about 20%, about 30%, about 40%, about 50%, about 60%, about 70%, about 80%, about 90%, or about 100%, as compared to in the absence of the Protein S antibodies.

In some embodiments, the antibodies are capable of promoting clotting of blood by reducing an ability of Protein S to act as a cofactor for both APC and TFPI. For example, clotting of blood may be promoted by reducing both APC activity and TFPI activity by about 10%, about 20%, about 30%, about 40%, about 50%, about 60%, about 70%, about 80%, about 90%, or about 100%, as compared to in the absence of the Protein S antibodies.

In some embodiments, the Protein S antibodies provided herein are capable of promoting the generation of a marker associated with coagulation activity, and this can be exhibited in vitro (e.g. in a sample) and/or in vivo (e.g. upon administration to a subject). Such markers include, but are not limited to, thrombin, fibrin, D-dimer, clot formation, thrombin-antithrombin complex, fibrin degradation products, and prothrombin fragment F1.2.

In some embodiments, the Protein S antibodies provided herein are capable of promoting thrombin generation (e.g. includes restoring thrombin generation or restoring the levels of thrombin, e.g., in a subject in need thereof, or in a sample). In some embodiments, the antibodies are capable of promoting generation of thrombin in a subject in need thereof. In some embodiments, the generation of thrombin does not exceed a predetermined threshold level. In some embodiments, the generation of thrombin is partially restored. In some embodiments, the generation of thrombin does not exceed a predetermined percentage of a maximum thrombin generation. In some embodiments, the generation of thrombin does not exceed a predetermined percentage of an area under the curve of the maximum thrombin generation. In some embodiments, thrombin generation may be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies. Exemplary antibodies that promote thrombin generation are described in greater detail below, and include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the Protein S antibodies provided herein can restore or promote thrombin generation in a subject who is deficient in coagulation factors. In some exemplary embodiments, the coagulation factor deficiency is congenital. In some exemplary embodiments, the coagulation factor deficiency is acquired. In some embodiments, the Protein S antibodies provided herein can promote thrombin generation in a subject who is deficient in Factor VII, Factor VIII, Factor IX, Factor XI. For example, thrombin generation can be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies, when used to promote thrombin generation in a sample from a subject with a factor deficiency.

In some embodiments, the Protein S antibodies provided herein can promote thrombin generation in a subject who suffers from von Willebrand Disease (vWD) disease. In some embodiments, the vWD is a subtype selected from: vWD Type 1, vWD Type 2A, vWD Type 2B, vWD Type 2N, vWD Type 2M, vWD Type 3, and acquired vWD. In some exemplary embodiments, the vWD is a subtype selected from Type 1, Type 2, or Type 3. For example, thrombin generation can be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies, when used to promote thrombin generation in a sample from a subject with vWD disease.

Exemplary antibodies that may promote thrombin generation in a subject who is deficient in a coagulation factor (such as Factor VII, Factor VIII, Factor IX, Factor XI) or who has von Willebrand disease (such as Type 1, Type 2A, Type 2B, Type 2M, Type 2N or Type 3) include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the Protein S antibodies provided herein are capable of promoting fibrin generation, e.g., in a subject in need thereof, or in a sample. In some embodiments, the Protein S antibodies provided herein are capable of promoting fibrin deposition e.g., in a sample. In some embodiments, the Protein S antibodies provided herein are capable of promoting coagulation activity, wherein the coagulation activity is marked by a promotion of fibrin generation. For example, fibrin generation may be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies. as compared to in the absence of the Protein S antibodies. Exemplary antibodies that may promote fibrin generation include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the Protein S antibodies provided herein are capable of promoting increasing D-dimer levels, e.g., in a subject in need thereof, or in a sample. In some embodiments, the Protein S antibodies provided herein are capable of promoting coagulation activity, wherein the coagulation activity is marked by an increase in D-dimer levels. For example, D-dimer levels may be increased by about two-fold to about 10,000-fold. Exemplary antibodies that may promote an increase in D-dimer levels include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the Protein S antibodies provided herein are capable of promoting coagulation in a sample or in a subject. In some embodiments, the Protein S antibodies provided herein alter the levels of markers associated with coagulation activity in a sample or in a subject. For example, in some embodiments, the antibodies are capable of restoring or promoting thrombin generation in a sample, or in a subject. In some embodiments, the antibodies are capable of restoring fibrin deposition in a sample, or in a subject. In some embodiments, the antibodies provided herein are capable of promoting a restoration of fibrin deposition. In some embodiments, the antibodies provided herein are capable of increasing the levels of D-dimer in a sample, or in a subject. In some embodiments, the antibodies provided herein are capable of promoting an increase of D-dimer. In some embodiments, activity of the antibodies provided herein is dose-dependent. In some embodiments, activity of the antibodies provided herein is measured in vitro. In some embodiments, activity of the antibodies provided herein is measured in vivo.

In some embodiments, the Protein S antibodies provided herein are administered to a subject, wherein the antibody remains active in the subject for a period of time.

Figure 24B:
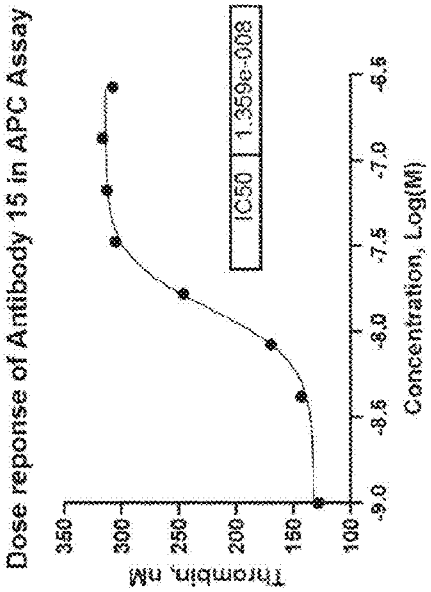
FIGS. 24A-24B depict exemplary dose response curves exhibited by antibodies 19 and 15 in an APC cofactor screening assay. The antibodies exhibit graded inhibition and switch-like inhibition, respectively, in the assay.
Figure 24A:
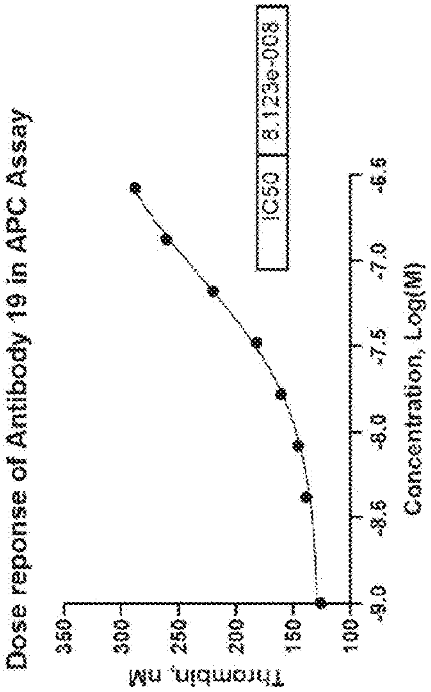

In some embodiments, the Protein S antibodies provided herein are administered to a subject, wherein the effect of the antibody is dose-dependent, such antibodies exhibit graded inhibition. FIG. 24A (Antibody 19) depicts an exemplary dose response curve of thrombin generation resulting from an antibody exhibiting graded inhibition. Antibodies exhibiting graded inhibition show concentration-dependent inhibition in vitro, where increasing concentrations of antibody result in incremental increases in thrombin generation over a wide concentration range. Exemplary antibodies that exhibit such graded inhibition include, but are not limited to, antibodies that comprise (a) the CDR amino acid sequences of SEQ ID NO: 1, SEQ ID NO: 12, SEQ ID NO: 21, SEQ ID NO: 33, SEQ ID NO: 45, and SEQ ID NO: 57; or (b) the CDR amino acid sequences of SEQ ID NO: 10, SEQ ID NO: 16, SEQ ID NO: 31, SEQ ID NO: 43, SEQ ID NO: 55, SEQ ID NO: 67.

In such embodiments, the graded inhibition can allow for increasing the dose of administration of the Protein S antibodies to a subject for added efficacy, or decreasing the dose to prevent excess thrombin generation, and/or potential thromboembolic complications, for example. Effectively, the dose can be adjusted to achieve the desired level of inhibition.

In some embodiments, the Protein S antibodies provided herein exhibit switch-like inhibition, wherein inhibition can be switched on or off. FIG. 24B (Antibody 15) depicts an exemplary dose response curve resulting from an antibody exhibiting switch-like inhibition. Antibodies exhibiting switch-like inhibition show abrupt concentration-dependent increases in thrombin generation in vitro, where upon reaching a concentration capable of promoting thrombin generation, achieves maximal thrombin generated within a narrow concentration range. Exemplary antibodies that exhibit such graded inhibition include, but are not limited to, antibodies that comprise (a) the CDR amino acid sequences of SEQ ID NO: 2, SEQ ID NO: 13, SEQ ID NO: 22, SEQ ID NO: 34, SEQ ID NO: 46, and SEQ ID NO: 58; or (b) the CDR amino acid sequences of SEQ ID NO: 1, SEQ ID NO: 15, SEQ ID NO: 24, SEQ ID NO: 36, SEQ ID NO: 48, and SEQ ID NO: 60.

In some embodiments, the Protein S antibodies provided herein are antibody fragments. In some embodiments, the antibody fragments are antigen-binding fragments (Fab), variable fragments (Fv) containing VH and VL, single chain variable fragments (scFv) containing VH and VL linked together in one chain, or other antibody variable region fragments, such as Fab', F(ab)2, F(ab')2, dsFv diabody, Fc, and Fd polypeptide fragments. The antibody fragments contain a Fc domain.

In some embodiments, the Protein S antibodies provided herein are monoclonal antibodies (mAbs). In some embodiments, the Protein S antibodies provided herein are human antibodies. In some embodiments, the Protein S antibodies provided herein are monoclonal human antibodies. In some embodiments, the Protein S antibodies provided herein are humanized antibodies. In some embodiments, the Protein S antibodies provided herein are monoclonal humanized antibodies. In some embodiments, the Protein S antibodies provided herein are chimeric antibodies. In some embodiments, the Protein S antibodies provided herein are monoclonal chimeric antibodies.

In some embodiments, the Protein S antibodies provided herein are full-length antibodies.

In some embodiments, the Protein S antibodies provided herein contain an Fc domain (either are full-length or for example, a single chain antibody linked to a Fc domain).

In some embodiments, the constant region (herein referred to also as a Fc domain, a Fc sequence or simply as a Fc) of a Protein S antibody is a human Fc domain. In some embodiments, the Fc domain of a full-length Protein S antibody is human IgG1, human IgG2, human IgG3, or human IgG4. In some embodiments, the Fc domain of a full-length Protein S antibody is that of a rat. In some embodiments, the Fc domain of a full-length Protein S antibody is rat IgG1 or rat IgG2b. In some embodiments, the Fc domain of a full-length Protein S antibody is that of a non-human primate, e.g. it is a cynomolgus monkey Fc domain.

In some embodiments, the Protein S antibodies provided herein are chimeric and comprise a variable region from one species, and a constant region from another species, e.g. comprise a human variable region and a rat constant region. In some embodiments, the rat constant region is rat IgG1 or IgG2b. In some embodiments, the antibodies comprise a human variable region and a human constant region. In exemplary embodiments, the human constant region is human IgG1, or human IgG4.

In some embodiments, the Protein S antibody contains an Fc domain, and the Fc domain of the antibody is a human IgG1 Fc. Exemplary, but non-limiting, human IgG1 Fc domain sequences are provided as SEQ ID NOS: 217.

```
                                  (SEQ ID NO: 217)
  1 ASTKGPSVFP LAPSSKSTSG GTAALGCLVK
    DYFPEPVTVS WNSGALTSGV HTFPAVLQSS
 61 GLYSLSSVVT VPSSSLGTQT YICNVNHKPS
    NTKVDKKVEP KSCDKTHTCP PCPAPELLGG
121 PSVFLFPPKP KDTLMISRTP EVTCVVVDVS
    HEDPEVKFNW YVDGVEVHNA KTKPREEQYN
181 STYRVVSVLT VLHQDWLNGK EYKCKVSNKA
    LPAPIEKTIS KAKGQPREPQ VYTLPPSRDE
241 LTKNQVSLTC LVKGFYPSDI AVEWESNGQP
    ENNYKTTPPV LDSDGSFFLY SKLTVDKSRW
301 QQGNVFSCSV MHEALHNHYT QKSLSLSPGK
```

In some embodiments, the Protein S antibody contains an Fc domain, and the Fc domain of the antibody is a human IgG4 Fc. An exemplary human IgG4 heavy chain Fc domain sequence is provided as SEQ ID NO: 218.

(SEQ ID NO: 218)

```
ASTKGPSVFPLAPCSRSTSESTAALGCLVKDYFPEPVT
VSWNSGALTSGVHTFPAVLQSSGLYSLSSVVTVPSSSL
GTKTYTCNVDHKPSNTKVDKRVESKYGPPCPSCPAPEF
LGGPSVFLFPPKPKDTLMISRTPEVTCVVVDVSQEDPE
VQFNWYVDGVEVHNAKTKPREEQFNSTYRVVSVLTVLH
QDWLNGKEYKCKVSNKGLPSSIEKTISKAKGQPREPQV
YTLPPSQEEMTKNQVSLTCLVKGFYPSDIAVEWESNGQ
PENNYKTTPPVLDSDGSFFLYSRLTVDKSRWQEGNVFS
CSVMHEALHNHYTQKSLSLSLGK
```

The EU numbering scheme is one of many available antibody numbering schemes based on the residue numbers assigned to a canonical antibody sequence. Accordingly, a skilled artisan would understand that reference to a particular residue using the EU numbering scheme may or may not be exactly the residue in one of the antibodies of the disclosure. For example, if a Protein S antibody of the disclosure comprises a V215A substitution in the Fc, wherein the position number of the amino acid residue is of the EU numbering scheme, the residue may not be the actual residue 215 in that particular Protein S antibody. It may be actual residue number 213, or 214, or 215, or 216. Accordingly a skilled artisan will understand how to correspond the recited residue using the EU numbering scheme, to the actual residue in a Protein S antibody of the disclosure. The EU numbering system for antibodies is known in the art and is described, for example, at imgt.org/IMGTScientificChart/Numbering/Hu_IGHGnber.html.

In some embodiments, the Fc domain of a Protein S antibody is an IgG1 or IgG4 human Fc domain, and Fc variants comprise at least one amino acid substitution at a position selected from the group consisting of: 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 396, 428, 430, 433, 434, and 440, wherein the position numbers of the amino acid residues are of the EU numbering scheme.

In some embodiments, the Fc domain of a Protein S antibody is a human IgG1, and substitutions are introduced to reduce effector function, including N297A, N297Q, N297G, L235E, L234A, and L235A, wherein the position numbers of the amino acid residues are of the EU numbering scheme. In some embodiments, the Fc domain of a full-length Protein S antibody is human IgG4, and substitutions are introduced to reduce effector function, including L235E, and F234A/L235A, wherein the position numbers of the amino acid residues are of the EU numbering scheme. In some embodiments, the Fc domain of a full-length Protein S antibody is human IgG2, and substitutions are introduced to reduce effector function, including H268Q/V309L/A330S/P331S and V234A/G237A/P238S/H268A/V309L/A330S/P331S, wherein the position numbers of the amino acid residues are of the EU numbering scheme.

In some embodiments, the Fc domain of a Protein S antibody is a human IgG1, and substitutions are introduced to increase effector function, including G236A/S239D, /I332E, K326W/E333S, S267E/H268F/S324T, and E345R/E430G/S440Y, wherein the position numbers of the amino acid residues are of the EU numbering scheme.

In some embodiments, the Fc domain of a Protein S antibody is an IgG4 human Fc domain, and the antibody is prone to the dynamic process of Fab-arm exchange. Accordingly, in some embodiments the IgG4 Fc domain comprises a S228P substitution, resulting in the reduction of this process, wherein the position number of the amino acid residues are of the EU numbering scheme.

In other embodiments, the Fc domain of a Protein S antibody is altered to increase its serum half-life. Such alterations include substitutions of a human IgG1 (e.g. SEQ ID NO: 217) such as T250Q/M428L, M252Y/S254T/T256E, M428L/N434S, S267E/L328F, N325S/L328F, and H433K/N434F, wherein the position number of the amino acid residues are of the EU numbering scheme.

In other embodiments, the Fc domain of a Protein S antibody is altered to increase its serum half-life. Such alterations include substitutions of a human IgG4 (e.g. SEQ ID NO: 218) such as T250Q/M428L, M252Y/S254T/T256E, M428L/N434S, S267E/L328F, N325S/L328F, and H433K/N434F, wherein the position number of the amino acid residues are of the EU numbering scheme.

In some embodiments, the Fc domain of a Protein S antibody is an IgG1 human Fc domain, and substitutions are introduced enhance effector function, including F243L/R292P/Y300L/V3051/P396L, S239D/I332E, S298A/E333A/K334A, L234Y/L235Q/G236W/S239M/H268D/D270E/S298A, D270E/K326D/A330M/K334E, wherein the position number of the amino acid residues are of the EU numbering scheme.

Exemplary Protein S Antibodies—CDR Sequences

Provided herein are exemplary CDR sequences of the Protein S antibodies disclosed herein.

Exemplary CDR sequences presented in Tables 1A-1C and 2A-2C below. As referred below, a light chain variable (VL) domain CDR1 region is referred to as CDR-L1; a VL CDR2 region is referred to as CDR-L2; a VL CDR3 region is referred to as CDR-L3; a heavy chain variable (VH) domain CDR1 region is referred to as CDR-H1; a VH CDR2 region is referred to as CDR-H2; and a VH CDR3 region is referred to as CDR-H3.

TABLE 1A

| Exemplary Protein S Antibody CDR-L1 Sequences |
|---|
| KLGDKY (SEQ ID NO: 1) |
| SLRNYY (SEQ ID NO: 2) |
| SSDVGGYEF (SEQ ID NO: 3) |
| QSVSIY (SEQ ID NO: 4) |
| QRINSN (SEQ ID NO: 5) |
| QSLLHSNGYNY (SEQ ID NO: 6) |
| TGAVTASNY (SEQ ID NO: 9) |
| QSVTSN (SEQ ID NO: 10) |
| QSLVHSDGNTY (SEQ ID NO: 11) |
| QGINNY (SEQ ID NO: 117) |
| QSISTF (SEQ ID NO: 127) |
| QSVGSSY (SEQ ID NO: 136) |
| QNIHMW (SEQ ID NO: 141) |
| QSISSY (SEQ ID NO: 174) |

TABLE 1A-continued

| Exemplary Protein S Antibody CDR-L1 Sequences |
|---|
| NIGGKS (SEQ ID NO: 184) |
| KLGDKY (SEQ ID NO: 194) |
| KLGDKY (SEQ ID NO: 204) |

TABLE IB

| Exemplary Protein S Antibody CDR-L2 Sequences |
|---|
| QDT (SEQ ID NO: 12) |
| GKN (SEQ ID NO: 13) |
| DVS (SEQ ID NO: 14) |
| QNS (SEQ ID NO: 15) |
| DAS (SEQ ID NO: 16) |
| GAS (SEQ ID NO: 17) |
| LGS (SEQ ID NO: 18) |
| STN (SEQ ID NO: 19) |
| KIS (SEQ ID NO: 20) |
| AAS (SEQ ID NO: 118) |
| ATS (SEQ ID NO: 128) |
| KTS (SEQ ID NO: 142) |
| AAS (SEQ ID NO: 175) |
| DDS (SEQ ID NO: 185) |
| QDS (SEQ ID NO: 195) |
| QDN (SEQ ID NO: 205) |

TABLE 1C

| Exemplary Protein S Antibody CDR-L3 Sequences |
|---|
| QAWDSNTVV (SEQ ID NO: 21) |
| NSRDSSGNHVV (SEQ ID NO: 22) |
| SSYTRSSTVV (SEQ ID NO: 23) |
| QAWDSSTWV (SEQ ID NO: 24) |
| QQRSNWPLT (SEQ ID NO: 25) |
| QQYDNWPLT (SEQ ID NO: 26) |
| MQALQTFT (SEQ ID NO: 27) |
| ALWYSDHFV (SEQ ID NO: 30) |
| QQYNNWPT (SEQ ID NO: 31) |
| MQATQFPHLT (SEQ ID NO: 32) |
| QQYNSYPRT (SEQ ID NO: 119) |
| QQYNSYPIT (SEQ ID NO: 123) |
| QQSYSTPRT (SEQ ID NO: 129) |

TABLE 1C-continued

| Exemplary Protein S Antibody CDR-L3 Sequences |
|---|
| QQYGSSPYT (SEQ ID NO: 137) |
| LQGQSYPFT (SEQ ID NO: 143) |
| QQSYSSLT (SEQ ID NO: 176) |
| QVWEITSDHPA (SEQ ID NO: 186) |
| QAWDSSTVG (SEQ ID NO: 196) |
| QAWDSSTAV (SEQ ID NO: 206) |

TABLE 2A

| Exemplary Protein S Antibody CDR-H1 Sequences |
|---|
| GGSISSSSYY (SEQ ID NO: 33) |
| GGTFSSYS (SEQ ID NO: 34) |
| GGSITSDGYH (SEQ ID NO: 35) |
| GFTFDDYA (SEQ ID NO: 36) |
| GFTFSTYG (SEQ ID NO: 37) |
| GYSISSGYY (SEQ ID NO: 38) |
| GDTFSNHA (SEQ ID NO: 39) |
| GHTFTGYY (SEQ ID NO: 42) |
| GGSISSTNW (SEQ ID NO: 43) |
| GGSISNYY (SEQ ID NO: 44) |
| GGSITNSNYY (SEQ ID NO: 120) |
| GFTFSSYN (SEQ ID NO: 124) |
| GGSISGNY (SEQ ID NO: 130) |
| GDSVSNNNAA (SEQ ID NO: 138) |
| GYTFTNHW (SEQ ID NO: 144) |
| GISFSNAW (SEQ ID NO: 179) |
| GFTFSSYS (SEQ ID NO: 189) |
| GYTFTNYY (SEQ ID NO: 199) |
| GYTFTSYY (SEQ ID NO: 209) |

TABLE 2B

| Exemplary Protein S Antibody CDR-H2 Sequences |
|---|
| IYYSGNT (SEQ ID NO: 45) |
| IIPIFGTT (SEQ ID NO: 46) |
| IYYTGNT (SEQ ID NO: 47) |
| ITWNSGNI (SEQ ID NO: 48) |
| IYYDGINK (SEQ ID NO: 49) |
| IYYSGST (SEQ ID NO: 50) |
| YIPIFGTT (SEQ ID NO: 51) |
| INPNSGDT (SEQ ID NO: 54) |

TABLE 2B-continued

| Exemplary Protein S Antibody CDR-H2 Sequences |
|---|
| IYQTGST (SEQ ID NO: 55) |
| IYYIGIT (SEQ ID NO: 56) |
| VYYSGTT (SEQ ID NO: 121) |
| ISSSSSYI (SEQ ID NO: 125) |
| TYYRSKWYN (SEQ ID NO: 139) |
| IYPGGGYT (SEQ ID NO: 145) |
| IKANPDGGTT (SEQ ID NO: 180) |
| ISSSTRTI (SEQ ID NO: 190) |
| ITPSGGTT (SEQ ID NO: 200) |
| TSPSGRST (SEQ ID NO: 210 |

TABLE 2C

| Exemplary Protein S Antibody CDR-H3 Sequences |
|---|
| ARCSGYGYSSGRSYFDY (SEQ ID NO: 57) |
| EGGRVGADFDY (SEQ ID NO: 58) |
| ARRLSTGPYFDY (SEQ ID NO: 59) |
| AKGRAVSDTFDI (SEQ ID NO: 60) |
| AESDLDY (SEQ ID NO: 61) |
| ATTYSDIVTGYYNDAFDI (SEQ ID NO: 62) |
| ARGGLAGSHYKNYYYDGMDV (SEQ ID NO: 63) |
| ARDSQILWFGELGY (SEQ ID NO: 66) |
| ARRFGELDY (SEQ ID NO: 67) |
| AALSGDHAFDI (SEQ ID NO: 68) |
| VRESESYYYYGSDV (SEQ ID NO: 122) |
| ARDEEWELLTGFDY (SEQ ID NO: 126) |
| ARDLDYFTWGAYSDWYFDL (SEQ ID NO: 131) |
| ARGSSWYRFFDY (SEQ ID NO: 140) |
| SRFGDQNWAWFAY (SEQ ID NO: 146) |
| TTELDILLWFTSFDY (SEQ ID NO: 181) |
| ARERSAFDY (SEQ ID NO: 191) |
| ARAGVQLDRRGWFDP (SEQ ID NO: 201) |
| ARGGVTIHLERRGYFDY (SEQ ID NO: 211) |

In some embodiments, the Protein S antibodies provided herein include any one or more of the amino acid sequences of the CDR sequences provided in Tables 1A, 1B, 1C, 2A, 2B, and 2C.

In some embodiments, provided herein are Protein S antibodies, wherein the antibodies comprise:

(a) any one of the CDR-L1 amino acid sequences of Table 1A;

(b) any one of the CDR-L2 amino acid sequences of Table 1B;

(c) any one of the CDR-L3 amino acid sequences of Table 1C;

(d) any one of the CDR-H1 amino acid sequences of Table 2A;

(e) any one of the CDR-H2 amino acid sequences of Table 2B; and (f) any one of the CDR-H3 amino acid sequences of Table 2C.

In some embodiments, provided herein are Protein S antibodies, wherein the light chain variable domain of the antibodies comprises:

(a) a CDR-L1 comprising the amino acid sequence of any one of SEQ ID NOs: 1-6, 9-11, 117, 127, 136, 141, 174, 184, 194, and 204;

(b) a CDR-L2 comprising the amino acid sequence of any one of SEQ ID NOs: 12-20, 118, 128, 142, 175, 185, 195, and 205; and (c) a CDR-L3 comprising the amino acid sequence of any one of SEQ ID NOs: 21-27, 30-32, 119, 123, 129, 137, 143, 176, 186, 196, and 206.

In some embodiments, provided herein are Protein S antibodies, wherein the heavy chain variable domain of the antibodies comprises:

(a) a CDR-H1 comprising the amino acid sequence of any one of SEQ ID NOs: 33-39, 42-44, 120, 124, 130, 138, 144, 179, 189, 199, and 209;

(b) a CDR-H2 comprising the amino acid sequence of any one of SEQ ID NOs: 45-51, 54-56, 121, 125, 139, 145, 180, 190, 200, and 210;

(c) a CDR-H3 comprising the amino acid sequence of any one of SEQ ID NOs: 57-63, 66-68, 122, 126, 131, 140, 146, 181, 191, 201, and 211.

In some embodiments, provided herein are Protein S antibodies, wherein the light chain variable domain of the antibody comprises:

(a) a CDR-L1 comprising the amino acid sequence of SEQ ID NO: 1;

(b) a CDR-L2 comprising the amino acid sequence of SEQ ID NO: 12; and (c) a CDR-L3 comprising the amino acid sequence of SEQ ID NO: 21.

In some embodiments, provided herein are Protein S antibodies, wherein the light chain variable domain of the antibody comprises:

(a) a CDR-L1 comprising the amino acid sequence of SEQ ID NO: 2;

(b) a CDR-L2 comprising the amino acid sequence of SEQ ID NO: 13; and (c) a CDR-L3 comprising the amino acid sequence of SEQ ID NO: 22.

In some embodiments, provided herein are Protein S antibodies, wherein the light chain variable domain of the antibody comprises:

(a) a CDR-L1 comprising the amino acid sequence of SEQ ID NO: 3;

(b) a CDR-L2 comprising the amino acid sequence of SEQ ID NO: 14; and (c) a CDR-L3 comprising the amino acid sequence of SEQ ID NO: 23.

In some embodiments, provided herein are Protein S antibodies, wherein the light chain variable domain of the antibody comprises:

(a) a CDR-L1 comprising the amino acid sequence of SEQ ID NO: 1;

(b) a CDR-L2 comprising the amino acid sequence of SEQ ID NO: 15; and (c) a CDR-L3 comprising the amino acid sequence of SEQ ID NO: 24.

In some embodiments, provided herein are Protein S antibodies, wherein the light chain variable domain of the antibody comprises:

(a) a CDR-L1 comprising the amino acid sequence of SEQ ID NO: 4;

(b) a CDR-L2 comprising the amino acid sequence of SEQ ID NO: 16; and (c) a CDR-L3 comprising the amino acid sequence of SEQ ID NO: 25.

In some embodiments, provided herein are Protein S antibodies, wherein the light chain variable domain of the antibody comprises:

(a) a CDR-L1 comprising the amino acid sequence of SEQ ID NO: 5;

(b) a CDR-L2 comprising the amino acid sequence of SEQ ID NO: 17; and (c) a CDR-L3 comprising the amino acid sequence of SEQ ID NO: 26.

In some embodiments, provided herein are Protein S antibodies, wherein the light chain variable domain of the antibody comprises:

(a) a CDR-L1 comprising the amino acid sequence of SEQ ID NO: 6;

(b) a CDR-L2 comprising the amino acid sequence of SEQ ID NO: 18; and (c) a CDR-L3 comprising the amino acid sequence of SEQ ID NO: 27.

In some embodiments, provided herein are Protein S antibodies, wherein the light chain variable domain of the antibody comprises:

(a) a CDR-L1 comprising the amino acid sequence of SEQ ID NO: 9;

(b) a CDR-L2 comprising the amino acid sequence of SEQ ID NO: 19; and (c) a CDR-L3 comprising the amino acid sequence of SEQ ID NO: 30.

In some embodiments, provided herein are Protein S antibodies, wherein the light chain variable domain of the antibody comprises:

(a) a CDR-L1 comprising the amino acid sequence of SEQ ID NO: 10;

(b) a CDR-L2 comprising the amino acid sequence of SEQ ID NO: 16; and (c) a CDR-L3 comprising the amino acid sequence of SEQ ID NO: 31.

In some embodiments, provided herein are Protein S antibodies, wherein the light chain variable domain of the antibody comprises:

(a) a CDR-L1 comprising the amino acid sequence of SEQ ID NO: 11;

(b) a CDR-L2 comprising the amino acid sequence of SEQ ID NO: 20; and (c) a CDR-L3 comprising the amino acid sequence of SEQ ID NO: 32.

In some embodiments, provided herein are Protein S antibodies, wherein the light chain variable domain of the antibody comprises:

(a) a CDR-L1 comprising the amino acid sequence of SEQ ID NO: 117;

(b) a CDR-L2 comprising the amino acid sequence of SEQ ID NO: 118; and (c) a CDR-L3 comprising the amino acid sequence of SEQ ID NO: 119.

In some embodiments, provided herein are Protein S antibodies, wherein the light chain variable domain of the antibody comprises:

(a) a CDR-L1 comprising the amino acid sequence of SEQ ID NO: 117;

(b) a CDR-L2 comprising the amino acid sequence of SEQ ID NO: 118; and (c) a CDR-L3 comprising the amino acid sequence of SEQ ID NO: 123.

(d)

In some embodiments, provided herein are Protein S antibodies, wherein the light chain variable domain of the antibody comprises:

(a) a CDR-L1 comprising the amino acid sequence of SEQ ID NO: 127;

(b) a CDR-L2 comprising the amino acid sequence of SEQ ID NO: 128; and (c) a CDR-L3 comprising the amino acid sequence of SEQ ID NO: 129.

In some embodiments, provided herein are Protein S antibodies, wherein the light chain variable domain of the antibody comprises:

(a) a CDR-L1 comprising the amino acid sequence of SEQ ID NO: 136;

(b) a CDR-L2 comprising the amino acid sequence of SEQ ID NO: 17; and (c) a CDR-L3 comprising the amino acid sequence of SEQ ID NO: 137.

In some embodiments, provided herein are Protein S antibodies, wherein the light chain variable domain of the antibody comprises:

(a) a CDR-L1 comprising the amino acid sequence of SEQ ID NO: 141;

(b) a CDR-L2 comprising the amino acid sequence of SEQ ID NO: 142; and (c) a CDR-L3 comprising the amino acid sequence of SEQ ID NO: 143.

In some embodiments, provided herein are Protein S antibodies, wherein the light chain variable domain of the antibody comprises:

(a) a CDR-L1 comprising the amino acid sequence of SEQ ID NO: 174;

(b) a CDR-L2 comprising the amino acid sequence of SEQ ID NO: 175; and (c) a CDR-L3 comprising the amino acid sequence of SEQ ID NO: 176.

In some embodiments, provided herein are Protein S antibodies, wherein the light chain variable domain of the antibody comprises:

(a) a CDR-L1 comprising the amino acid sequence of SEQ ID NO: 184;

(b) a CDR-L2 comprising the amino acid sequence of SEQ ID NO: 185; and (c) a CDR-L3 comprising the amino acid sequence of SEQ ID NO: 186.

In some embodiments, provided herein are Protein S antibodies, wherein the light chain variable domain of the antibody comprises:

(a) a CDR-L1 comprising the amino acid sequence of SEQ ID NO: 194;

(b) a CDR-L2 comprising the amino acid sequence of SEQ ID NO: 195; and (c) a CDR-L3 comprising the amino acid sequence of SEQ ID NO: 196.

In some embodiments, provided herein are Protein S antibodies, wherein the light chain variable domain of the antibody comprises:

(a) a CDR-L1 comprising the amino acid sequence of SEQ ID NO: 204;

(b) a CDR-L2 comprising the amino acid sequence of SEQ ID NO: 205; and (c) a CDR-L3 comprising the amino acid sequence of SEQ ID NO: 206.

In some embodiments, provided herein are Protein S antibodies, wherein the heavy chain variable domain of the antibodies comprises:

(a) a CDR-H1 comprising the amino acid sequence of SEQ ID NO: 33;

(b) a CDR-H2 comprising the amino acid sequence of SEQ ID NO: 45; and (c) a CDR-H3 comprising the amino acid sequence of SEQ ID NO: 57.

In some embodiments, provided herein are Protein S antibodies, wherein the heavy chain variable domain of the antibodies comprises:

(a) a CDR-H1 comprising the amino acid sequence of SEQ ID NO: 34;

(b) a CDR-H2 comprising the amino acid sequence of SEQ ID NO: 46; and (c) a CDR-H3 comprising the amino acid sequence of SEQ ID NO: 58.

In some embodiments, provided herein are Protein S antibodies, wherein the heavy chain variable domain of the antibodies comprises:

(a) a CDR-H1 comprising the amino acid sequence of SEQ ID NO: 35;

(b) a CDR-H2 comprising the amino acid sequence of SEQ ID NO: 47; and (c) a CDR-H3 comprising the amino acid sequence of SEQ ID NO: 59.

In some embodiments, provided herein are Protein S antibodies, wherein the heavy chain variable domain of the antibodies comprises:

(a) a CDR-H1 comprising the amino acid sequence of SEQ ID NO: 36;

(b) a CDR-H2 comprising the amino acid sequence of SEQ ID NO: 48; and (c) a CDR-H3 comprising the amino acid sequence of SEQ ID NO: 60.

In some embodiments, provided herein are Protein S antibodies, wherein the heavy chain variable domain of the antibodies comprises:

(a) a CDR-H1 comprising the amino acid sequence of SEQ ID NO: 37;

(b) a CDR-H2 comprising the amino acid sequence of SEQ ID NO: 49; and (c) a CDR-H3 comprising the amino acid sequence of SEQ ID NO: 61.

In some embodiments, provided herein are Protein S antibodies, wherein the heavy chain variable domain of the antibodies comprises:

(a) a CDR-H1 comprising the amino acid sequence of SEQ ID NO: 38;

(b) a CDR-H2 comprising the amino acid sequence of SEQ ID NO: 50; and (c) a CDR-H3 comprising the amino acid sequence of SEQ ID NO: 62.

In some embodiments, provided herein are Protein S antibodies, wherein the heavy chain variable domain of the antibodies comprises:

(a) a CDR-H1 comprising the amino acid sequence of SEQ ID NO: 39;

(b) a CDR-H2 comprising the amino acid sequence of SEQ ID NO: 51; and (c) a CDR-H3 comprising the amino acid sequence of SEQ ID NO: 63.

In some embodiments, provided herein are Protein S antibodies, wherein the heavy chain variable domain of the antibodies comprises:

(a) a CDR-H1 comprising the amino acid sequence of SEQ ID NO: 42;

(b) a CDR-H2 comprising the amino acid sequence of SEQ ID NO: 54; and (c) a CDR-H3 comprising the amino acid sequence of SEQ ID NO: 66.

In some embodiments, provided herein are Protein S antibodies, wherein the heavy chain variable domain of the antibodies comprises:

(a) a CDR-H1 comprising the amino acid sequence of SEQ ID NO: 43;

(b) a CDR-H2 comprising the amino acid sequence of SEQ ID NO: 55; and (c) a CDR-H3 comprising the amino acid sequence of SEQ ID NO: 67.

In some embodiments, provided herein are Protein S antibodies, wherein the heavy chain variable domain of the antibodies comprises:

(a) a CDR-H1 comprising the amino acid sequence of SEQ ID NO: 44;

(b) a CDR-H2 comprising the amino acid sequence of SEQ ID NO: 56; and (c) a CDR-H3 comprising the amino acid sequence of SEQ ID NO: 68.

In some embodiments, provided herein are Protein S antibodies, wherein the heavy chain variable domain of the antibodies comprises:

(a) a CDR-H1 comprising the amino acid sequence of SEQ ID NO: 120;

(b) a CDR-H2 comprising the amino acid sequence of SEQ ID NO: 121; and (c) a CDR-H3 comprising the amino acid sequence of SEQ ID NO: 122.

In some embodiments, provided herein are Protein S antibodies, wherein the heavy chain variable domain of the antibodies comprises:

(a) a CDR-H1 comprising the amino acid sequence of SEQ ID NO: 124;

(b) a CDR-H2 comprising the amino acid sequence of SEQ ID NO: 125; and (c) a CDR-H3 comprising the amino acid sequence of SEQ ID NO: 126.

In some embodiments, provided herein are Protein S antibodies, wherein the heavy chain variable domain of the antibodies comprises:

(a) a CDR-H1 comprising the amino acid sequence of SEQ ID NO: 130;

(b) a CDR-H2 comprising the amino acid sequence of SEQ ID NO: 50; and (c) a CDR-H3 comprising the amino acid sequence of SEQ ID NO: 131.

In some embodiments, provided herein are Protein S antibodies, wherein the heavy chain variable domain of the antibodies comprises:

(a) a CDR-H1 comprising the amino acid sequence of SEQ ID NO: 138;
(b) a CDR-H2 comprising the amino acid sequence of SEQ ID NO: 139; and
(c) a CDR-H3 comprising the amino acid sequence of SEQ ID NO: 140.

In some embodiments, provided herein are Protein S antibodies, wherein the heavy chain variable domain of the antibodies comprises:

(a) a CDR-H1 comprising the amino acid sequence of SEQ ID NO: 144;
(b) a CDR-H2 comprising the amino acid sequence of SEQ ID NO: 145; and
(c) a CDR-H3 comprising the amino acid sequence of SEQ ID NO: 146.

In some embodiments, provided herein are Protein S antibodies, wherein the heavy chain variable domain of the antibodies comprises:

(a) a CDR-H1 comprising the amino acid sequence of SEQ ID NO: 179;
(b) a CDR-H2 comprising the amino acid sequence of SEQ ID NO: 180; and
(c) a CDR-H3 comprising the amino acid sequence of SEQ ID NO: 181.

In some embodiments, provided herein are Protein S antibodies, wherein the heavy chain variable domain of the antibodies comprises:

(a) a CDR-H1 comprising the amino acid sequence of SEQ ID NO: 189;
(b) a CDR-H2 comprising the amino acid sequence of SEQ ID NO: 190; and
(c) a CDR-H3 comprising the amino acid sequence of SEQ ID NO: 191.

In some embodiments, provided herein are Protein S antibodies, wherein the heavy chain variable domain of the antibodies comprises:

(a) a CDR-H1 comprising the amino acid sequence of SEQ ID NO: 199;
(b) a CDR-H2 comprising the amino acid sequence of SEQ ID NO: 200; and
(c) a CDR-H3 comprising the amino acid sequence of SEQ ID NO: 201.

In some embodiments, provided herein are Protein S antibodies, wherein the heavy chain variable domain of the antibodies comprises:

(a) a CDR-H1 comprising the amino acid sequence of SEQ ID NO: 209;
(b) a CDR-H2 comprising the amino acid sequence of SEQ ID NO: 210; and
(c) a CDR-H3 comprising the amino acid sequence of SEQ ID NO: 211.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:

(a) a CDR-H1 comprising the amino acid sequence of SEQ ID NO: 33;
(b) a CDR-H2 comprising the amino acid sequence of SEQ ID NO: 45; and
(c) a CDR-H3 comprising the amino acid sequence of SEQ ID NO: 57.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:

(a) a CDR-H1 comprising the amino acid sequence of SEQ ID NO: 34;
(b) a CDR-H2 comprising the amino acid sequence of SEQ ID NO: 46; and
(c) a CDR-H3 comprising the amino acid sequence of SEQ ID NO: 58.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:

(a) a CDR-H1 comprising the amino acid sequence of SEQ ID NO: 35;
(b) a CDR-H2 comprising the amino acid sequence of SEQ ID NO: 47; and
(c) a CDR-H3 comprising the amino acid sequence of SEQ ID NO: 59.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:

(a) a CDR-H1 comprising the amino acid sequence of SEQ ID NO: 36;
(b) a CDR-H2 comprising the amino acid sequence of SEQ ID NO: 48; and
(c) a CDR-H3 comprising the amino acid sequence of SEQ ID NO: 60.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:

(a) a CDR-H1 comprising the amino acid sequence of SEQ ID NO: 37;
(b) a CDR-H2 comprising the amino acid sequence of SEQ ID NO: 49; and
(c) a CDR-H3 comprising the amino acid sequence of SEQ ID NO: 61.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:

(a) a CDR-H1 comprising the amino acid sequence of SEQ ID NO: 38;
(b) a CDR-H2 comprising the amino acid sequence of SEQ ID NO: 50; and
(c) a CDR-H3 comprising the amino acid sequence of SEQ ID NO: 62.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:

(a) a CDR-H1 comprising the amino acid sequence of SEQ ID NO: 39;
(b) a CDR-H2 comprising the amino acid sequence of SEQ ID NO: 51; and
(c) a CDR-H3 comprising the amino acid sequence of SEQ ID NO: 63.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 42;
(b) a CDR-H2 comprising the amino acid sequence of SEQ ID NO: 54; and
(c) a CDR-H3 comprising the amino acid sequence of SEQ ID NO: 66.

In some embodiments, provided herein are Protein S antibodies, wherein the light chain variable domain of the antibodies comprises any one or more of the sequences provided in Tables 1A, 1B, and 1C, and wherein the heavy chain variable domain of the antibodies comprises:
(a) a CDR-H1 comprising the amino acid sequence of SEQ ID NO: 43;
(b) a CDR-H2 comprising the amino acid sequence of SEQ ID NO: 55; and
(c) a CDR-H3 comprising the amino acid sequence of SEQ ID NO: 67.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 44;
(b) a CDR-H2 comprising the amino acid sequence of SEQ ID NO: 56; and
(c) a CDR-H3 comprising the amino acid sequence of SEQ ID NO: 68.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 120;
(b) a CDR-H2 comprising the amino acid sequence of SEQ ID NO: 121; and
(c) a CDR-H3 comprising the amino acid sequence of SEQ ID NO: 122.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 124;
(b) a CDR-H2 comprising the amino acid sequence of SEQ ID NO: 125; and
(c) a CDR-H3 comprising the amino acid sequence of SEQ ID NO: 126.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 130;
(b) a CDR-H2 comprising the amino acid sequence of SEQ ID NO: 50; and
(c) a CDR-H3 comprising the amino acid sequence of SEQ ID NO: 131.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the (a) a CDR-H1 comprising the amino acid sequence of SEQ ID NO: 138;
(b) a CDR-H2 comprising the amino acid sequence of SEQ ID NO: 139; and
(c) a CDR-H3 comprising the amino acid sequence of SEQ ID NO: 140.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 144;
(b) a CDR-H2 comprising the amino acid sequence of SEQ ID NO: 145; and
(c) a CDR-H3 comprising the amino acid sequence of SEQ ID NO: 146.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(d) a CDR-H1 comprising the amino acid sequence of SEQ ID NO: 179;
(e) a CDR-H2 comprising the amino acid sequence of SEQ ID NO: 180; and
(f) a CDR-H3 comprising the amino acid sequence of SEQ ID NO: 181.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 189;
(b) a CDR-H2 comprising the amino acid sequence of SEQ ID NO: 190; and
(c) a CDR-H3 comprising the amino acid sequence of SEQ ID NO: 191.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 199;
(b) a CDR-H2 comprising the amino acid sequence of SEQ ID NO: 200; and (c) a CDR-H3 comprising the amino acid sequence of SEQ ID NO: 201.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:

(a) a CDR-H1 comprising the amino acid sequence of SEQ ID NO: 209;

(b) a CDR-H2 comprising the amino acid sequence of SEQ ID NO: 210; and (c) a CDR-H3 comprising the amino acid sequence of SEQ ID NO: 211.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 1;

(b) a CDR-L2 comprising the amino acid sequence of SEQ ID NO: 12; and (c) a CDR-L3 comprising the amino acid sequence of SEQ ID NO: 21.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the (a) a CDR-L1 comprising the amino acid sequence of SEQ ID NO: 2;

(b) a CDR-L2 comprising the amino acid sequence of SEQ ID NO: 13; and (c) a CDR-L3 comprising the amino acid sequence of SEQ ID NO: 22.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 3;

(b) a CDR-L2 comprising the amino acid sequence of SEQ ID NO: 14; and (c) a CDR-L3 comprising the amino acid sequence of SEQ ID NO: 23.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 1;

(b) a CDR-L2 comprising the amino acid sequence of SEQ ID NO: 15; and (c) a CDR-L3 comprising the amino acid sequence of SEQ ID NO: 24.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 4;

(b) a CDR-L2 comprising the amino acid sequence of SEQ ID NO: 16; and (c) a CDR-L3 comprising the amino acid sequence of SEQ ID NO: 25.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 5;

(b) a CDR-L2 comprising the amino acid sequence of SEQ ID NO: 17; and (c) a CDR-L3 comprising the amino acid sequence of SEQ ID NO: 26.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 6;

(b) a CDR-L2 comprising the amino acid sequence of SEQ ID NO: 18; and (c) a CDR-L3 comprising the amino acid sequence of SEQ ID NO: 27.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comp comprises rise:

(a) a CDR-L1 comprising the amino acid sequence of SEQ ID NO: 9;

(b) a CDR-L2 comprising the amino acid sequence of SEQ ID NO: 19; and (c) a CDR-L3 comprising the amino acid sequence of SEQ ID NO: 30.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the (a) a CDR-L1 comprising the amino acid sequence of SEQ ID NO: 10;

(b) a CDR-L2 comprising the amino acid sequence of SEQ ID NO: 16; and (c) a CDR-L3 comprising the amino acid sequence of SEQ ID NO: 31.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 11;

(b) a CDR-L2 comprising the amino acid sequence of SEQ ID NO: 20; and (c) a CDR-L3 comprising the amino acid sequence of SEQ ID NO: 32.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 117;

(b) a CDR-L2 comprising the amino acid sequence of SEQ ID NO: 118; and (c) a CDR-L3 comprising the amino acid sequence of SEQ ID NO: 119.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 117;

(b) a CDR-L2 comprising the amino acid sequence of SEQ ID NO: 118; and (c) a CDR-L3 comprising the amino acid sequence of SEQ ID NO: 123.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 127;

(b) a CDR-L2 comprising the amino acid sequence of SEQ ID NO: 128; and (c) a CDR-L3 comprising the amino acid sequence of SEQ ID NO: 129.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 136;

(b) a CDR-L2 comprising the amino acid sequence of SEQ ID NO: 17; and (c) a CDR-L3 comprising the amino acid sequence of SEQ ID NO: 137.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 141;

(b) a CDR-L2 comprising the amino acid sequence of SEQ ID NO: 142; and (c) a CDR-L3 comprising the amino acid sequence of SEQ ID NO: 143.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the (a) a CDR-L1 comprising the amino acid sequence of SEQ ID NO: 174;

(b) a CDR-L2 comprising the amino acid sequence of SEQ ID NO: 175; and (c) a CDR-L3 comprising the amino acid sequence of SEQ ID NO: 176.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 184;

(b) a CDR-L2 comprising the amino acid sequence of SEQ ID NO: 185; and (c) a CDR-L3 comprising the amino acid sequence of SEQ ID NO: 186.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 194;

(b) a CDR-L2 comprising the amino acid sequence of SEQ ID NO: 195; and (c) a CDR-L3 comprising the amino acid sequence of SEQ ID NO: 196.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 204;

(b) a CDR-L2 comprising the amino acid sequence of SEQ ID NO: 205; and (c) a CDR-L3 comprising the amino acid sequence of SEQ ID NO: 206.

In some embodiments, provided herein are Protein S antibodies, wherein the antibodies comprise the CDR amino acid sequences of SEQ ID NO: 1, SEQ ID NO: 12, SEQ ID NO: 21, SEQ ID NO: 33, SEQ ID NO: 45, and SEQ ID NO: 57.

In some embodiments, provided herein are Protein S antibodies, wherein the antibodies comprise the CDR amino acid sequences of SEQ ID NO: 2, SEQ ID NO: 13, SEQ ID NO: 22, SEQ ID NO: 34, SEQ ID NO: 46, and SEQ ID NO: 58.

In some embodiments, provided herein are Protein S antibodies, wherein the antibodies comprise the CDR amino acid sequences of SEQ ID NO: 3, SEQ ID NO: 14, SEQ ID NO: 23, SEQ ID NO: 35, SEQ ID NO: 47, and SEQ ID NO: 59.

In some embodiments, provided herein are Protein S antibodies, wherein the antibodies comprise the CDR amino acid sequences of SEQ ID NO: 1, SEQ ID NO: 15, SEQ ID NO: 24, SEQ ID NO: 36, SEQ ID NO: 48, and SEQ ID NO: 60.

In some embodiments, provided herein are Protein S antibodies, wherein the antibodies comprise the CDR amino acid sequences of SEQ ID NO: 4, SEQ ID NO: 16, SEQ ID NO: 25, SEQ ID NO: 37, SEQ ID NO: 49, and SEQ ID NO: 61.

In some embodiments, provided herein are Protein S antibodies, wherein the antibodies comprise the CDR amino acid sequences of SEQ ID NO: 5, SEQ ID NO: 17, SEQ ID NO: 26, SEQ ID NO: 38, SEQ ID NO: 50, and SEQ ID NO: 62.

In some embodiments, provided herein are Protein S antibodies, wherein the antibodies comprise the CDR amino acid sequences of SEQ ID NO: 6, SEQ ID NO: 18, SEQ ID NO: 27, SEQ ID NO: 39, SEQ ID NO: 51, and SEQ ID NO: 63.

In some embodiments, provided herein are Protein S antibodies, wherein the antibodies comprise the CDR amino acid sequences of SEQ ID NO: 9, SEQ ID NO: 19, SEQ ID NO: 30, SEQ ID NO: 42, SEQ ID NO: 54, and SEQ ID NO: 66.

In some embodiments, provided herein are Protein S antibodies, wherein the antibodies comprise the CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, provided herein are Protein S antibodies, wherein the antibodies comprise the CDR amino acid sequences of SEQ ID NO: 11, SEQ ID NO: 20, SEQ ID NO: 32, SEQ ID NO: 44, SEQ ID NO: 56, and SEQ ID NO: 68.

In some embodiments, provided herein are Protein S antibodies, wherein the antibodies comprise the CDR amino acid sequences of SEQ ID NO: 117, SEQ ID NO: 118, SEQ ID NO: 119, SEQ ID NO: 120, SEQ ID NO: 121, and SEQ ID NO: 122.

In some embodiments, provided herein are Protein S antibodies, wherein the antibodies comprise the CDR amino acid sequences of SEQ ID NO: 117, SEQ ID NO: 118, SEQ ID NO: 123, SEQ ID NO: 124, SEQ ID NO: 125, and SEQ ID NO: 126.

In some embodiments, provided herein are Protein S antibodies, wherein the antibodies comprise the CDR amino acid sequences of SEQ ID NO: 127, SEQ ID NO: 128, SEQ ID NO: 129, SEQ ID NO: 130, SEQ ID NO: 50, and SEQ ID NO: 131.

In some embodiments, provided herein are Protein S antibodies, wherein the antibodies comprise the CDR amino acid sequences of SEQ ID NO: 136, SEQ ID NO: 17, SEQ ID NO: 137, SEQ ID NO: 138, SEQ ID NO: 139, and SEQ ID NO: 140.

In some embodiments, provided herein are Protein S antibodies, wherein the antibodies comprise the CDR amino acid sequences of SEQ ID NO: 141, SEQ ID NO: 142, SEQ ID NO: 143, SEQ ID NO: 144, SEQ ID NO: 145, and SEQ ID NO: 146.

In some embodiments, provided herein are Protein S antibodies, wherein the antibodies comprise the CDR amino acid sequences of SEQ ID NO: 174, SEQ ID NO: 175, SEQ ID NO: 176, SEQ ID NO: 179, SEQ ID NO: 180, and SEQ ID NO: 181.

In some embodiments, provided herein are Protein S antibodies, wherein the antibodies comprise the CDR amino acid sequences of SEQ ID NO: 184, SEQ ID NO: 185, SEQ ID NO: 186, SEQ ID NO: 189, SEQ ID NO: 190, and SEQ ID NO: 191.

In some embodiments, provided herein are Protein S antibodies, wherein the antibodies comprise the CDR amino acid sequences of SEQ ID NO: 194, SEQ ID NO: 195, SEQ ID NO: 196, SEQ ID NO: 199, SEQ ID NO: 200, and SEQ ID NO: 201.

In some embodiments, provided herein are Protein S antibodies, wherein the antibodies comprise the CDR amino acid sequences of SEQ ID NO: 204, SEQ ID NO: 205, SEQ ID NO: 206, SEQ ID NO: 209, SEQ ID NO: 210, and SEQ ID NO: 211.

Exemplary Protein S Antibodies—Kappa and Lambda Light Chains

Provided herein are amino acid sequences for the kappa and lambda light chain constant regions of exemplary Protein S antibodies of the disclosure. Any of the Protein S antibodies provided herein (provided in the preceding section) may have a kappa light chain constant region or a lambda light chain constant region. The sequences of the kappa and lambda light chain constant regions are provided in Table 3.

TABLE 3

| | |
|---|---|
| Kappa light chain sequence | RTVAAPSVFIFPPSDEQLKSGTASV VCLLNNFYPREAKVQWKVDNALQS GNSQESVTEQDSKDSTYSLSSTLT LSKADYEKHKVYACEVTHQGLSSP VTKSFNRGEC (SEQ ID NO: 214) |
| Lambda light chain sequence | GQPKAAPSVTLFPPSSEELQANKAT LVCLISDFYPGAVTVAWKADSSPVK AGVETTTPSKQSNNKYAASSYLSLT PEQWKSHRSYSCQVTHEGSTVEKTV APTECS (SEQ ID NO: 215) |

In exemplary embodiments, the Protein S antibody having the light chain sequence of SEQ ID NO: 214 comprises CDRs having the amino acid sequences as set forth in SEQ ID NO: 2, SEQ ID NO: 13, SEQ ID NO: 22, SEQ ID NO: 34, SEQ ID NO: 46, and SEQ ID NO: 58.

In exemplary embodiments, the Protein S antibody having the light chain sequence of SEQ ID NO: 215 comprises CDRs having the amino acid sequences as set forth in SEQ ID NO: 2, SEQ ID NO: 13, SEQ ID NO: 22, SEQ ID NO: 34, SEQ ID NO: 46, and SEQ ID NO: 58.

In exemplary embodiments, the Protein S antibody having the light chain sequence of SEQ ID NO: 214 comprises CDRs having the amino acid sequences as set forth in SEQ ID NO: 10, SEQ ID NO: 16, SEQ ID NO: 31, SEQ ID NO: 43, SEQ ID NO: 55, and SEQ ID NO: 67.

In exemplary embodiments, the Protein S antibody having the light chain sequence of SEQ ID NO: 215 comprises CDRs having the amino acid sequences as set forth in SEQ ID NO: 10, SEQ ID NO: 16, SEQ ID NO: 31, SEQ ID NO: 43, SEQ ID NO: 55, and SEQ ID NO: 67.

In exemplary embodiments, the Protein S antibody having the light chain sequence of SEQ ID NO: 214 comprises CDRs having the amino acid sequences as set forth in SEQ ID NO: 174, SEQ ID NO: 175, SEQ ID NO: 176, SEQ ID NO: 179, SEQ ID NO: 180, and SEQ ID NO: 181.

In exemplary embodiments, the Protein S antibody having the light chain sequence of SEQ ID NO: 215 comprises CDRs having the amino acid sequences as set forth in SEQ ID NO: 174, SEQ ID NO: 175, SEQ ID NO: 176, SEQ ID NO: 179, SEQ ID NO: 180, and SEQ ID NO: 181.

In exemplary embodiments, the Protein S antibody having the light chain sequence of SEQ ID NO: 214 comprises the variable heavy and variable light chains having the amino acid sequences as set forth in SEQ ID NO: 71 and SEQ ID NO: 72.

In exemplary embodiments, the Protein S antibody having the light chain sequence of SEQ ID NO: 215 comprises the variable heavy and variable light chains having the amino acid sequences as set forth in SEQ ID NO: 71 and SEQ ID NO: 72.

In exemplary embodiments, the Protein S antibody having the light chain sequence of SEQ ID NO: 214 comprises the variable heavy and variable light chains having the amino acid sequences as set forth in SEQ ID NO: 89 and SEQ ID NO: 90.

In exemplary embodiments, the Protein S antibody having the light chain sequence of SEQ ID NO: 215 comprises the variable heavy and variable light chains having the amino acid sequences as set forth in SEQ ID NO: 89 and SEQ ID NO: 90.

In exemplary embodiments, the Protein S antibody having the light chain sequence of SEQ ID NO: 214 comprises the variable heavy and variable light chains having the amino acid sequences as set forth in SEQ ID NO: 177 and SEQ ID NO: 182.

In exemplary embodiments, the Protein S antibody having the light chain sequence of SEQ ID NO: 215 comprises the variable heavy and variable light chains having the amino acid sequences as set forth in SEQ ID NO: 177 and SEQ ID NO: 182.

Exemplary Protein S Antibodies—Variable Region Sequences

Provided herein are amino acid sequences for the variable domains of exemplary Protein S antibodies of the disclosure. The exemplary variable light chain amino acid sequences and exemplary variable heavy chain amino acid sequences are presented in Tables 4A and 4B below. Table 4C presents exemplary combinations of variable heavy and variable light chains.

Accordingly, in some embodiments, the Protein S antibodies of the disclosure comprise the variable chain amino acid sequence of any one of the combinations provided in Table 4C. In some embodiments, provided herein are Protein S antibodies, wherein the antibodies comprise a variable light chain comprising the amino acid sequence selected from SEQ ID NO: 69, 71, 73, 75, 77, 79, 81, 87, 89, 91, 148, 150, 152, 156 158, 177, 187, 197, and 207. In some embodiments, provided herein are Protein S antibodies, wherein the antibodies comprise a variable heavy chain comprising the amino acid sequence selected from SEQ ID NO: 70, 72, 74, 76, 78, 80, 82, 88, 90, 92, 149, 151, 153, 157 159, 182, 192, 202, and 212.

TABLE 4A

| Exemplary Variable Light Chain Amino Acid Sequences of Protein S Monoclonal Antibodies |
|---|
| SYELTQPPSVSVSPGQTASITCSGDKLGDKYACWY<br>QQKPGQSPVLVIYQDTKRPSGIPERFSGSNSGNTA<br>TLTISGTQAMDEADYYCQAWDSNTVVFGGGTKLTV<br>L<br>(SEQ ID NO: 69) |
| SSDLTQGPAVSVALGQTVRITCQGDSLRNYYASWY<br>QQKPGQAPVPVIYGKNDRPSGIPDRFSGSISGNTA<br>SLTITGAQAEDEAHYYCNSRDSSGNHVVFGGGTKL<br>TVL<br>(SEQ ID NO: 71) |
| QSALTQPASVSGSPGQSITISCTGTSSDVGGYEFV<br>SWYQHHPGKAPKLMIYDVSSRPSGVSNRFSGSKSG<br>NTASLTISGLQAEDEADYYCSSYTRSSTVVFGGGA<br>RLTVL<br>(SEQ ID NO: 73) |
| SYELNQPPSVSVSPGQTASITCSGDKLGDKYASWY<br>QQKPGQSPVVAIYQNSKRPSGIPERFSASNSGNTA<br>TLTISGTQALDEADYYCQAWDSSTWVFGGGTKLTV<br>L<br>(SEQ ID NO: 75) |
| EIVLTQSPATLSLSPGERATLSCRASQSVSIYLAW<br>YQQKPGQAPRLLIYDASNRATGIPARFSGSGSGTD<br>FTLTISSLEPEDFAVYYCQQRSNWPLTFGPGTKVD<br>IK<br>(SEQ ID NO: 77) |
| EIVMTQSPATLSVSPGERATLSCRASQRINSNLAW<br>YQQKPGQAPRLLIYGASTRATGIPARFSGSGSGTE<br>FTLTISSLQSEDFAAYYCQQYDNWPLTFGGGTKVE<br>IK<br>(SEQ ID NO: 79) |

TABLE 4A-continued

| Exemplary Variable Light Chain Amino Acid Sequences of Protein S Monoclonal Antibodies |
|---|
| DIVMTQSPLSLPVTPGEPASISCRSSQSLLHSNGY<br>NYLDWYLQKPGQSPQLLIYLGSNRASGVPDRFSGS<br>GSGTDFTLKISRVEAEDVGVYYCMQALQTFTFGPG<br>TKVDIK<br>(SEQ ID NO: 81) |
| QAVVTQESALTTSPGETVTLTCRSSTGAVTASNYA<br>NWVQEKPDHLFTGLIGSTNNRAPGVPARFSGSLIG<br>DKAALTITGAQTEDEAIYFCALWYSDHFVFGGGTK<br>LTVL<br>(SEQ ID NO: 87) |
| EIVMTQSPATLSVSPGERATLSCRASQSVTSNLAW<br>YQQKPGQAPRLLIYDASTRATGIPARFSGSGSGTE<br>FTLTISSLQSEDFAIYYCQQYNNWPTFGQGTRLEI<br>K<br>(SEQ ID NO: 89) |
| DIVMTQTPLSSPVTLGQPASISCRSSQSLVHSDGN<br>TYLSWLQQRPGQPPRLLIYKISNRFSGVPDRFSGS<br>GAGTDFTLKISRVEAEDVGVYYCMQATQFPHLTFG<br>GGTKVEIK<br>(SEQ ID NO: 91) |
| DIQMTQSPSSLSASVGDRVTITCRASQGINNYLAW<br>FQQKPGKAPKSLIYAASSLQSGVPSKFSGSGSGTD<br>FTLTISSLQPEDFATYYCQQYNSYPRTFGQGTKVE<br>IK<br>(SEQ ID NO: 148) |
| DIQMTQSPSSLSASVGDRVTITCRASQGINNYLAW<br>FQQKPGKAPKSLIYAASNLQSGVPLKFSGSGSGTD<br>FTLTISSLQPEDFATYYCQQYNSYPITFGQGTRLE<br>IK<br>(SEQ ID NO: 150) |
| DIQMTQSPSSLSASVGDRVTITCRASQSISTFLNW<br>YQQKPGKAPKLLIYATSSLRSGVPSRFSGSGSGTD<br>FTLTISSLQPEDFAIYYCQQSYSTPRTFGQGTQVE<br>IK<br>(SEQ ID NO: 152) |
| EIVLTQSPGTLSLSPGERATLSCRASQSVGSSYLA<br>WYQQKPGQAPRLLISGASGRATGIPDRFSGSGSGT<br>DFTLTISRLEPEDFTVYYCQQYGSSPYTFGQGTKL<br>EIK<br>(SEQ ID NO: 156) |
| DIQMNQSPSSLSASLGDTITITCRASQNIHMWLSW<br>YQQKPGNIPKLLIFKTSNLHTGVPSRFSGSGSGTD<br>FTLTISSLQPEDIATYYCLQGQSYPFTFGGGTKLE<br>IK<br>(SEQ ID NO: 158) |
| DIQMTQSPSSLSASVGDRVTITCRASQSISSYLNW<br>YQQKPGKAPKLLIYAASSLQSGVPSRFSGSGSGTD<br>FTLTISSLQPEDFATYYCQQSYSSLTFGQGTRLEI<br>K<br>(SEQ ID NO: 177) |
| SYVLTQPPSVSVAPGQTARITCGGDNIGGKSVHWY<br>QQKPGQAPVMVVYDDSDRPSGIPERFAGSNSGNTA<br>TLAISRVEAGDEADYYCQVWEITSDHPAFGGGTR<br>LTVL<br>(SEQ ID NO: 187) |
| SYELTQPPSVSVSPGQTASITCSGDKLGDKYVFWY<br>QQKPGQSPVLVIYQDSKRPSGIPERFSGSNSGNTA<br>TLTISGTQTMDEADYYCQAWDSSTVGFGGGTKLAV<br>L<br>(SEQ ID NO: 197) |

TABLE 4A-continued

| Exemplary Variable Light Chain Amino Acid Sequences of Protein S Monoclonal Antibodies |
|---|
| SYELTQPPSVSVSPGQTASITCSGDKLGDKYAFWY QQKPGQSPVLVIYQDNKRPSGIPERFSGSNSGNTA TLTISGTQAVDEADYYCQAWDSSTAVFGGGTKLTV L (SEQ ID NO: 207) |

TABLE 4B

| Exemplary Variable Heavy Chain Amino Acid Sequences of Protein S Monoclonal Antibodies |
|---|
| QLQLQESGPGLVKPSETLSLTCTVSGGSISSSSYY WGWIRQPPGKGLEWIGNIYYSGNTYYNPSLKSRVT ISVDTSKNQFSLKLSSMTAADTAVYYCARCSGYGY SSGRSYFDYWGQETLVTVSS (SEQ ID NO: 70) |
| QVQLVQSGAEVKKPGSSVKVSCKVSGGTFSSYSIS WVRQAPGQGLEWMGGIIPIFGTTNYAQKFQGRVTI TADESTSTAYMDLSSLKSEDTAMYYCEGGRVGADF DYWGQGTLVTVSS (SEQ ID NO: 72) |
| QVQLQESGPGLVKPSQTLSLTCTVSGGSITSDGYH WSWIRQYPGKGLDWIGYIYYTGNTYYNPSLKSRVT ISVGTSQNQFSLKLISVTAADTAVYYCARRLSTGP YFDYWGQGTLVTVSS (SEQ ID NO: 74) |
| EVQLVESGGGLVQPGRSLRLSCAASGFTFDDYAMH WVRQAPGKGLEWVSGITWNSGNIGYADSVI<GRFT ISRDNAI<NSLYLHMNSLRIEDTAFYYCAI<GRAV SDTFDIWGQGTMVTVSS (SEQ ID NO: 76) |
| QVQLVESGGGVVQPGRSLRLSCAASGFTFSTYGFH WVRQPPGKGLEWVAVIYYDGINKYYADSVKGRFTI SRDNSKNTLFLQMNSLRAEDTAVYYCAESDLDYWG QGTLVTVSS (SEQ ID NO: 78) |
| QVQLQESGPGLVKPSETLSLTCAVSGYSISSGYYW GWIRQPPGKGLDWIGSIYYSGSTYYNPSLKSRVTI SVDTSKNQISLKLSSVTAADTAVYYCATTYSDIVT GYYNDAFDIWGQGTMVTVSS (SEQ ID NO: 80) |
| QVQLVQSGAEVKKPGSSVKVSCKASGDTFSNHAIN WVRQAPGQGLEWMGGYIPIFGTTNSAQKFRGRVTI TADKSTNTAYMALSSLRSEDTAVYYCARGGLAGSH YKNYYYDGMDVWGQGTTVTVSS (SEQ ID NO: 82) |
| QVQLVQSGAEVKKPGASVKVSCKSSGHTFTGYYMH WVRQAPGQGLEWMGWINPNSGDTNYAQKFQGRVTM TRDTSISTAYMEMSRLRSDDTAVYYCARDSQILWF GELGYWGQGTLVTVSS (SEQ ID NO: 88) |
| QVQLQESGPGLVKPSETLSLTCGVSGGSISSTNWW SWVRQPPGKGLEWIGEIYQTGSTDYDPSLKSRVTI SIDKSKNQFSLKLYSVTAADTAVYYCARRFGELDY WGQGTLVTVSS (SEQ ID NO: 90) |
| QVQLQESGPGLVKPSETLSLTCTVSGGSISNYYWN WIRQPPGKGLEWIGYIYYIGITDYNPSLKSRVTIS VDTSKNQFSLKVTSVTAADTAVYYCAALSGDHAFD IWGQGTLVTVSS (SEQ ID NO: 92) |

TABLE 4B-continued

| Exemplary Variable Heavy Chain Amino Acid Sequences of Protein S Monoclonal Antibodies |
|---|
| QLQLQESGPGLVKPSETLSLTCTVSGGSITNSNYY WGWIRQPPGKGLEWIGSVYYSGTTYYNPSLKSRVT ISVDPSKNQFSLKLSSVTAADTAVYYCVRESESYY YYGSDVWGQGTTVTVSS (SEQ ID NO: 149) |
| EVQLVESGGGLVKPGGSLRLSCAASGFTFSSYNMN WVRQAPGRGLDWVSSISSSSSYIYYADSVKGRFTI SRDNAKNSLYLQMNTLRAEDTAVYYCARDEEWELL TGFDYWGQGTLVTVSS (SEQ ID NO: 151) |
| QVQLQESGPGLVKPSETLSLTCTVSGGSISGNYWS WIRQPPGKGLEWIGYIYYSGSTNYNPSLKSRVTIS VDTSKNQFSLKLSSVTAADTAVYYCARDLDYFTWG AYSDWYFDLWGRGTLVTVSS (SEQ ID NO: 153) |
| QVQLQQSGPGLVKPSQTLSLTCAISGDSVSNNNAA WNWIRQSPSRGLEWLGGTYYRSKWYNDYAVSVKSR IIINPVTSKNQFSLQLNSVTPEDTAVYYCARGSSW YRFFDYWGQGTLVTVSS (SEQ ID NO: 157) |
| QVQLQQSGTELVRPGTSVKMSCKAAGYTFTNHWIG WVKQRPGHGLEWIGDIYPGGGYTNYNEKFKGKASL TADTSSTTAYMQLSSLTSEDSAIYYCSRFGDQNWA WFAYWGQGTLVTVSA (SEQ ID NO: 159) |
| EVQLVESGGGLVKPGGSLRLSCAASGISFSNAWMS WVRQAPGKGLEWVGRIKANPDGGTTDYAAPVKGRF TISRDDSKNTLYLQMNSLKTEDTAVYYCTTELDIL LWFTSFDYWGQGTLVTVSS (SEQ ID NO: 182) |
| EVQLVESGGGLVQPGGSLRLSCAASGFTFSSYSMN WVRQAPGKGLEWVAYISSSTRTIFYADSVKGRFTI SRDNAKNSLYLQMNSLRDEDTAFYYCARERSAFDY WGQGTLVTVSS (SEQ ID NO: 192) |
| QVQLVQSGSEVKKPGASVKVSCKASGYTFTNYYIH WVRQAPGQGLEWMGIITPSGGTTSYAQKFQGRVTM TRDTSTNTVYMGLSSLRSEDTAMYYCARAGVQLDR RGWFDPWGQGTLVTVSS (SEQ ID NO: 202) |
| QVQLVQSGAEVKKPGASVKVSCKASGYTFTSYYIH WVRQAPGQGLEWMGVTSPSGRSTSFAQKFQGRVTM TRDTSTSAVYMDLDSLRSEDTAVYYCARGGVTIHL ERRGYFDYWGQGTLVIVSS (SEQ ID NO: 212) |

TABLE 4C

Exemplary Variable Light Chain and Variable Heavy Chain Amino Acid Sequence Combinations of Protein S Monoclonal Antibodies

| Combination Number | Variable Light Chain Amino Acid Sequence | Variable Heavy Chain Amino Acid Sequence |
|---|---|---|
| Combination 1 | SEQ ID NO: 69 | SEQ ID NO: 70 |
| Combination 2 | SEQ ID NO: 71 | SEQ ID NO: 72 |
| Combination 3 | SEQ ID NO: 73 | SEQ ID NO: 74 |
| Combination 4 | SEQ ID NO: 75 | SEQ ID NO: 76 |
| Combination 5 | SEQ ID NO: 77 | SEQ ID NO: 78 |
| Combination 6 | SEQ ID NO: 79 | SEQ ID NO: 80 |
| Combination 7 | SEQ ID NO: 81 | SEQ ID NO: 82 |
| Combination 10 | SEQ ID NO: 87 | SEQ ID NO: 88 |
| Combination 11 | SEQ ID NO: 89 | SEQ ID NO: 90 |
| Combination 12 | SEQ ID NO: 91 | SEQ ID NO: 92 |

TABLE 4C-continued

| Exemplary Variable Light Chain and Variable Heavy Chain Amino Acid Sequence Combinations of Protein S Monoclonal Antibodies | | |
|---|---|---|
| Combination Number | Variable Light Chain Amino Acid Sequence | Variable Heavy Chain Amino Acid Sequence |
| Combination 13 | SEQ ID NO: 148 | SEQ ID NO: 149 |
| Combination 14 | SEQ ID NO: 150 | SEQ ID NO: 151 |
| Combination 15 | SEQ ID NO: 152 | SEQ ID NO: 153 |
| Combination 17 | SEQ ID NO: 156 | SEQ ID NO: 157 |
| Combination 18 | SEQ ID NO: 158 | SEQ ID NO: 159 |
| Combination 19 | SEQ ID NO: 177 | SEQ ID NO: 182 |
| Combination 20 | SEQ ID NO: 187 | SEQ ID NO: 192 |
| Combination 21 | SEQ ID NO: 197 | SEQ ID NO: 202 |
| Combination 22 | SEQ ID NO: 207 | SEQ ID NO: 212 |

In some embodiments, the heavy and light chain variable domains of the Protein S antibodies provided herein include the amino acid sequence of any one of the numbered combinations presented in Table 4C.

In some embodiments, provided herein are Protein S antibodies, wherein the light chain variable domain of the antibodies comprise the amino acid sequence of SEQ ID NO: 69 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibodies comprise the amino acid sequence of SEQ ID NO: 70, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 69 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and wherein the heavy chain variable domain of the antibody comprises the amino acid sequence of SEQ ID NO: 70, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 1, SEQ ID NO: 12, SEQ ID NO: 21, SEQ ID NO: 33, SEQ ID NO: 45, and SEQ ID NO: 57.

In some embodiments, provided herein are Protein S antibodies, wherein the light chain variable domain of the antibodies comprise the amino acid sequence of SEQ ID NO: 71 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 72, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 71 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 72, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 2, SEQ ID NO: 13, SEQ ID NO: 22, SEQ ID NO: 34, SEQ ID NO: 46, and SEQ ID NO: 58.

In some embodiments, provided herein are Protein S antibodies, wherein the light chain variable domain of the antibodies comprise the amino acid sequence of SEQ ID NO: 73 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 74, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 73 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 74, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 3, SEQ ID NO: 14, SEQ ID NO: 23, SEQ ID NO: 35, SEQ ID NO: 47, and SEQ ID NO: 59.

In some embodiments, provided herein are Protein S antibodies, wherein the light chain variable domain of the antibodies comprise the amino acid sequence of SEQ ID NO: 75 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 76, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 75 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 76, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 1, SEQ ID NO: 15, SEQ ID NO: 24, SEQ ID NO: 36, SEQ ID NO: 48, and SEQ ID NO: 60.

In some embodiments, provided herein are Protein S antibodies, wherein the light chain variable domain of the antibodies comprise the amino acid sequence of SEQ ID NO: 77 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 78, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 77 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 78, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 4, SEQ ID NO: 16, SEQ ID NO: 25, SEQ ID NO: 37, SEQ ID NO: 49, and SEQ ID NO: 61.

In some embodiments, provided herein are Protein S antibodies, wherein the light chain variable domain of the antibodies comprise the amino acid sequence of SEQ ID NO: 79 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 80, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 79 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 80, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 5, SEQ ID NO: 17, SEQ ID NO: 26, SEQ ID NO: 38, SEQ ID NO: 50, and SEQ ID NO: 62.

In some embodiments, provided herein are Protein S antibodies, wherein the light chain variable domain of the antibodies comprise the amino acid sequence of SEQ ID NO: 81 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 82, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 81 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 82, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 6, SEQ ID NO: 18, SEQ ID NO: 27, SEQ ID NO: 39, SEQ ID NO: 51, and SEQ ID NO: 63.

In some embodiments, provided herein are Protein S antibodies, wherein the light chain variable domain of the antibodies comprise the amino acid sequence of SEQ ID NO: 87 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 88, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 87 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 88, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 9, SEQ ID NO: 19, SEQ ID NO: 30, SEQ ID NO: 42, SEQ ID NO: 54, and SEQ ID NO: 66.

In some embodiments, provided herein are Protein S antibodies, wherein the light chain variable domain of the antibodies comprise the amino acid sequence of SEQ ID NO: 89 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 90, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 89 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 90, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, provided herein are Protein S antibodies, wherein the light chain variable domain of the antibodies comprise the amino acid sequence of SEQ ID NO: 91 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 92, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 91 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 92, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 11, SEQ ID NO: 20, SEQ ID NO: 32, SEQ ID NO: 44, SEQ ID NO: 56, and SEQ ID NO: 68.

In some embodiments, provided herein are Protein S antibodies, wherein the light chain variable domain of the antibodies comprise the amino acid sequence of SEQ ID NO: 148 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 149, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 148 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 149, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 117, SEQ ID NO: 118, SEQ ID NO: 119, SEQ ID NO: 120, SEQ ID NO: 121, and SEQ ID NO: 122.

In some embodiments, provided herein are Protein S antibodies, wherein the light chain variable domain of the antibodies comprise the amino acid sequence of SEQ ID NO: 150 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 151, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 150 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 151, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 117, SEQ ID NO: 118, SEQ ID NO: 123, SEQ ID NO: 124, SEQ ID NO: 125, and SEQ ID NO: 126.

In some embodiments, provided herein are Protein S antibodies, wherein the light chain variable domain of the antibodies comprise the amino acid sequence of SEQ ID NO: 152 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 153, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 152 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 153, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 127, SEQ ID NO: 128, SEQ ID NO: 129, SEQ ID NO: 130, SEQ ID NO: 50, and SEQ ID NO: 131.

In some embodiments, provided herein are Protein S antibodies, wherein the light chain variable domain of the antibodies comprise the amino acid sequence of SEQ ID NO: 156 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 157, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 156 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 157, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 136, SEQ ID NO: 17, SEQ ID NO: 137, SEQ ID NO: 138, SEQ ID NO: 139, and SEQ ID NO: 140.

In some embodiments, provided herein are Protein S antibodies, wherein the light chain variable domain of the antibodies comprise the amino acid sequence of SEQ ID NO: 158 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 159, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 158 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 159, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 141, SEQ ID NO: 142, SEQ ID NO: 143, SEQ ID NO: 144, SEQ ID NO: 145, and SEQ ID NO: 146.

In some embodiments, provided herein are Protein S antibodies, wherein the light chain variable domain of the antibodies comprise the amino acid sequence of SEQ ID NO: 177 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 182, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 177 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 182, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 174, SEQ ID NO: 175, SEQ ID NO: 176, SEQ ID NO: 179, SEQ ID NO: 180, and SEQ ID NO: 181.

In some embodiments, provided herein are Protein S antibodies, wherein the light chain variable domain of the antibodies comprise the amino acid sequence of SEQ ID NO: 187 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 192, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 187 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 192, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 184, SEQ ID NO: 185, SEQ ID NO: 186, SEQ ID NO: 189, SEQ ID NO: 190, and SEQ ID NO: 191.

In some embodiments, provided herein are Protein S antibodies, wherein the light chain variable domain of the antibodies comprise the amino acid sequence of SEQ ID NO: 197, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 202, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 197 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 202, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 194, SEQ ID NO: 195, SEQ ID NO: 196, SEQ ID NO: 199, SEQ ID NO: 200, and SEQ ID NO: 201.

In some embodiments, provided herein are Protein S antibodies, wherein the light chain variable domain of the antibodies comprise the amino acid sequence of SEQ ID NO: 207, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 212, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 207, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 212, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 204, SEQ ID NO: 205, SEQ ID NO: 206, SEQ ID NO: 209, SEQ ID NO: 210, and SEQ ID NO: 211.

As noted above, Protein S comprises four domains: the γ-carboxy-glutamic acid domain (Gla-domain), the thrombin-sensitive region (TSR), the epidermal growth factor-like domain (EGF domain), and the sex hormone binding globulin-like domain (SHBG domain). FIG. 1 depicts the schematic diagram of Protein S showing these modular domains of Protein S. The TSR is within the heavy chain of Protein S. The heavy chain of Protein S represents amino acids 42-296 of Protein S, the TSR represents amino acids 88-116, the signal peptide represents amino acids 1-24 and the propeptide represents amino acids 25-41.

In some embodiments, the Protein S antibodies provided herein bind to the Gla domain of Protein S. In some embodiments, the Protein S antibodies provided herein bind to the Gla domain and inhibit the cofactor activity of Protein S for both APC and TFPI. Exemplary antibodies that bind to the Gla domain and inhibit the cofactor activity of Protein S for both APC and TFPI may comprise the light chain variable domain comprising the amino acid sequence of SEQ ID NO: 77 and the heavy chain variable domain comprising the amino acid sequence of SEQ ID NO: 78; or such antibodies may comprise the light and heavy CDR amino acid sequences of SEQ ID NO: 4, SEQ ID NO: 16, SEQ ID NO: 25, SEQ ID NO: 37, SEQ ID NO: 49, and SEQ ID NO: 61.

In some embodiments, the Protein S antibodies provided herein bind to EGF domain of Protein S. In some embodiments, the Protein S antibodies provided herein bind to the SHBG-like domain of Protein S. In some embodiments, the Protein S antibodies provided herein bind to the C-terminal region of Protein S. In some embodiments, the Protein S antibodies provided herein bind the C-terminal region of Protein S, and inhibit the cofactor activity of Protein S for TFPI.

In some embodiments, the Protein S antibodies provided herein bind to Protein S fragments. The Protein S fragments are referred to herein as the Protein S heavy chain when they are expressed recombinantly in a cell line, such as HEK293 cells, for example. The Protein S heavy chain comprises amino acids 42-296. In some embodiments, the Protein S antibodies provided herein bind the Protein S heavy chain. Exemplary antibodies that bind to the Protein S heavy chain may comprise the light chain variable domain comprising the amino acid sequence of SEQ ID NO: 69 and the heavy chain variable domain comprising the amino acid sequence of SEQ ID NO: 70, or may comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57. As another example, antibodies that bind to the Protein S heavy chain may comprise the light chain variable domain comprising the amino acid sequence of SEQ ID NO: 79 and the heavy chain variable domain comprising the amino acid sequence of SEQ ID NO: 80, or may comprise the light and heavy CDR amino acid sequences of SEQ ID NO: 5, SEQ ID NO: 17, SEQ ID NO: 26, SEQ ID NO: 38, SEQ ID NO: 50, and SEQ ID NO: 62.

In some embodiments, the Protein S antibodies provided herein bind to the Protein S heavy chain comprising the TSR. In some embodiments, the Protein S antibodies provided herein bind to the Protein S heavy chain not comprising the TSR.

In some embodiments, the Protein S antibodies provided herein bind to the TSR of Protein S. In some embodiments, the Protein S antibodies provided herein do not bind to the TSR. In some embodiments, the Protein S antibodies provided herein bind to the heavy chain of Protein S, but do not bind the TSR region of the heavy chain. In some embodiments, the Protein S antibodies provided are dual inhibitors of APC and TFPI, and bind to the TSR of Protein S. In some embodiments, the Protein S antibodies provided are dual inhibitors of APC and TFPI, and do not bind to the TSR of Protein S. In some embodiments, the Protein S antibodies provided are inhibitors of APC, and do not bind to the TSR of Protein S. In some embodiments, the Protein S antibodies provided are inhibitors of TFPI, and do not bind to the TSR of Protein S.

Exemplary antibodies that bind to the TSR and are dual inhibitors of APC and TFPI may comprise the light chain variable domain comprising the amino acid sequence of SEQ ID NO: 89 and the heavy chain variable domain comprising the amino acid sequence of SEQ ID NO: 90, or may comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67. As another example, antibodies that bind to the TSR and are dual inhibitors of APC and TFPI may comprise the light chain variable domain comprising the amino acid sequence of SEQ ID NO: 75 and the heavy chain variable domain comprising the amino acid sequence of SEQ ID NO: 76, or may comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60.

In some embodiments, the Protein S antibodies provided herein do not bind to the TSR of Protein S, and cause a dual inhibition of the activity of APC and TFPI. In some embodiments, the Protein S antibodies provided herein do not bind to the TSR of Protein S, and cause an inhibition of the activity of APC. In some embodiments, the Protein S antibodies provided herein do not bind to the TSR of Protein S, and cause an inhibition of the activity of TFPI.

Exemplary antibodies that do not bind to the TSR and are dual inhibitors of APC and TFPI may comprise the light chain variable domain comprising the amino acid sequence of SEQ ID NO: 73 and the heavy chain variable domain comprising the amino acid sequence of SEQ ID NO: 74, or may comprise the light and heavy CDR amino acid sequences of SEQ ID NO: 3, SEQ ID NO: 14, SEQ ID NO: 23, SEQ ID NO: 35, SEQ ID NO: 47, and SEQ ID NO: 59.

In some embodiments, the Protein S antibodies provided herein bind to a linear epitope of Protein S. Exemplary antibodies that bind to a linear epitope of Protein S may comprise the light chain variable domain comprising the amino acid sequence of SEQ ID NO: 77 and the heavy chain variable domain comprising the amino acid sequence of SEQ ID NO: 78, or may comprise the light and heavy CDR amino acid sequences of SEQ ID NO: 4, SEQ ID NO: 16, SEQ ID NO: 25, SEQ ID NO: 37, SEQ ID NO: 49, and SEQ ID NO: 61.

In some embodiments, the Protein S antibodies provided herein bind to a conformational epitope, i.e., an epitope that is non-linear. Exemplary antibodies that bind to a non-linear epitope and inhibit the cofactor activity of Protein S for APC may comprise the light chain variable domain comprising the amino acid sequence of SEQ ID NO: 91 and the heavy chain variable domain comprising the amino acid sequence of SEQ ID NO: 92, or may comprise the light and heavy CDR amino acid sequences of SEQ ID NO: 11, SEQ ID NO: 20, SEQ ID NO: 32, SEQ ID NO: 44, SEQ ID NO: 56, and SEQ ID NO: 68. Exemplary antibodies that bind to a non-linear epitope and inhibit the cofactor activity of Protein S for APC and TFPI may comprise the light chain variable domain comprising the amino acid sequence of SEQ ID NO: 89 and the heavy chain variable domain comprising the amino acid sequence of 90, or may comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

As discussed above, Protein S can be found in a free form, or in a complexed form. Protein S can form a complex with at least TFPI, or with C4b-binding protein (C4BP). In some embodiments, the Protein S antibodies provided herein are capable of binding to Protein S in a free form, but not when in complexed form. In some embodiments, the Protein S antibodies provided herein are capable of binding to Protein S when Protein S is complexed, but not in free form. In some embodiments, the Protein S antibodies provided herein are capable of binding to Protein S that is either in free or complexed form. In some embodiments, the Protein S antibodies provided herein bind to a complexed Protein S, wherein the Protein S is bound to TFPI. In some embodiments, the Protein S antibodies provided herein bind to a complexed Protein S, wherein the Protein S is bound to C4BP.

In some embodiments, the Protein S antibodies provided herein bind Protein S, and the binding affinity of the antibodies to Protein S is calcium-dependent. In some embodiments, the Protein S antibodies provided herein bind Protein S, and the binding affinity of the antibodies to Protein S is not calcium-dependent. In some embodiments, the Protein S antibodies provided herein are dual inhibitors of APC and TFPI, and the binding affinity of the antibodies to Protein S is calcium-dependent. In some embodiments, the Protein S antibodies provided herein are dual inhibitors of APC and TFPI, and the binding affinity of the antibodies to Protein S is calcium-independent. In some embodiments, the Protein S antibodies provided herein are inhibitors of APC, and the binding affinity of the antibodies to Protein S is calcium-dependent. In some embodiments, the Protein S antibodies provided herein are inhibitors of APC, and the binding affinity of the antibodies to Protein S is calcium-independent. In some embodiments, the Protein S antibodies provided herein are inhibitors of TFPI, and the binding affinity of the antibodies to Protein S is calcium-independent. In some embodiments, the Protein S antibodies provided herein are inhibitors of TFPI, and the binding affinity of the antibodies to Protein S is calcium-dependent.

Exemplary antibodies that are dual inhibitors of the Protein S cofactor activity of APC and TFPI, wherein the binding affinity of the antibodies to Protein S is calcium-independent, may comprise the light chain variable domain comprising the amino acid sequence of SEQ ID NO: 71 and the heavy chain variable domain comprising the amino acid sequence of 72, or may comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58.

Exemplary antibodies that are inhibitors of the Protein S cofactor activity of TFPI, wherein the wherein the binding affinity of the antibodies to Protein S is calcium-independent, may comprise the light chain variable domain comprising the amino acid sequence of SEQ ID NO: 87 and the heavy chain variable domain comprising the amino acid sequence of 88, or may comprise the light and heavy CDR amino acid sequences of SEQ ID NO: 9, SEQ ID NO: 19, SEQ ID NO: 30, SEQ ID NO: 42, SEQ ID NO: 54, and SEQ ID NO: 66.

Exemplary antibodies that are inhibitors of the Protein S cofactor activity of APC, wherein the wherein the binding affinity of the antibodies to Protein S is calcium-dependent, may comprise the light chain variable domain comprising the amino acid sequence of SEQ ID NO: 91 and the heavy chain variable domain comprising the amino acid sequence of 92, or may comprise the light and heavy CDR amino acid sequences of SEQ ID NO: 11, SEQ ID NO: 20, SEQ ID NO: 32, SEQ ID NO: 44, SEQ ID NO: 56, and SEQ ID NO: 68.

Exemplary antibodies that are dual inhibitors of the Protein S cofactor activity of APC and TFPI, wherein the wherein the binding affinity of the antibodies to Protein S is calcium-dependent, may comprise the light chain variable domain comprising the amino acid sequence of SEQ ID NO: 89 and the heavy chain variable domain comprising the amino acid sequence of 90, or may comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

B. Generation of Protein S Antibodies

Production of the Protein S antibodies provided herein may be by use of any method known to those of ordinary skill in the art. In some embodiments, the antibodies are produced by hybridomas. In some embodiments, the antibodies are encoded by a nucleic acid and are expressed, purified, and isolated.

Accordingly, provided herein are nucleic acids encoding any of the antibodies disclosed herein, vectors comprising any of the nucleic acids encoding such antibodies, and host cells comprising such vectors. Also provided herein are exemplary nucleic acid sequences encoding for the variable heavy chains and variable light chains of the Protein S antibodies disclosed herein.

Tables 5A and 5B provide exemplary variable light chain nucleic acid sequences and exemplary variable heavy chain nucleic acid sequences. Exemplary combinations of nucleic acid sequences encoding for the variable heavy and light chain domains of the Protein S antibodies disclosed herein are presented in Table 5C. The exemplary amino acid sequences of Tables 4A-4C correspond to the nucleic acid sequences of Tables 5A-5C. The exemplary combinations of Table 5C correspond to the numbered combinations presented in Table 4C.

The person of ordinary skill in the art will appreciate that, because of redundancy in the triplet code, multiple nucleic acids may encode the same amino acid sequence. Thus, nucleic acid sequences that are not identical to those set forth in the tables below may still encode the Protein S antibodies of the disclosure.

TABLE 5A

| Exemplary Variable Light Chain Nucleic Acid Sequences of Anti-Protein S Monoclonal Antibodies |
|---|
| TCCTATGAGCTGACTCAGCCACCCTCAGTGTCCGT<br>GTCCCCAGGACAGACAGCCAGCATCACCTGCTCTG<br>GAGATAAATTGGGGGATAAATATGCTTGCTGGTAT<br>CAGCAGAAGCCAGGCCAGTCCCCTGTACTGGTCAT<br>CTATCAAGATACTAAGCGGCCCTCAGGGATCCCTG<br>AGCGATTCTCTGGCTCCAACTCTGGGAACACAGCC<br>ACTCTGACCATCAGCGGGACCCAGGCTATGGATGA<br>GGCTGACTATTACTGTCAGGCGTGGGACAGCAACA<br>CTGTGGTCTTCGGCGGAGGGACCAAGCTGACCGTC<br>CTA<br>(SEQ ID NO: 93) |
| TCCTCTGACCTGACTCAGGGCCCTGCTGTGTCTGT<br>GGCCCTGGGACAGACAGTCAGGATCACATGCCAAG<br>GAGACAGCCTCAGAAACTATTATGCAAGCTGGTAC<br>CAGCAGAAGCCAGGACAGGCCCCTGTACCTGTCAT<br>CTATGGTAAAAACGACCGGCCCTCAGGGATCCCAG<br>ACCGATTCTCTGGCTCCATCTCAGGAAACACAGCT<br>TCCTTGACCATCACTGGGGCTCAGGCGGAAGATGA<br>GGCTCACTATTACTGTAACTCCCGGGACAGCAGTG<br>GTAACCATGTGGTATTCGGCGGAGGGACCAAGCTG<br>ACCGTCCTG<br>(SEQ ID NO: 95) |
| CAGTCTGCCCTGACTCAGCCTGCCTCCGTGTCTGG<br>GTCTCCTGGACAGTCGATCACCATCTCCTGCACTG<br>GAACCAGCAGTGACGTTGGTGGTTATGAATTTGTC<br>TCCTGGTACCAACATCACCCAGGCAAAGCCCCCAA<br>ACTCATGATTTATGATGTCAGTAGTCGGCCCTCAG<br>GGGTTTCTAATCGCTTCTCTGGCTCCAAGTCTGGC<br>AACACGGCCTCCCTGACCATCTCTGGGCTCCAGGC<br>TGAGGACGAGGCTGATTATTACTGCAGCTCATATA<br>CGCGCAGCAGCACTGTGGTGTTCGGCGGCGGGGCC<br>AGGCTGACCGTCCTA<br>(SEQ ID NO: 97) |
| TCCTATGAGCTGAATCAGCCACCCTCAGTGTCCGT<br>GTCCCCAGGACAGACAGCCAGCATCACCTGCTCTG<br>GAGATAAATTGGGGGATAAATATGCTTCCTGGTAT<br>CAGCAGAAGCCAGGCCAGTCCCCTGTGGTGGCCAT<br>CTATCAAAATAGCAAGCGGCCCTCAGGGATCCCTG<br>AGCGATTCTCTGCCTCCAACTCTGGGAACACAGCC<br>ACTCTGACCATCAGCGGGACCCAGGCTTTGGATGA<br>GGCTGACTATTACTGTCAGGCGTGGGACAGCAGCA<br>CTTGGGTGTTCGGCGGAGGGACCAAGCTGACCGTC<br>CTA<br>(SEQ ID NO: 99) |
| GAAATTGTGTTGACACAGTCTCCAGCCACCCTGTC<br>TTTGTCTCCAGGGGAAAGAGCCACCCTCTCCTGCA<br>GGGCCAGTCAGAGTGTTAGTATCTACTTAGCCTGG |

TABLE 5A-continued

| Exemplary Variable Light Chain Nucleic Acid Sequences of Anti-Protein S Monoclonal Antibodies |
|---|
| TACCAACAGAAACCTGGCCAGGCTCCCAGGCTCCT<br>CATCTATGATGCATCCAACAGGGCCACTGGCATCC<br>CAGCCAGGTTCAGTGGCAGTGGGTCTGGGACAGAC<br>TTCACTCTCACCATCAGCAGCCTAGAGCCTGAAGA<br>TTTTGCAGTTTATTACTGTCAGCAGCGTAGCAACT<br>GGCCCCTCACTTTCGGCCCTGGGACCAAAGTGGAT<br>ATCAAA<br>(SEQ ID NO: 101) |
| GAAATAGTGATGACGCAGTCTCCAGCCACCCTGTC<br>TGTGTCTCCAGGGGAAAGAGCCACCCTCTCCTGCA<br>GGGCCAGTCAGAGGATTAACAGCAACTTAGCCTGG<br>TACCAGCAGAAACCTGGCCAGGCTCCCAGGCTCCT<br>CATCTATGGTGCATCCACCAGGGCCACTGGTATCC<br>CCGCCAGGTTCAGTGGCAGTGGGTCTGGGACAGAG<br>TTCACTCTCACCATCAGCAGCCTGCAGTCTGAAGA<br>TTTTGCAGCTTATTACTGTCAGCAGTATGATAACT<br>GGCCGCTCACTTTCGGCGGAGGGACCAAGGTGGAG<br>ATCAAA<br>(SEQ ID NO: 103) |
| GATATTGTGATGACTCAGTCTCCACTCTCCCTGCC<br>CGTCACCCCTGGAGAGCCGGCCTCCATCTCCTGCA<br>GGTCTAGTCAGAGCCTCCTGCATAGTAATGGATAC<br>AACTATTTGGATTGGTACCTGCAGAAGCCAGGGCA<br>GTCTCCACAGCTCCTGATCTATTTGGGTTCTAATC<br>GGGCCTCCGGGGTCCCTGACAGGTTCAGTGGCAGT<br>GGATCAGGCACAGATTTTACACTGAAAATCAGCAG<br>AGTGGAGGCTGAGGATGTTGGGGTTTATTATTGTA<br>TGCAAGCTCTACAAACTTTCACTTTCGGCCCTGGG<br>ACCAAAGTGGATATCAAA<br>(SEQ ID NO: 105) |
| CAGGCTGTTGTGACTCAGGAATCTGCACTCACCAC<br>ATCACCTGGTGAAACAGTCACACTCACTTGTCGCT<br>CAAGTACTGGGGCTGTTACAGCTAGTAACTATGCC<br>AACTGGGTCCAAGAAAAACCAGATCATTTGTTCAC<br>TGGTCTAATAGGTAGTACCAATAACCGAGCTCCAG<br>GTGTTCCTGCCAGATTCTCAGGCTCCCTGATTGGA<br>GACAAGGCTGCCCTCACCATCACAGGGGCACAGAC<br>TGAGGATGAGGCAATATATTTCTGTGCTCTATGGT<br>ACAGCGACCATTTCGTGTTCGGTGGAGGAACCAAA<br>CTGACTGTCCTA<br>(SEQ ID NO: 111) |
| GAAATAGTGATGACGCAGTCTCCAGCCACCCTGTC<br>TGTGTCTCCAGGGGAAAGAGCCACCCTCTCCTGCA<br>GGGCCAGTCAGAGTGTTACCAGCAACTTAGCCTGG<br>TACCAGCAGAAACCTGGCCAGGCTCCCAGGCTCCT<br>CATCTATGATGCATCCACCAGGGCCACTGGTATCC<br>CAGCCAGGTTCAGTGGCAGTGGGTCTGGGACAGAG<br>TTCACTCTCACCATCAGCAGCCTGCAGTCTGAAGA<br>TTTTGCAATTTATTACTGTCAGCAGTATAATAACT<br>GGCCCACCTTCGGCCAAGGGACACGACTGGAGATT<br>AAA<br>(SEQ ID NO: 113) |
| GATATTGTGATGACCCAGACTCCACTCTCCTCACC<br>TGTCACCCTTGGACAGCCGGCCTCCATCTCCTGCA<br>GGTCTAGTCAAAGCCTCGTACACAGTGATGGAAAC<br>ACCTACTTGAGTTGGCTTCAGCAGAGGCCAGGCCA<br>GCCTCCAAGACTCCTAATTTATAAGATTTCTAACC<br>GGTTCTCTGGGGTCCCAGACAGATTCAGTGGCAGT<br>GGGGCAGGGACAGATTTCACACTGAAAATCAGCAG<br>GGTGGAAGCTGAGGATGTCGGGGTTTATTACTGCA<br>TGCAAGCTACACAATTTCCCCATCTCACTTTCGGC<br>GGAGGGACCAAGGTGGAGATCAAA<br>(SEQ ID NO: 115) |
| GACATCCAGATGACCCAGTCTCCATCCTCACTGTC<br>TGCATCTGTAGGAGACAGAGTCACCATCACTTGTC<br>GGGCGAGTCAGGGCATTAACAATTATTTAGCCTGG<br>TTTCAGCAGAAACCAGGGAAAGCCCCTAAGTCCCT<br>GATCTATGCTGCATCCAGTTTGCAAAGTGGGGTCC<br>CATCAAAGTTCAGCGGCAGTGGATCTGGGACAGAT<br>TTCACTCTCACCATCAGCAGCCTGCAGCCTGAAGA |

TABLE 5A-continued

| Exemplary Variable Light Chain Nucleic Acid Sequences of Anti-Protein S Monoclonal Antibodies |
|---|
| TTTTGCAACTTATTACTGCCAACAGTATAATAGTT ACCCTCGGACGTTCGGCCAAGGGACCAAGGTGGAA ATCAAA (SEQ ID NO: 162) |
| GACATCCAGATGACCCAGTCTCCATCCTCACTGTC TGCATCTGTAGGAGACAGAGTCACCATCACTTGTC GGGCGAGTCAGGGCATTAACAATTATTTAGCCTGG TTTCAGCAGAAACCAGGGAAAGCCCCTAAGTCCCT GATCTATGCTGCATCCAATTTGCAAAGTGGGGTCC CATTAAAGTTCAGCGGCAGTGGATCTGGGACAGAT TTCACTCTCACCATCAGCAGCCTGCAGCCTGAAGA TTTTGCAACTTATTACTGCCAACAGTATAATAGTT ACCCGATCACCTTCGGCCAAGGGACACGACTGGAG ATTAAA (SEQ ID NO: 164) |
| GACATCCAGATGACCCAGTCTCCATCCTCCCTGTC TGCATCTGTAGGAGACAGAGTCACCATCACTTGCC GGGCAAGTCAGAGCATTAGCACCTTTTTAAATTGG TATCAGCAGAAACCAGGGAAAGCCCCTAAACTCCT GATCTATGCTACATCCAGTTTGCGAAGTGGGGTCC CATCAAGGTTCAGTGGCAGTGGATCTGGGACAGAT TTCACTCTCACCATCAGCAGTCTGCAACCTGAAGA TTTTGCAATTTATTATTGTCAACAGAGTTACAGTA CCCCTCGGACGTTCGGCCAAGGGACCCAGGTGGAA ATCAAA (SEQ ID NO: 166) |
| GAAATTGTGTTGACGCAGTCTCCAGGCACCCTGTC TTTGTCTCCAGGGGAAAGAGCCACCCTCTCCTGCA GGGCCAGTCAGAGTGTTGGCAGCAGCTACTTAGCC TGGTACCAGCAGAAACCTGGCCAGGCTCCCAGGCT CCTCATCTCTGGTGCATCCGGCAGGGCCACTGGCA TCCCAGACAGGTTCAGTGGCAGTGGGTCTGGGACA GACTTCACTCTCACCATCAGCAGACTGGAGCCTGA AGATTTTACAGTGTATTACTGTCAGCAGTATGGTA GCTCACCGTACACTTTTGGCCAGGGGACCAAGCTG GAGATCAAA (SEQ ID NO: 170) |
| GACATCCAGATGAACCAGTCTCCATCCAGTCTGTC TGCATCCCTCGGAGACACAATTACCATCACTTGCC GTGCCAGTCAGAACATTCATATGTGGTTAAGCTGG TACCAGCAGAAACCAGGAAATATTCCTAAACTATT GATCTTTAAGACTTCCAATTTGCACACAGGCGTCC CATCAAGGTTTAGTGGCAGTGGATCTGGAACAGAT TTCACATTAACCATCAGCAGTCTGCAGCCTGAAGA CATTGCCACTTACTACTGTCTACAGGGTCAAAGTT ATCCGTTCACGTTCGGAGGGGGGACCAAGCTGGAA ATAAAG (SEQ ID NO: 172) |
| GACATCCAGATGACCCAGTCTCCATCCTCCCTGTC TGCATCTGTAGGAGACAGAGTCACCATCACTTGCC GGGCAAGTCAGAGCATTAGCAGCTATTTAAATTGG TATCAGCAGAAACCAGGGAAAGCCCCTAAGCTCCT GATCTATGCTGCATCCAGTTTGCAAAGTGGGGTCC CATCAAGGTTCAGTGGCAGTGGATCTGGGACAGAT TTCACTCTCACCATCAGCAGTCTGCAACCTGAAGA TTTTGCAACTTACTACTGTCAACAGAGTTACAGTT CCCTCACCTTCGGCCAAGGGACACGACTGGAGATT AAA (SEQ ID NO: 178) |
| TCCTATGTGCTGACTCAGCCACCCTCGGTGTCAGT GGCCCCAGGACAGACGGCCAGGATTACCTGTGGGG GAGACAACATTGGAGGTAAAAGTGTGCACTGGTAC CAGCAGAAGCCAGGCCAGGCCCCTGTGATGGTCGT CTATGATGATAGCGACCGGCCCTCAGGGATCCCTG AGCGATTCGCTGGCTCCAATTCTGGGAACACGGCC ACCCTGGCCATCAGCAGGGTCGAAGCCGGGGATGA GGCCGACTATTACTGTCAGGTGTGGGAGATAACTA GTGATCATCCGGCATTCGGCGGAGGGACCAGGCTG ACCGTCCTA (SEQ ID NO: 188) |
| TCCTATGAGCTGACTCAGCCACCCTCAGTGTCCGT GTCCCCAGGACAGACAGCCAGCATCACCTGCTCTG GAGATAAATTGGGGGATAAATATGTTTTCTGGTAT CAGCAGAAGCCAGGCCAGTCCCCTGTGTTGGTCAT CTATCAAGATAGCAAGCGGCCCTCAGGGATCCCTG AGCGATTCTCTGGCTCCAACTCTGGGAACACAGCC ACTCTGACCATCAGCGGGACCCAGACTATGGATGA GGCTGACTATTACTGTCAGGCGTGGGACAGCAGCA CTGTGGGATTCGGCGGAGGGACCAAGCTGGCCGTC CTG (SEQ ID NO: 198) |
| TCCTATGAGCTGACTCAGCCACCCTCAGTGTCCGT GTCCCCGGGACAGACAGCCAGCATCACCTGCTCTG GAGATAAATTGGGGGATAAATATGCTTTCTGGTAT CAGCAGAAGCCAGGCCAGTCCCCTGTGCTGGTCAT CTATCAAGATAACAAGCGGCCCTCAGGGATCCCTG AGCGATTCTCTGGCTCCAACTCTGGGAACACAGCC ACTCTAACCATCAGCGGGACCCAGGCTGTGGATGA GGCTGACTATTACTGTCAGGCGTGGGACAGCAGCA CTGCGGTATTCGGCGGAGGGACCAAGCTGACCGTC CTA (SEQ ID NO: 208) |

TABLE 5B

| Exemplary Variable Heavy Chain Nucleic Acid Sequences of Anti-Protein S Monoclonal Antibodies |
|---|
| CAGCTGCAGCTGCAGGAGTCGGGCCCAGGACTGGT GAAGCCTTCGGAGACCCTGTCCCTCACCTGCACTG TCTCTGGTGGCTCCATCAGCAGTAGTAGTTACTAC TGGGGCTGGATCCGCCAGCCCCCGGGGAAGGGACT GGAGTGGATTGGGAATATCTATTATAGTGGGAACA CCTACTACAACCCGTCCCTCAAGAGTCGAGTCACC ATATCCGTAGACACGTCCAAGAACCAGTTCTCCCT GAAGCTGAGCTCTATGACCGCCGCAGACACGGCTG TGTATTACTGTGCGAGATGTAGTGGCTACGGGTAT AGCAGTGGCCGGTCCTACTTTGACTACTGGGGCCA GGAAACCCTGGTCACCGTCTCCTCA (SEQ ID NO: 94) |
| CAGGTGCAGCTGGTGCAGTCTGGGGCTGAGGTGAA GAAGCCTGGGTCCTCGGTGAAGGTCTCCTGCAAGG TTTCTGGAGGCACCTTCAGCAGCTATTCTATCAGC TGGGTGCGACAGGCCCCTGGACAAGGGCTTGAGTG GATGGGAGGGATCATCCCTATATTTGGTACAACAA ACTACGCACAGAAGTTCCAGGGCAGAGTCACGATC ACCGCGGACGAATCCACGAGCACAGCCTACATGGA TCTGAGCAGCCTGAAATCTGAGGACACGGCCATGT ATTACTGTGAGGGGGGTAGAGTGGGAGCGGACTTT GACTACTGGGGCCAGGGAACCCTGGTCACCGTCTC CTCA (SEQ ID NO: 96) |
| CAGGTGCAGCTGCAGGAGTCGGGCCCAGGACTGGT GAAGCCTTCACAGACCCTGTCCCTCACCTGCACTG TCTCTGGTGGCTCCATCACCAGTGATGGTTACCAC TGGAGCTGGATCCGCCAGTACCCAGGGAAGGGCCT GGACTGGATTGGATACATCTATTACACTGGGAACA CCTACTACAACCCGTCCCTCAAGAGTCGAGTGACC ATATCAGTAGGCACGTCTCAGAACCAGTTCTCCCT GAAGCTGATCTCTGTGACTGCCGCGGACACGGCCG TTTATTACTGTGCGAGAAGGCTGTCGACTGGGCCC TACTTTGACTACTGGGGCCAGGGAACCCTGGTCAC CGTCTCCTCC (SEQ ID NO: 98) |
| GAAGTGCAGCTGGTGGAGTCTGGGGGAGGCTTGGT ACAGCCTGGCAGGTCCCTGAGACTCTCCTGTGCAG CCTCTGGATTCACCTTTGATGATTATGCCATGCAC |

TABLE 5B-continued

Exemplary Variable Heavy Chain Nucleic Acid Sequences of Anti-Protein S Monoclonal Antibodies TGGGTCCGGCAAGCTCCAGGGAAGGGCCTGGAATG
GGTCTCAGGTATTACTTGGAATAGTGGTAACATAG
GCTATGCGGACTCTGTGAAGGGCCGATTCACCATC
TCCAGAGACAACGCCAAGAACTCCCTGTATCTGCA
CATGAACAGTCTGAGAATTGAGGACACGGCCTTCT
ATTACTGTGCAAAAGGCCGAGCAGTGTCTGATACT
TTTGATATCTGGGGCCAAGGGACAATGGTCACCGT
CTCTTCA
(SEQ ID NO: 100)

CAGGTGCAGTTGGTGGAATCTGGGGGAGGCGTGGT
CCAGCCTGGGAGGTCCCTGAGACTCTCCTGTGCAG
CGTCTGGATTCACCTTCAGTACCTATGGCTTTCAC
TGGGTCCGCCAGCCTCCAGGCAAGGGACTGGAGTG
GGTGGCAGTTATATATTATGATGGAATTAATAAAT
ATTATGCAGACTCCGTGAAGGGCCGATTCACCATC
TCCAGAGACAATTCCAAGAACACGCTGTTTCTTCA
AATGAACAGCCTGAGAGCCGAGGACACGGCTGTGT
ATTACTGTGCGGAGTCCGACTTGGACTACTGGGGC
CAGGGAACCCTGGTCACCGTCTCCTCA
(SEQ ID NO:
102)

CAGGTGCAGCTGCAGGAGTCGGGCCCAGGACTGGT
GAAGCCTTCGGAGACCCTGTCCCTCACCTGCGCTG
TCTCTGGTTATTCCATCAGCAGTGGTTACTACTGG
GGCTGGATCCGGCAGCCCCCAGGGAAGGGGCTGGA
CTGGATTGGGAGTATCTATTATAGTGGGAGTACCT
ACTACAACCCGTCCCTCAAGAGTCGAGTCACCATA
TCAGTTGACACGTCCAAGAACCAGATCTCCCTGAA
GCTGAGCTCTGTGACCGCCGCAGACACGGCCGTGT
ATTACTGTGCGACCACGTATTCCGATATTGTGACT
GGTTATTATAATGATGCTTTTGATATCTGGGGCCA
AGGGACAATGGTCACCGTGTCTTCA
(SEQ ID NO: 104)

CAGGTGCAGCTGGTGCAGTCTGGGGCTGAGGTGAA
GAAGCCTGGGTCCTCGGTGAAGGTCTCCTGTAAGG
CTTCTGGAGACACCTTCAGCAACCATGCTATCAAC
TGGGTGCGACAGGCCCCTGGACAAGGGCTTGAGTG
GATGGGAGGGTACATCCCTATCTTTGGTACAACAA
ACTCCGCACAGAAGTTCCGGGGCAGAGTCACGATT
ACCGCGGACAAATCCACGAACACAGCCTACATGGC
GCTGAGCAGCCTGAGATCTGAGGACACGGCCGTTT
ATTACTGTGCGAGAGGGGGGCTCGCGGGGAGTCAT
TATAAGAACTACTACTATGACGGTATGGACGTCTG
GGGCCAGGGGACCACGGTCACCGTCTCCTCA
(SEQ ID NO: 106)

CAGGTGCAACTGGTGCAGTCTGGGGCTGAGGTGAA
GAAGCCTGGGGCCTCAGTGAAGGTCTCCTGCAAGT
CTTCTGGCCACACCTTCACCGGCTACTATATGCAC
TGGGTGCGACAGGCCCCTGGACAAGGGCTTGAGTG
GATGGGATGGATCAACCCTAACAGTGGTGACACAA
ACTACGCACAGAAGTTTCAGGGCAGGGTCACCATG
ACCAGGGACACGTCCATCAGCACAGCCTACATGGA
GATGAGCAGGCTGAGATCTGACGACACGGCCGTGT
ATTACTGTGCGAGAGACTCCCAAATACTATGGTTC
GGGGAGTTAGGCTACTGGGGCCAGGGAACCCTGGT
CACCGTCTCCTCC
(SEQ ID NO: 112)

CAGGTGCAGCTGCAGGAGTCGGGCCCAGGACTGGT
GAAGCCTTCGGAGACCCTGTCCCTCACCTGCGGTG
TCTCTGGTGGCTCCATCAGCAGTACTAACTGGTGG
AGTTGGGTCCGCCAGCCCCCAGGGAAGGGGCTGGA
GTGGATTGGGGAAATCTATCAAACTGGGAGTACCG
ACTACGACCCGTCCCTCAAGAGTCGAGTCACCATA
TCAATAGACAAGTCCAAGAACCAGTTCTCCCTGAA
GCTGTACTCTGTGACCGCCGCGGACACGGCCGTGT
ATTACTGTGCGAGAAGGTTCGGGGAGTTAGACTAC
TGGGGCCAGGGAACCCTGGTCACCGTCTCCTCA
(SEQ
ID NO: 114)

TABLE 5B-continued

Exemplary Variable Heavy Chain Nucleic Acid Sequences of Anti-Protein S Monoclonal Antibodies CAGGTGCAGCTGCAGGAGTCGGGCCCAGGACTGGT
GAAGCCTTCGGAGACCCTGTCCCTCACCTGCACTG
TCTCTGGTGGCTCCATCAGTAATTACTACTGGAAC
TGGATCCGGCAGCCCCCAGGGAAGGGACTGGAGTG
GATTGGGTATATCTATTACATTGGGATCACCGACT
ACAACCCCTCCCTCAAGAGTCGAGTCACCATATCA
GTAGACACGTCCAAGAACCAGTTCTCCCTGAAGGT
GACCTCTGTGACCGCTGCGGACACGGCCGTGTATT
ACTGTGCGGCTCTAAGTGGGGATCATGCTTTTGAC
ATCTGGGGCCAAGGGACACTGGTCACCGTCTCTTC
A
(SEQ ID NO: 116)

CAGCTGCAGCTGCAGGAGTCGGGCCCAGGACTGGT
GAAGCCTTCGGAGACCCTGTCCCTCACCTGCACTG
TCTCTGGTGGCTCCATCACCAATAGTAATTACTAC
TGGGGCTGGATCCGCCAGCCCCCAGGGAAGGGACT
GGAGTGGATTGGGAGTGTCTATTATAGTGGGACCA
CCTACTACAACCCGTCCCTCAAGAGTCGAGTCACC
ATATCCGTAGACCCGTCCAAGAACCAGTTCTCCCT
GAAGCTGAGCTCTGTGACCGCCGCAGACACGGCTG
TGTATTACTGTGTGAGAGAGAGTGAGAGCTACTAC
TACTACGGTTCGGACGTCTGGGGCCAAGGGACCAC
GGTCACCGTCTCCTCA
(SEQ ID NO: 163)

GAGGTGCAGCTGGTTGAGTCTGGGGGAGGCCTGGT
CAAGCCTGGGGGGTCCCTGAGACTCTCCTGTGCAG
CCTCTGGATTCACCTTCAGTAGCTATAACATGAAC
TGGGTCCGCCAGGCTCCAGGGAGGGGGCTGGACTG
GGTCTCATCCATTAGTAGTAGTAGTAGTTACATAT
ACTACGCAGACTCAGTGAAGGGCCGATTCACCATC
TCCAGAGACAACGCCAAGAACTCACTGTATCTGCA
AATGAATACCCTGAGAGCCGAGGACACGGCTGTTT
ATTACTGTGCGAGAGATGAGGAGTGGGAGCTACTG
ACGGGCTTTGACTACTGGGGCCAGGGAACCCTGGT
CACCGTCTCCTCA
(SEQ ID NO: 165)

CAGGTGCAGCTGCAGGAGTCGGGCCCAGGACTGGT
GAAGCCTTCGGAGACCCTGTCCCTCACCTGCACTG
TCTCTGGTGGCTCCATCAGTGGTAACTACTGGAGC
TGGATCCGGCAGCCCCCAGGGAAGGGACTGGAGTG
GATTGGGTATATCTATTACAGTGGGAGCACCAACT
ACAATCCCTCCCTCAAGAGTCGAGTCACCATATCA
GTTGACACGTCCAAGAACCAGTTCTCCCTGAAGCT
GAGCTCTGTGACCGCTGCGGATACGGCCGTGTATT
ACTGTGCGAGAGATCTTGATTACTTTACTTGGGGG
GCTTATTCTGACTGGTACTTCGATCTCTGGGGCCG
TGGCACCCTGGTCACTGTCTCCTCA
(SEQ ID NO: 167)

CAGGTACAGCTGCAGCAGTCAGGTCCAGGACTGGT
GAAGCCCTCGCAGACCCTCTCACTCACCTGTGCCA
TCTCCGGGGACAGTGTCTCTAACAACAATGCTGCT
TGGAACTGGATCAGGCAGTCCCCATCGAGAGGCCT
TGAGTGGCTGGGAGGGACATACTACAGGTCCAAGT
GGTATAATGATTATGCAGTATCTGTGAAAAGTCGA
ATAATCATCAACCCAGTCACATCCAAGAACCAGTT
CTCCCTACAGCTGAACTCTGTGACTCCCGAGGACA
CGGCTGTGTATTACTGTGCAAGAGGCAGCAGCTGG
TACAGGTTTTTTGACTACTGGGGCCAGGGAACCCT
GGTCACCGTCTCCTCA
(SEQ ID NO: 171)

CAGGTCCAGCTGCAGCAGTCTGGAACTGAGCTGGT
AAGGCCTGGGACTTCAGTGAAGATGTCCTGTAAGG
CTGCTGGATACACCTTCACTAACCACTGGATAGGT
TGGGTAAAGCAGAGGCCTGGACATGGCCTTGAGTG
GATTGGAGATATTTACCCTGGAGGTGGTTATACTA
ACTACAATGAGAAGTTCAAGGGCAAGGCCTCACTG
ACTGCAGACACATCCTCCACCACAGCCTACATGCA

TABLE 5B-continued

| Exemplary Variable Heavy Chain Nucleic Acid Sequences of Anti-Protein S Monoclonal Antibodies |
|---|
| GCTCAGCAGCCTGACATCTGAGGACTCTGCCATCT<br>ATTACTGTTCAAGATTCGGGGATCAAAACTGGGCC<br>TGGTTTGCTTACTGGGGCCAAGGGACTCTGGTCAC<br>TGTCTCTGCA<br>(SEQ ID NO: 173) |
| GAGGTGCAGCTGGTGGAGTCTGGGGGAGGCTTGGT<br>AAAGCCTGGGGGGTCCCTTAGACTCTCCTGTGCAG<br>CCTCTGGAATCAGTTTCAGTAACGCCTGGATGAGC<br>TGGGTCCGCCAGGCTCCAGGGAAGGGGCTGGAATG<br>GGTTGGCCGTATTAAAGCCAATCCTGATGGTGGGA<br>CAACAGACTACGCTGCACCCGTGAAAGGCAGATTC<br>ACCATCTCAAGAGATGATTCAAAAAACACGCTATA<br>TCTGCAAATGAACAGCCTGAAAACCGAGGACACAG<br>CCGTGTATTACTGTACCACAGAGTTGGACATTTTA<br>CTATGGTTCACCTCCTTTGACTACTGGGGCCAGGG<br>AACCCTGGTCACCGTCTCCTCA<br>(SEQ ID NO: 183) |
| GAGGTGCAGCTGGTGGAGTCTGGGGGAGGCTTGGT<br>ACAGCCTGGGGGGTCCCTGAGACTCTCCTGTGCAG<br>CCTCTGGATTCACCTTCAGTAGCTATAGCATGAAC<br>TGGGTCCGCCAGGCTCCAGGGAAGGGGCTGGAGTG<br>GGTTGCATACATTAGTAGTAGTACTCGTACCATAT<br>TCTACGCAGACTCTGTGAAGGGCCGATTCACCATC<br>TCCAGAGACAATGCCAAGAACTCACTGTATCTGCA<br>AATGAACAGCCTGAGAGACGAGGACACGGCTTTTT<br>ATTATTGTGCGAGAGAACGTTCGGCCTTTGACTAC<br>TGGGGCCAGGGAACCCTGGTCACCGTCTCCTCA<br>(SEQ ID NO: 193) |
| CAGGTGCAGCTGGTGCAGTCTGGGTCTGAGGTGAA<br>GAAGCCTGGGGCCTCAGTGAAGGTTTCCTGCAAGG<br>CATCTGGATACACCTTCACCAACTACTATATACAC<br>TGGGTGCGGCAGGCCCCTGGACAAGGGCTTGAGTG<br>GATGGGAATAATCACCCCTAGTGGTGGTACCACAA<br>GCTACGCACAGAAGTTCCAGGGCAGAGTCACTATG<br>ACCAGGGACACGTCCACGAACACAGTCTACATGGG<br>GCTGAGCAGCCTGAGATCTGAGGACACGGCCATGT<br>ATTACTGTGCGAGAGCCGGGGTACAACTGGATCGA<br>CGAGGGTGGTTCGACCCCTGGGGCCAGGGAACCCT<br>GGTCACCGTCTCCTCA<br>(SEQ ID NO: 203) |
| CAGGTGCAGCTGGTGCAGTCTGGGGCTGAGGTGAA<br>GAAGCCTGGGGCCTCAGTGAAGGTTTCCTGCAAGG<br>CATCTGGATACACCTTCACCAGCTACTATATACAC<br>TGGGTACGACAGGCCCCTGGACAAGGGCTTGAGTG<br>GATGGGAGTAACCAGCCCTAGTGGTCGTAGCACAA<br>GCTTCGCACAGAAGTTCCAGGGCAGAGTCACCATG<br>ACCAGGGACACGTCCACGAGCGCAGTCTATATGGA<br>CCTGGACAGCCTGAGATCTGAGGACACGGCCGTGT<br>ATTACTGTGCGAGAGGGGGAGTGACGATACACCTG<br>GAACGACGGGGCTACTTTGACTACTGGGGCCAGGG<br>AACCCTGGTCATTGTCTCCTCA<br>(SEQ ID NO: 213) |

TABLE 5C

Exemplary Variable Light Chain and Variable Heavy Chain Nucleic Acid Sequences of Anti-Protein S Monoclonal Antibodies

| Combination Number | Variable Light Chain Nucleic Acid Sequence | Variable Heavy Chain Nucleic Acid Sequence |
|---|---|---|
| Combination 1 | SEQ ID NO: 93 | SEQ ID NO: 94 |
| Combination 2 | SEQ ID NO: 95 | SEQ ID NO: 96 |
| Combination 3 | SEQ ID NO: 97 | SEQ ID NO: 98 |
| Combination 4 | SEQ ID NO: 99 | SEQ ID NO: 100 |
| Combination 5 | SEQ ID NO: 101 | SEQ ID NO: 102 |
| Combination 6 | SEQ ID NO: 103 | SEQ ID NO: 104 |
| Combination 7 | SEQ ID NO: 105 | SEQ ID NO: 106 |

TABLE 5C-continued

Exemplary Variable Light Chain and Variable Heavy Chain Nucleic Acid Sequences of Anti-Protein S Monoclonal Antibodies

| Combination Number | Variable Light Chain Nucleic Acid Sequence | Variable Heavy Chain Nucleic Acid Sequence |
|---|---|---|
| Combination 10 | SEQ ID NO: 111 | SEQ ID NO: 112 |
| Combination 11 | SEQ ID NO: 113 | SEQ ID NO: 114 |
| Combination 12 | SEQ ID NO: 115 | SEQ ID NO: 116 |
| Combination 13 | SEQ ID NO: 162 | SEQ ID NO: 163 |
| Combination 14 | SEQ ID NO: 164 | SEQ ID NO: 165 |
| Combination 15 | SEQ ID NO: 166 | SEQ ID NO: 167 |
| Combination 17 | SEQ ID NO: 170 | SEQ ID NO: 171 |
| Combination 18 | SEQ ID NO: 172 | SEQ ID NO: 173 |
| Combination 19 | SEQ ID NO: 178 | SEQ ID NO: 183 |
| Combination 20 | SEQ ID NO: 188 | SEQ ID NO: 193 |
| Combination 21 | SEQ ID NO: 198 | SEQ ID NO: 203 |
| Combination 22 | SEQ ID NO: 208 | SEQ ID NO: 213 |

In some embodiments, provided herein are nucleic acids encoding any of the Protein S antibodies disclosed herein. In some embodiments, provided herein are nucleic acids comprising any one or more of the nucleic acid sequences of Tables 5A-5B. In some embodiments, the heavy chain and light chain variable domains of the Protein S antibodies disclosed herein are encoded by a nucleic acid comprising any one or more of the nucleic acid sequences of Tables 5A-5B.

In some embodiments, the variable domain of the Protein S antibodies of the disclosure are encoded by a nucleic acid, wherein the light chain variable domain of the antibody is encoded by the nucleic acid sequence of SEQ ID NO: 93 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 94, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 93 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 94, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 95 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 96, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 95 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 96, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 97 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 98, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 97 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 98, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 99 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 100, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 99 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 100, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 101 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 102, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 101 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 102, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 103 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 104, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 103 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 104, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 105 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 106, or a nucleic acid sequence with at least 80%, 81%, 82%, 83%, 84%, 85%, 86%, 87%, 88%, 89%, 90%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 105 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 106, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 111 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 112, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 111 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 112, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 113 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 114, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 113 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 114, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 115 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 116, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 115 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 116, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 162 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 163, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 162 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 163, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 164 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 165, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 164 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 165, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 166 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 167, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 166 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 167, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 170 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 171, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 170 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 171, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 172 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 173, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 172 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 173, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 178 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 183, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 178 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 183, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 188 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 193, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 188 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 193, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 198 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 203, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 198 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 203, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 208 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 213, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 208 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 213, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

The disclosure also provides vectors comprising any nucleic acid of the disclosure. In some embodiments, the nucleic acid of the vector comprises any one or more of the nucleic acid sequences provided in Tables 5A-5B. In some embodiments, the vector is an expression vector or an expression construct. In some embodiments, the vector is a mammalian vector. In some embodiments, the vector is a viral vector.

In some embodiments, the Protein S antibodies provided herein are produced by culturing a cell under suitable conditions for leading to the expression of the Protein S antibody, wherein the cell comprises a vector.

II. USES OF PROTEIN S ANTIBODIES

A. Therapeutic Protein S Antibodies

Provided herein are antibodies that recognize and selectively and/or specifically bind to Protein S, including Protein S fragments. The antibodies disclosed herein may be used for therapeutics in a subject. In some embodiments, the subject is a mammalian subject. In some embodiments, the mammalian subject is a human subject. In some embodiments, the mammalian subject is a non-human primate, e.g. a cynomolgus monkey.

In some embodiments, the Protein S antibodies provided herein are useful for treating a condition in a subject, wherein the condition is associated with the coagulation cascade. In some embodiments, the Protein S antibodies provided herein are useful for reducing an ability of Protein S to act as a cofactor within the coagulation cascade for the treatment of a condition in a subject.

In some embodiments, the Protein S antibodies provided herein are useful for reducing an ability of Protein S to act as a cofactor for APC, TFPI, or APC and TFPI for the treatment of a bleeding disorder or other diseases, e.g., a platelet disorder.

In some embodiments, provided herein is a method of promoting the coagulation of blood, the method comprising contacting any one of the Protein S antibodies disclosed herein with Protein S. In some embodiments, the contacting takes place in plasma. In some embodiments, the method is in vitro. In some embodiments, the method is in vivo. In some embodiments, the method is in vivo, and the method further comprises administering any one of the Protein S antibodies disclosed herein to a subject in need thereof.

In some embodiments, provided herein is a method of promoting the coagulation of blood, the method comprising contacting any one of the Protein S antibodies disclosed herein with a blood sample. Exemplary antibodies that may be used in a method for promoting the coagulation of blood include, but are not limited to, antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the coagulation of blood is marked by an increase in thrombin generation. Exemplary antibodies wherein use of the antibodies in the method for promoting the coagulation of blood, and wherein the coagulation of blood is marked by an increase in thrombin generation, include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the coagulation of blood is marked by an increase in fibrin generation. Exemplary antibodies wherein use of the antibodies in the method of promoting the coagulation of blood, and wherein the coagulation of blood is marked by an increase in fibrin generation include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the coagulation of blood is marked by an increase in D-dimer.

In some embodiments, the blood sample is obtained from a subject having a coagulation factor deficiency or von Willebrand disease (vWD), or a platelet disorder. In some embodiments, the vWD is a subtype selected from: vWD Type 1, vWD Type 2A, vWD Type 2B, vWD Type 2N, vWD Type 2M, vWD Type 3, and acquired vWD. Exemplary antibodies wherein use of the antibodies for a method for promoting coagulation of blood, and wherein the blood is a blood sample obtained from a subject having a coagulation factor deficiency (e.g. such as Factor VII deficiency, Factor VIII deficiency, Factor IX deficiency, Factor XI deficiency) or von Willebrand disease may comprise the light chain variable domain comprising the amino acid sequence of SEQ ID NO: 75 and the heavy chain variable domain comprising the amino acid sequence of SEQ ID NO: 76, or may comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60.

In some embodiments, provided herein is a method of promoting the coagulation of blood in a subject in need thereof, the method comprising administering to the subject any one of the Protein S antibodies disclosed herein, or any one of the pharmaceutical compositions disclosed herein. In some embodiments, the antibody remains active in the subject for a period of time, wherein the period of time is antibody dose-dependent. In some embodiments, the period of time is about 50 hours to about 170 hours. Exemplary antibodies wherein use of the antibodies for a method of promoting the coagulation of blood in a subject in need thereof, wherein the activity of the antibody is dose-dependent, may comprise the light chain variable domain comprising the amino acid sequence of SEQ ID NO: 71 and the heavy chain variable domain comprising the amino acid sequence of SEQ ID NO: 72, or may comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58.

In some embodiments, provided herein is a method of promoting generation of thrombin in a subject in need thereof, the method comprising administering to the subject any one of the Protein S antibodies disclosed herein, or any one of the pharmaceutical compositions disclosed herein. In some embodiments, the subject suffers from a disease or condition selected from the group consisting of bleeding disorders, and platelet disorders. In some embodiments, the subject suffers from trauma and/or bleeding resulting from a surgery or a medical procedure. For example, the medical procedure may be a procedure in which bleeding may occur, but not necessarily so. In some embodiments, the medical procedure is a dental procedure. Exemplary antibodies that may be used in a method of promoting generation of thrombin in a subject in need thereof may comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, or may comprise the amino acid sequence of SEQ ID NO: 75 and the heavy chain variable domain comprising the amino acid sequence of SEQ ID NO: 76, or may comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, or may comprise the amino acid sequence of SEQ ID NO: 69 and the heavy chain variable domain comprising the amino acid sequence of SEQ ID NO: 70, and may comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57.

In some embodiments, provided herein is a method of treating a condition in a subject in need thereof, wherein the disease is selected from the group consisting of bleeding disorders, and platelet disorders, and the method comprises administering to the subject any one of the Protein S antibodies disclosed herein, or any one of the pharmaceutical compositions disclosed herein. In some embodiments, the condition is a bleeding disorder. In some embodiments, the bleeding disorder is selected from the group consisting of hemophilia A, hemophilia B, von Willebrand disease (vWD, which may be a subtype selected from: vWD Type 1, vWD Type 2A, vWD Type 2B, vWD Type 2N, vWD Type 2M, vWD Type 3, and acquired vWD), menorrhagia including menorrhagia due to a congenital or acquired factor deficiency, Factor I deficiency, Factor II deficiency, Factor V deficiency, Factor VII deficiency, Factor X deficiency, Factor XI deficiency (hemophilia C), Factor VIII deficiency (hemophilia A), Factor IX deficiency (hemophilia B), trauma, and hereditary hemorrhagic telangiectasia. In some embodiments, the bleeding is associated with surgery, e.g. in a subject with a type of hemophilia. In some embodiments, the bleeding is associated with a medical procedure, e.g., a dental procedure. In some embodiments, the bleeding disorder is vWD, and the subject also suffers from menorrhagia. In some embodiments, the bleeding disorder is vWD, and the subject is undergoing a prophylactic treatment. In some embodiments, the subject suffers from menorrhagia associated with any one or more bleeding disorders and/or platelet disorders. In some embodiments, the subject is a hemophilia carrier. In some embodiments, the subject is a hemophilia carrier, and suffers from menorrhagia. In some embodiments, the condition is a platelet disorder. In some embodiments, the platelet disorder includes but is not limited to Bernard-Soulier syndrome, Glanzmann's thrombasthenia, and platelet storage pool deficiencies. In some embodiments, the platelet disorder is a platelet storage pool deficiency. In some embodiments, the platelet storage pool deficiency includes but is not limited to: Gray platelet syndrome, Quebec platelet disorder, and MYH9-related thrombocytopenia (MYH9RD). In some embodiments, the subject has a bleeding disorder, and has inhibitors. In some embodiments, the bleeding disorder is hemophilia A or hemophilia B, wherein the subject has inhibitors. In some embodiments, the bleeding disorder is vWD. For example, the inhibitors may be developed in the subject as a response to factor replacement therapy. Exemplary antibodies that may be used for a method of treating a condition in a subject in need thereof, wherein the disease is selected from the group consisting of bleeding disorders, and platelet disorders, include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, a subject in need thereof may be treated with any of the Protein S antibodies provided herein, wherein the treatment is a routine prophylaxis to prevent or reduce the frequency of bleeding episodes. In some embodiments, a subject in need thereof may be treated with any of the Protein S antibodies provided herein, wherein the treatment is an on-demand treatment used for the control of bleeding episodes. In some embodiments, a subject in need thereof may be treated with any of the Protein S antibodies provided herein, wherein the treatment is a perioperative management of bleeding. For example, a perioperative management treatment may be used for treating a subject prior to, during, and/or after surgery or other medical procedure, or prior to, during, and/or after trauma.

In some embodiments, the treatment with any of the Protein S antibodies provided herein is provided as a chronic therapy, with dosing occurring continuously over time. In some embodiments, the treatment with any of the Protein S antibodies provided herein is provided as an intermittent therapy, with dosing occurring at irregular intervals. As an example, such an intermittent therapy can be used for a subject having menorrhagia. In some embodiments, the treatment with any of the Protein S antibodies provided herein is provided as an acute therapy, with dosing occurring for a short finite period of time. For example, the acute therapy may be administered for spontaneous bleeding episodes, or in conjunction with a surgery or other medical procedure, or after experiencing a trauma.

In some embodiments, the method of treatment of a subject may be a combination one of the above, e.g., the method of treatment may be prophylactic, and on-demand. In some embodiments, a prophylactic method of treatment may be a chronic therapy. In some embodiments, a prophylactic method of treatment may be an acute therapy. In some embodiments, a prophylactic method of treatment may be an intermittent therapy. In some embodiments, an on-demand treatment may be an acute therapy. In some embodiments, an on-demand treatment may be an intermittent treatment.

In some embodiments, treatment of a subject in need thereof comprises administering to the subject any of the Protein S antibodies provided herein, wherein the Protein S antibodies provided herein are Fab fragments. Without being bound to any theory, in some embodiments a shorter half-life of a Fab fragment, in relation to a full-length antibody with the same VH/VL may be beneficial for an acute treatment or on-demand. In some embodiments, the Fab fragment Protein S antibodies are administered to a subject in need thereof to reduce risk of bleeding.

B. Combination Therapies

The administration of any one of the therapeutic Protein S antibodies provided herein may be a monotherapy, or may be in combination with any other known drugs or treatments for diseases or conditions. In some embodiments, the other known drugs or treatments are useful for treating disorders, diseases, or conditions associated with reduced or impaired clotting. In some embodiments, the disorder, condition is a bleeding disorder. In some embodiments, the disorder, disease, or condition is a bleeding disorder or a platelet disorder.

In some embodiments, the administration of any of the therapeutic Protein S antibodies provided herein may be with a factor replacement therapy. In some embodiments, the administration of any of the therapeutic Protein S antibodies provided herein may be with the administration of a recombinant Factor VII.

C. Administration of Therapeutic Protein S Antibodies

The in vivo administration of the therapeutic Protein S antibodies described herein may be carried out intravenously, intramuscularly, subcutaneously, topically, orally, transdermally, intraperitoneally, intraorbitally, intrathecally, intraventricularly, intranasally, transmucosally, through implantation, or through inhalation. Administration of the therapeutic Protein S antibodies may be performed with any suitable excipients, carriers, or other agents to provide suitable or improved tolerance, transfer, delivery, and the like.

In some embodiments, the in vivo administration of any of the therapeutic Protein S antibodies provided herein may be an intravenous administration. In some embodiments, the intravenous administration may be provided as a prophylactic treatment. In some embodiments, the prophylactic treatment may be a routine prophylaxis. In some embodiments, the routine prophylaxis may have a regular dosing schedule. In some exemplary embodiments, the regular dosing schedule may be once weekly, twice weekly, once monthly, twice monthly, or three times monthly. In some embodiments, the intravenous administration may be provided as an on-demand treatment. In some embodiments, the intravenous administration may be provided as a chronic therapy. In some embodiments, the intravenous administration may be provided as an intermittent therapy. In some embodiments, the intravenous administration may be provided as an acute therapy. In some embodiments, an intermittent therapy may have a regular dosing schedule for the duration of the intermittent therapy. In some embodiments, an acute therapy may have a regular dosing schedule for the duration of the acute therapy. For example, administration of any of the therapeutic Protein S antibodies provided herein for an acute therapy by intravenous administration may occur on a regular dosing schedule for a predetermined duration of days, e.g., 7 days, 14 days, or more. Exemplary antibodies that may be used for an in vivo intravenous administration include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the in vivo administration of any of the therapeutic Protein S antibodies provided herein may be a subcutaneous administration. In some embodiments, the subcutaneous administration may be provided as a prophylactic treatment. In some embodiments, the prophylactic treatment may be a routine prophylaxis. In some embodiments, the routine prophylaxis may have a regular dosing schedule. In some exemplary embodiments, the regular dosing schedule may be once weekly, twice weekly, once monthly, twice monthly, or three times monthly. In some embodiments, the subcutaneous administration may be provided as an on-demand treatment. In some embodiments, the subcutaneous administration may be provided as a chronic therapy. In some embodiments, the subcutaneous administration may be provided as an intermittent therapy. In some embodiments, the subcutaneous administration may be provided as an acute therapy. In some embodiments, an intermittent therapy may have a regular dosing schedule for the duration of the intermittent therapy. In some embodiments, an acute therapy may have a regular dosing schedule for the duration of the acute therapy. For example, administration of any of the therapeutic Protein S antibodies provided herein for an acute therapy by subcutaneous administration may occur on a regular dosing schedule for a predetermined duration of days, e.g., 7 days, 14 days, or more. Exemplary antibodies that may be used for an in vivo subcutaneous administration include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the Protein S antibodies provided herein may be provided in a small volume amenable for injection, such as for subcutaneous administration. In some embodiments, the Protein S antibodies provided herein may be provided in a small volume amenable for injection by use of a pen-like auto-injector device. In some embodiments, the device is a syringe, for example a pre-filled syringe.

In some embodiments provided herein are single-dose vials useful for either subcutaneous or intravenous administration.

Accordingly, a therapeutically effective amount of the Protein S antibodies provided herein may be provided in a small volume for subcutaneous administration to a subject in need thereof. In some embodiments, the Protein S antibodies provided herein may be provided in a large volume amenable for administration by a subcutaneous infusion device, for subcutaneous infusion to a subject in need thereof.

D. Pharmaceutical Compositions

The disclosure also provides pharmaceutical compositions comprising any one of the Protein S antibodies disclosed herein, and optionally a pharmaceutical acceptable excipient or carrier. In some embodiments, the pharmaceutical composition is sterile. The pharmaceutical compositions may be formulated to be compatible with their intended routes of administration. In some embodiments, the pharmaceutical compositions of the disclosure are suitable for administration to a human subject.

E. Diagnostic Antibodies

The antibodies provided herein may also be used for diagnostic purposes. For example, diagnostic antibodies could be used for detecting protein S deficiencies, or for detecting protein S levels in plasma prior to dosing (e.g. as a companion diagnostic).

Accordingly, in some embodiments, a Protein S antibody of the disclosure is conjugated to a label, for example a detectable label, a spin label, a colorimetric label, a radioactive label, an enzymatic label, a fluorescent label, or a magnetic label. The label may be detectable by spectroscopic, photochemical, biochemical, immunochemical, fluorescent, electrical, optical or chemical methods. Useful labels include, but are not limited to, magnetic beads (e.g. DYNABEADS®), fluorescent dyes (e.g., fluorescein isothiocyanate, red, rhodamine, and the like), radiolabels (e.g., 3H, 125I, 35S, 14C, or 32P), enzymes (e.g., LacZ, CAT, horseradish peroxidase, alkaline phosphatase and others, commonly used as detectable enzymes, either as marker gene products or in an ELISA), biotin, avidin, or streptavidin and colorimetric labels such as colloidal gold colored glass or plastic (e.g. polystyrene, polypropylene, latex, etc.) beads, and nanoparticles. In some embodiments, provided herein are substrates to which one or more Protein S antibodies of the disclosure is attached.

Detection may be carried out on any biological sample obtained from a subject. Biological samples include, but are not limited to whole blood, plasma, serum, saliva, urine, feces, synovial fluid, cerebrospinal fluid, bronchial lavage, ascites fluid, bone marrow aspirate, pleural effusion, tissue, cells, a biopsy, interstitial fluid, lymphatic fluid, or fractions thereof derived from a subject. In some embodiments, the biological sample comprises cells and the cells are in culture, in a suspension, on a slide, in intact tissue, or in preparation ready for a FACs analysis.

III. KITS AND ARTICLES OF MANUFACTURE

The disclosure also provides a kit or article of manufacture comprising any one of the antibodies disclosed herein, or any pharmaceutical composition disclosed herein. In some embodiments, the kits may further include instructional materials for carrying out any of the methods disclosed herein. In some embodiments, the kits may further include sterile containers or vials for holding the antibodies and/or pharmaceutical compositions disclosed herein. In some embodiments, the kits may further include sterile delivery devices for administering the antibodies and/or pharmaceutical compositions disclosed herein. In some embodiments, an article of manufacture comprises any pharmaceutical composition of the disclosure.

IV. EXEMPLARY ENUMERATED EMBODIMENTS

Exemplary enumerated embodiments of the disclosure are as follows.

1. An antibody that binds Protein S, wherein the antibody is an inhibitor of the cofactor activity of Protein S for activated Protein C (APC), an inhibitor of the cofactor activity of Protein S for tissue factor pathway inhibitor (TFPI), or an inhibitor of the cofactor activity of Protein S for both APC and TFPI, and wherein the antibody is human, humanized, or chimeric.
2. An antibody that binds Protein S, wherein the antibody is capable of promoting coagulation and/or modulating a component in the coagulation cascade.
3. The antibody of any one of Enumerated Embodiments 1-2, wherein the antibody is an inhibitor for the cofactor activity of Protein S for APC.
4. The antibody of any one of Enumerated Embodiments 1-2, wherein the antibody is an inhibitor for the cofactor activity of Protein S for TFPI.
5. The antibody of any one of Enumerated Embodiments 1-2, wherein the antibody is an inhibitor for the cofactor activity of Protein S for both APC and TFPI.
6. The antibody of Enumerated Embodiment 3, wherein the capability of the antibody for inhibiting the cofactor activity of Protein S for TFPI is negligible.

7. The antibody of Enumerated Embodiment 4, wherein the capability of the antibody for inhibiting the cofactor activity of Protein S for APC is negligible.
8. The antibody of any one of Enumerated Embodiments 1-7, wherein the antibody binds to the C-terminus of Protein S.
9. The antibody of any one of Enumerated Embodiments 1-7, wherein the antibody binds to the N-terminus of Protein S.
10. The antibody of any one of Enumerated Embodiments 1-9, wherein the antibody binds to a thrombin-sensitive region of the Protein S.
11. The antibody of any one of Enumerated Embodiments 1-9, wherein the antibody binds to an EGF region of the Protein S.
12. The antibody of any one of Enumerated Embodiments 1-9, wherein the antibody binds to an SHBG region of Protein S.
13. The antibody of any one of Enumerated Embodiments 1-12, wherein the antibody is capable of promoting generation of a marker associated with coagulation activity.
14. The antibody of any one of Enumerated Embodiments 1-13, wherein the antibody is capable of promoting thrombin generation.
15. The antibody of any one of Enumerated Embodiments 1-14, wherein the antibody is capable of promoting D-dimer levels.
16. The antibody of any one of Enumerated Embodiments 1-15, wherein the antibody is capable of promoting fibrin generation.
17. The antibody of any one of Enumerated Embodiments 1-16, wherein activity of the antibody is dose-dependent.
18. The antibody of any one of Enumerated Embodiments 1-17, wherein activity of the antibody is measured in vitro.
19. The antibody of any one of Enumerated Embodiments 1-17, wherein activity of the antibody is measured in vivo.
20. The antibody of any one of Enumerated Embodiments 1-19, wherein the binding affinity of the antibody to Protein S is calcium-dependent.
21. The antibody of any one of Enumerated Embodiments 1-19, wherein the binding affinity of the antibody to Protein S is calcium-independent.
22. The antibody of any one of Enumerated Embodiments 1-21, wherein the antibody binds to free Protein S.
23. The antibody of any one of Enumerated Embodiments 1-21, wherein the antibody binds to complexed Protein S.
24. The antibody of Enumerated Embodiment 23, wherein the Protein S is complexed with C4BP.
25. The antibody of Enumerated Embodiment 23, wherein the Protein S is complexed with TFPI.
26. The antibody of any one of Enumerated Embodiments 1-25, wherein the antibody is a monoclonal antibody.
27. The antibody of any one of Enumerated Embodiments 1-26, wherein the antibody is a full-length antibody.
28. The antibody of any one of Enumerated Embodiments 1-26, wherein the antibody is an antibody fragment.
29. The antibody of any one of Enumerated Embodiments 1-28, wherein the antibody is a humanized antibody.
30. The antibody of any of Enumerated Embodiments 1-29, wherein the antibody comprises a Fc domain.
31. The antibody of Enumerated Embodiment 30, wherein the Fc domain is human.
32. The antibody of Enumerated Embodiment 31, wherein the human Fc domain is IgG1, IgG2, IgG3, or IgG4.
33. The antibody of Enumerated Embodiment 32, wherein the Fc domain of the antibody is human IgG4, optionally SEQ ID NO: 218, and comprises at least one amino acid substitution at a position selected from the group consisting of: 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 396, 428, 430, 433, 434, and 440, or comprises one or more of the substitutions selected from the group consisting of T250Q/M428L, M252Y/S254T/T256E, M428LN434S, S267E/L328F, N325S/L328F, and H433K/N434F, wherein the position numbers of the amino acid residues are of the EU numbering scheme.
34. The antibody of Enumerated Embodiment 27, wherein the antibody is a human antibody.
35. The antibody of Enumerated Embodiment 27, wherein the antibody is a chimeric antibody.
36. The antibody of any one of Enumerated Embodiments 1-35, wherein the antibody is conjugated.
37. The antibody of Enumerated Embodiment 36, wherein the antibody is conjugated to a label.
38. The antibody of any one of Enumerated Embodiments 1-37, wherein the antibody comprises any one or more of the amino acid sequences of the CDR sequences provided in Tables 1A, 1B, 1C, 2A, 2B, and 2C.
39. The Protein S antibody of any one of Enumerated Embodiments 1-38, wherein the antibody comprises:
(a) any one of the CDR-L1 amino acid sequences of Table 1A;
(b) any one of the CDR-L2 amino acid sequences of Table 1B;
(c) any one of the CDR-L3 amino acid sequences of Table 1C;
(d) any one of the CDR-H1 amino acid sequences of Table 2A;
(e) any one of the CDR-H2 amino acid sequences of Table 2B; and
(f) any one of the CDR-H3 amino acid sequences of Table 2C.
40. The Protein S antibody of any one of Enumerated Embodiments 1-39, wherein the light chain variable domain of the antibody comprises:
(a) a CDR-L1 comprising the amino acid sequence of any one of SEQ ID NOs: 1-6, 9-11, 117, 127, 136, 141, 174, 184, 194, and 204;
(b) a CDR-L2 comprising the amino acid sequence of any one of SEQ ID NOs: 12-20, 118, 128, 142, 175, 185, 195, and 205; and
(c) a CDR-L3 comprising the amino acid sequence of any one of SEQ ID NOs: 21-27, 30-32, 119, 123, 129, 137, 143, 176, 186, 196, and 206.
41. The Protein S antibody of any one of Enumerated Embodiments 1-40, wherein the heavy chain variable domain of antibody comprises:
(a) a CDR-H1 comprising the amino acid sequence of any one of SEQ ID NOs: 33-39, 42-44, 120, 124, 130, 138, 144, 179, 189, 199, and 209;
(b) a CDR-H2 comprising the amino acid sequence of any one of SEQ ID NOs: 45-51, 54-56, 121, 125, 139, 145, 180, 190, 200, and 210; and
(c) a CDR-H3 comprising the amino acid sequence of any one of SEQ ID NOs: 57-63, 66-68, 122, 126, 131, 140, 146, 181, 191, 201, and 211.

42. The Protein S antibody of any one of Enumerated Embodiments 1-41, wherein the light chain variable domain of the antibody comprises:
(a) a CDR-L1 comprising the amino acid sequence of SEQ ID NO: 1;
(b) a CDR-L2 comprising the amino acid sequence of SEQ ID NO: 12; and
(c) a CDR-L3 comprising the amino acid sequence of SEQ ID NO: 21.

43. The Protein S antibody of any one of Enumerated Embodiments 1-41, wherein the light chain variable domain of the antibody comprises:
(a) a CDR-L1 comprising the amino acid sequence of SEQ ID NO: 2;
(b) a CDR-L2 comprising the amino acid sequence of SEQ ID NO: 13; and
(c) a CDR-L3 comprising the amino acid sequence of SEQ ID NO: 22.

44. The Protein S antibody of any one of Enumerated Embodiments 1-41, wherein the light chain variable domain of the antibody comprises:
(a) a CDR-L1 comprising the amino acid sequence of SEQ ID NO: 3;
(b) a CDR-L2 comprising the amino acid sequence of SEQ ID NO: 14; and
(c) a CDR-L3 comprising the amino acid sequence of SEQ ID NO: 23.

45. The Protein S antibody of any one of Enumerated Embodiments 1-41, wherein the light chain variable domain of the antibody comprises:
(a) a CDR-L1 comprising the amino acid sequence of SEQ ID NO: 1;
(b) a CDR-L2 comprising the amino acid sequence of SEQ ID NO: 15; and
(c) a CDR-L3 comprising the amino acid sequence of SEQ ID NO: 24.

46. The Protein S antibody of any one of Enumerated Embodiments 1-41, wherein the light chain variable domain of the antibody comprises:
(a) a CDR-L1 comprising the amino acid sequence of SEQ ID NO: 4;
(b) a CDR-L2 comprising the amino acid sequence of SEQ ID NO: 16; and
(c) a CDR-L3 comprising the amino acid sequence of SEQ ID NO: 25.

47. The Protein S antibody of any one of Enumerated Embodiments 1-41, wherein the light chain variable domain of the antibody comprises:
(a) a CDR-L1 comprising the amino acid sequence of SEQ ID NO: 5;
(b) a CDR-L2 comprising the amino acid sequence of SEQ ID NO: 17; and
(c) a CDR-L3 comprising the amino acid sequence of SEQ ID NO: 26.

48. The Protein S antibody of any one of Enumerated Embodiments 1-41, wherein the light chain variable domain of the antibody comprises:
(a) a CDR-L1 comprising the amino acid sequence of SEQ ID NO: 6;
(b) a CDR-L2 comprising the amino acid sequence of SEQ ID NO: 18; and
(c) a CDR-L3 comprising the amino acid sequence of SEQ ID NO: 27.

49. The Protein S antibody of any one of Enumerated Embodiments 1-41, wherein the light chain variable domain of the antibody comprises:
(a) a CDR-L1 comprising the amino acid sequence of SEQ ID NO: 9;
(b) a CDR-L2 comprising the amino acid sequence of SEQ ID NO: 19; and
(c) a CDR-L3 comprising the amino acid sequence of SEQ ID NO: 30.

50. The Protein S antibody of any one of Enumerated Embodiments 1-41, wherein the light chain variable domain of the antibody comprises:
(a) a CDR-L1 comprising the amino acid sequence of SEQ ID NO: 10;
(b) a CDR-L2 comprising the amino acid sequence of SEQ ID NO: 16; and
(c) a CDR-L3 comprising the amino acid sequence of SEQ ID NO: 31.

51. The Protein S antibody of any one of Enumerated Embodiments 1-41, wherein the light chain variable domain of the antibody comprises:
(a) a CDR-L1 comprising the amino acid sequence of SEQ ID NO: 11;
(b) a CDR-L2 comprising the amino acid sequence of SEQ ID NO: 20; and
(c) a CDR-L3 comprising the amino acid sequence of SEQ ID NO: 32.

52. The Protein S antibody of any one of Enumerated Embodiments 1-41, wherein the light chain variable domain of the antibody comprises:
(a) a CDR-L1 comprising the amino acid sequence of SEQ ID NO: 117;
(b) a CDR-L2 comprising the amino acid sequence of SEQ ID NO: 118; and
(c) a CDR-L3 comprising the amino acid sequence of SEQ ID NO: 119.

53. The Protein S antibody of any one of Enumerated Embodiments 1-41, wherein the light chain variable domain of the antibody comprises:
(a) a CDR-L1 comprising the amino acid sequence of SEQ ID NO: 117;
(b) a CDR-L2 comprising the amino acid sequence of SEQ ID NO: 118; and
(c) a CDR-L3 comprising the amino acid sequence of SEQ ID NO: 123.

54. The Protein S antibody of any one of Enumerated Embodiments 1-41, wherein the light chain variable domain of the antibody comprises:
(a) a CDR-L1 comprising the amino acid sequence of SEQ ID NO: 127;
(b) a CDR-L2 comprising the amino acid sequence of SEQ ID NO: 128; and
(c) a CDR-L3 comprising the amino acid sequence of SEQ ID NO: 129.

55. The Protein S antibody of any one of Enumerated Embodiments 1-41, wherein the light chain variable domain of the antibody comprises:
(a) a CDR-L1 comprising the amino acid sequence of SEQ ID NO: 136;
(b) a CDR-L2 comprising the amino acid sequence of SEQ ID NO: 17; and
(c) a CDR-L3 comprising the amino acid sequence of SEQ ID NO: 137.

56. The Protein S antibody of any one of Enumerated Embodiments 1-41, wherein the light chain variable domain of the antibody comprises:
(a) a CDR-L1 comprising the amino acid sequence of SEQ ID NO: 141;
(b) a CDR-L2 comprising the amino acid sequence of SEQ ID NO: 142; and (c) a CDR-L3 comprising the amino acid sequence of SEQ ID NO: 143.

57. The Protein S antibody of any one of Enumerated Embodiments 1-41, wherein the light chain variable domain of the antibody comprises:

(a) a CDR-L1 comprising the amino acid sequence of SEQ ID NO: 174;

(b) a CDR-L2 comprising the amino acid sequence of SEQ ID NO: 175; and (c) a CDR-L3 comprising the amino acid sequence of SEQ ID NO: 176.

58. The Protein S antibody of any one of Enumerated Embodiments 1-41, wherein the light chain variable domain of the antibody comprises:

(a) a CDR-L1 comprising the amino acid sequence of SEQ ID NO: 184;

(b) a CDR-L2 comprising the amino acid sequence of SEQ ID NO: 185; and (c) a CDR-L3 comprising the amino acid sequence of SEQ ID NO: 186.

59. The Protein S antibody of any one of Enumerated Embodiments 1-41, wherein the light chain variable domain of the antibody comprises:

(a) a CDR-L1 comprising the amino acid sequence of SEQ ID NO: 194;

(b) a CDR-L2 comprising the amino acid sequence of SEQ ID NO: 195; and (c) a CDR-L3 comprising the amino acid sequence of SEQ ID NO: 196.

60. The Protein S antibody of any one of Enumerated Embodiments 1-41, wherein the light chain variable domain of the antibody comprises:

(a) a CDR-L1 comprising the amino acid sequence of SEQ ID NO: 204;

(b) a CDR-L2 comprising the amino acid sequence of SEQ ID NO: 205; and (c) a CDR-L3 comprising the amino acid sequence of SEQ ID NO: 206.

61. The Protein S antibody of any one of Enumerated Embodiments 1-60, wherein the heavy chain variable domain of the antibody comprises:

(a) a CDR-H1 comprising the amino acid sequence of SEQ ID NO: 33;

(b) a CDR-H2 comprising the amino acid sequence of SEQ ID NO: 45; and (c) a CDR-H3 comprising the amino acid sequence of SEQ ID NO: 57.

62. The Protein S antibody of any one of Enumerated Embodiments 1-60, wherein the heavy chain variable domain of the antibody comprises:

(a) a CDR-H1 comprising the amino acid sequence of SEQ ID NO: 34;

(b) a CDR-H2 comprising the amino acid sequence of SEQ ID NO: 46; and (c) a CDR-H3 comprising the amino acid sequence of SEQ ID NO: 58.

63. The Protein S antibody of any one of Enumerated Embodiments 1-60, wherein the heavy chain variable domain of the antibody comprises:

(a) a CDR-H1 comprising the amino acid sequence of SEQ ID NO: 35;

(b) a CDR-H2 comprising the amino acid sequence of SEQ ID NO: 47; and (c) a CDR-H3 comprising the amino acid sequence of SEQ ID NO: 59.

64. The Protein S antibody of any one of Enumerated Embodiments 1-60, wherein the heavy chain variable domain of the antibody comprises:

(a) a CDR-H1 comprising the amino acid sequence of SEQ ID NO: 36;

(b) a CDR-H2 comprising the amino acid sequence of SEQ ID NO: 48; and (c) a CDR-H3 comprising the amino acid sequence of SEQ ID NO: 60.

65. The Protein S antibody of any one of Enumerated Embodiments 1-60, wherein the heavy chain variable domain of the antibody comprises:

(a) a CDR-H1 comprising the amino acid sequence of SEQ ID NO: 37;

(b) a CDR-H2 comprising the amino acid sequence of SEQ ID NO: 49; and (c) a CDR-H3 comprising the amino acid sequence of SEQ ID NO: 61.

66. The Protein S antibody of any one of Enumerated Embodiments 1-60, wherein the heavy chain variable domain of the antibody comprises:

(a) a CDR-H1 comprising the amino acid sequence of SEQ ID NO: 38;

(b) a CDR-H2 comprising the amino acid sequence of SEQ ID NO: 50; and (c) a CDR-H3 comprising the amino acid sequence of SEQ ID NO: 62.

67. The Protein S antibody of any one of Enumerated Embodiments 1-60, wherein the heavy chain variable domain of the antibody comprises:

(a) a CDR-H1 comprising the amino acid sequence of SEQ ID NO: 39;

(b) a CDR-H2 comprising the amino acid sequence of SEQ ID NO: 51; and (c) a CDR-H3 comprising the amino acid sequence of SEQ ID NO: 63.

68. The Protein S antibody of any one of Enumerated Embodiments 1-60, wherein the heavy chain variable domain of the antibody comprises:

(a) a CDR-H1 comprising the amino acid sequence of SEQ ID NO: 42;

(b) a CDR-H2 comprising the amino acid sequence of SEQ ID NO: 54; and (c) a CDR-H3 comprising the amino acid sequence of SEQ ID NO: 66.

69. The Protein S antibody of any one of Enumerated Embodiments 1-60, wherein the heavy chain variable domain of the antibody comprises:

(a) a CDR-H1 comprising the amino acid sequence of SEQ ID NO: 43;

(b) a CDR-H2 comprising the amino acid sequence of SEQ ID NO: 55; and (c) a CDR-H3 comprising the amino acid sequence of SEQ ID NO: 67.

70. The Protein S antibody of any one of Enumerated Embodiments 1-60, wherein the heavy chain variable domain of the antibody comprises:

(a) a CDR-H1 comprising the amino acid sequence of SEQ ID NO: 44;

(b) a CDR-H2 comprising the amino acid sequence of SEQ ID NO: 56; and (c) a CDR-H3 comprising the amino acid sequence of SEQ ID NO: 68.

71. The Protein S antibody of any one of Enumerated Embodiments 1-60, wherein the heavy chain variable domain of the antibody comprises:

(a) a CDR-H1 comprising the amino acid sequence of SEQ ID NO: 120;

(b) a CDR-H2 comprising the amino acid sequence of SEQ ID NO: 121; and (c) a CDR-H3 comprising the amino acid sequence of SEQ ID NO: 122.

72. The Protein S antibody of any one of Enumerated Embodiments 1-60, wherein the heavy chain variable domain of the antibody comprises:

(a) a CDR-H1 comprising the amino acid sequence of SEQ ID NO: 124;

(b) a CDR-H2 comprising the amino acid sequence of SEQ ID NO: 125; and (c) a CDR-H3 comprising the amino acid sequence of SEQ ID NO: 126.

73. The Protein S antibody of any one of Enumerated Embodiments 1-60, wherein the heavy chain variable domain of the antibody comprises:

(a) a CDR-H1 comprising the amino acid sequence of SEQ ID NO: 130;

(b) a CDR-H2 comprising the amino acid sequence of SEQ ID NO: 50; and (c) a CDR-H3 comprising the amino acid sequence of SEQ ID NO: 131.

74. The Protein S antibody of any one of Enumerated Embodiments 1-60, wherein the heavy chain variable domain of the antibody comprises:

(a) a CDR-H1 comprising the amino acid sequence of SEQ ID NO: 138;

(b) a CDR-H2 comprising the amino acid sequence of SEQ ID NO: 139; and (c) a CDR-H3 comprising the amino acid sequence of SEQ ID NO: 140.

75. The Protein S antibody of any one of Enumerated Embodiments 1-60, wherein the heavy chain variable domain of the antibody comprises:

(a) a CDR-H1 comprising the amino acid sequence of SEQ ID NO: 144;

(b) a CDR-H2 comprising the amino acid sequence of SEQ ID NO: 145; and (c) a CDR-H3 comprising the amino acid sequence of SEQ ID NO: 146.

76. The Protein S antibody of any one of Enumerated Embodiments 1-60, wherein the heavy chain variable domain of the antibody comprises:

(a) a CDR-H1 comprising the amino acid sequence of SEQ ID NO: 179;

(b) a CDR-H2 comprising the amino acid sequence of SEQ ID NO: 180; and (c) a CDR-H3 comprising the amino acid sequence of SEQ ID NO: 181.

77. The Protein S antibody of any one of Enumerated Embodiments 1-60, wherein the heavy chain variable domain of the antibody comprises:

(a) a CDR-H1 comprising the amino acid sequence of SEQ ID NO: 189;

(b) a CDR-H2 comprising the amino acid sequence of SEQ ID NO: 190; and (c) a CDR-H3 comprising the amino acid sequence of SEQ ID NO: 191.

78. The Protein S antibody of any one of Enumerated Embodiments 1-60, wherein the heavy chain variable domain of the antibody comprises:

(a) a CDR-H1 comprising the amino acid sequence of SEQ ID NO: 199;

(b) a CDR-H2 comprising the amino acid sequence of SEQ ID NO: 200; and (c) a CDR-H3 comprising the amino acid sequence of SEQ ID NO: 201.

79. The Protein S antibody of any one of Enumerated Embodiments 1-60, wherein the heavy chain variable domain of the antibody comprises:

(a) a CDR-H1 comprising the amino acid sequence of SEQ ID NO: 209;

(b) a CDR-H2 comprising the amino acid sequence of SEQ ID NO: 210; and (c) a CDR-H3 comprising the amino acid sequence of SEQ ID NO: 211.

80. The Protein S antibody of any one of Enumerated Embodiments 1-41, wherein the antibody comprises the light and heavy CDR amino acid sequences of SEQ ID NO: 1, SEQ ID NO: 12, SEQ ID NO: 21, SEQ ID NO: 33, SEQ ID NO: 45, and SEQ ID NO: 57.

81. The Protein S antibody of any one of Enumerated Embodiments 1-41, wherein the antibody comprises the light and heavy CDR amino acid sequences of SEQ ID NO: 2, SEQ ID NO: 13, SEQ ID NO: 22, SEQ ID NO: 34, SEQ ID NO: 46, and SEQ ID NO: 58.

82. The Protein S antibody of any one of Enumerated Embodiments 1-41, wherein the antibody comprises the light and heavy CDR amino acid sequences of SEQ ID NO: 3, SEQ ID NO: 14, SEQ ID NO: 23, SEQ ID NO: 35, SEQ ID NO: 47, and SEQ ID NO: 59.

83. The Protein S antibody of any one of Enumerated Embodiments 1-41, wherein the antibody comprises the light and heavy CDR amino acid sequences of SEQ ID NO: 1, SEQ ID NO: 15, SEQ ID NO: 24, SEQ ID NO: 36, SEQ ID NO: 48, and SEQ ID NO: 60.

84. The Protein S antibody of any one of Enumerated Embodiments 1-41, wherein the antibody comprises the light and heavy amino acid sequences of SEQ ID NO: 4, SEQ ID NO: 16, SEQ ID NO: 25, SEQ ID NO: 37, SEQ ID NO: 49, and SEQ ID NO: 61.

85. The Protein S antibody of any one of Enumerated Embodiments 1-41, wherein the antibody comprises the light and heavy CDR amino acid sequences of SEQ ID NO: 5, SEQ ID NO: 17, SEQ ID NO: 26, SEQ ID NO: 38, SEQ ID NO: 50, and SEQ ID NO: 62.

86. The Protein S antibody of any one of Enumerated Embodiments 1-41, wherein the antibody comprises the light and heavy CDR amino acid sequences of SEQ ID NO: 6, SEQ ID NO: 18, SEQ ID NO: 27, SEQ ID NO: 39, SEQ ID NO: 51, and SEQ ID NO: 63.

87. The Protein S antibody of any one of Enumerated Embodiments 1-41, wherein the antibody comprises the light and heavy CDR amino acid sequences of SEQ ID NO: 9, SEQ ID NO: 19, SEQ ID NO: 30, SEQ ID NO: 42, SEQ ID NO: 54, and SEQ ID NO: 66.

88. The Protein S antibody of any one of Enumerated Embodiments 1-41, wherein the antibody comprises the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

89. The Protein S antibody of any one of Enumerated Embodiments 1-41, wherein the antibody comprises the light and heavy CDR amino acid sequences of SEQ ID NO: 11, SEQ ID NO: 20, SEQ ID NO: 32, SEQ ID NO: 44, SEQ ID NO: 56, and SEQ ID NO: 68.

90. The Protein S antibody of any one of Enumerated Embodiments 1-41, wherein the antibody comprises the light and heavy CDR amino acid sequences of SEQ ID NO: 117, SEQ ID NO: 118, SEQ ID NO: 119, SEQ ID NO: 120, SEQ ID NO: 121, and SEQ ID NO: 122.

91. The Protein S antibody of any one of Enumerated Embodiments 1-41, wherein the antibody comprises the light and heavy CDR amino acid sequences of SEQ ID NO: 117, SEQ ID NO: 118, SEQ ID NO: 123, SEQ ID NO: 124, SEQ ID NO: 125, and SEQ ID NO: 126.
92. The Protein S antibody of any one of Enumerated Embodiments 1-41, wherein the antibody comprises the light and heavy CDR amino acid sequences of SEQ ID NO: 127, SEQ ID NO: 128, SEQ ID NO: 129, SEQ ID NO: 130, SEQ ID NO: 50, and SEQ ID NO: 131.
93. The Protein S antibody of any one of Enumerated Embodiments 1-41, wherein the antibody comprises the light and heavy CDR amino acid sequences of SEQ ID NO: 136, SEQ ID NO: 17, SEQ ID NO: 137, SEQ ID NO: 138, SEQ ID NO: 139, and SEQ ID NO: 140.
94. The Protein S antibody of any one of Enumerated Embodiments 1-41, wherein the antibody comprises the light and heavy CDR amino acid sequences of SEQ ID NO: 141, SEQ ID NO: 142, SEQ ID NO: 143, SEQ ID NO: 144, SEQ ID NO: 145, and SEQ ID NO: 146.
95. The Protein S antibody of any one of Enumerated Embodiments 1-41, wherein the antibody comprises the light and heavy CDR amino acid sequences of SEQ ID NO: 174, SEQ ID NO: 175, SEQ ID NO: 176, SEQ ID NO: 179, SEQ ID NO: 180, and SEQ ID NO: 181.
96. The Protein S antibody of any one of Enumerated Embodiments 1-41, wherein the antibody comprises the light and heavy CDR amino acid sequences of SEQ ID NO: 184, SEQ ID NO: 185, SEQ ID NO: 186, SEQ ID NO: 189, SEQ ID NO: 190, and SEQ ID NO: 191.
97. The Protein S antibody of any one of Enumerated Embodiments 1-41, wherein the antibody comprises the light and heavy CDR amino acid sequences of SEQ ID NO: 194, SEQ ID NO: 195, SEQ ID NO: 196, SEQ ID NO: 199, SEQ ID NO: 200, and SEQ ID NO: 201.
98. The Protein S antibody of any one of Enumerated Embodiments 1-41, wherein the antibody comprises the light and heavy CDR amino acid sequences of SEQ ID NO: 204, SEQ ID NO: 205, SEQ ID NO: 206, SEQ ID NO: 209, SEQ ID NO: 210, and SEQ ID NO: 211.
99. The Protein S antibody of any one of Enumerated Embodiments 1-98, wherein the antibody comprises the variable chain amino acid sequence of any one of the amino acid sequences provided in Table 4A, and/or the variable chain amino acid sequence of any one of the amino acid sequences provided in Table 4B.
100. The Protein S antibody of any one of Enumerated Embodiments 1-99, wherein the antibody comprises the light and heavy variable chain amino acid sequence of any one of the amino acid sequence combinations provided in Table 4C.
101. The Protein S antibody of any one of Enumerated Embodiments 1-100, wherein the light chain variable domain of the antibody comprises the amino acid sequence of SEQ ID NO: 69 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and wherein the heavy chain variable domain of the antibody comprises the amino acid sequence of SEQ ID NO: 70, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.
102. The Protein S antibody of one of Enumerated Embodiments 1-100, wherein the light chain variable domain of the antibody comprises the amino acid sequence of SEQ ID NO: 71 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 72, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.
103. The Protein S antibody of any one of Enumerated Embodiments 1-100, wherein the light chain variable domain of the antibody comprises the amino acid sequence of SEQ ID NO: 73 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 74, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.
104. The Protein S antibody of any one of Enumerated Embodiments 1-100, wherein the light chain variable domain of the antibody comprises the amino acid sequence of SEQ ID NO: 75 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 76, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.
105. The Protein S antibody of any one of Enumerated Embodiments 1-100, wherein the light chain variable domain of the antibody comprises the amino acid sequence of SEQ ID NO: 77 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 78, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.
106. The Protein S antibody of any one of Enumerated Embodiments 1-100, wherein the light chain variable domain of the antibody comprises the amino acid sequence of SEQ ID NO: 79 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 80, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.
107. The Protein S antibody of any one of Enumerated Embodiments 1-100, wherein the light chain variable domain of the antibody comprises the amino acid sequence of SEQ ID NO: 81 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 82, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

108. The Protein S antibody of any one of Enumerated Embodiments 1-100, wherein the light chain variable domain of the antibody comprises the amino acid sequence of SEQ ID NO: 87 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 88, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

109. The Protein S antibody of any one of Enumerated Embodiments 1-100, wherein the light chain variable domain of the antibody comprises In some embodiments, provided herein are Protein S antibodies, wherein the light chain variable domain of the antibodies comprise the amino acid sequence of SEQ ID NO: 89 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 90, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

110. The Protein S antibody of any one of Enumerated Embodiments 1-100, wherein the light chain variable domain of the antibody comprises the amino acid sequence of SEQ ID NO: 91 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 92, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

111. The Protein S antibody of any one of Enumerated Embodiments 1-100, wherein the light chain variable domain of the antibody comprises the amino acid sequence of SEQ ID NO: 148 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 149, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

112. The Protein S antibody of any one of Enumerated Embodiments 1-100, wherein the light chain variable domain of the antibody comprises the amino acid sequence of SEQ ID NO: 150 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 151, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

113. The Protein S antibody of any one of Enumerated Embodiments 1-100, wherein the light chain variable domain of the antibody comprises the amino acid sequence of SEQ ID NO: 152 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 153, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

114. The Protein S antibody of any one of Enumerated Embodiments 1-100, wherein the light chain variable domain of the antibody comprises the amino acid sequence of SEQ ID NO: 156 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 157, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

115. The Protein S antibody of any one of Enumerated Embodiments 1-100, wherein the light chain variable domain of the antibody comprises the amino acid sequence of SEQ ID NO: 158 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 159, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

116. The Protein S antibody of any one of Enumerated Embodiments 1-100, wherein the light chain variable domain of the antibody comprises the amino acid sequence of SEQ ID NO: 177 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 182, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

117. The Protein S antibody of any one of Enumerated Embodiments 1-100, wherein the light chain variable domain of the antibody comprises the amino acid sequence of SEQ ID NO: 187 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 192, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

118. The Protein S antibody of any one of Enumerated Embodiments 1-41, wherein the light chain variable domain of the antibody comprises the amino acid sequence of SEQ ID NO: 197 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 202, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

119. The Protein S antibody of any one of Enumerated Embodiments 1-100, wherein the light chain variable domain of the antibody comprises the amino acid sequence of SEQ ID NO: 207 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 212, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

120. The Protein S antibody of any one of Enumerated Embodiments 1-119, wherein the light chain comprises the amino acid sequence of SEQ ID NO: 214.

121. The Protein S antibody of any one of Enumerated Embodiments 1-119, wherein the light chain comprises the amino acid sequence of SEQ ID NO: 215.

122. A pharmaceutical composition comprising any one of the antibodies of Enumerated Embodiments 1-121, and optionally a pharmaceutically acceptable excipient.

123. A complex comprising Protein S and the antibody of any one of Enumerated Embodiments 1-119, wherein the antibody is bound to the Protein S, and the Protein S is free.

124. A complex comprising Protein S and the antibody of any one of Enumerated Embodiments 1-119, wherein the antibody is bound to the Protein S, and the Protein S is complexed.

125. The complex of Enumerated Embodiment 124, wherein the Protein S is bound to C4BP.

126. The complex of Enumerated Embodiment 124, wherein the Protein S is bound to TFPI.

127. A nucleic acid encoding for any one of the antibodies of Enumerated Embodiments 1-121.

128. The nucleic acid of Enumerated Embodiment 127, comprising any one of the nucleic acid sequences selected from Table 5A.

129. The nucleic acid of any one of Enumerated Embodiments 127-128, comprising any one of the nucleic acid sequences selected from Table 5B.

130. The nucleic acid of any one of Enumerated Embodiments 127-129, wherein the nucleic acid comprises the nucleic acid sequence of any one of the nucleic acid sequence combinations provided in Table 5C.

131. The nucleic acid of any one of Enumerated Embodiments 127-130, wherein the light chain variable domain of the Protein S antibody is encoded by the nucleic acid sequence of SEQ ID NO: 93 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 94, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

132. The nucleic acid of any one of Enumerated Embodiments 127-130, wherein the light chain variable domain of the Protein S antibody is encoded by the nucleic acid sequence of SEQ ID NO: 95 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 96, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

133. The nucleic acid of any one of Enumerated Embodiments 127-130, wherein the light chain variable domain of the Protein S antibody is encoded by the nucleic acid sequence of SEQ ID NO: 97 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 98, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

134. The nucleic acid of any one of Enumerated Embodiments 127-130, wherein the light chain variable domain of the Protein S antibody is encoded by the nucleic acid sequence of SEQ ID NO: 99 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 100, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

135. The nucleic acid of any one of Enumerated Embodiments 127-130, wherein the light chain variable domain of the Protein S antibody is encoded by the nucleic acid sequence of SEQ ID NO: 101 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 102, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

136. The nucleic acid of any one of Enumerated Embodiments 127-130, wherein the light chain variable domain of the Protein S antibody is encoded by the nucleic acid sequence of SEQ ID NO: 103 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 104, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

137. The nucleic acid of any one of Enumerated Embodiments 127-130, wherein the light chain variable domain of the Protein S antibody is encoded by the nucleic acid sequence of SEQ ID NO: 105 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 106, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

138. The nucleic acid of any one of Enumerated Embodiments 127-130, wherein the light chain variable domain of the Protein S antibody is encoded by the nucleic acid sequence of SEQ ID NO: 111 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 112, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

139. The nucleic acid of any one of Enumerated Embodiments 127-130, wherein the light chain variable domain of the Protein S antibody is encoded by the nucleic acid sequence of SEQ ID NO: 113 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 114, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

140. The nucleic acid of any one of Enumerated Embodiments 127-130, wherein the light chain variable domain of the Protein S antibody is encoded by the nucleic acid sequence of SEQ ID NO: 115 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 116, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

141. The nucleic acid of any one of Enumerated Embodiments 127-130, wherein the light chain variable domain of the Protein S antibody is encoded by the nucleic acid sequence of SEQ ID NO: 162 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 163, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

142. The nucleic acid of any one of Enumerated Embodiments 127-130, wherein the light chain variable domain of the Protein S antibody is encoded by the nucleic acid sequence of SEQ ID NO: 164 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 165, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

143. The nucleic acid of any one of Enumerated Embodiments 127-130, wherein the light chain variable domain of the Protein S antibody is encoded by the nucleic acid sequence of SEQ ID NO: 166 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 167, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

144. The nucleic acid of any one of Enumerated Embodiments 127-130, wherein the light chain variable domain of the Protein S antibody is encoded by the nucleic acid sequence of SEQ ID NO: 170 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 171, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

145. The nucleic acid of any one of Enumerated Embodiments 127-130, wherein the light chain variable domain of the Protein S antibody is encoded by the nucleic acid sequence of SEQ ID NO: 172 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 173, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

146. The nucleic acid of any one of Enumerated Embodiments 127-130, wherein the light chain variable domain of the Protein S antibody is encoded by the nucleic acid sequence of SEQ ID NO: 178 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 183, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

147. The nucleic acid of any one of Enumerated Embodiments 127-130, wherein the light chain variable domain of the Protein S antibody is encoded by the nucleic acid sequence of SEQ ID NO: 188 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 193, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

148. The nucleic acid of any one of Enumerated Embodiments 127-130, wherein the light chain variable domain of the Protein S antibody is encoded by the nucleic acid sequence of SEQ ID NO: 198 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 203, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

149. The nucleic acid of any one of Enumerated Embodiments 127-130, wherein the light chain variable domain of the Protein S antibody is encoded by the nucleic acid sequence of SEQ ID NO: 208 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 213, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

150. A vector comprising the nucleic acid of any one of Enumerated Embodiments 127-149.

151. An in vitro method of promoting the coagulation of blood, comprising contacting the antibody of any one of Enumerated Embodiments 1-121 with a blood sample.

152. The method of Enumerated Embodiment 151, wherein the blood sample comprises plasma.

153. The method of any one of Enumerated Embodiments 151-152, wherein a marker associated with coagulation activity is increased.

154. The method of any one of Enumerated Embodiments 151-153, wherein thrombin generation is promoted.

155. The method of any one of Enumerated Embodiments 151-154, wherein fibrin generation is promoted.

156. The method of any one of Enumerated Embodiments 151-155, wherein D-dimer levels are promoted.

157. The method of any one of Enumerated Embodiments 151-156, wherein the blood sample is obtained from a subject having a coagulation factor deficiency, von Willebrand disease, or a platelet disorder.

158. A method of promoting the coagulation of blood in a subject in need thereof, comprising administering to the subject the antibody of any one of Enumerated Embodiments 1-121 or the pharmaceutical composition of Enumerated Embodiment 122.

159. The method of Enumerated Embodiment 158, wherein a marker associated with coagulation activity is increased.

160. The method of any of Enumerated Embodiments 158-159, wherein thrombin generation is promoted in the subject.

161. The method of any of Enumerated Embodiments 158-160, wherein fibrin generation is promoted in the subject.

162. The method of any of Enumerated Embodiments 153-161, wherein D-dimer levels are increased in the subject.

163. The method of any of Enumerated Embodiments 153-162, wherein the antibody remains active in the subject for a period of time.

164. method of any of Enumerated Embodiments 151-163, wherein activity of the antibody is dose-dependent.

165. A method of promoting the generation of thrombin in a subject in need thereof, comprising administering to the subject the antibody of any one of Enumerated Embodiments 1-121 or the pharmaceutical composition of Enumerated Embodiment 122.

166. The method of Enumerated Embodiment 165, wherein the subject has a coagulation factor deficiency, von Willebrand disease, or a platelet disorder, and the antibody restores or promotes the generation of thrombin.

167. A method of treating a condition in a subject in need thereof, comprising administering to the subject the antibody of Enumerated Embodiments 1-121 or the pharmaceutical composition of Enumerated Embodiment 122, wherein the condition is selected from the group consisting of: bleeding disorders, platelet disorders, trauma, and bleeding resulting from a surgery or a medical procedure.

168. The method of Enumerated Embodiment 167, wherein the method of treating is prophylactic.

169. The method of Enumerated Embodiment 167, wherein the method of treating is on-demand.

170. The method of any one of Enumerated Embodiments 167-169, wherein the method is prophylactic and on-demand.

171. The method of any one of Enumerated Embodiments 168 or 170, wherein the prophylactic method of treating is a routine prophylaxis.

172. The method of any one of Enumerated Embodiments 167-171, wherein the administration of the antibody of any one of Enumerated Embodiments 1-119 is a subcutaneous administration.

173. The method of any one of Enumerated Embodiments 158-172, wherein the method of treating is acute.

174. The method of any one of Enumerated Embodiments 158-172, wherein the method of treating is chronic.

175. The method of any one of Enumerated Embodiments 158-172, wherein the method of treating is perioperative.

176. The method of any one of Enumerated Embodiments 158-172, wherein the method of treating is intermittent.

177. The method of any one of Enumerated Embodiments 158-176, wherein the antibody exhibits graded inhibition.

178. The method of any one of Enumerated Embodiments 158-176, wherein the antibody exhibits switch-like inhibition.

179. The method of any one of Enumerated Embodiments 167-178, wherein the subject suffers from two or more conditions selected from the group consisting of: bleeding disorders, platelet disorders, trauma, and bleeding resulting from a surgery or a medical procedure.

180. The method of any one of Enumerated Embodiments 165-179, wherein the subject suffers from a bleeding disorder selected from the group consisting of: hemophilia A, hemophilia B, von Willebrand disease (vWD) disease, menorrhagia, Factor I deficiency, Factor II deficiency, Factor V deficiency, Factor VII deficiency, Factor X deficiency, Factor XI deficiency, Factor VIII deficiency (hemophilia A), Factor IX deficiency (hemophilia B), trauma, and hereditary hemorrhagic telangiectasia.

181. The method of any one of Enumerated Embodiments 158-180, wherein the subject is a hemophilia carrier.

182. The method of any one of Enumerated Embodiments 165-181, wherein the subject suffers from menorrhagia.

183. The method of any one of Enumerated Embodiments 158-182, wherein the subject suffers from menorrhagia associated with one or more of the bleeding disorders or the platelet disorders.

184. The method of Enumerated Embodiment 180, wherein the bleeding disorder is vWD, and wherein the subject is undergoing a prophylactic treatment.

185. The method of Enumerated Embodiment 180, wherein the bleeding disorder is vWD, and the vWD is a subtype selected from: vWD Type 1, vWD Type 2A, vWD Type 2B, vWD Type 2N, vWD Type 2M, vWD Type 3, and acquired vWD.

186. The method of any one of Enumerated Embodiments 167-185, wherein the condition is a platelet disorder selected from the group consisting of: Bernard-Soulier syndrome, Glanzmann's thrombasthenia, and platelet storage pool deficiency.

187. The method of Enumerated Embodiment 186, wherein the platelet disorder is a platelet storage pool deficiency selected from the group consisting of: Gray platelet syndrome, Quebec platelet disorder, and MYH9-related thrombocytopenia (MYH9RD).

188. The method of Enumerated Embodiment 180, wherein the bleeding disorder is selected from Factor I deficiency, Factor II deficiency, Factor V deficiency, Factor VII deficiency, Factor X deficiency, Factor XI deficiency, Factor VIII deficiency (hemophilia A), Factor IX deficiency (hemophilia B), and vWD disease, and wherein the subject has inhibitors.

189. The method of any one of Enumerated Embodiments 167-188, wherein the antibody or the pharmaceutical composition is capable of promoting thrombin generation in the subject.

190. The method of any one of Enumerated Embodiments 165-166, wherein the thrombin generation does not exceed a predetermined threshold level.

191. The method of any one of Enumerated Embodiments 165-166 and 190, wherein the thrombin generation is antibody concentration-dependent.

193. A kit or article of manufacture comprising an antibody of any one of Enumerated Embodiments 1-121 or the pharmaceutical composition of Enumerated Embodiment 122.

193. Use of the antibody of any one of Enumerated Embodiments 1-121 or the pharmaceutical composition of Enumerated Embodiment 122 for the treatment of a condition in a subject in need thereof.

194. Use of the antibody of any one of Enumerated Embodiments 1-121 or the pharmaceutical composition of Enumerated Embodiment 122 for the manufacture of a medicament for the treatment of a condition in a subject in need thereof.

The present invention is not limited in scope by the specific embodiments described herein, which are intended as illustrations of individual aspects or embodiments of the invention. Functionally equivalent methods and components are within the scope of the invention. Various modifications of the invention, in addition to those described here, are apparent to those skilled in the art from the foregoing description and accompanying drawings. Such modifications fall within the scope of the invention.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the antibodies of the present invention and practice the claimed methods. The following examples therefore, specifically point out the preferred embodiments of the present invention, and are not to be construed as limiting in any way the remainder of the disclosure.

EXAMPLES

Example 1

Generation of Protein S Antibodies

The Protein S antibodies of the disclosure were generated as follows. Animals (e.g., mice, rats) were immunized with a full-length purified human plasma Protein S. Three immunization campaigns were carried out and standard techniques were used to generate hybridoma libraries from the animals. Flow cytometry and single cell sorting was used to generate single cell clones. Supernatants from these single clones were then screened for binding to both human and cynomolgus monkey Protein S. Clones that exhibited binding to both human and cynomolgus monkey Protein S were selected for expanded growth. The expanded cultures were then purified over Protein G or Protein A Sepharose using standard techniques. These purified antibody preparations were used in subsequent functional assays. The selected Protein S antibodies had a human or mouse variable region and a rat Fc domain, or a mouse Fc domain.

Antibodies having a human variable region and a rat or mouse Fc domain were made into fully human antibodies maintaining the human variable domain as the parent antibody, but with a human IgG4 Fc domain. Table 6 below lists the Antibody number used to designate the human antibodies in the first column and the corresponding parental rodent antibodies (with the human variable region) in the second column. The second column also includes a single antibody with a mouse variable domain and a mouse Fc domain. The subsequent columns provide the variable light chain/variable heavy chain amino acid sequences and nucleic acid sequences, and the last column provides the amino acid sequences of the set of six CDRs that map to each Antibody.

TABLE 6

| Human Antibody: Protein S Antibody with Human Fc | Rat Antibody: Protein S Antibody with Rat Fc | Variable Light Chain, Variable Heavy Chain (Amino Acid Sequences) | Variable Light Chain, Variable Heavy Chain (Nucleic Acid Sequences) | CDR Combination (Amino Acid Sequences) |
|---|---|---|---|---|
| Antibody 1 | Antibody 13 | SEQ ID NO: 71, SEQ ID NO: 72 | SEQ ID NO: 95, SEQ ID NO: 96 | SEQ ID NO: 2, SEQ ID NO: 13, SEQ ID NO: 22, SEQ ID NO: 34, SEQ ID NO: 46, SEQ ID NO: 58 |
| Antibody 2 | Antibody 14 | SEQ ID NO: 73, SEQ ID NO: 74 | SEQ ID NO: 97, SEQ ID NO: 98 | SEQ ID NO: 3, SEQ ID NO: 14, SEQ ID NO: 23, SEQ ID NO: 35, SEQ ID NO: 47, SEQ ID NO: 59 |
| Antibody 3 | Antibody 15 | SEQ ID NO: 75, SEQ ID NO: 76 | SEQ ID NO: 99, SEQ ID NO: 100 | SEQ ID NO: 1, SEQ ID NO: 15, SEQ ID NO: 24, SEQ ID NO: 36, SEQ ID NO: 48, SEQ ID NO: 60 |
| Antibody 4 | Antibody 16 | SEQ ID NO: 77, SEQ ID NO: 78 | SEQ ID NO: 101, SEQ ID NO: 102 | SEQ ID NO: 4, SEQ ID NO: 16, SEQ ID NO: 25, SEQ ID NO: 37, SEQ ID NO: 49, SEQ ID NO: 61 |
| Antibody 6 | Antibody 18 | SEQ ID NO: 91, SEQ ID NO: 92 | SEQ ID NO: 115, SEQ ID NO: 116 | SEQ ID NO: 11, SEQ ID NO: 20, SEQ ID NO: 32, SEQ ID NO: 44, SEQ ID NO: 56, SEQ ID NO: 68 |
| Antibody 7 | Antibody 19 | SEQ ID NO: 69, SEQ ID NO: 70 | SEQ ID NO: 93, SEQ ID NO: 94 | SEQ ID NO: 1, SEQ ID NO: 12, SEQ ID NO: 21, SEQ ID NO: 33, SEQ ID NO: 45, SEQ ID NO: 57 |
| Antibody 8 | Antibody 20 | SEQ ID NO: 79, SEQ ID NO: 80 | SEQ ID NO: 103, SEQ ID NO: 104 | SEQ ID NO: 5, SEQ ID NO: 17, SEQ ID NO: 26, SEQ ID NO: 38, SEQ ID NO: 50, SEQ ID NO: 62 |
| Antibody 9 | Antibody 21 | SEQ ID NO: 81, SEQ ID NO: 82 | SEQ ID NO: 105, SEQ ID NO; 106 | SEQ ID NO: 6, SEQ ID NO: 18, SEQ ID NO: 27, SEQ ID NO: 39, SEQ ID NO: 51, SEQ ID NO: 63 |
| Antibody 11 | Antibody 23 | SEQ ID NO: 87, SEQ ID NO: 88 | SEQ ID NO: 111, SEQ ID NO: 112 | SEQ ID NO: 9, SEQ ID NO: 19, SEQ ID NO: 30, SEQ ID NO: 42, SEQ ID NO: 54, SEQ ID NO: 66 |
| Antibody 12 | Antibody 24 | SEQ ID NO: 89, SEQ ID NO: 90 | SEQ ID NO: 113, SEQ ID NO: 114 | SEQ ID NO: 10, SEQ ID NO: 16, |

TABLE 6-continued

| Human Antibody: Protein S Antibody with Human Fc | Rat Antibody: Protein S Antibody with Rat Fc | Variable Light Chain, Variable Heavy Chain (Amino Acid Sequences) | Variable Light Chain, Variable Heavy Chain (Nucleic Acid Sequences) | CDR Combination (Amino Acid Sequences) |
|---|---|---|---|---|
| | | | | SEQ ID NO: 31, SEQ ID NO: 43, SEQ ID NO: 55, SEQ ID NO: 67 |
| Antibody 29 | Antibody 35 | SEQ ID NO: 148, SEQ ID NO: 149 | SEQ ID NO: 162, SEQ ID NO: 163 | SEQ ID NO: 117, SEQ ID NO: 118, SEQ ID NO: 119, SEQ ID NO: 120, SEQ ID NO: 121, SEQ ID NO: 122 |
| Antibody 30 | Antibody 36 | SEQ ID NO: 150, SEQ ID NO: 151 | SEQ ID NO: 164, SEQ ID NO: 165 | SEQ ID NO: 117, SEQ ID NO: 118, SEQ ID NO: 123, SEQ ID NO: 124, SEQ ID NO: 125, SEQ ID NO: 126 |
| Antibody 25 | Antibody 31 | SEQ ID NO: 152, SEQ ID NO: 153 | SEQ ID NO: 166, SEQ ID NO: 167 | SEQ ID NO: 127, SEQ ID NO: 128, SEQ ID NO: 129, SEQ ID NO: 130, SEQ ID NO: 50, SEQ ID NO: 131 |
| Antibody 27 | Antibody 33 | SEQ ID NO: 156, SEQ ID NO: 157 | SEQ ID NO: 170, SEQ ID NO: 171 | SEQ ID NO: 136, SEQ ID NO: 17, SEQ ID NO: 137, SEQ ID NO: 138, SEQ ID NO: 139, SEQ ID NO: 140 |
| Antibody 28 | Antibody 34* (*mouse variable region/mouse Fc) | SEQ ID NO: 158, SEQ ID NO: 159 | SEQ ID NO: 172, SEQ ID NO: 173 | SEQ ID NO: 141, SEQ ID NO: 142, SEQ ID NO: 143, SEQ ID NO: 144, SEQ ID NO: 145, SEQ ID NO: 146 |
| Antibody 37 | Antibody 38 | SEQ ID NO: 177, SEQ ID NO: 182 | SEQ ID NO: 178, SEQ ID NO: 183 | SEQ ID NO: 174, SEQ ID NO: 175, SEQ ID NO: 176, SEQ ID NO: 179, SEQ ID NO: 180, SEQ ID NO: 181 |
| Antibody 39 | Antibody 40 | SEQ ID NO: 187, SEQ ID NO: 192 | SEQ ID NO: 188, SEQ ID NO: 193 | SEQ ID NO: 184, SEQ ID NO: 185, SEQ ID NO: 186, SEQ ID NO: 189, SEQ ID NO: 190, SEQ ID NO: 191 |
| Antibody 41 | Antibody 42 | SEQ ID NO: 197, SEQ ID NO: 202 | SEQ ID NO: 198, SEQ ID NO: 203 | SEQ ID NO: 194, SEQ ID NO: 195, SEQ ID NO: 196, SEQ ID NO: 199, SEQ ID NO: 200, SEQ ID NO: 201 |
| Antibody 43 | Antibody 44 | SEQ ID NO: 207, SEQ ID NO: 212 | SEQ ID NO: 208, SEQ ID NO: 213 | SEQ ID NO: 204, SEQ ID NO: 205, SEQ ID NO: 206, SEQ ID NO: 209, SEQ ID NO: 210, SEQ ID NO: 211 |

Example 2

Figure 2A:
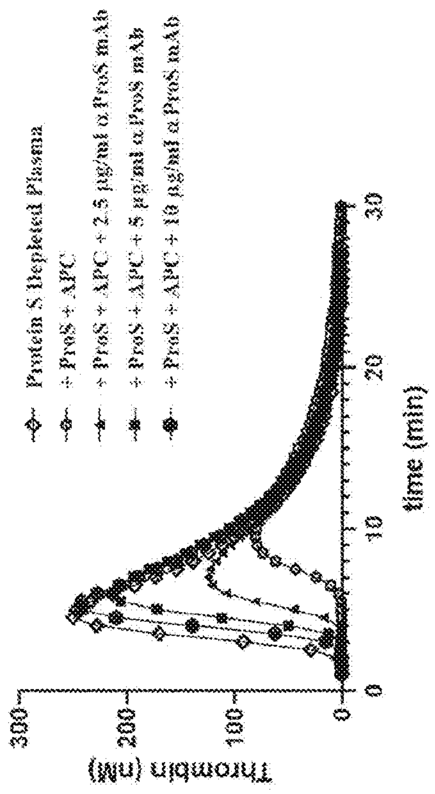
FIGS. 2A-2B depict the results of screening assays performed to assess APC and TFPI cofactor activity, respectively, using control Protein S antibodies. In this and subsequent figures, ProS=Protein S; mAb=monoclonal antibody; pAb=polyclonal antibody; PRP=platelet rich plasma.
Figure 2B:
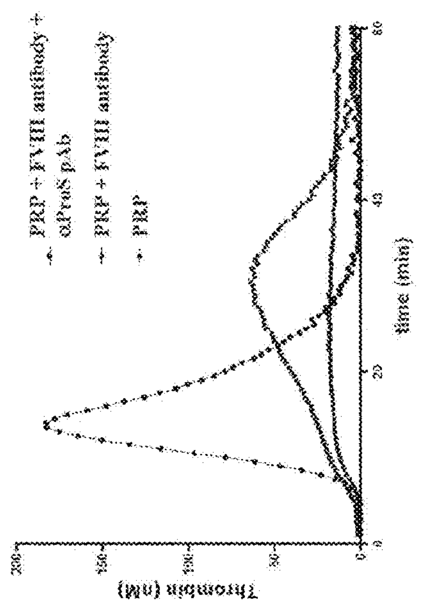

Assessing Thrombin Generation in APC and TFPI Cofactor Activity Screening Assays Assessing APC and TFPI Cofactor Activity with Screening Assays FIGS. 2A-2B depict exemplary assays performed to assess APC and TFPI cofactor activity, respectively and demonstrate how a APC cofactor inhibitor and a TFPI cofactor inhibitor would behave in the assay.

FIGS. 2A-2B depict assays performed to assess APC and TFPI cofactor activity, respectively. For the APC cofactor activity screening assay depicted in FIG. 2A, the following were tested: Protein S depleted platelet poor plasma, Protein S depleted plasma reconstituted with a Protein S and APC mixture, and Protein S depleted plasma reconstituted with a Protein S and APC mixture in the presence of varying concentrations of an anti-Protein S monoclonal antibody (mAb). The Protein S and APC mixture was made by pre-mixing Protein S and APC and adding to the Protein S depleted plasma to create a Protein S-dependent assay, due to APC not showing inhibition of thrombin generation in the absence of Protein S. As shown, the addition of the premixed Protein S and APC mixture to Protein S depleted plasma shows significantly less tissue factor-induced thrombin generation than the Protein S depleted plasma alone. Addition of anti-Protein S mAbs to the Protein S depleted plasma+Protein S and APC mixture restored tissue factor-induced thrombin generation in a concentration-dependent manner.

For the TFPI cofactor activity screening assay depicted in FIG. 2B, the following were tested: platelet rich plasma with no treatment (also referred to herein as platelet-rich plasma, or PRP), a commercial Factor VIII (FVIII) neutralizing antibody, and a FVIII antibody and Protein S polyclonal antibody (pAB) mixture. The FVIII antibody acts as a neutralizing antibody and inhibits tissue factor induced thrombin generation. Addition of the neutralizing Protein S antibodies enhanced thrombin generation in the presence of the FVIII antibody. Neutralizing Protein C antibodies did not show an effect on thrombin generation in the TFPI cofactor activity assay, suggesting that endogenous Protein C or activated Protein C does not inhibit thrombin generation in this assay.

Figure 3:
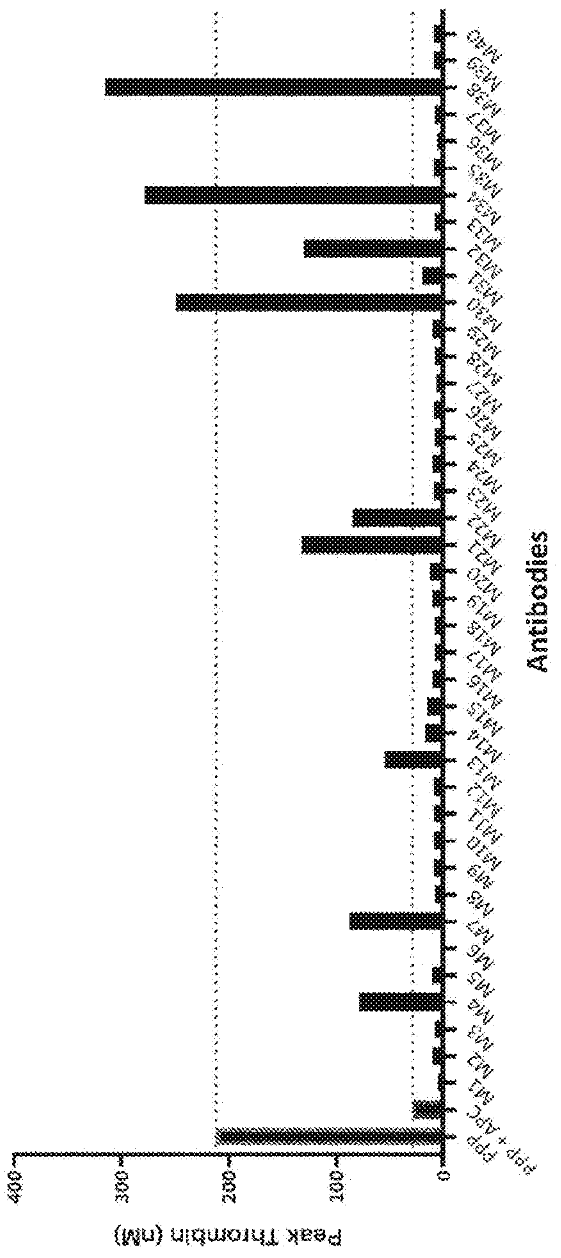
FIGS. 3-4 depict peak thrombin levels generated by Protein S monoclonal antibodies, identified from hybridoma libraries, in the APC cofactor and TFPI cofactor screening assays, respectively.
Figure 4:
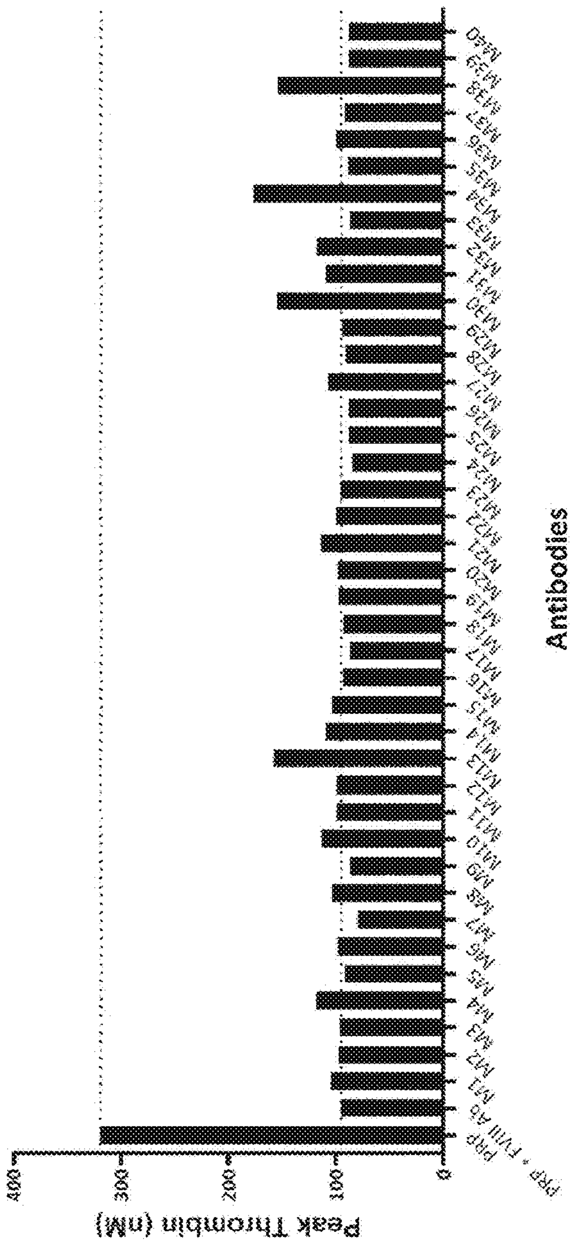

Clones M1-M40 were generated from a rat hybridoma library described in Example 1. The cofactor activity assays performed as described when referring to FIGS. 2A-2B were used to measure the amount of thrombin generation in the presence of clones M1-M40 generated from a rat hybridoma library. FIGS. 3-4 depict the peak thrombin levels generated from an APC cofactor screening assay (APC assay) and a TFPI cofactor screening assay, respectively, of the clones M1-M40. Controls used for the APC assay depicted in FIG. 3 were platelet-poor plasma ("PPP") alone and PPP with APC. Controls used for the TFPI assay depicted in FIG. 4 were platelet-rich plasma ("PRP") alone and PRP with a commercial neutralizing FVIII antibody.

Example 3

Characterization of Selected Protein S Antibodies

Characterization of Inhibitor Type by Cofactor Activity Assays

As a general matter, Protein S antibodies can be identified as either a dual inhibitor of Protein S cofactor activity for both APC and TFPI, for APC only (APC cofactor inhibitor), or for TFPI (TFPI cofactor inhibitor) only. The antibodies can be categorized by assessment of the thrombin generation profiles shown when assaying each antibody using the cofactor activity assays described in FIGS. 2A-2B.

Figure 5:
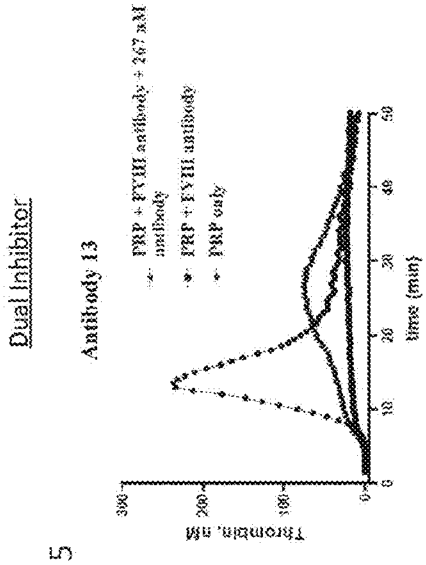
FIGS. 5-10 depict the prototypic thrombin generation profiles of a dual inhibitor of APC and TFPI (Antibody 13.
Figure 6:
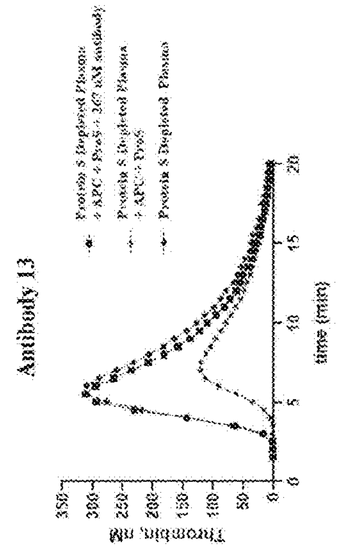

FIGS. 5-6 depict thrombin generation in the presence of Antibody 13 in the TFPI cofactor assay (FIG. 5) and the APC cofactor assay (FIG. 6). As shown in the TFPI cofactor activity assay using PRP, robust thrombin generation occurred in the absence of FVIII antibody and was reduced by addition of the FVIII antibody. Addition of 267 nM Antibody 13 promoted thrombin generation in the presence of the FVIII antibody. As shown in the APC cofactor activity assay, thrombin generation was reduced by addition of both APC and Protein S to Protein S depleted plasma. Addition of 267 nM Antibody 13 to Protein S depleted plasma containing APC and Protein S rescued thrombin generation. Since Antibody 13 induced thrombin generation in both the TFPI and APC cofactor assays, Antibody 13 was characterized as a dual inhibitor.

Figure 7:
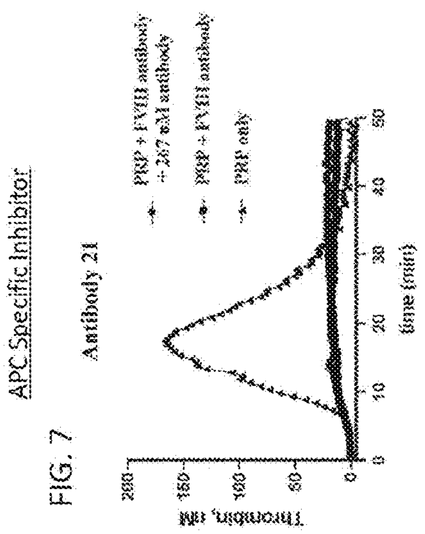
Figure 8:
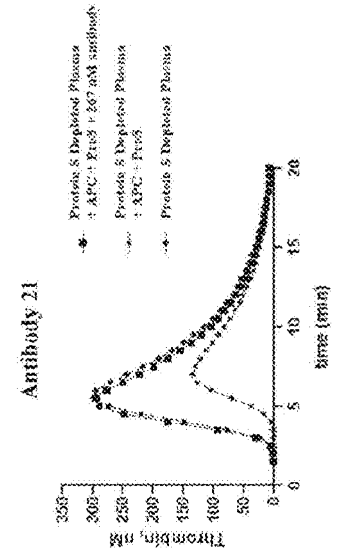

FIGS. 7-8 depict the thrombin generation of Antibody 21 when using a TFPI cofactor assay (FIG. 7) and an APC cofactor assay (FIG. 8). As shown in the TFPI cofactor activity assay depicted in FIG. 7, in PRP, robust thrombin generation occurred in the absence of FVIII antibody. Thrombin generation was reduced by addition of the FVIII antibody only. Addition of 267 nM Antibody 21 showed no rescue of the thrombin generation. As shown in the APC cofactor activity assay depicted in FIG. 8, thrombin generation was reduced by addition of a mixture of APC and Protein S, which was rescued by the addition of 267 nM Antibody 21. Because Antibody 21 did not induce thrombin generation in the TFPI cofactor assay but did rescue thrombin generation in the APC cofactor assay, Antibody 21 was characterized as an APC cofactor inhibitor.

Figure 9:
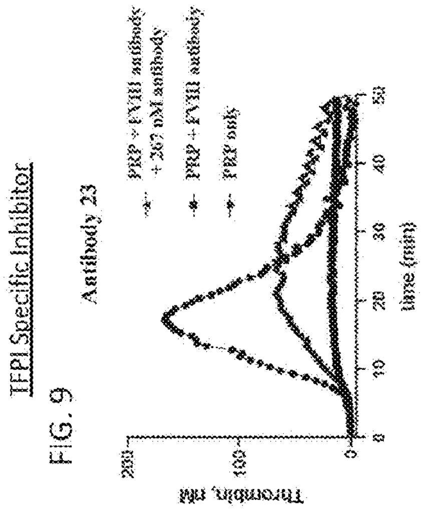
Figure 10:
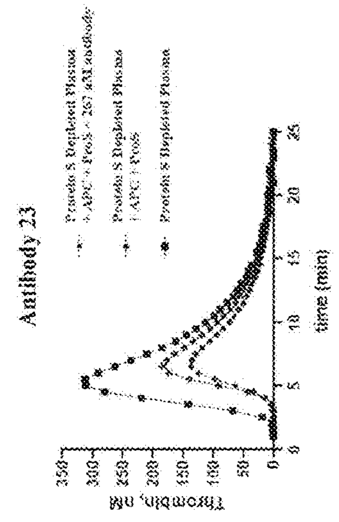

FIGS. 9-10 depict the thrombin generation of Antibody 23 when using a TFPI cofactor assay (FIG. 9) and an APC cofactor assay (FIG. 10). As shown in the TFPI cofactor activity assay depicted in FIG. 9, in PRP, robust thrombin generation occurred in the absence of FVIII antibody. Thrombin generation was reduced by addition of the FVIII antibody only. Addition of 267 nM Antibody 23 promoted thrombin generation. As shown in the APC cofactor activity assay depicted in FIG. 10, in Protein S depleted plasma, thrombin generation was reduced by addition of a mixture of APC and Protein S. Addition of 267 nM Antibody 23 to Protein S depleted plasma with APC+Protein S showed limited rescue of the thrombin generation. Since Antibody 23 induced thrombin generation in the TFPI cofactor assay but not in the APC cofactor assay, Antibody 23 was characterized as a TFPI cofactor inhibitor.

Characterization of Protein S Antibodies

The assay results depicted in FIGS. 11A-20H were used to characterize the exemplary Protein S antibodies provided herein. The antibodies were characterized as an inhibitor of APC cofactor activity (APC cofactor inhibitor), an inhibitor of TFPI cofactor activity (TFPI cofactor inhibitor), or a dual inhibitor. Binding regions and calcium dependence were also determined. The results of the characterization assays are summarized in Tables 7 and 8 below and described in further detail in the below sections.

TABLE 7

| Protein S Antibody | Fc | Pathway Inhibitor (APC, TFPI, or Dual) | IC50 APC (nM) | Hill Coefficient | IC50 TFPI (nM) | Hill Coefficient |
|---|---|---|---|---|---|---|
| Antibody 13 | Rat | Dual | 5.30E−09 | 2.56 | 5.11E−08 | 5.62 |
| Antibody 14 | Rat | Dual | 8.76E−09 | 2.26 | 7.33E−08 | 2.46 |
| Antibody 15 | Rat | Dual | 1.35E−08 | 2.80 | 7.73E−08 | 3.79 |
| Antibody 16 | Rat | Dual | 1.40E−08 | 2.69 | 4.63E−08 | 3.9 |

TABLE 7-continued

| Protein S Antibody | Fc | Pathway Inhibitor (APC, TFPI, or Dual) | IC50 APC (nM) | Hill Coefficient | IC50 TFPI (nM) | Hill Coefficient |
|---|---|---|---|---|---|---|
| Antibody 18 | Rat | APC only | 1.28E−08 | 2.7 | N/A | N/A |
| Antibody 19 | Rat | Dual | 8.12E−08 | 1.06 | 1.05E−07 | 1.39 |
| Antibody 20 | Rat | Dual | 1.28E−08 | 2.70 | N/A | N/A |
| Antibody 21 | Rat | APC only | 6.23E−09 | 2.10 | N/A | N/A |
| Antibody 23 | Rat | TFPI only | N/A | N/A | <4.4E−09 | N/A |
| Antibody 24 | Rat | Dual | 1.79E−08 | 1.6 | 7.36E−08 | 1.59 |
| Antibody 31 | Rat | APC only | 9.90E−08 | 1.12 | N/A | N/A |
| Antibody 33 | Rat | Dual | 5.81E−08 | 2.48 | 3.4E−08 | 2.21 |
| Antibody 34 | Mouse | APC only | 9.58E−08 | 2.28 | N/A | N/A |
| Antibody 35 | Rat | APC only | 3.71E−07 | 0.68 | N/A | N/A |
| Antibody 36 | Rat | Dual | 1.53E−08 | 1.55 | 6.05E−09 | 3.53 |
| Antibody 38 | Rat | APC only | 8.40E−08 | 0.70 | N/A | N/A |
| Antibody 40 | Rat | APC only | 1.19E−08 | 2.82 | N/A | N/A |
| Antibody 42 | Rat | APC only | 2.15E−07 | 1.37 | N/A | N/A |
| Antibody 44 | Rat | APC only | 4.92E−07 | 0.87 | N/A | N/A |

TABLE 8

| Protein S Antibody with Rat Fc | Pathway Inhibitor | Binds Heavy Chain | Calcium-Dependent Binding | Binds Thrombin-Sensitive Region of Protein S |
|---|---|---|---|---|
| Antibody 13 | Dual | Yes | No | No |
| Antibody 14 | Dual | Yes | No | No |
| Antibody 15 | Dual | Yes | Yes | Yes |
| Antibody 16 | Dual | Yes | Yes | No |
| Antibody 19 | Dual | Yes | Yes | Yes |
| Antibody 20 | Dual | Yes | Yes | No |
| Antibody 24 | Dual | Yes | Yes | Yes |
| Antibody 18 | APC | Yes | Yes | No |
| Antibody 21 | APC | Yes | No | No |
| Antibody 23 | TFPI | No | No | No |
| Antibody 31 | APC | No | No | No |
| Antibody 33 | Dual | No | Yes | No |
| Antibody 34 | APC | No | Yes | No |
| Antibody 35 | APC | No | Yes | No |
| Antibody 36 | Dual | No | Yes | No |
| Antibody 38 | APC | No | Yes | No |
| Antibody 40 | APC | No | Yes | No |
| Antibody 42 | APC | No | No | No |
| Antibody 44 | APC | Yes | No | No |

Binding characteristics of the Protein S antibodies were also determined. Binding interaction analysis was obtained by Surface Plasmon Resonance in a Biacore X100 instrument. The human anti-IgG (Fc) antibody was immobilized to the carboxymethylated dextran membrane on the sensor chip surface (CM5) via the free amine method for a contact time of 420 seconds. Human anti-IgG antibody at 25 μg/mL in 0.15 M NaCl was immobilized to 9,785 RU in 10 mM sodium acetate pH 5.0. Each tested monoclonal antibody (Antibody 1-12) was captured at a fixed concentration (0.25 μg/mL) with immobilized human anti-IgG antibody. Experimentally, the capture ligand level for the antibodies tested was determined to be 66-99 RL, corresponding to a $R_{max}$ of 61-91 RU. No signs of mass transport limitation were observed.

The following experimental conditions were used: purified Protein S was injected at concentrations: 2-128 nM, 1:2-fold dilution. Dilution and running buffer were as follows: Hbs−EP+5 mM $CaCl_2$. Regeneration was obtained by 3 M $MgCl_2$. Binding constants (ka, kd, and KD) were determined using the Biacore X100 evaluation software, assuming a 1:1 interaction of Protein S and the tested monoclonal antibody under investigation. The resulting data are presented in Table 9 below.

TABLE 9

| | Ka (1/MS) | Kd (1/S) | KD nM |
|---|---|---|---|
| Antibody 1 | 2.90E+05 | 3.90E−04 | 1.33 |
| Antibody 2 | 3.46E+05 | 5.60E−04 | 1.63 |
| Antibody 3 | 2.53E+05 | 5.69E−04 | 2.24 |
| Antibody 4 | 3.99E+05 | 1.65E−03 | 4.13 |
| Antibody 6 | 2.80E+05 | 1.60E−03 | 5.79 |
| Antibody 7 | 2.52E+05 | 5.00E−03 | 20.00 |
| Antibody 8 | 1.32E+05 | 8.23E−04 | 6.25 |
| Antibody 9 | 2.12E+05 | 3.36E−03 | 15.90 |
| Antibody 11 | 1.16E+05 | 1.13E−03 | 9.60 |
| Antibody 12 | 6.57E+05 | 9.47E−03 | 14.40 |

Binding characteristics of the Protein S antibodies were also further characterized using Octet. Using the Octet System (Sartorius), the binding of each antibody to both human and cynomolgus monkey ("cyno" in Table 10) Protein S was determined. The human Fc antibodies were immobilized onto anti-human Fc capture probes by placing the probes into 10 μg/ml antibody solution in 10 mg/ml bovine serum albumin, 20 mM Tris pH 7.0, 150 mM NaCl, and 4 mM calcium chloride. Next, the bound antibodies were placed into solutions containing 500 nM, 250 nM, 125 nM 62.5 nM, 31.25 nM, 15.625 nM and 7.81 nM Protein S and the association rates were measured. Next, the probes were placed into buffer and the dissociation rates were measured. A summary of the resulting data is provided in Table 10 below.

TABLE 10

| Antibody | $k_{on}$ (l/Ms) | kdis (1/s) | KD (human) (M) | $k_{on}$ (1/Ms) | kdis (1/s) | KD (cyno) (M) |
|---|---|---|---|---|---|---|
| Antibody 1 | 1.69E+05 | <1.0E−07 | <1.0E−12 | 1.39E+05 | <1.0E−07 | <1.0E−12 |
| Antibody 2 | 2.07E+05 | <1.0E−07 | <1.0E−12 | 1.54E+05 | <1.0E−07 | <1.0E−12 |
| Antibody 3 | 1.64E+05 | 8.86E−06 | 5.42E−11 | 1.27E+05 | <1.0E−07 | <1.0E−12 |
| Antibody 4 | 2.71E+05 | 7.08E−04 | 2.62E−09 | 2.01E+05 | 3.08E−03 | 1.53E−08 |
| Antibody 6 | 2.26E+05 | 3.32E−04 | 1.47E−09 | 1.40E+05 | 3.94E−04 | 2.81E−09 |
| Antibody 7 | 1.72E+05 | 1.41E−03 | 8.18E−09 | 1.37E+05 | 2.32E−03 | 1.69E−08 |
| Antibody 8 | 1.31E+05 | 6.70E−05 | 5.14E−10 | 8.58E+04 | 1.33E−04 | 1.55E−09 |
| Antibody 9 | 3.04E+05 | 1.62E−04 | 5.33E−10 | 1.66E+05 | 4.42E−05 | 2.66E−10 |
| Antibody 11 | 8.52E+04 | 3.40E−05 | 3.99E−10 | 8.21E+04 | <1.0E−07 | <1.0E−12 |
| Antibody 12 | 3.09E+05 | 2.32E−03 | 7.49E−09 | 2.58E+05 | 2.91E−03 | 1.13E−08 |
| Antibody 25 | 1.43E+05 | <1.0E−07 | <1.0E−12 | 1.24E+05 | <1.0E−07 | <1.0E−12 |
| Antibody 27 | 2.77E+05 | 1.59E−04 | 5.74E−10 | 6.79E+04 | 2.33E−03 | 3.43E−08 |
| Antibody 28 | 1.56E+05 | 1.06E−03 | 6.78E−09 | 1.09E+05 | 1.06E−03 | 9.81E−09 |
| Antibody 29 | 8.19E+04 | 1.73E−03 | 2.11E−08 | 8.82E+04 | 1.77E−03 | 2.00E−08 |
| Antibody 30 | 2.42E+04 | 2.79E−04 | 1.15E−08 | 3.50E+04 | 7.30E−04 | 2.09E−08 |
| Antibody 37 | 2.18E+05 | 8.32E−05 | 3.82E−10 | 1.77E+05 | 1.19E−04 | 6.72E−10 |
| Antibody 39 | 2.34E+05 | 5.84E−05 | 2.50E−10 | 1.91E+05 | 8.02E−05 | 4.19E−10 |
| Antibody 41 | 8.00E+04 | 1.10E−03 | 1.38E−08 | 9.64E+04 | 1.88E−03 | 1.95E−08 |
| Antibody 43 | 3.20E+05 | 6.36E−04 | 1.99E−09 | 2.68E+05 | 1.04E−03 | 3.88E−09 |

TABLE 11

| Antibody | Binding to heavy chain (OD) |
|---|---|
| Antibody 13 | 1.63 |
| Antibody 14 | 2.03 |
| Antibody 15 | 1.78 |
| Antibody 16 | 1.67 |
| Antibody 18 | 0.60 |
| Antibody 19 | 0.61 |
| Antibody 20 | 1.54 |
| Antibody 21 | 1.58 |
| Antibody 23 | 0.10 |
| Antibody 24 | 0.71 |
| Antibody 31 | 0.13 |
| Antibody 33 | 0.11 |
| Antibody 34 | 0.16 |

Antibody 19 and Antibody 7

FIGS. 11A-11H depict the characterization of Antibody 19 and Antibody 7. Antibody 19 and Antibody 7 both comprise the same human variable regions, while Antibody 19 comprises a rat Fc domain and Antibody 7 comprises a human IgG4 Fc domain.

Figure 11C:
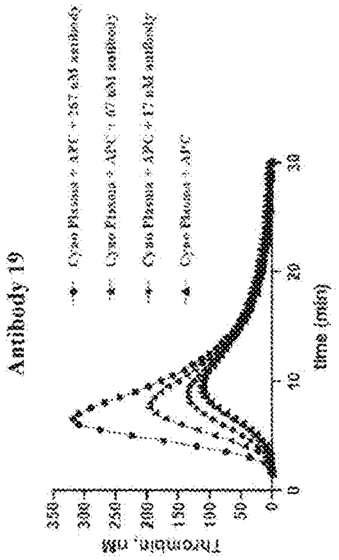
FIGS. 11A-11H depict the characterization of Antibody 19 and Antibody 7, antibodies sharing the same human variable region, and are characterized as dual inhibitors.
Figure 11B:
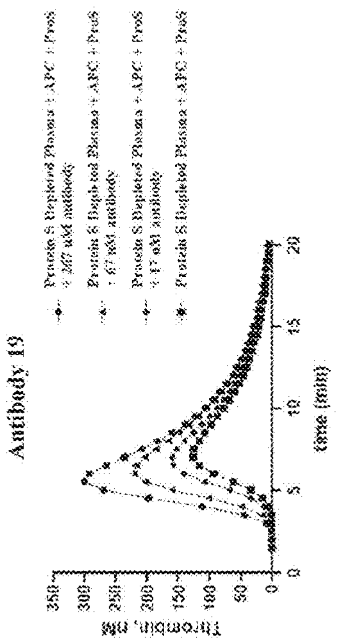
Figure 11D:
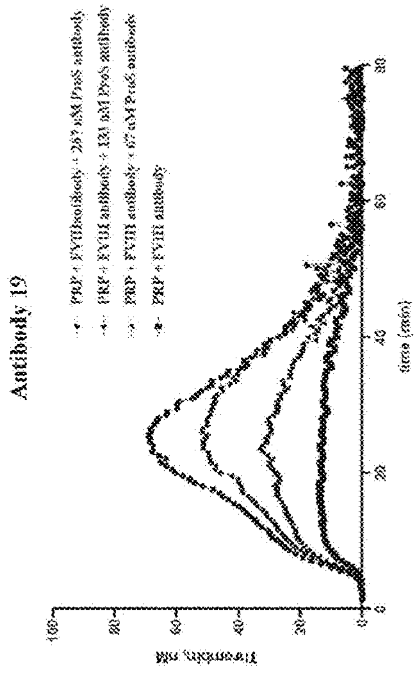
Figure 11A:
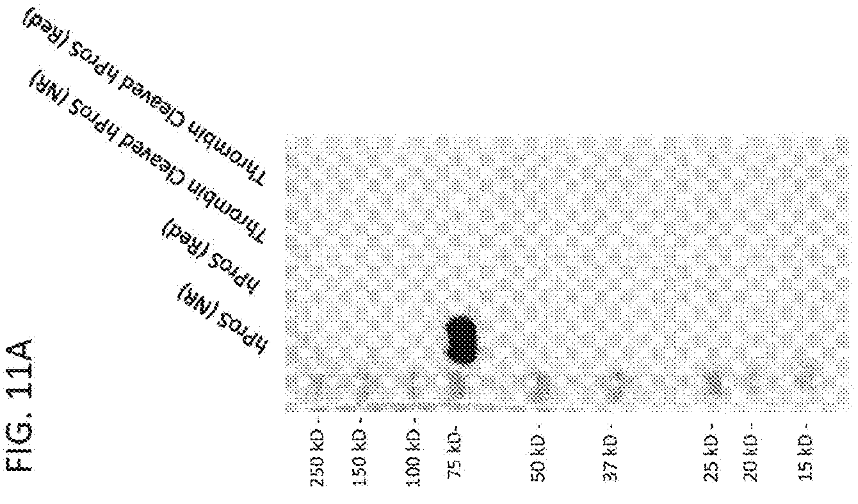

FIG. 11A depicts a Western blot showing that Antibody 19 binds Protein S in the Thrombin Sensitive Region (TSR) of Protein S. A full-length human Protein S protein (Reduced (Red) and Non-reduced (NR)) and a thrombin-cleaved Protein S fragment (cleaved in the Thrombin Sensitive Region (TSR), NR and Red) were used. By Western blot, Antibody 19 bound the full Protein S, but not the thrombin-cleaved Protein S, indicating that Antibody 19 binds at the TSR. Because no signal was observed with the reduced Protein S, the epitope for this antibody is not a linear epitope.

Binding to the heavy chain of Protein S was determined using an ELISA based method. Briefly, high binding ELISA plates were coated with recombinant heavy chain Protein S expressed and purified from HEK293 cells. The "heavy chain" of Protein S represents a fragment of Protein S spanning amino acids 42-296. The coated plate was blocked with 1% casein solution. Then, buffer containing 1 μml of antibody was applied to the well with buffer containing 1 mM calcium chloride. For antibodies that bound this fragment of Protein S, it was concluded that the epitope on Protein S for that antibody is between amino acids 42-296 of Protein S. Table 11 below summarizes the results of the heavy chain binding assay for all Antibodies. (antibodies that do bind this region have ODs greater than about 0.48 OD).

TABLE 11-continued

| Antibody | Binding to heavy chain (OD) |
|---|---|
| Antibody 35 | 0.08 |
| Antibody 36 | 0.08 |
| Antibody 38 | 0.10 |
| Antibody 40 | 0.11 |
| Antibody 42 | 0.11 |
| Antibody 44 | 0.48 |

Calcium dependence of binding was determined using an ELISA based method. Briefly, high binding ELISA plates were coated with human Protein S. Then, buffer containing 1 μg/ml of antibody was applied to the well with either buffer containing 1 mM EDTA or 1 mM calcium chloride. If the level of binding of Protein S was reduced dramatically (greater than 85% of the absorbance observed in the presence of calcium) when EDTA was added, it was concluded that the binding was calcium-dependent. Table 12 summarizes the results of the calcium dependence assay for all Antibodies.

TABLE 12

| | Binding to Protein S in EDTA (OD) | Binding to Protein S in CaCl2 (OD) |
|---|---|---|
| Antibody 13 | 0.48 | 1.77 |
| Antibody 14 | 0.75 | 2.03 |
| Antibody 15 | 0.07 | 1.86 |

TABLE 12-continued

| | Binding to Protein S in EDTA (OD) | Binding to Protein S in CaCl2 (OD) |
|---|---|---|
| Antibody 16 | 0.17 | 1.95 |
| Antibody 18 | 0.10 | 1.96 |
| Antibody 19 | 0.06 | 1.68 |
| Antibody 20 | 0.26 | 1.93 |
| Antibody 21 | 1.40 | 1.92 |
| Antibody 23 | 0.26 | 0.57 |
| Antibody 24 | 0.06 | 1.72 |
| Antibody 31 | 0.63 | 1.03 |
| Antibody 33 | 0.20 | 1.23 |
| Antibody 34 | 0.06 | 0.51 |
| Antibody 35 | 0.11 | 0.96 |
| Antibody 36 | 0.03 | 0.60 |
| Antibody 38 | 0.09 | 1.38 |
| Antibody 40 | 0.11 | 0.51 |
| Antibody 42 | 0.53 | 0.67 |
| Antibody 44 | 0.89 | 1.17 |

FIGS. 11B-11D depict the results of an APC cofactor assay for Antibody 19 using Protein S deficient human PPP, cynomolgus monkey PPP, and a TFPI cofactor assay using human PRP, respectively.

Figure 11E:
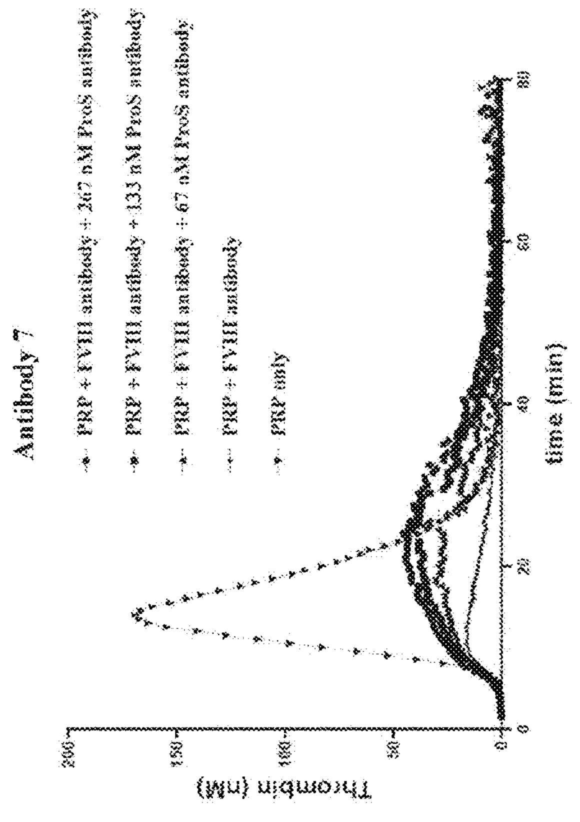
Figure 11F:
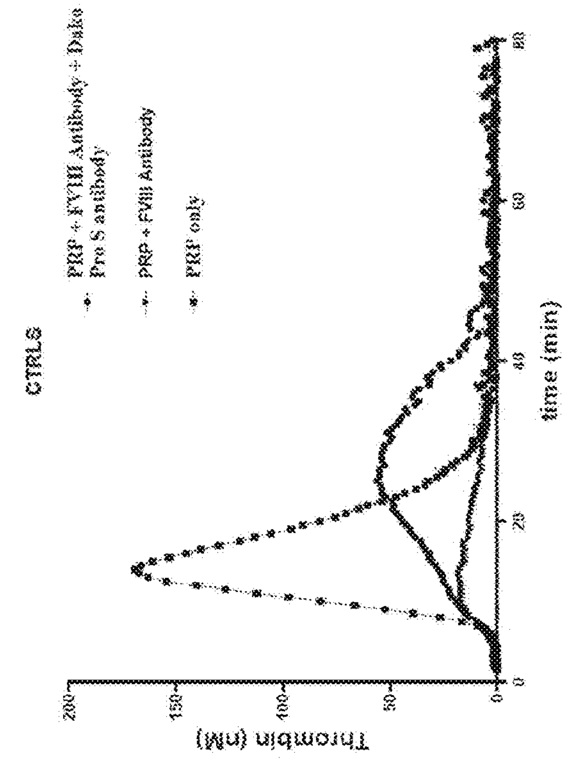

FIGS. 11E and 11F depict the results of a TFPI cofactor assay in human PRP using Antibody 7 and controls, respectively. A rabbit polyclonal human Protein S antibody labeled Dako was used as a positive control.

Figure 11H:
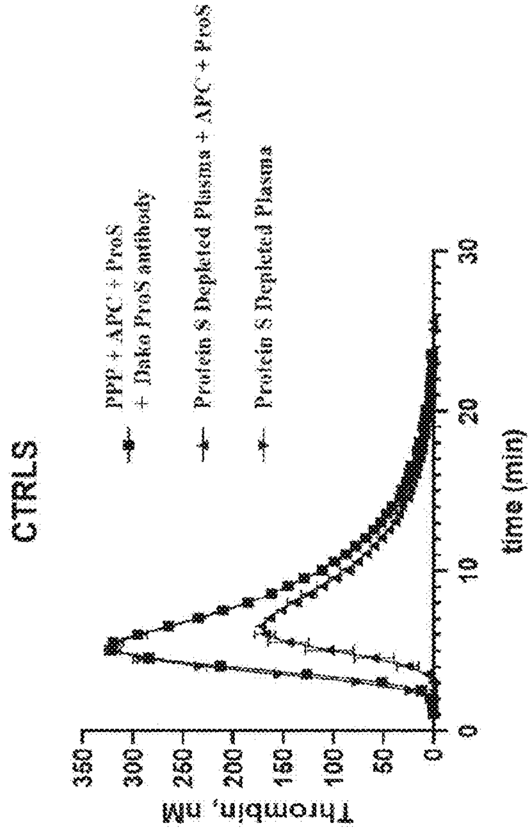
Figure 11G:
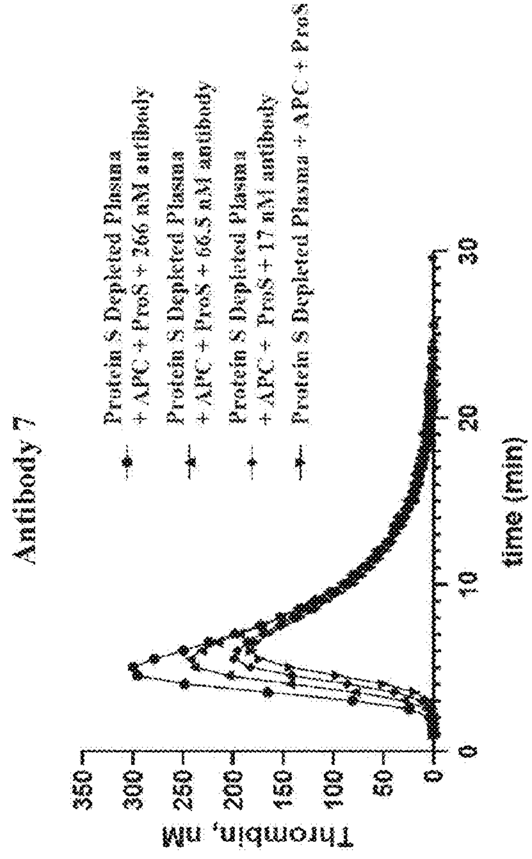

FIGS. 11G-11H depict the results of a PPP with APC assay performed with Antibody 7, and controls, respectively.

These results indicate that Antibody 19 and Antibody 7 are dual inhibitors.

Antibody 13 and Antibody 1

FIGS. 12A-12H depict the characterization of Antibody 13 and Antibody 1, antibodies sharing the same human variable region, and are characterized as dual inhibitors.

Figure 12A:
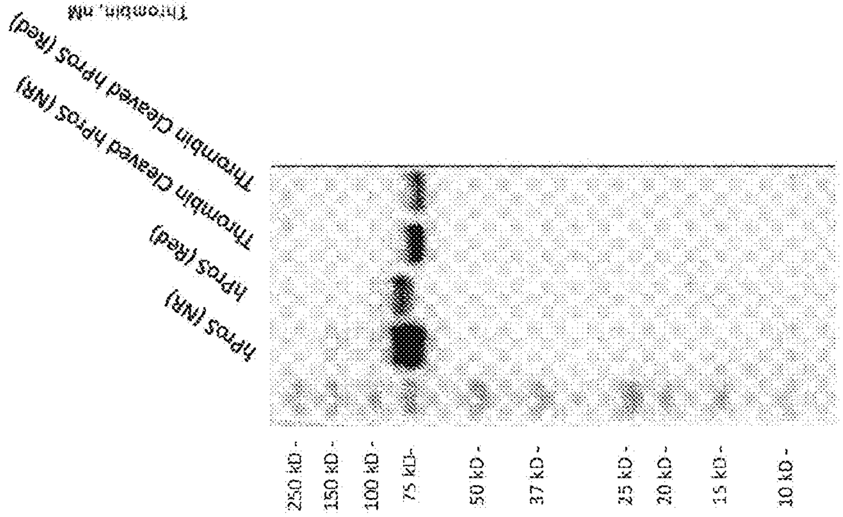
FIGS. 12A-12H depict the characterization of Antibody 13 and Antibody 1, antibodies sharing the same human variable region, and are characterized as dual inhibitors.

FIG. 12A depicts a Western blot showing that Antibody 13 does not bind to Protein S in the TSR of Protein S. The Western blot was carried out as described for FIG. 11A. By Western blot, Antibody 13 bound the full Protein S, the thrombin-cleaved Protein S, the reduced Protein S, and the reduced thrombin-cleaved Protein S, indicating that Antibody 13 does not bind Protein S at the TSR. Binding to reduced Protein S showed that the epitope for Antibody 13 is a linear epitope.

Binding to the heavy chain of Protein S was determined using an ELISA based method, as described herein. Antibody 13 was determined to bind to the heavy chain of Protein S. Calcium dependence was determined, also as described above, and Antibody 13 showed calcium-independent binding.

Figure 12B:
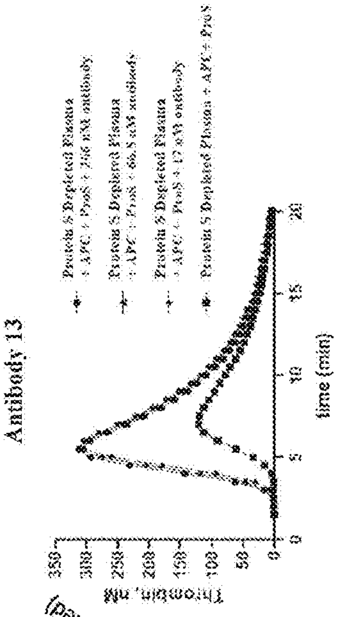
Figure 12C:
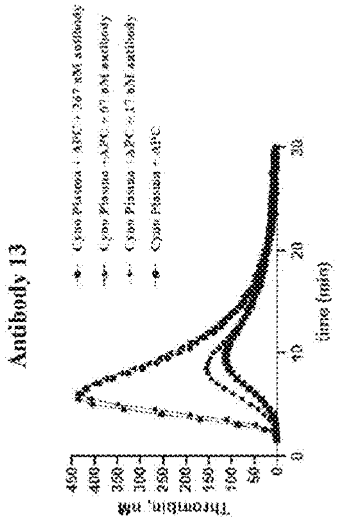
Figure 12D:
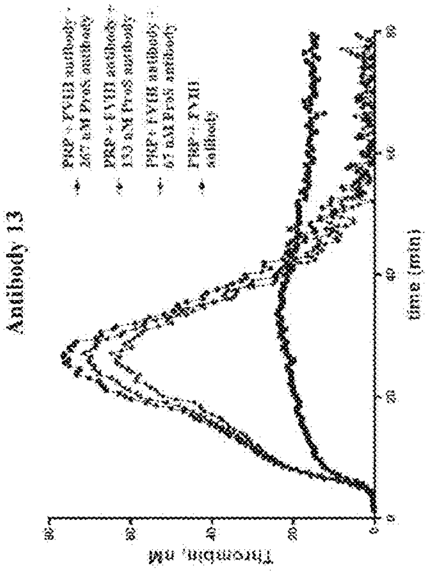

FIGS. 12B-12D depict the results of an APC cofactor assay for Antibody 13 using Protein S deficient human PPP, cynomolgus monkey PPP, and a TFPI cofactor assay using human PRP, respectively.

Figure 12F:
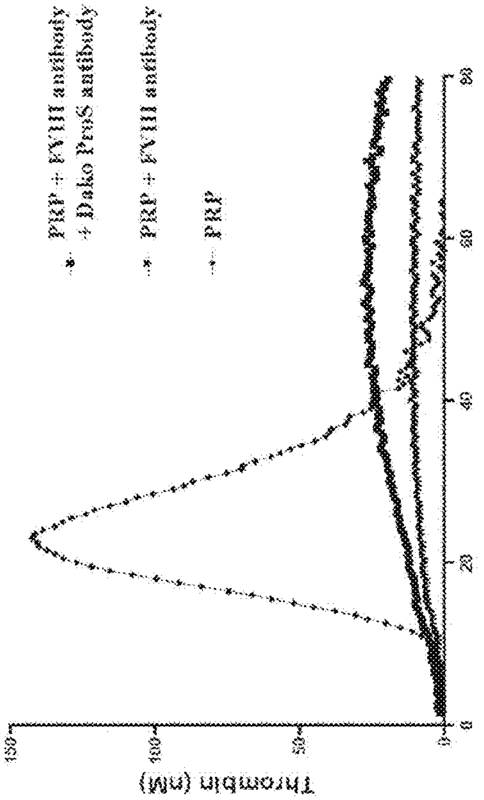
Figure 12E:
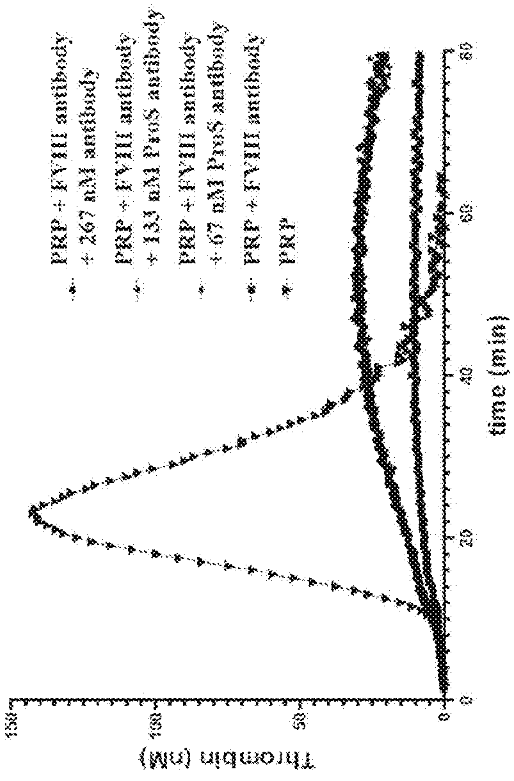

FIGS. 12E and 12F depict the results of a TFPI cofactor assay in human PRP using Antibody 1 and controls, respectively. A rabbit polyclonal human Protein S antibody labeled Dako was used as a positive control.

Figure 12H:
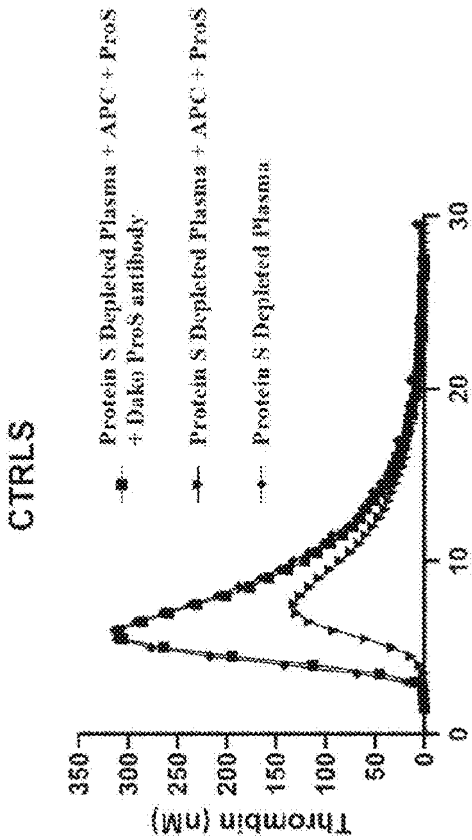
Figure 12G:
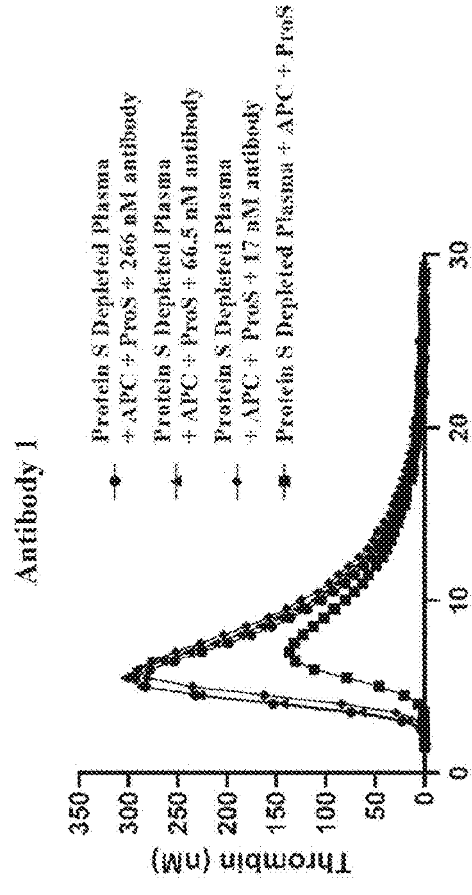

FIGS. 12G-12H depict the results of the APC cofactor assay performed with Antibody 1, and controls, respectively.

These results indicate that Antibody 13 and Antibody 1 are dual inhibitors.

Antibody 14 and Antibody 2

FIGS. 13A-13H depict the characterization of Antibody 14 and Antibody 2, antibodies sharing the same human variable region, and are characterized as dual inhibitors.

Figure 13A:
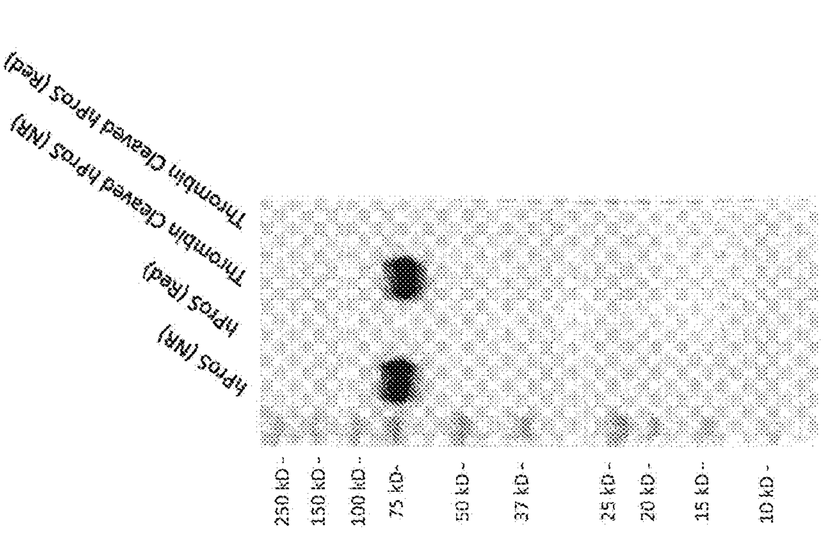
FIGS. 13A-13H depict the characterization of Antibody 14 and Antibody 2, antibodies sharing the same human variable region, and are characterized as dual inhibitors.

FIG. 13A depicts a Western blot showing that Antibody 14 does not bind Protein S in the TSR of Protein S. The Western blot was carried out as described for FIG. 11A. By Western blot, Antibody 14 bound the full Protein S and the thrombin-cleaved Protein S, but did not bind the reduced Protein S, and the reduced thrombin-cleaved Protein S. These results indicate that Antibody 14 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 14 was determined to bind to the heavy chain of Protein S. Calcium dependence was determined, also as described above, and Antibody 14 showed binding that was calcium-independent.

Figure 13B:
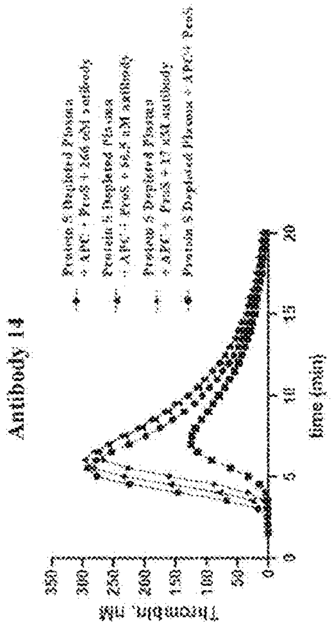
Figure 13C:
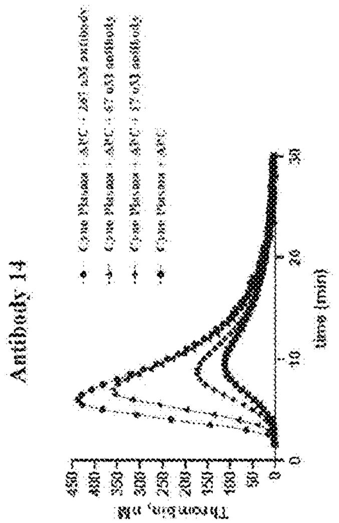
Figure 13D:
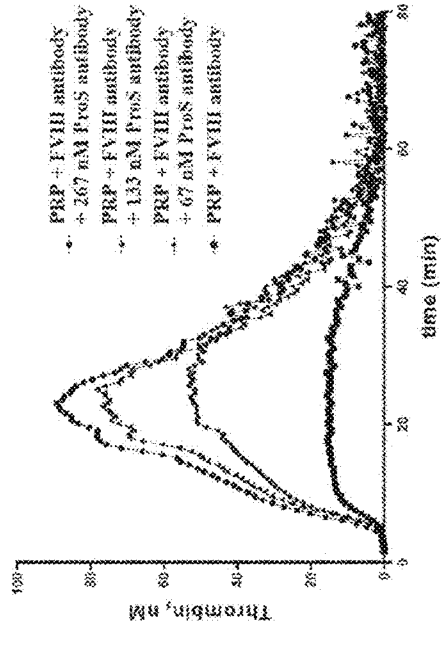

FIGS. 13B-13D depict the results of an APC cofactor assay for Antibody 14 using Protein S deficient human PPP, cynomolgus monkey PPP, and a TFPI cofactor assay using human PRP, respectively.

Figure 13F:
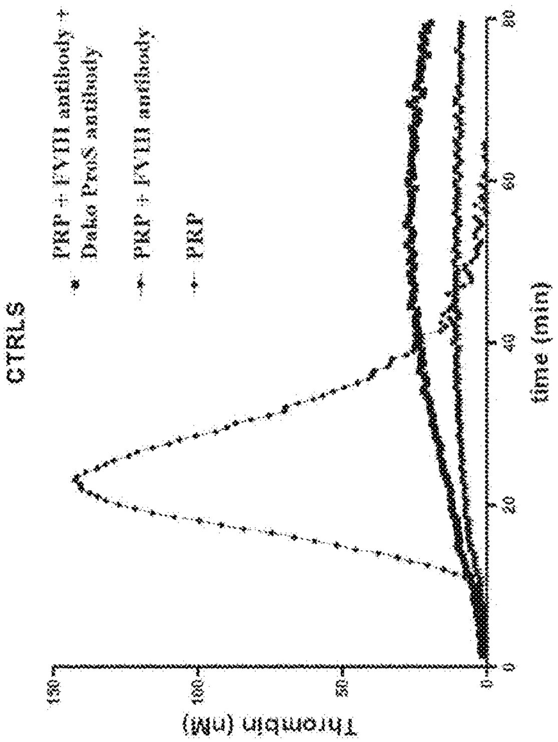
Figure 13E:
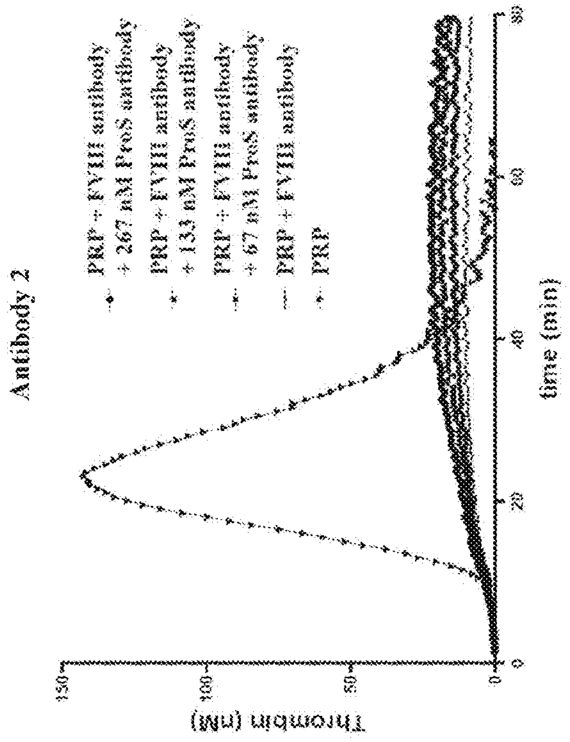

FIGS. 13E and 13F depict the results of a TFPI cofactor assay in human PRP using Antibody 2 and controls, respectively. A rabbit polyclonal human Protein S antibody labeled Dako was used as a positive control.

Figure 13H:
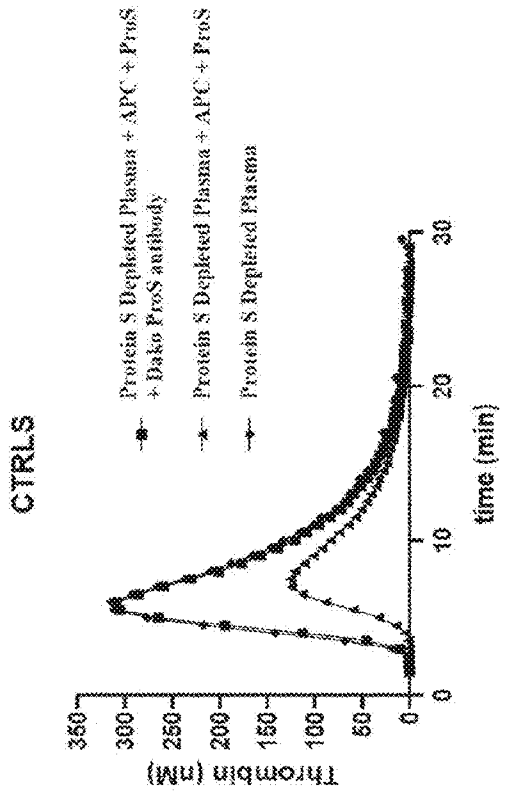
Figure 13G:
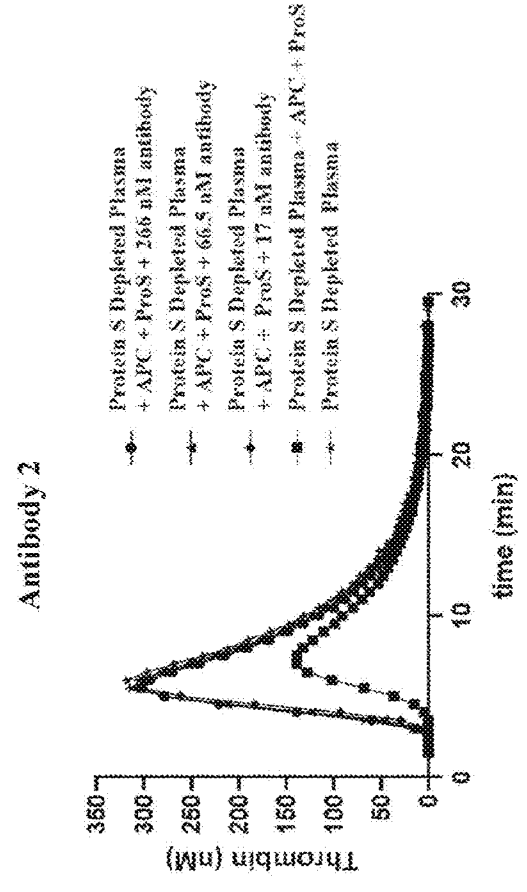

FIGS. 13G-13H depict the results of the APC cofactor assay performed with Antibody 2 and controls, respectively.

These results indicate that Antibody 14 and Antibody 2 are dual inhibitors.

Antibody 15 and Antibody 3

FIGS. 14A-14H depict the characterization of Antibody 15 and Antibody 3, antibodies sharing the same human variable region, and are characterized as dual inhibitors.

Figure 14A:
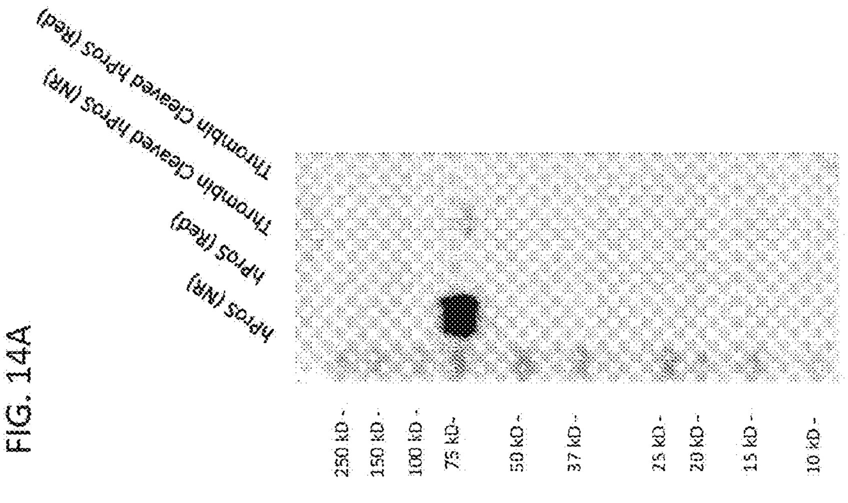
FIGS. 14A-14H depict the characterization of Antibody 15 and Antibody 3, antibodies sharing the same human variable region, and are characterized as dual inhibitors.

FIG. 14A depicts a Western blot showing that Antibody 15 binds Protein S in the TSR region of Protein S. The Western blot was carried out as described for FIG. 11A. By Western blot, Antibody 15 bound the full Protein S and showed a small band for the thrombin-cleaved Protein S, but did not bind the reduced Protein S, and the reduced thrombin-cleaved Protein S. These results indicate that Antibody 15 binds Protein S at the TSR, and the lack of signal observed with the reduced Protein S showed that the epitope for this antibody is not a linear epitope.

Binding to the heavy chain of Protein S was determined using an ELISA based method, as described above. Antibody 15 was determined to bind to the heavy chain of Protein S. Calcium dependence was determined, also as described above, and Antibody 15 showed binding that was calcium-dependent.

Figure 14B:
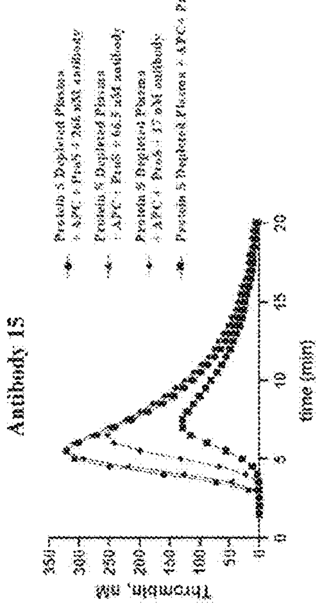
Figure 14C:
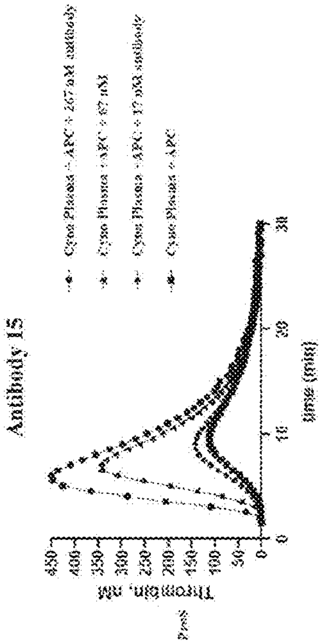
Figure 14D:
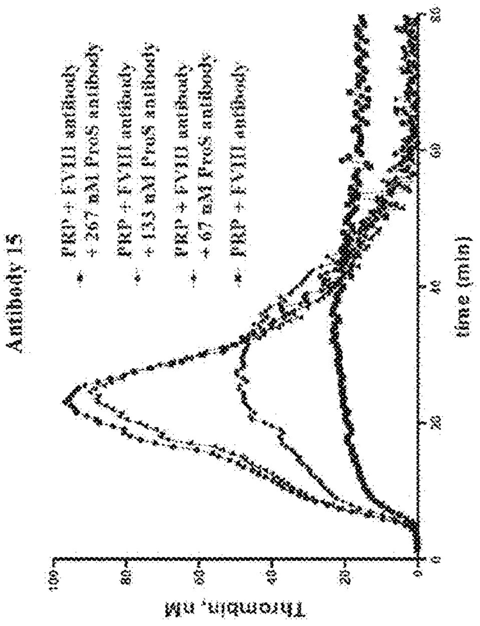

FIGS. 14B-14D depict the results of an APC cofactor assay for Antibody 15 using Protein S deficient human PPP, cynomolgus monkey PPP, and a TFPI cofactor assay using human PRP, respectively.

Figure 14E:
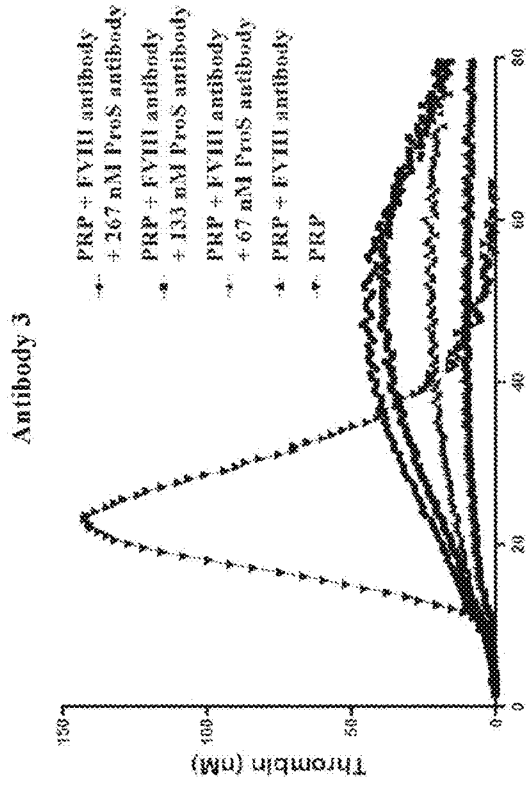
Figure 14F:
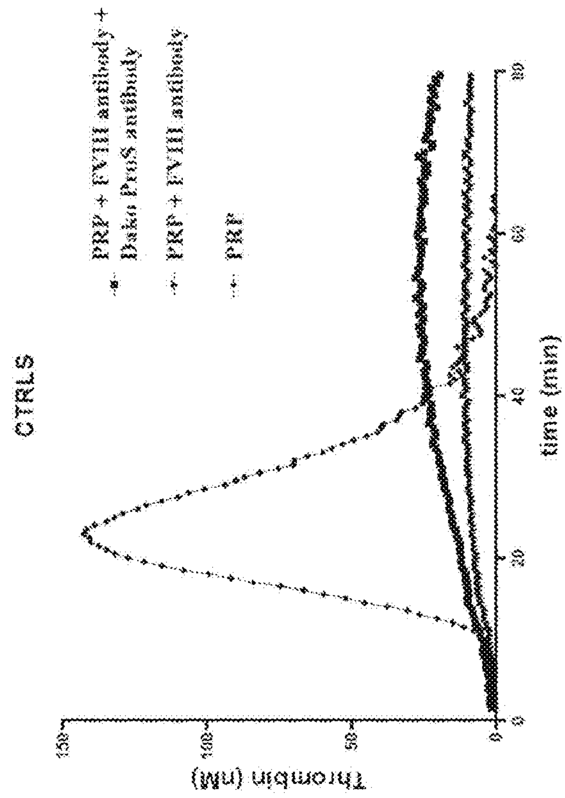

FIGS. 14E and 14F depict the results of a TFPI cofactor assay in human PRP using Antibody 3 and controls, respectively. A rabbit polyclonal human Protein S antibody labeled Dako was used as a positive control.

Figure 14H:
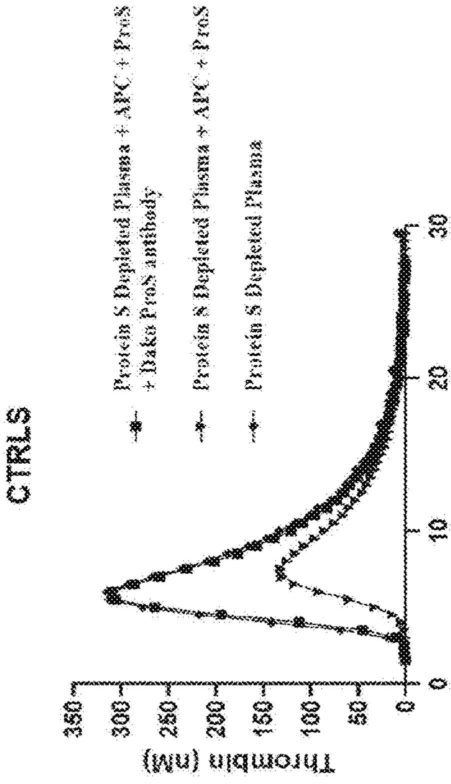
Figure 14G:
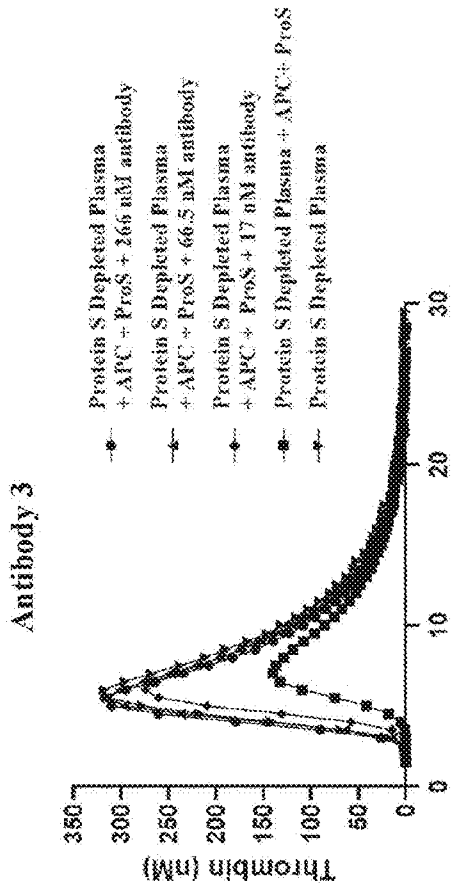

FIGS. 14G-14H depict the results of the APC cofactor assay performed with Antibody 3 and controls, respectively.

These results indicate that Antibody 15 and Antibody 3 are dual inhibitors.

Antibody 16 and Antibody 4

FIGS. 15A-15H depict the characterization of Antibody 16 and Antibody 4, antibodies sharing the same human variable region, and are characterized as dual inhibitors.

Figure 15A:
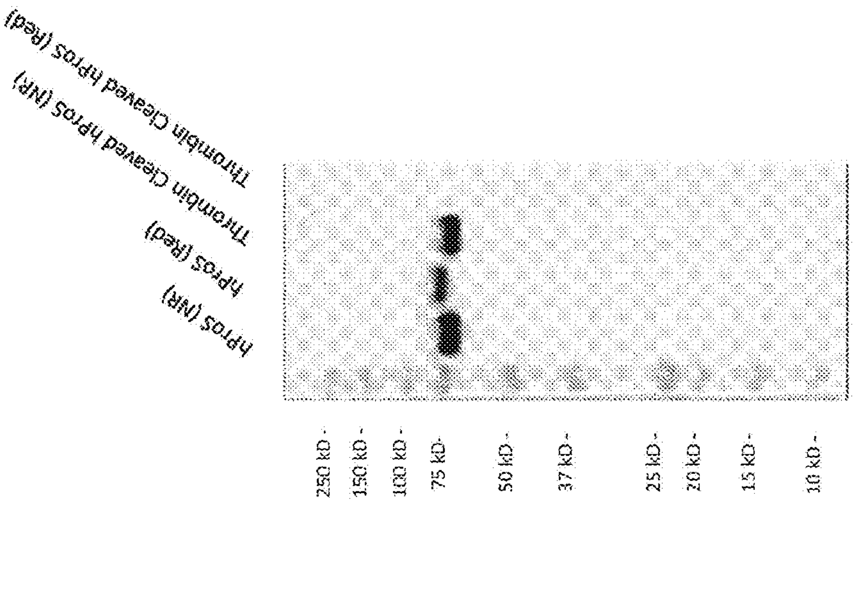
FIGS. 15A-15H depict the characterization of Antibody 16 and Antibody 4, antibodies sharing the same human variable region, and are characterized as dual inhibitors.

FIG. 15A depicts a Western blot showing that Antibody 16 binds Protein S in the Gla-domain of Protein S. The Western blot was carried out as described for FIG. 11A. By Western blot, Antibody 16 bound the full Protein S, the thrombin-cleaved Protein S, the reduced Protein S, but did not bind the reduced thrombin-cleaved Protein S. These results indicate that Antibody 16 binds Protein S at the Gla-domain, and the signal observed with the reduced Protein S showed that the epitope for this antibody is a linear epitope.

Binding to the heavy chain of Protein S was determined using an ELISA based method, as described herein. Antibody 16 was determined to bind to the heavy chain of Protein S. Calcium dependence was determined, also as described herein, and Antibody 16 showed binding that was calcium-dependent.

Figure 15B:
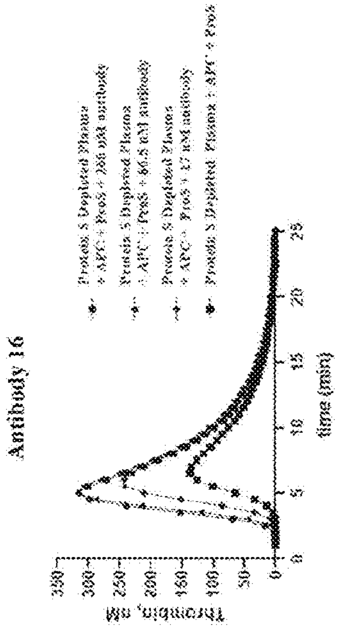
Figure 15C:
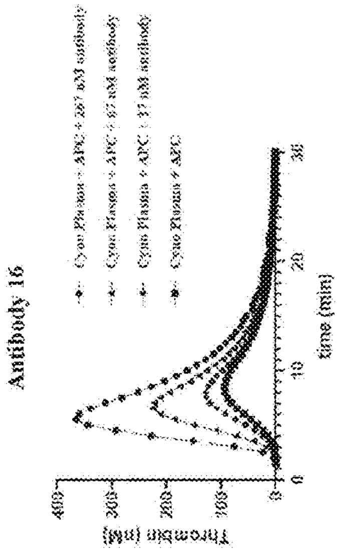
Figure 15D:
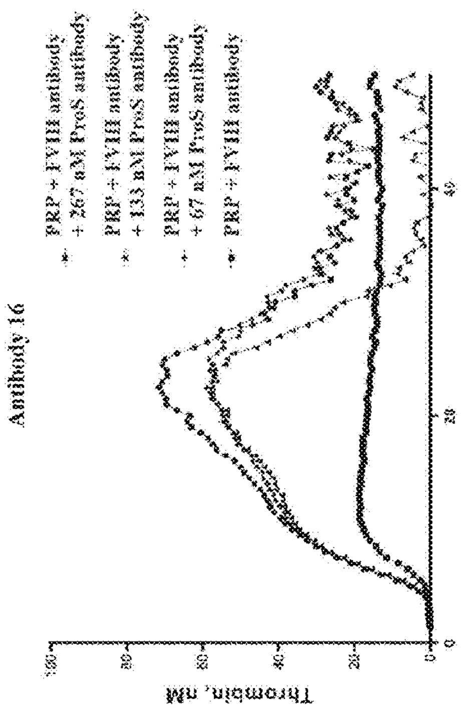

FIGS. 15B-15D depict the results of an APC cofactor assay for Antibody 16 using Protein S deficient human PPP, cynomolgus monkey PPP, and a TFPI cofactor assay using human PRP, respectively.

Figure 15E:
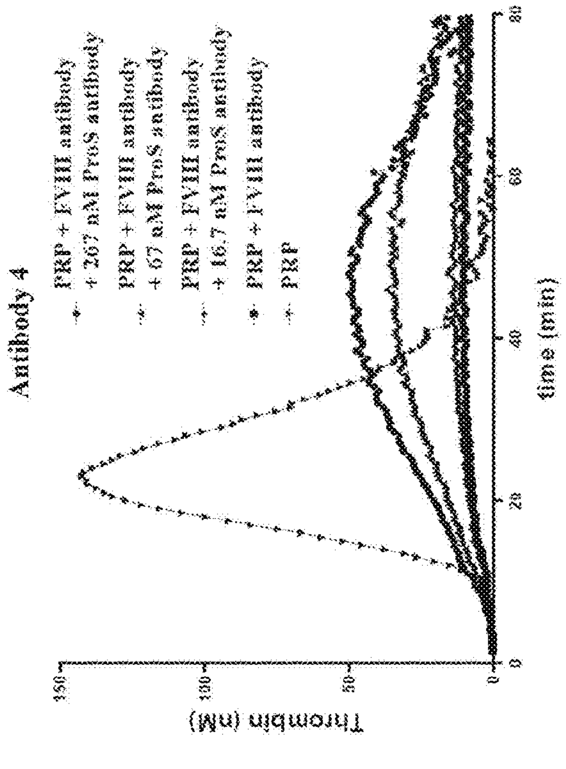
Figure 15F:
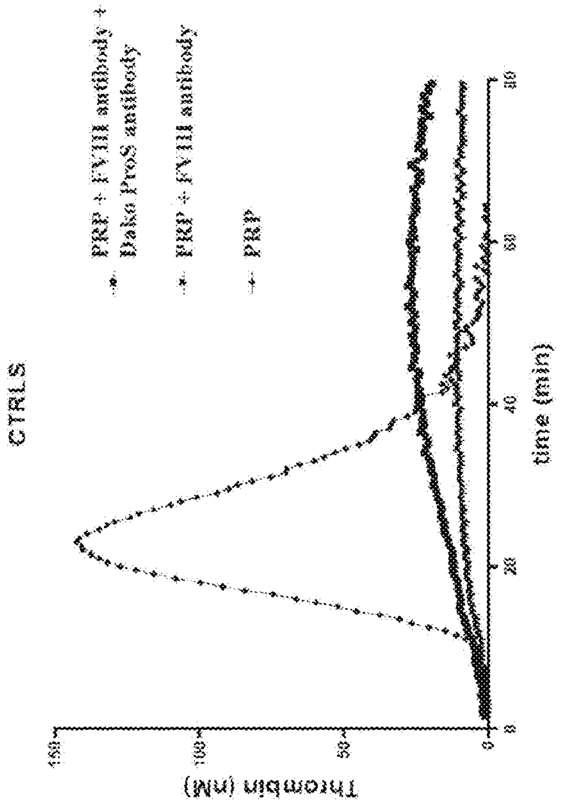

FIGS. 15E and 15F depict the results of a TFPI cofactor assay in human PRP using Antibody 4 and controls, respectively. A rabbit polyclonal human Protein S antibody labeled Dako was used as a positive control.

Figure 15H:
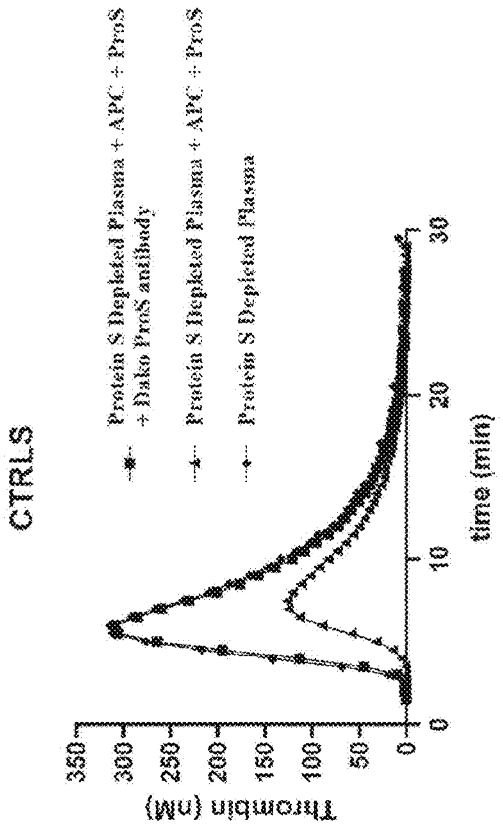
Figure 15G:
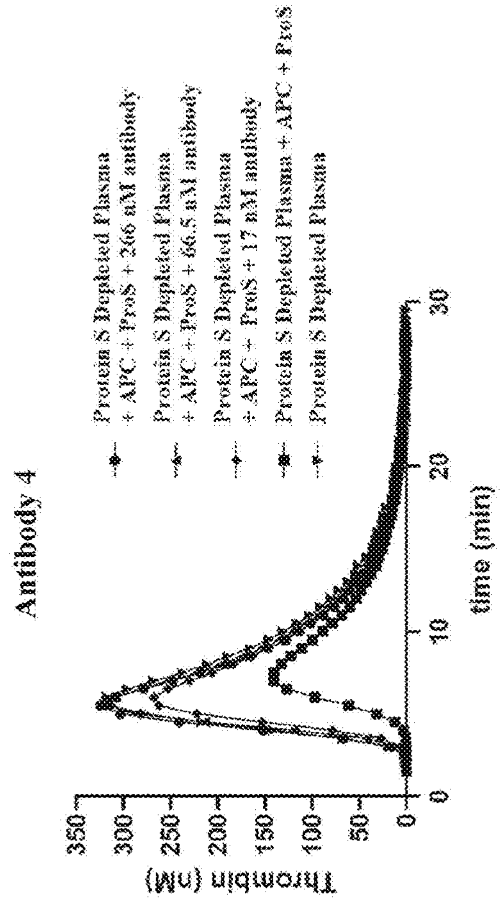

FIGS. 15G-15H depict the results of the APC cofactor assay performed with Antibody 4, and controls, respectively.

These results indicate that Antibody 16 and Antibody 4 are dual inhibitors.

Antibody 20 and Antibody 8

FIGS. 16A-16H depict the characterization of Antibody 20 and Antibody 8, antibodies sharing the same human variable region, and are characterized as dual inhibitors.

Figure 16C:
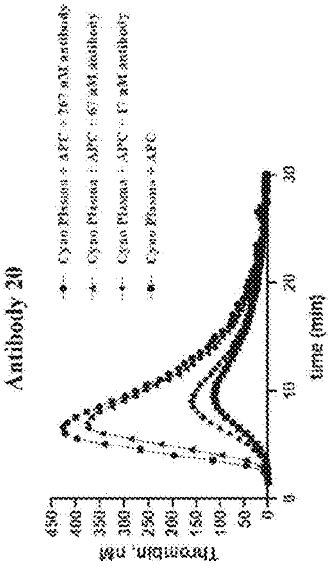
FIGS. 16A-16H depict the characterization of Antibody 20 and Antibody 8, antibodies sharing the same human variable region, and are characterized as dual inhibitors.
Figure 16B:
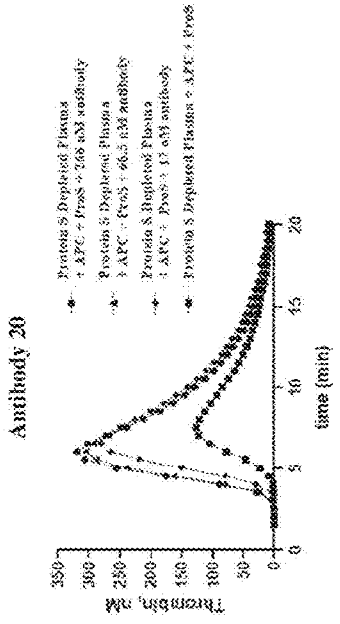
Figure 16D:
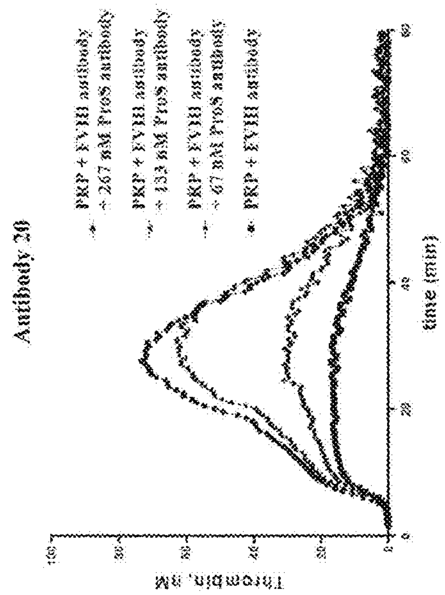
Figure 16A:
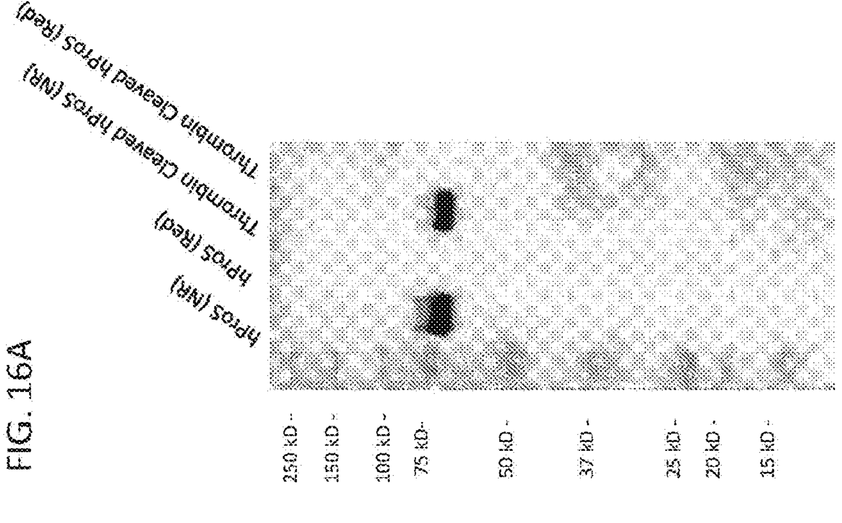

FIG. 16A depicts a Western blot showing that Antibody 20 does not bind Protein S in the TSR of Protein S. The Western blot was carried out as described for FIG. 11A. By Western blot, Antibody 20 bound the full Protein S and the thrombin-cleaved Protein S, but did not bind the reduced Protein S or the reduced thrombin-cleaved Protein S. These results indicate that Antibody 20 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 20 was determined to bind to the heavy chain of Protein S. Calcium dependence was determined, also as described herein, and Antibody 20 showed binding that was calcium-dependent.

FIGS. 16B-16D depict the results of an APC cofactor assay for Antibody 20 using Protein S deficient human PPP, cynomolgus monkey PPP, and a TFPI cofactor assay using human PRP, respectively.

Figure 16E:
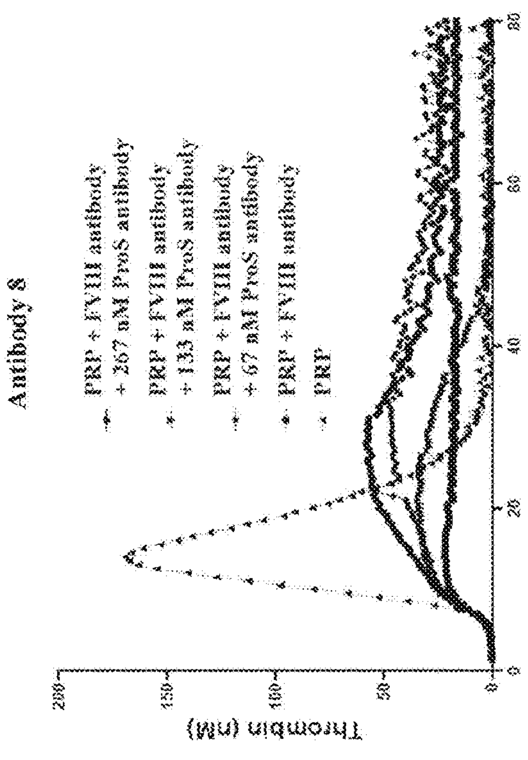
Figure 16F:
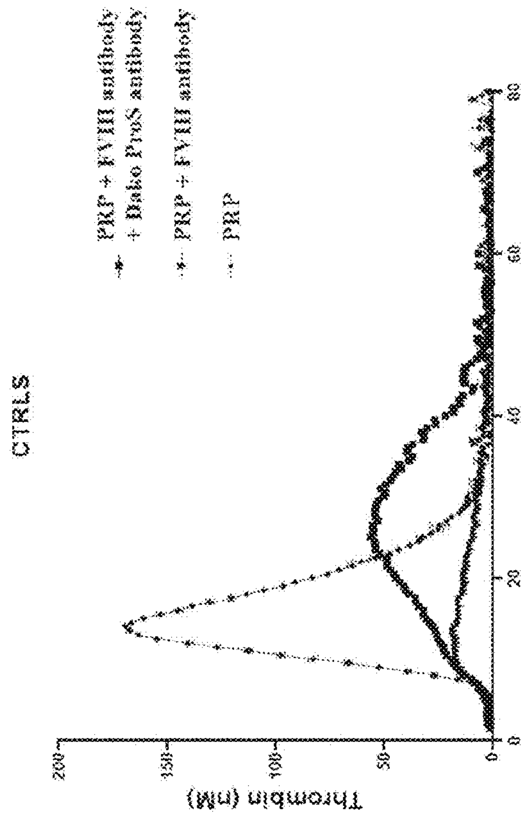

FIGS. 16E and 16F depict the results of a TFPI cofactor assay in human PRP using Antibody 8 and controls, respectively. A rabbit polyclonal human Protein S antibody labeled Dako was used as a positive control.

Figure 16G:
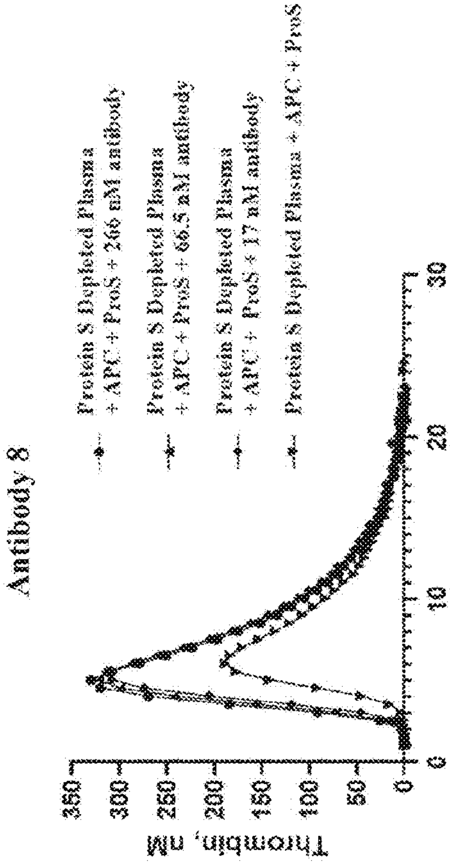
Figure 16H:
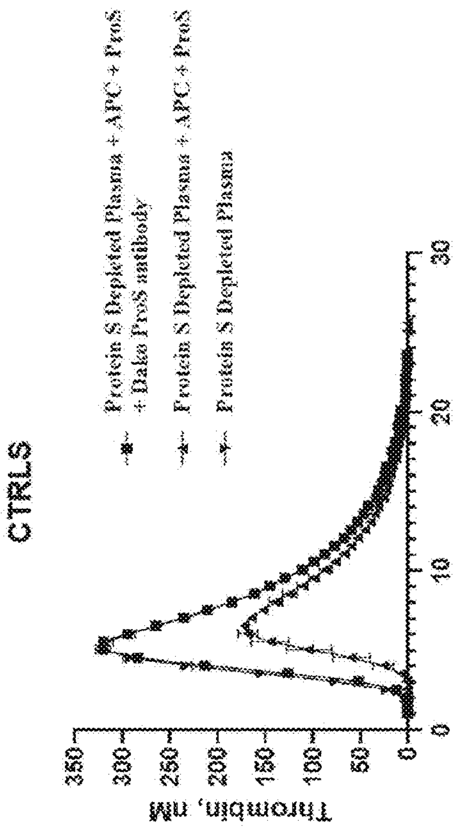

FIGS. 16G-16H depict the results of the APC cofactor assay performed with Antibody 8 and controls, respectively.

These results indicate that Antibody 20 and Antibody 8 are dual inhibitors.

Antibody 21 and Antibody 9

FIGS. 17A-17H depict the characterization of Antibody 21 and Antibody 9, antibodies sharing the same human variable region, and are characterized as APC cofactor inhibitors.

Figures 17A, 17B, 17C, 17D:
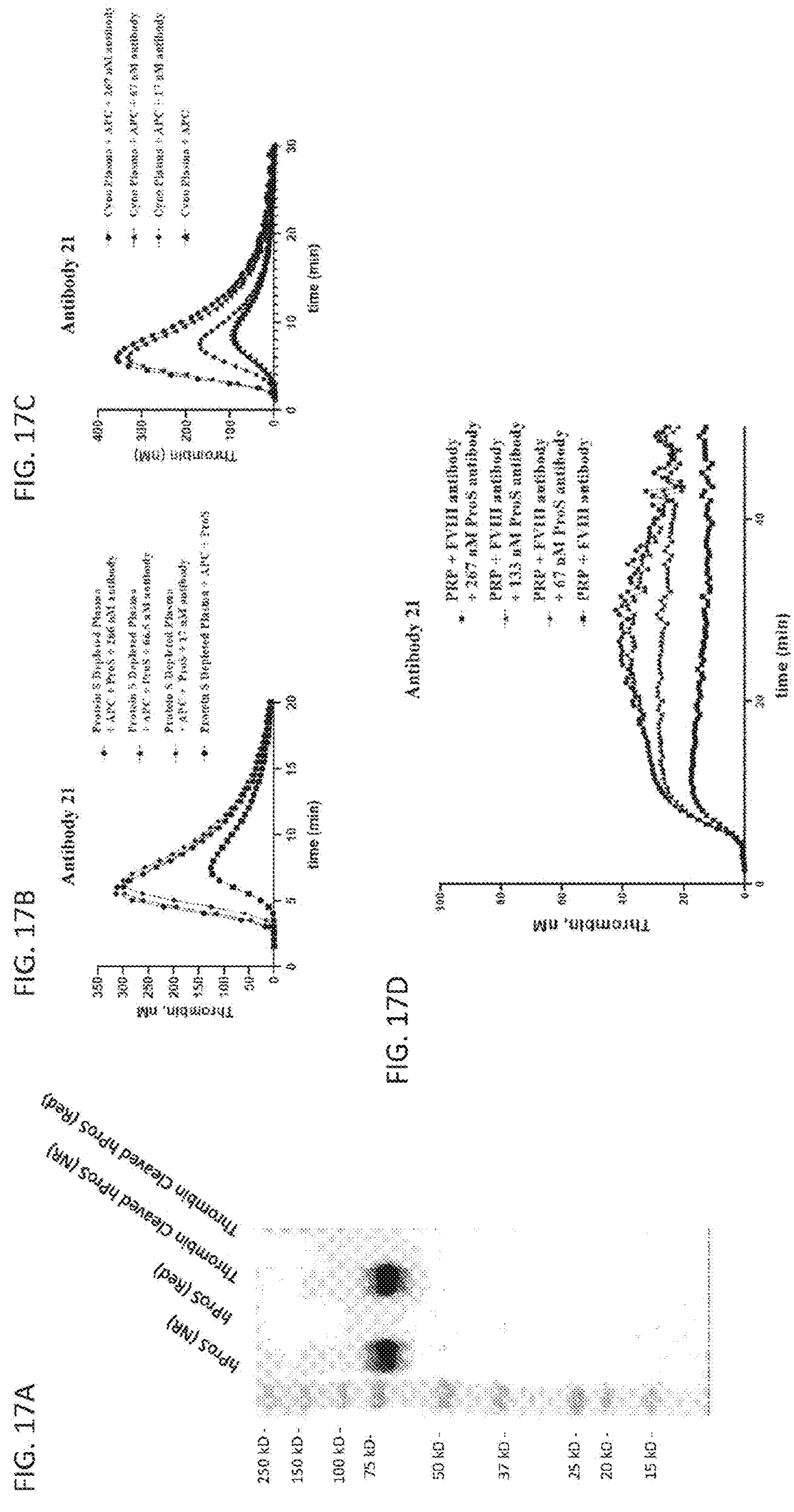
FIGS. 17A-17H depict the characterization of Antibody 21 and Antibody 9, antibodies sharing the same human variable region, and are characterized as APC cofactor inhibitors.

FIG. 17A depicts a Western blot showing that Antibody 21 does not bind Protein S in the TSR of Protein S. The Western blot was carried out as described for FIG. 11A. By Western blot, Antibody 21 bound the full Protein S and the thrombin-cleaved Protein S, but did not bind the reduced Protein S or the reduced thrombin-cleaved Protein S. These results indicate that Antibody 21 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 21 was determined to bind to the heavy chain of Protein S. Calcium dependence was determined, also as described herein, and Antibody 21 showed binding that was calcium-independent.

FIGS. 17B-17D depict the results of an APC cofactor assay for Antibody 21 using Protein S deficient human PPP, cynomolgus monkey PPP, and a TFPI cofactor assay using human PRP, respectively.

Figure 17E:
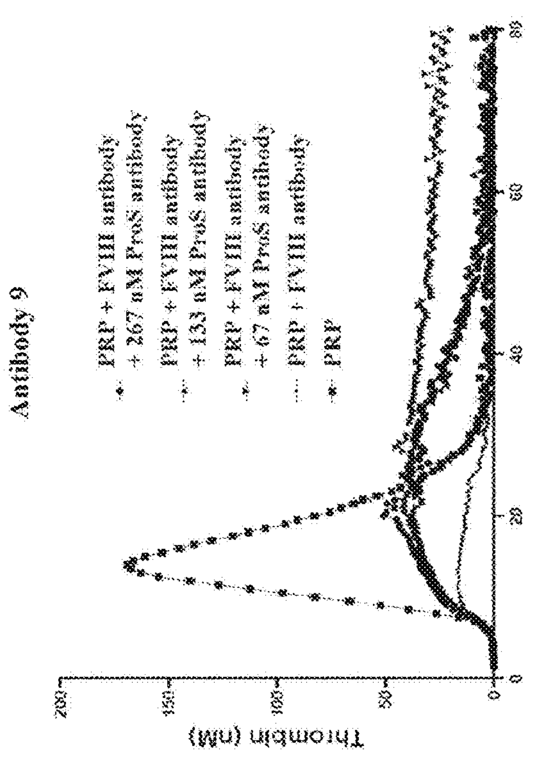
Figure 17F:
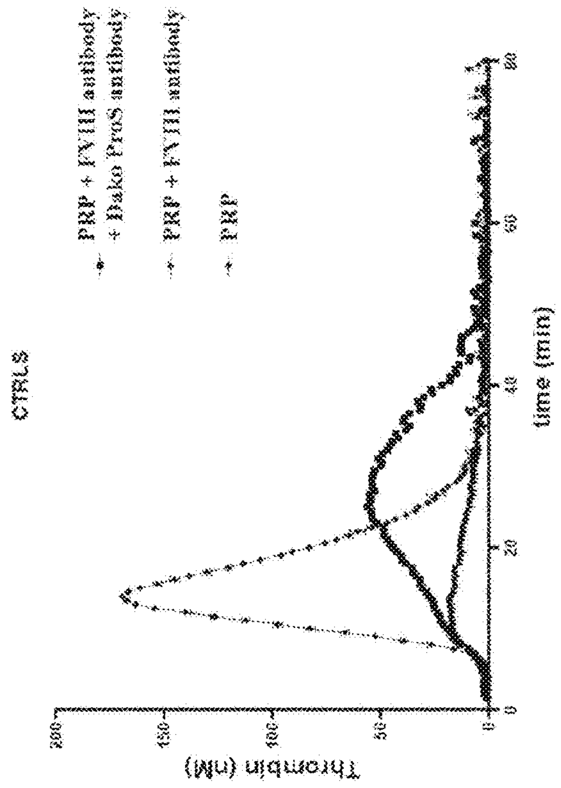

FIGS. 17E and 17F depict the results of a TFPI cofactor assay in human PRP using Antibody 9 and controls, respectively. A rabbit polyclonal human Protein S antibody labeled Dako was used as a positive control.

Figure 17G:
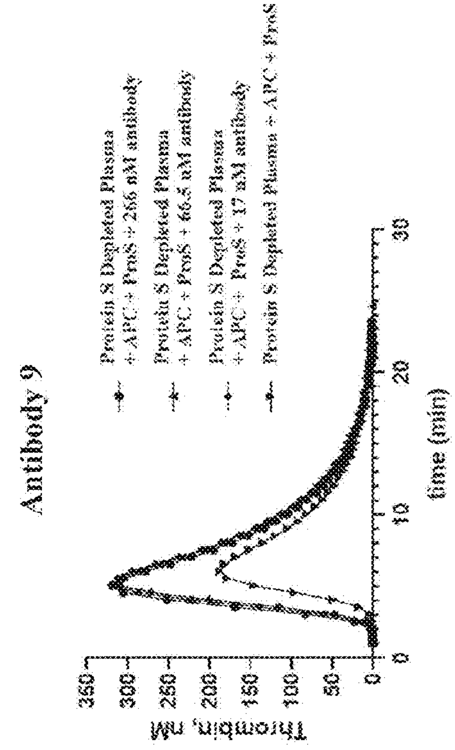
Figure 17H:
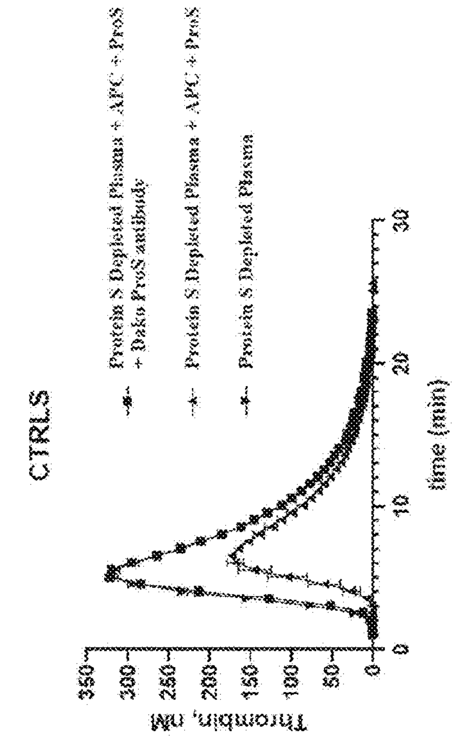

FIGS. 17G-17H depict the results of the APC cofactor assay performed with Antibody 9 and controls, respectively.

These results indicate that Antibody 21 and Antibody 9 are APC cofactor inhibitors.

Antibody 23 and Antibody 11

FIGS. 18A-18G depict the characterization of Antibody 23 and Antibody 11, antibodies sharing the same human variable region, and are characterized as TFPI cofactor inhibitors.

Binding to the heavy chain of Protein S was determined using an ELISA based method, as described herein. Antibody 23 was determined to not bind to the heavy chain of Protein S. Calcium dependence was determined, also as described herein, and Antibody 23 showed binding that was calcium-independent.

Figure 18A:
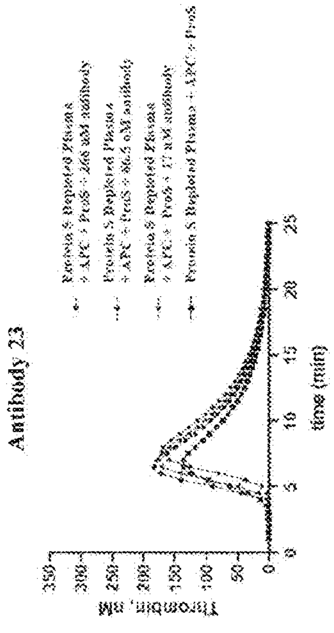
FIGS. 18A-18G depict the characterization of Antibody 23 and Antibody 11, antibodies sharing the same human variable region, and are characterized as TFPI cofactor inhibitors.
Figure 18B:
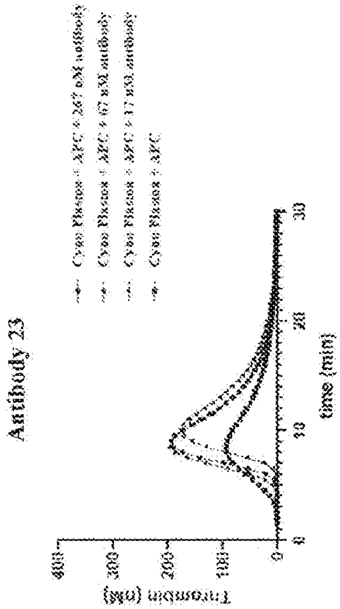
Figure 18C:
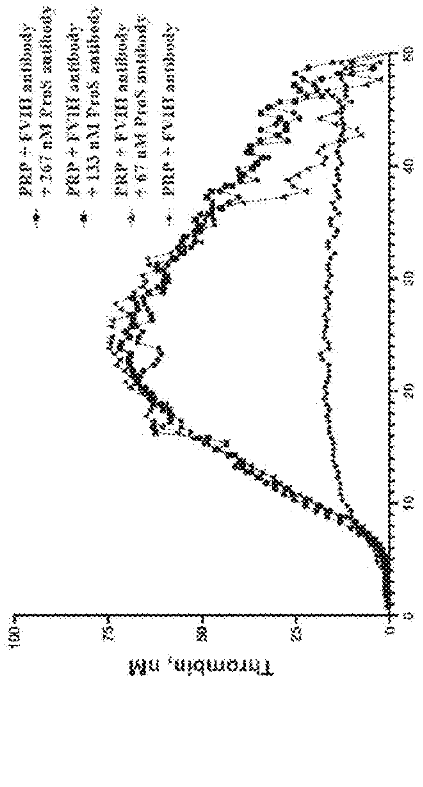

FIGS. 18A-18C depict the results of a APC cofactor assay for Antibody 23 using Protein S deficient human PPP, cynomolgus monkey PPP, and a TFPI cofactor assay using human PRP, respectively.

Figure 18E:
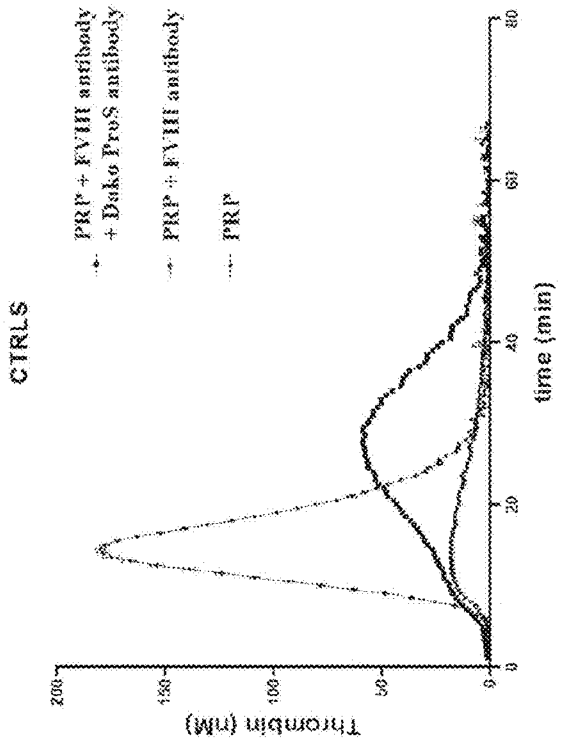
Figure 18D:
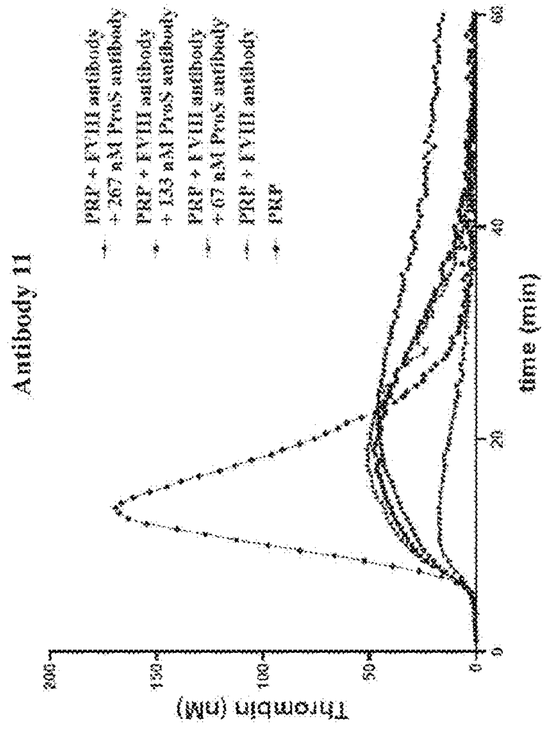

FIGS. 18D and 18E depict the results of a TFPI cofactor assay in human PRP using Antibody 11 and controls, respectively.

Figure 18F:
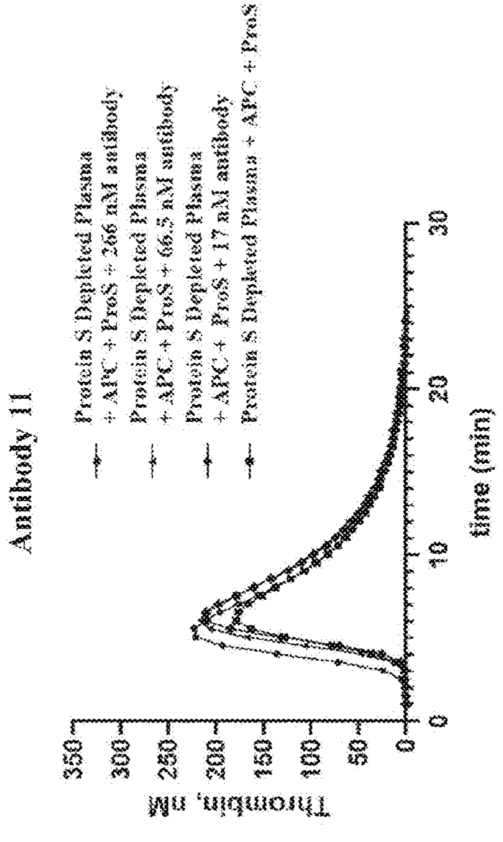
Figure 18G:
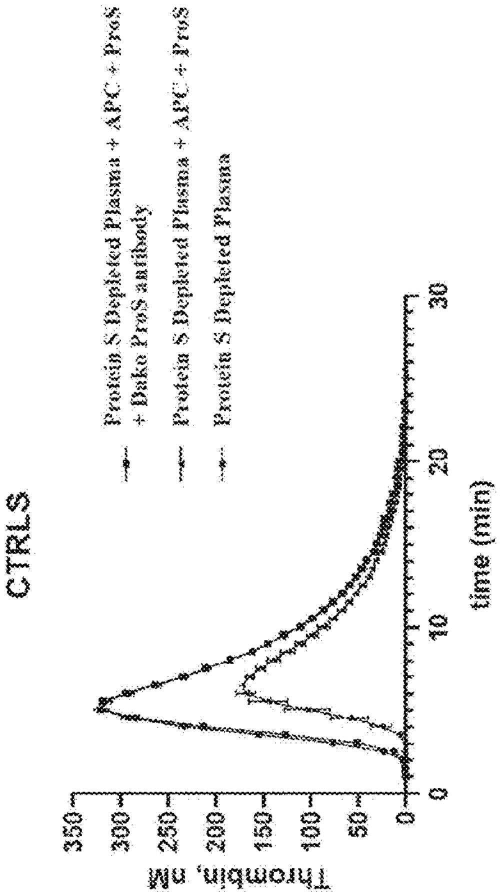

FIGS. 18F and 180G depict the results of a APC cofactor assay with Antibody 11 and controls, respectively.

These results indicate that Antibody 23 and Antibody 11 are TFPI cofactor inhibitors.

Antibody 24 and Antibody 12

FIGS. 19A-19H depict the characterization of Antibody 24 and Antibody 12, antibodies sharing the same human variable region, and are characterized as dual inhibitors.

FIG. 191A depicts a Western blot showing that Antibody 24 binds Protein S in the TSR of Protein S. The Western blot was carried out as described for FIG. 11A. By Western blot, Antibody 24 bound the full Protein S but did not bind the thrombin-cleaved Protein S. Antibody 24 did not bind the reduced Protein S or the reduced thrombin-cleaved Protein S. These results indicate that Antibody 24 binds Protein S at the TSR, and the lack of signal observed with the reduced Protein S showed that the epitope for this antibody is not a linear epitope.

Binding to the heavy chain of Protein S was determined using an ELISA based method, as described herein. Antibody 24 was determined to bind to the heavy chain of Protein S. Calcium dependence was determined, also as described herein, and Antibody 24 showed binding that was calcium-dependent.

Figure 19A:
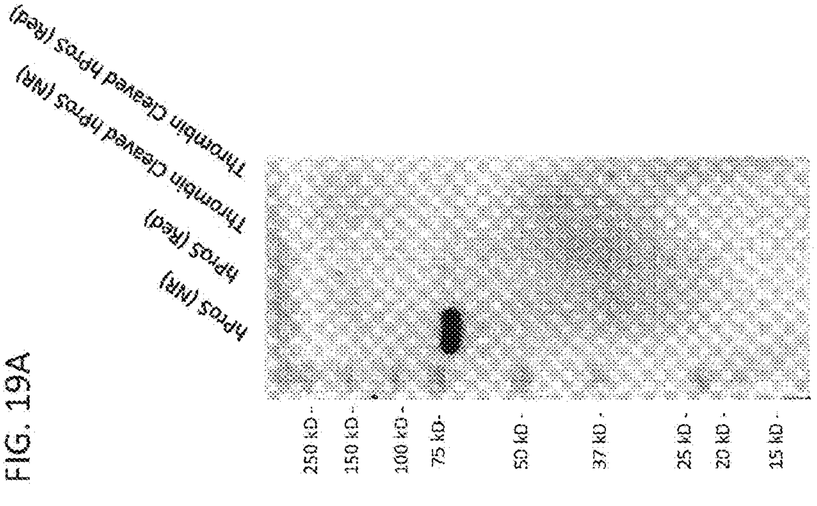
FIGS. 19A-19H depict the characterization of Antibody 24 and Antibody 12, antibodies sharing the same human variable region, and are characterized as dual inhibitors.
Figure 19B:
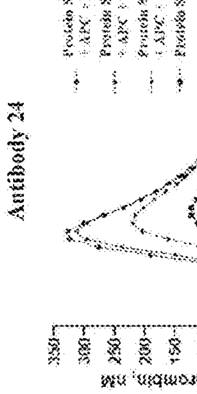
Figure 19C:
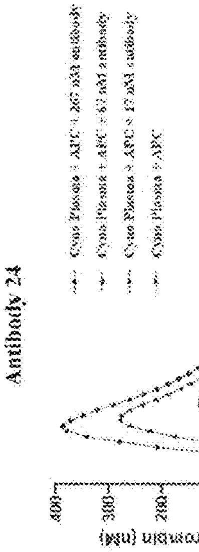
Figure 19D:
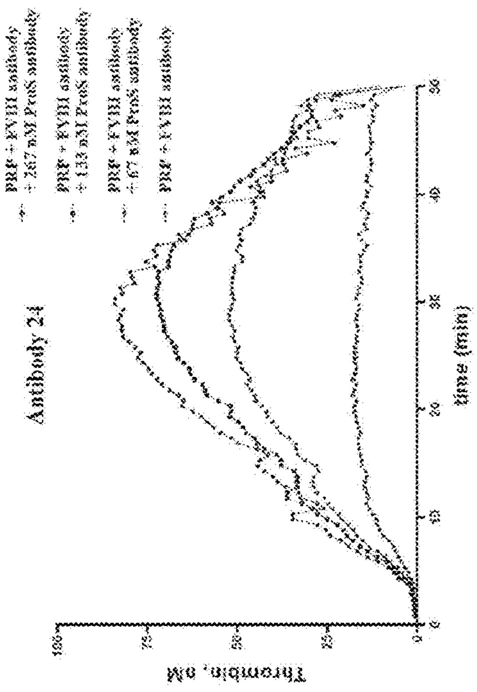

FIGS. 19B-19D depict the results of a APC cofactor assay for Antibody 24 using Protein S deficient human PPP, cynomolgus monkey PPP, and a TFPI cofactor assay using human PRP, respectively.

Figure 19F:
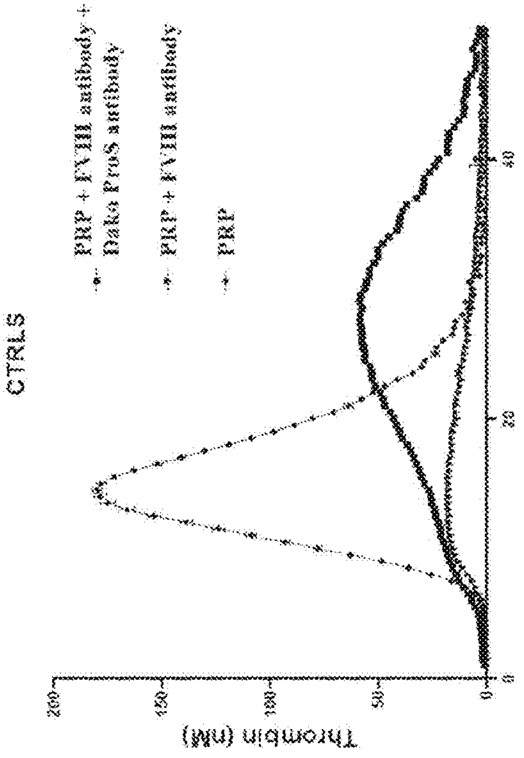
Figure 19E:
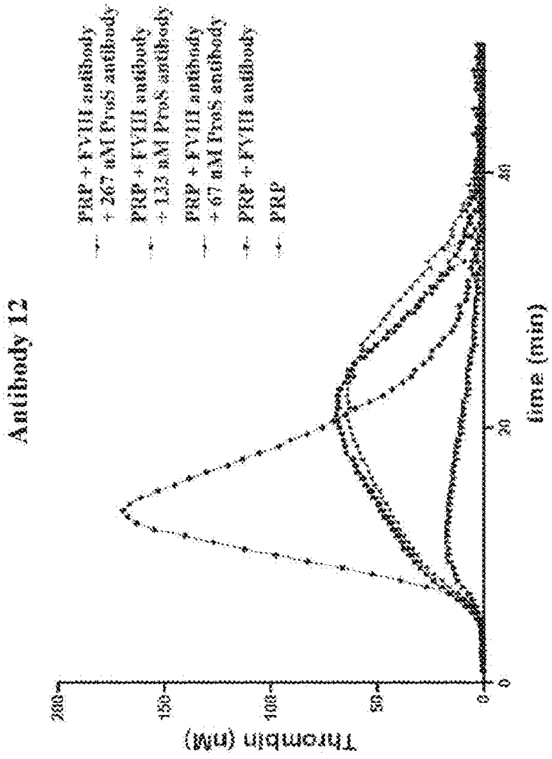

FIGS. 19E and 19F depict the results of a TFPI cofactor assay in human PRP using Antibody 12 and controls, respectively.

Figure 19H:
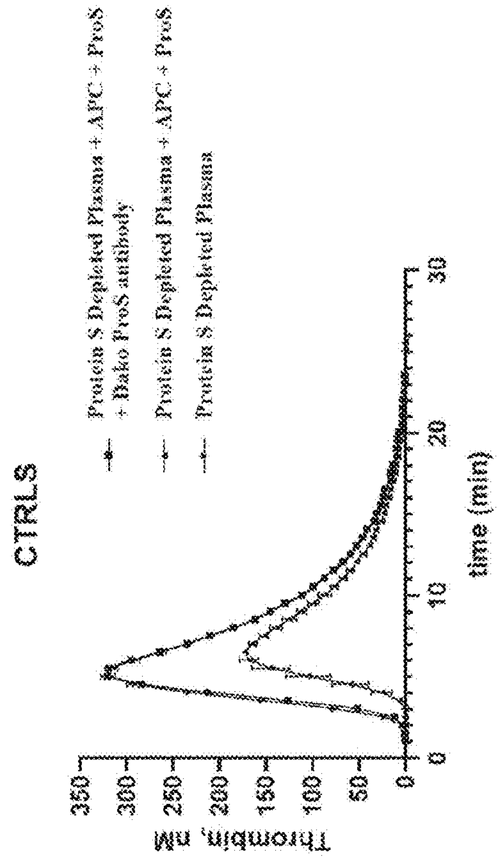
Figure 19G:
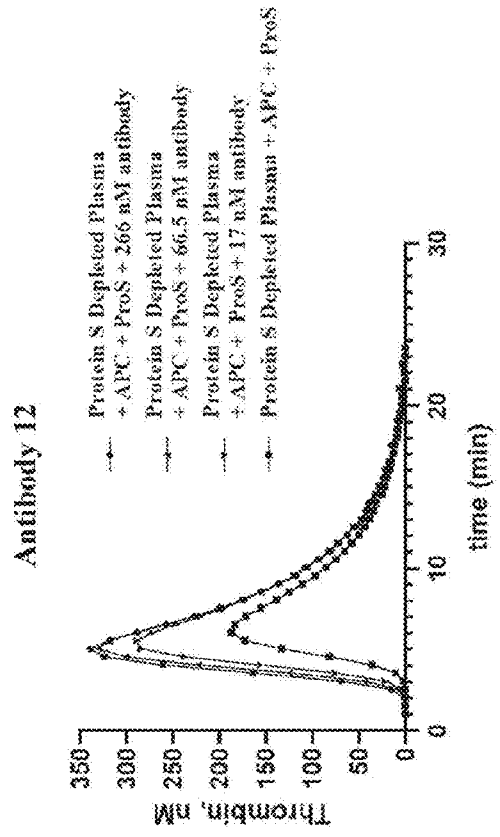

FIGS. 19G and 19H depict the results of a APC cofactor assay with Antibody 12 and controls, respectively.

These results indicate that Antibody 24 and Antibody 12 are dual inhibitors.

Antibody 18 and Antibody 6

FIGS. 20A-20H depict the characterization of Antibody 18 and Antibody 6, antibodies sharing the same human variable region, and are characterized as APC cofactor inhibitors.

Figure 20C:
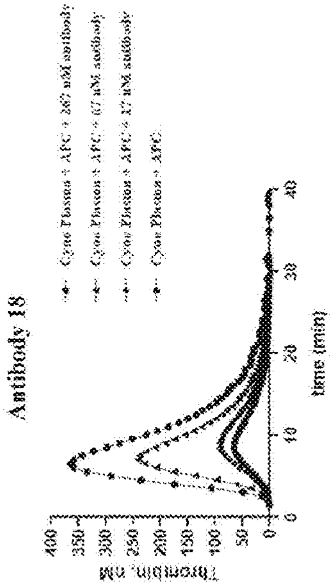
FIGS. 20A-20H depict the characterization of Antibody 18 and Antibody 6, antibodies sharing the same human variable region, and are characterized as APC cofactor inhibitors.
Figure 20B:
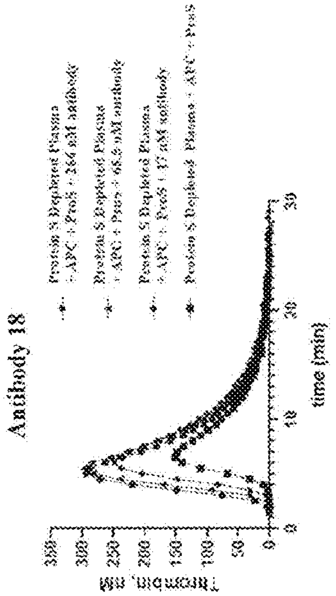
Figure 20D:
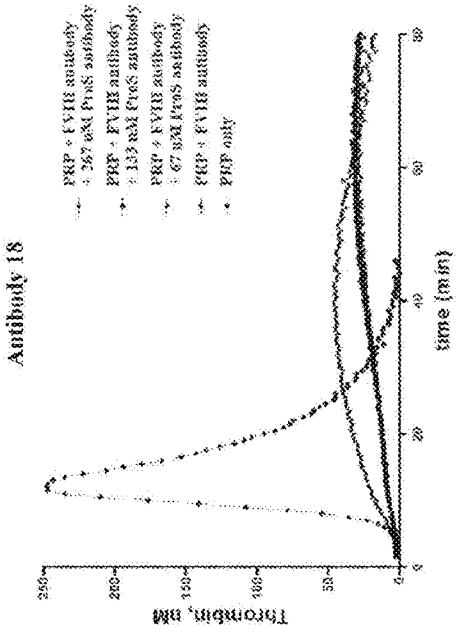
Figure 20A:
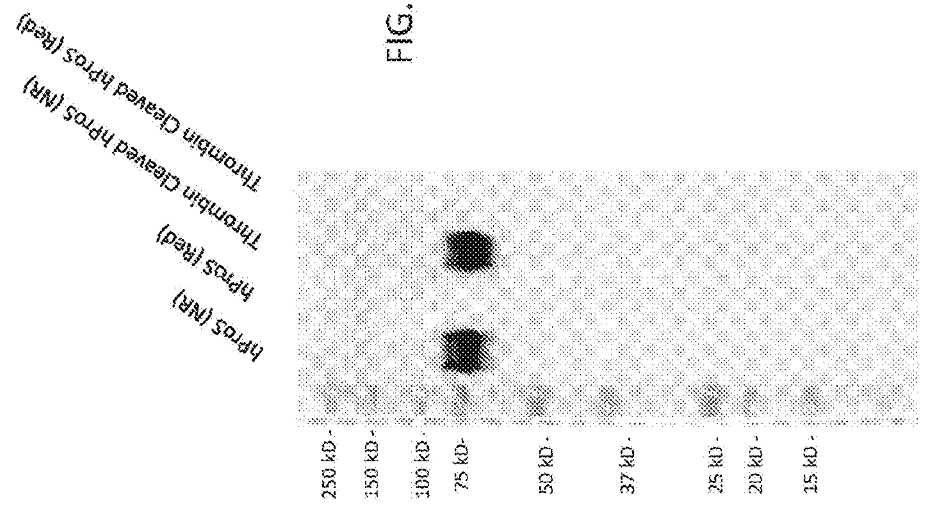

FIG. 20A depicts a Western blot showing that Antibody 18 does not bind Protein S in the TSR of Protein S. The Western blot was carried out as described for FIG. 20A. By Western blot, Antibody 18 bound the full Protein S and the thrombin-cleaved Protein S, but did not bind the reduced Protein S or the reduced thrombin-cleaved Protein S. These results indicate that Antibody 18 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 18 was determined to bind to the heavy chain of Protein S. Calcium dependence was determined, also as described herein, and Antibody 18 showed binding that was calcium-dependent.

FIGS. 20B-20D depict the results of a APC cofactor assay for Antibody 18 using Protein S deficient human PPP, cynomolgus monkey PPP, and a TFPI cofactor assay using human PRP, respectively.

Figure 20F:
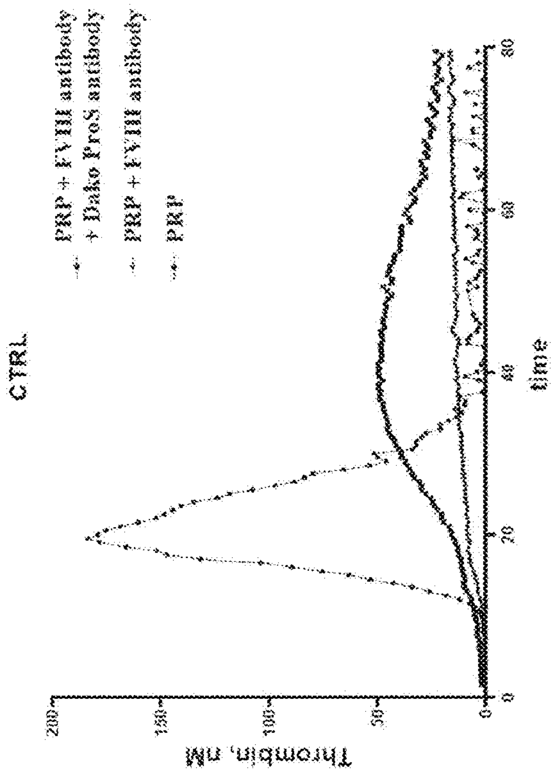
Figure 20E:
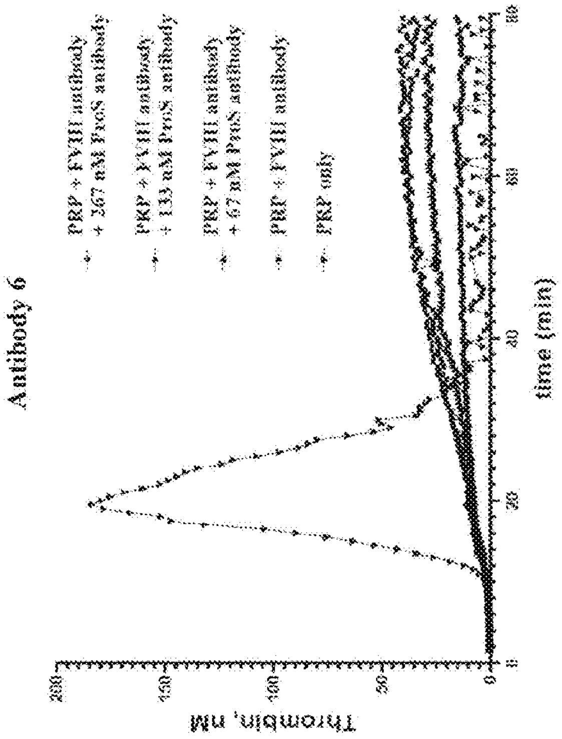

FIGS. 20E and 20F depict the results of a TFPI cofactor assay in human PRP using Antibody 6 and controls, respectively.

Figure 20G:
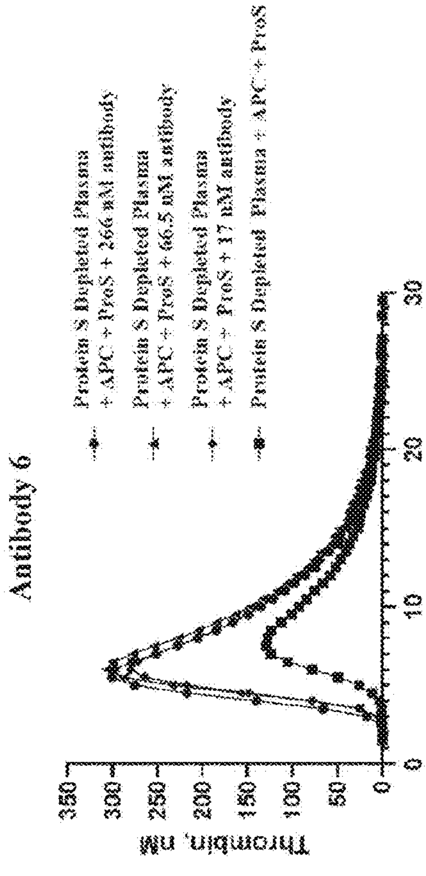
Figure 20H:
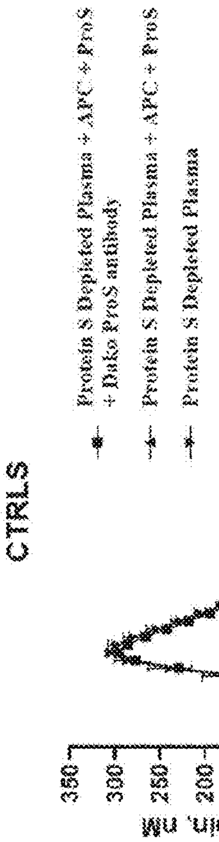

FIGS. 20G and 20H depict the results of a APC cofactor assay with Antibody 6 and controls, respectively.

These results indicate that Antibody 18 and Antibody 6 are APC cofactor inhibitors.

A summary of the characterizations exemplified above is presented in Table 13 below.

TABLE 13

| Human Antibody: Corresponding Protein S Antibody with Human Fc | Rat Antibody: Protein S Antibody with Rat Fc | Inhibitor Type |
|---|---|---|
| Antibody 1 | Antibody 13 | Dual |
| Antibody 2 | Antibody 14 | Dual |
| Antibody 3 | Antibody 15 | Dual |
| Antibody 4 | Antibody 16 | Dual |
| Antibody 6 | Antibody 18 | APC cofactor |
| Antibody 7 | Antibody 19 | Dual |
| Antibody 8 | Antibody 20 | Dual |
| Antibody 9 | Antibody 21 | APC cofactor |
| Antibody 11 | Antibody 23 | TFPI cofactor |
| Antibody 12 | Antibody 24 | Dual |

Example 4

Thrombin Generation Improvement in Plasma Samples from Patients with Various Factor Deficiencies and Von Willebrand Disease FIGS. 21A-21G depict enhanced thrombin generation when Antibody 15 is added to various samples of congenital factor deficient plasma containing soluble thrombomodulin, a cofactor of thrombin that is involved in conversion of thrombin to an anti-coagulant enzyme. Plasma samples were taken from patients having various factor deficiencies and conditions: Factor VII, Factor VIII, Factor IX, or Factor XI deficiencies, and von Willebrand disease (vWD) type 1, 2, or 3.

Figure 21A:
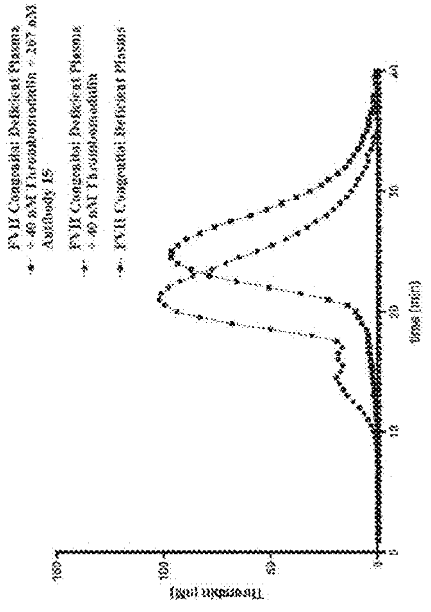
FIGS. 21A-21G depict enhanced thrombin generation when Antibody 15 is added to various samples of congenital factor deficient plasma containing soluble thrombomodulin.
Figure 21B:
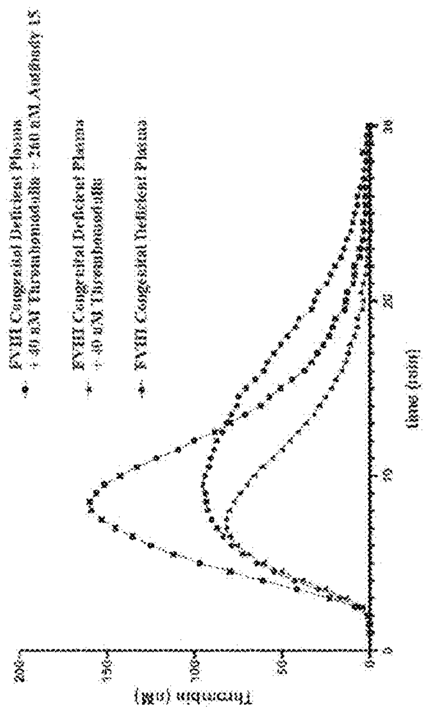
Figure 21C:
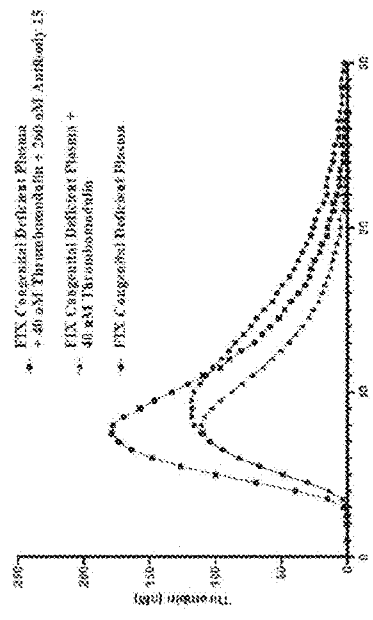
Figure 21E:
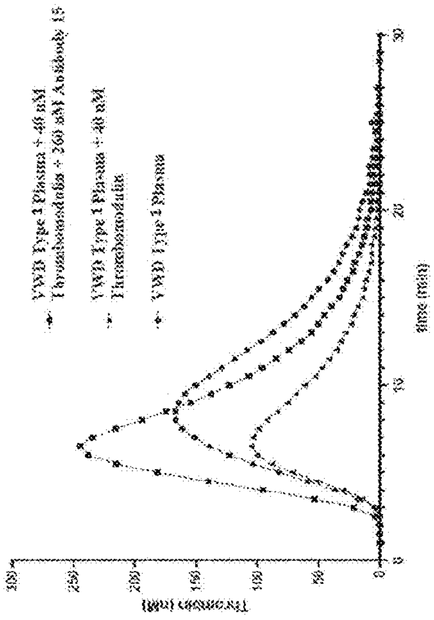
Figure 21D:
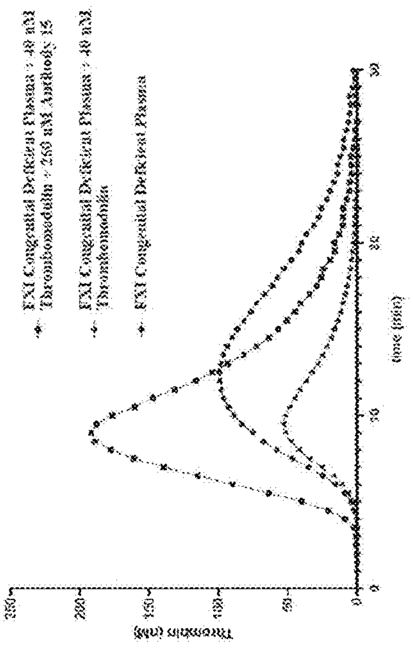
Figure 21F:
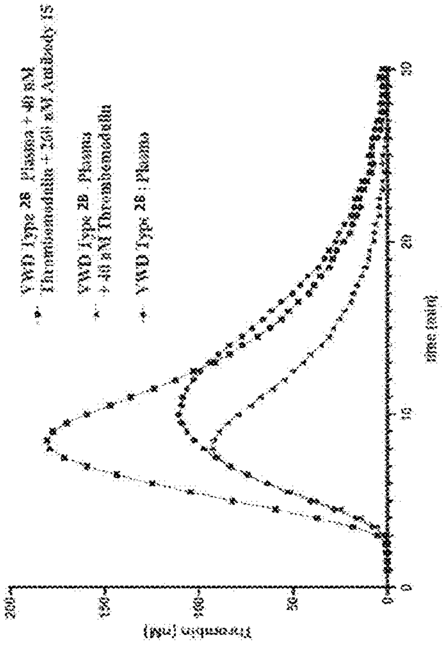
Figure 21G:
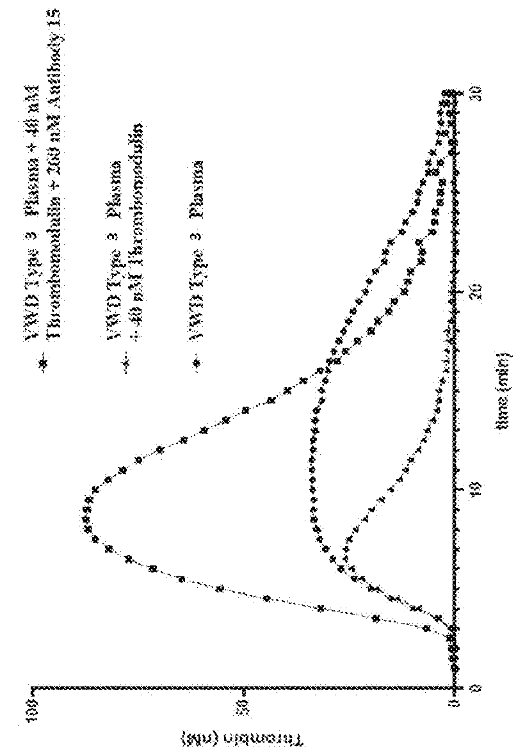

FIG. 21A depicts soluble tissue factor added to congenital Factor VII deficient plasma in the presence or absence of 40 nM soluble thrombomodulin. The level of thrombin generated is measured over time. When Antibody 15 is added to the deficient plasma containing thrombomodulin, increased thrombin was observed. FIGS. 21B-21G depict data generated from experiments performed in a similar manner, but using congenital Factor VIII deficient plasma, congenital Factor IX deficient plasma, congenital Factor XI deficient plasma, vWD type 1 plasma, vWD type 2B plasma or vWD type 3 plasma, respectively. These results show that the tested antibodies were able to promote thrombin generation in samples having a factor deficiency or vWD disease.

Example 5

Figure 22B:
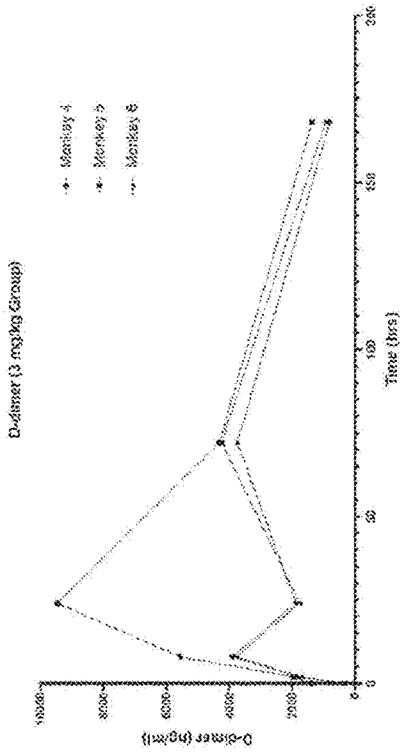
FIGS. 22A-22B depict the levels of D-dimer, as a marker of coagulation activity, observed over time in cynomolgus monkeys injected with either 1 mg/kg or 3 mg/kg of Antibody 1.
Figure 22A:
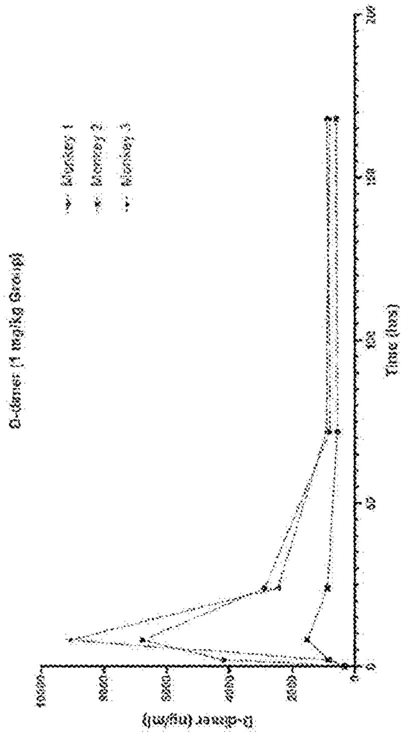

Activity of Protein S Antibodies Post-Treatment in Cynomolgus Monkeys Using D-Dimer as a Marker FIGS. 22A and 22B depict D-dimer levels observed in cynomolgus monkeys treated with 1 mg/kg or 3 mg/kg, respectively, of Antibody 1. At varying times post-injection of the antibody, blood was collected in sodium citrate tubes. Plasma samples were analyzed for the presence of D-dimer, a fibrin degradation product which acts as a marker of coagulation. Increases in the levels of D-dimer indicated that the tested antibodies activate the coagulation cascade and remain active in vivo for a period of time after treatment. FIG. 22A shows that treatment with 1 mg/kg of Antibody 1 showed activity for approximately 70 hours after treatment, and FIG. 22B shows that treatment with 3 mg/kg of Antibody 1 showed activity for approximately 105-110 hours after treatment.

Example 6

Restoration of Fibrin Deposition by Protein S Antibodies

Figure 23A:
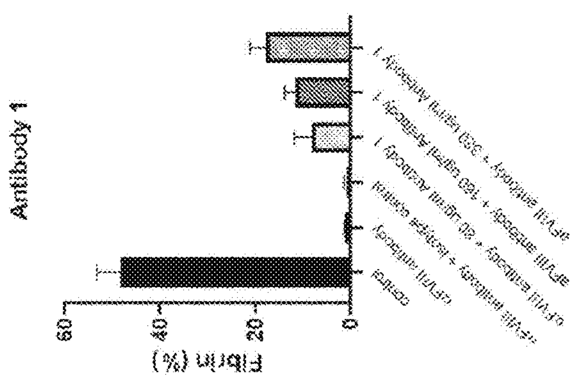
FIGS. 23A-23C depict the level of fibrin deposited onto collagen coated spots in Factor VIII (FVIII) neutralized blood treated with various Protein S antibodies, showing a restoration of fibrin deposition activity by the Protein S antibodies in the FVIII neutralized blood.
Figure 23B:
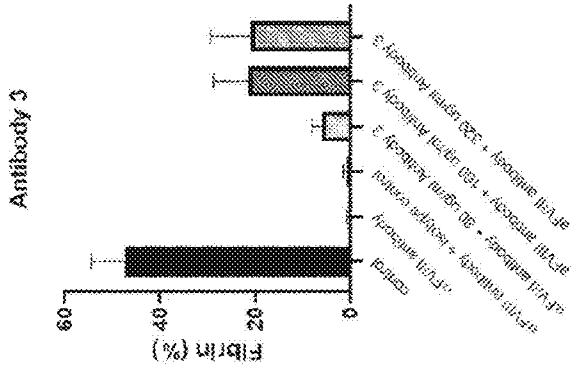
Figure 23C:
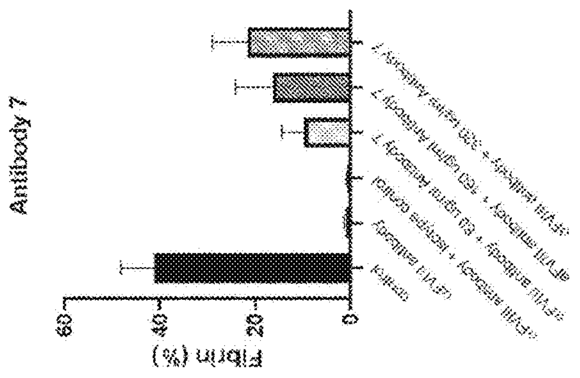

FIGS. 23A-23C depict the level of fibrin deposited onto collagen spots in a microfluidic system. Certain coagulation factor deficiencies can cause fibrin deposition to be at levels lower than that of subjects not having a factor deficiency. The microfluidic system can allow measurement of coagulation occurring during flow of blood.

Normal human blood, from a patient without any factor deficiencies, was untreated or treated with Factor VIII (FVIII) neutralizing antibody. This was then passed over collagen spots in a microfluidic system. Strong fibrin deposition was observed in untreated blood, but not in treated blood. When Antibodies 1, 3 and 7 were added to the treated blood, fibrin deposition was restored in a dose dependent manner. These results show that in blood neutralized with FVIII antibody, the Protein S antibodies disclosed herein may be used for restoration of fibrin formation or deposition, which may serve as a desired marker for coagulation activity.

Example 7

Binding of Protein S Antibodies to the Protein S-C4BP Complex

The Octet assay was used to determine the capability of the Protein S antibodies provided herein to bind to Protein S either alone, or when complexed to C4BP. A summary of the binding to Protein S or the Protein S-C4BP complex is provided in Table 14. Table 14 presents an X where a tested antibody was able to bind to either the Protein S-C4BP Complex, and/or the Protein S alone. A dash indicates that the binding did not occur.

Using the Octet System (Sartorius), the binding of each antibody to both Protein S and Protein S in complex with C4BP was determined. It had previously been determined that the C4BP preparation from Complement Technologies contains Protein S precomplexed to human C4BP. Therefore, this preparation represented the Protein S-C4BP complex and plasma purified Protein S from Haematologic Technologies was used as the source of free Protein S. The human Fc antibodies were immobilized onto anti-human Fc capture probes by placing the probes into 10 μg/ml antibody solution in 10 mg/ml bovine serum albumin, 20 mM Tris pH 7.0, 150 mM NaCl, and 4 mM calcium chloride. Then the bound antibodies were placed into solutions containing either 75 μg/ml Protein S or 100 μg/ml C4BP (C4BP-Protein S complex). With antibodies that do not bind Protein S in complex with C4BP, no binding is observed. With antibodies that bind Protein S in free form or in complex with C4BP, an association is observed under both conditions. All antibodies tested bound free Protein S, as depicted in Table 14.

TABLE 14

| Antibody with Human Fc | Binding to ProS-C4BP Complex | Binding to ProS |
|---|---|---|
| Antibody 1 | X | X |
| Antibody 2 | X | X |
| Antibody 3 | X | X |
| Antibody 4 | X | X |
| Antibody 6 | X | X |
| Antibody 7 | X | X |
| Antibody 8 | X | X |
| Antibody 9 | X | X |
| Antibody 11 | — | X |
| Antibody 12 | X | X |
| Antibody 25 | — | X |
| Antibody 27 | X | X |
| Antibody 28 | X | X |
| Antibody 29 | — | X |
| Antibody 30 | — | X |
| Antibody 37 | — | X |
| Antibody 39 | — | X |
| Antibody 41 | — | X |
| Antibody 43 | X | X |

Example 8

Effects of Protein S Antibodies on Fibrin Deposition

These experiments were carried out as follows. Bioflux 1000z 48-well high shear microfluidics plates (0-200 dynes/cm2) employed in the experiments were purchased from Bioflux. The device has the #1.5 borosilicate glass coverslip which forms the floor of the microfluidic channel engineer to facilitate the coated of collagen. Collagen type 1 was purchase from Chrono-Par collagen (chrono-Log Corp, Havertown, PA). Collagen was perfused from the wells at room temperature and incubated for 1 hour. Precoated plates with collagen type 1 were rinsed with PBS and channels were blocked with 0.5% (v/v) BSA for 10 min in PBS prior to the addition of the labeled blood to the wells. Sodium citrate anti-coagulated whole human blood (ALLCells, Oakland, CA) was used within 4-8 h of collection. Whole blood was incubated for 1 hour with 100 μg/mL Sheep anti-Human Factor VIII (Haematologic Technologies, Essex, VT). The antibodies were added and incubated with whole blood. Fibrinogen from human plasma, Alexa Fluor 546 (Invitrogen, Carlsbad, CA) was added at a final concentration of 50 μg/mL prior to biological experiments. Whole blood was added to the input wells and perfused at 30 dyn/cm2 using the BioFlux Controller and software. The samples were illuminated for no more than 30 ms for each capture. The BioFlux software imaging module was used to control the image acquisition settings and to process the fluorescence intensity measurements. Fluorescent micrographs were captured with the blood under flow using an inverted microscope (ZEISS Axio Observer 7) and sCMOS Camera. Images were timelapse recorded using the BioFlux 1000 imaging system (Fluxion Biosciences). Data was processed using BioFlux Montage Software.

Figure 25A:
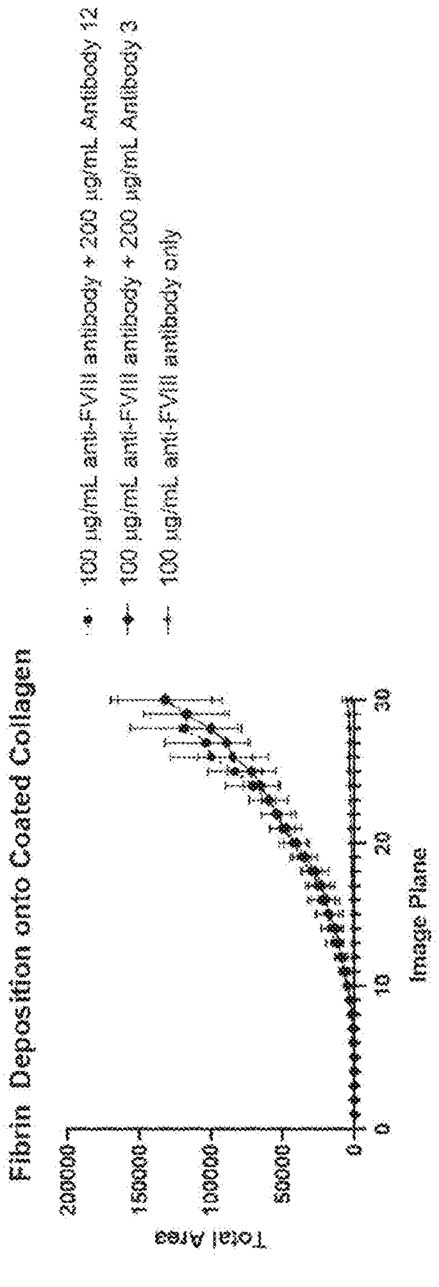
FIGS. 25A-25B depict the effect of selected Protein S antibodies on fibrin deposition.
Figure 25B:
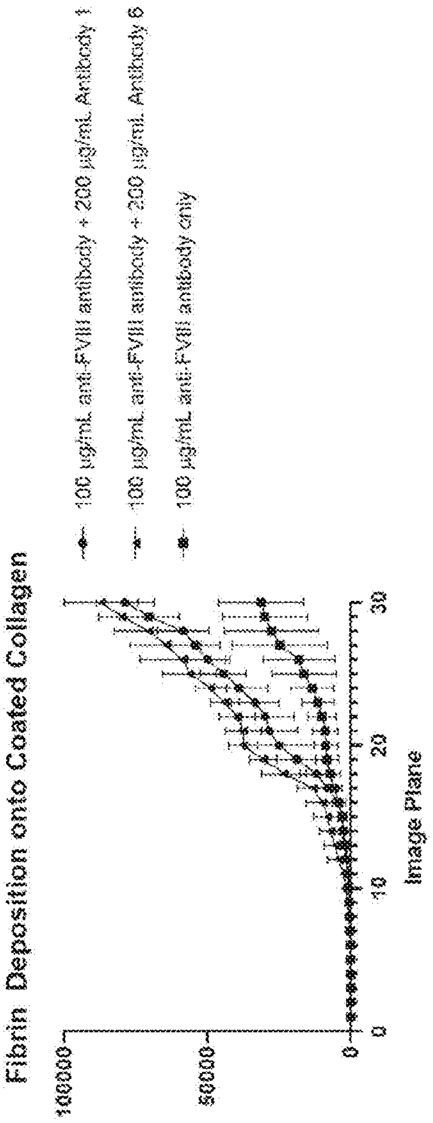

FIGS. 25A-25B depict the level of fibrin deposition resulting from the Protein S antibodies added to whole blood treated with Factor VIII neutralizing antibodies. This experiment tests the ability of the Protein S antibodies to restore or increase fibrin deposition in an in vitro microfluidic Hemophilia A model. Whole blood was treated with Factor VIII antibody to decrease fibrin deposition. FIG. 25A depicts the effects of Antibodies 12, and 3, and a control on fibrin deposition in anti-FVIII treated human plasma, and FIG. 25B depicts the effects of Antibodies 1 and 6 and a control on fibrin deposition in anti-FVIII treated human plasma. These results demonstrate that the Protein S antibodies 12, 3, 1 and 6 could restore or increase fibrin deposition in an in vitro microfluidic Hemophilia A model.

Example 9

Effect of Protein S Antibodies in an In Vitro Microfluidics Hemophilia A Bleeding Model These experiments were carried out using a fully endothelialized microfluidic system that was coupled to a microengineered pneumatic valve that mimics vascular damage (Sakurai, et al. Nature Communications 2018). Briefly, whole blood collected from healthy volunteers were treated with a sheep anti-human FVIII antibody to mimic whole blood from a hemophilia A patient. After treatment, the whole blood was perfused into the microfluidics system at which time an “injury” was introduced using the pneumatic valve. The localization of both platelets and fibrin at the site of “injury” was monitored and the time to cessation of “bleeding” was measured.

Figure 26A:
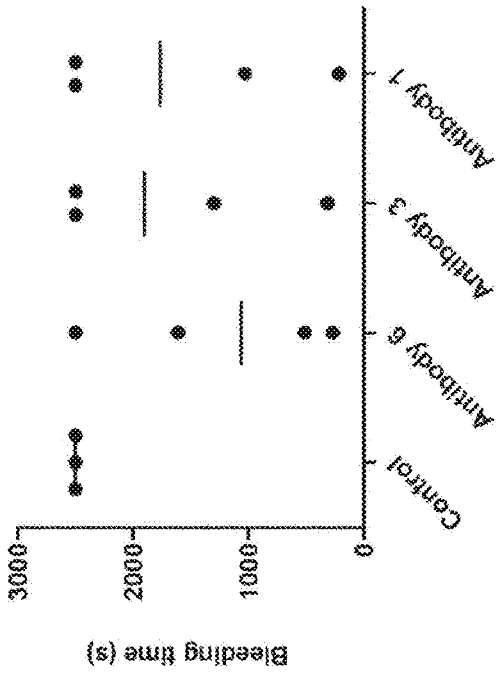
FIGS. 26A-26B depict the effects of Protein S antibodies in an in vitro microfluidic Hemophilia A bleeding model.
Figure 26B:
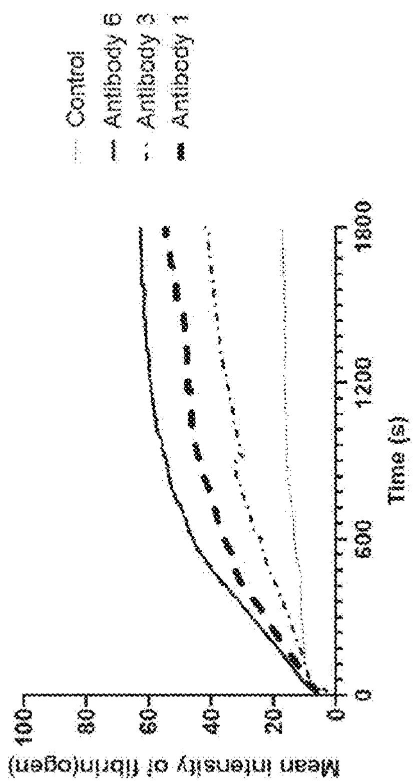

FIGS. 26A-26B depict the effects of Protein S antibodies in an in vitro microfluidics Hemophilia A bleeding model, measured by microfluidics experiments. These experiments were performed to measure the time of various Protein S antibodies to stop bleeding, and to determine the extent to which these antibodies induced fibrin deposition, respectively, in a microengineered, vascularized Hemophilia A bleeding model. The tested antibodies were Antibodies 6, 3, and 1. These results demonstrate that the antibodies were able to restore or increase fibrin deposition in a Hemophilia A bleeding model and therefore stop bleeding.

Example 10

Effect of Protein S Antibodies on Thrombin Generation

These experiments were carried out as follows. The Thrombin Generation Assay (TGA) was performed using a Thermo Fluoroskan Ascent Microplate Fluorometer and Thrombinoscope software. The PPP low reagent (Diagnostica Stago) was used in this experiment. Briefly, plasma from von Willebrand diseased patients was mixed with increasing levels of Protein S antibodies and incubated at room temperature. Then soluble human thrombomodulin was added prior to initiation of the reaction. To start the reaction, PPP low reagent was added along with calcium and the thrombin substrate. The levels of thrombin were then monitored.

FIGS. 27A-27F depict various results of enhanced dose-dependent thrombin generation when Protein S antibodies were added to plasma obtained from patients with various types of von Willebrand disease, with thrombomodulin added. These results demonstrate that the Protein S antibodies could effectively increase thrombin generation in a dose-dependent manner, and that different Protein S antibodies were more efficacious for different types of von Willebrand disease. Generally, the tested antibodies were more effective at increasing thrombin generation for Type 1 than Types 2A, 2B, and 3.

Figure 27A:
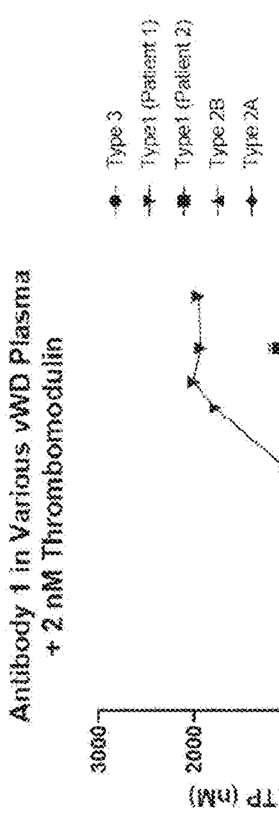
FIGS. 27A-27F depict the effect of selected Protein S antibodies on enhanced dose-dependent thrombin generation, wherein the Protein S antibodies were added to plasma obtained from patients with various types of von Willebrand disease.
Figure 27B:
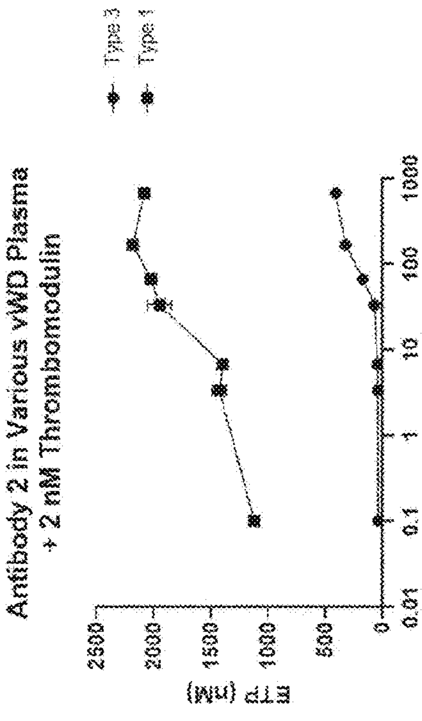
Figure 27D:
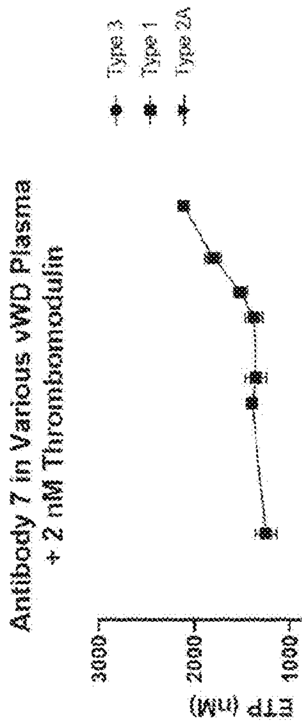
Figure 27C:
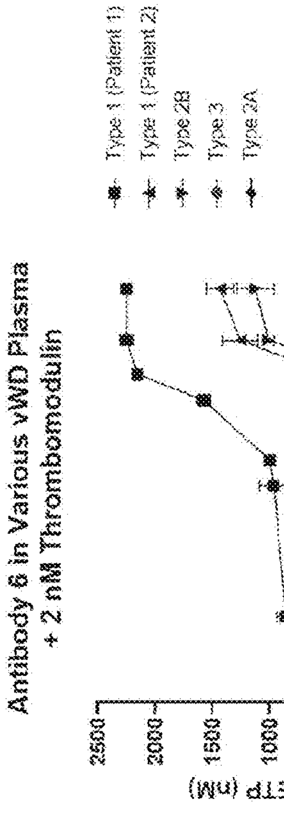
Figure 27E:
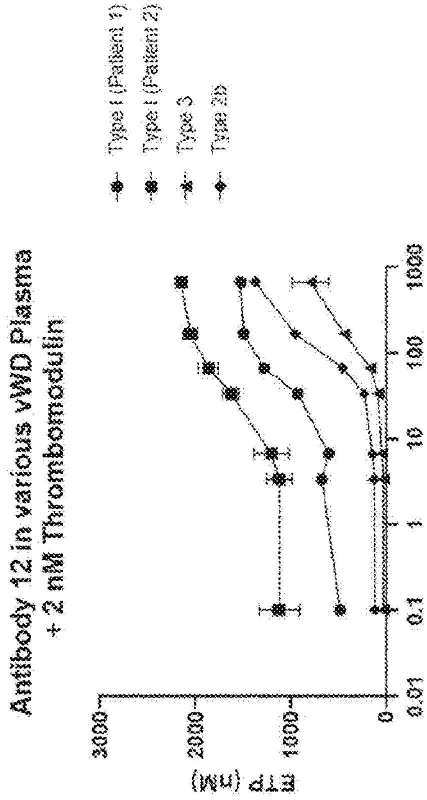
Figure 27F:
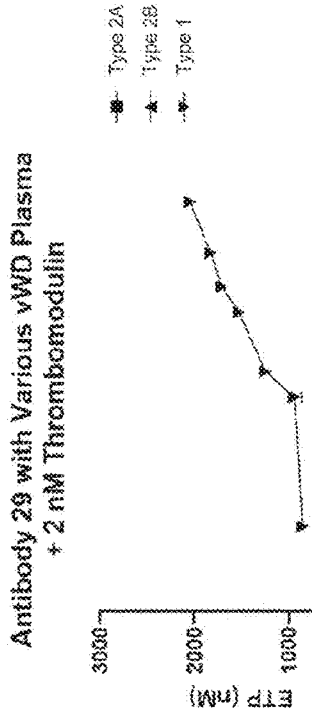

FIGS. 27A-27B depict enhanced dose-dependent thrombin generation when Antibodies 1 and 2 were added to plasma obtained from patients with various types of von Willebrand disease. FIGS. 27C-27D depict enhanced dose-dependent thrombin generation when Antibodies 6 and 7 were added to plasma obtained from patients with various types of von Willebrand disease, with thrombomodulin added. FIGS. 27E-27F depict enhanced dose-dependent thrombin generation when Antibodies 12 and 29 were added to plasma obtained from patients with various types of von Willebrand disease, with thrombomodulin added.

Example 11

APC Cofactor Assay in Cynomolgus Monkeys with Subcutaneous and Intravenous Injection The APC cofactor assay was performed using a Thermo Fluoroskan Ascent Microplate Fluorometer and Thrombinoscope software. The PPP reagent (Diagnostica Stago) was used in this experiment. Briefly, cynomolgus monkey plasma was mixed with PPP reagent and 5 μg/ml of activated Protein C along with calcium and substrate and the levels of thrombin generation was monitored over 1 hour. The PK assay was performed by incubating diluted cynomolgus monkey plasma onto plates immobilized with human Protein S. The plates used were MSD 96-well plates. 30 μl of 2 μg/ml plasma purified Protein S in Tris buffer containing calcium was used to coat the plate overnight. After blocking, the wells were incubated with samples, standards and QCs. 25 μl per well of 2 μg/ml sulfo-tagged goat anti-human IgG, monkey ads and incubated at room temperature for 1 hr. After washing, 150 μl of 1×MSD Read Buffer T in water was added to each well and the plate was read on a MSD plate reader. The levels of D-dimer were measured using the D-dimer assay kit from Diagnostica Stago following manufacturer's recommended protocol.

Figure 28B:
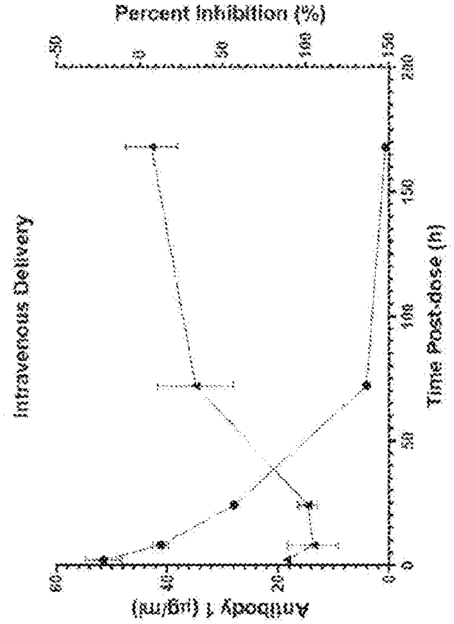
FIGS. 28A-28N depict the results of thrombin generation assays (ex vivo pharmacodynamic assay) as well as pharmacokinetic assays used to measure free antibody, in cynomolgus monkeys injected subcutaneously or intravenously with Protein S antibodies. These figures also depict levels of D-dimer, used as a marker of coagulation activity, observed in the monkeys.
Figure 28A:
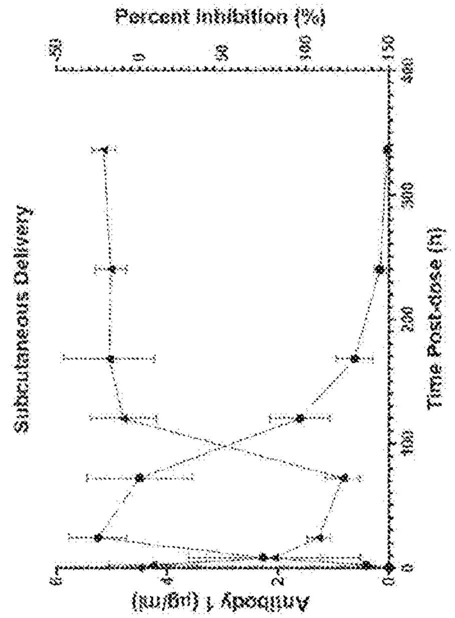
Figure 28C:
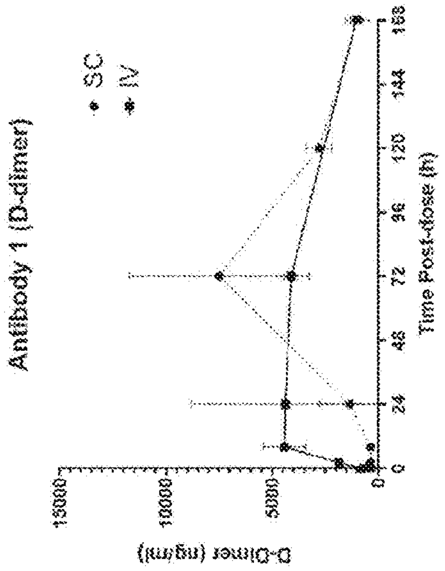
Figure 28D:
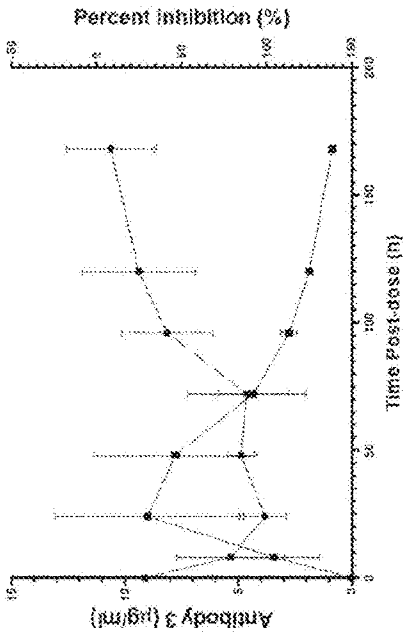
Figure 28E:
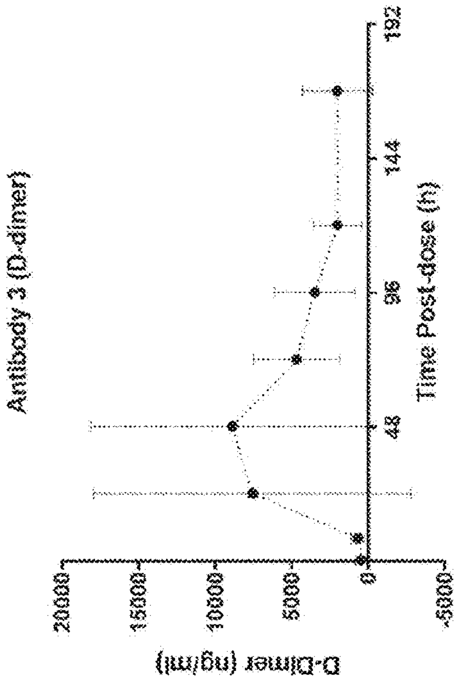
Figure 28G:
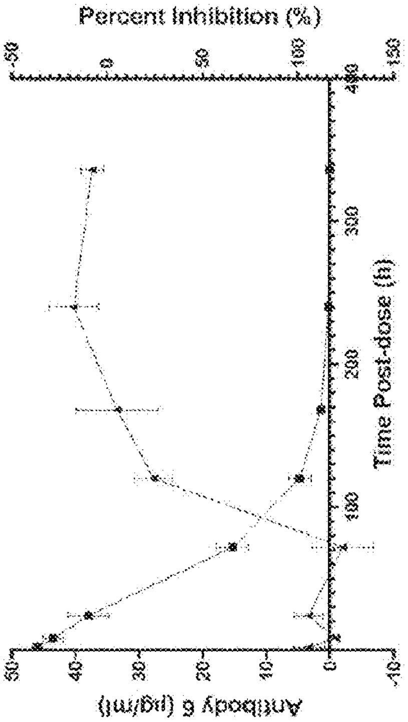
Figure 28H:
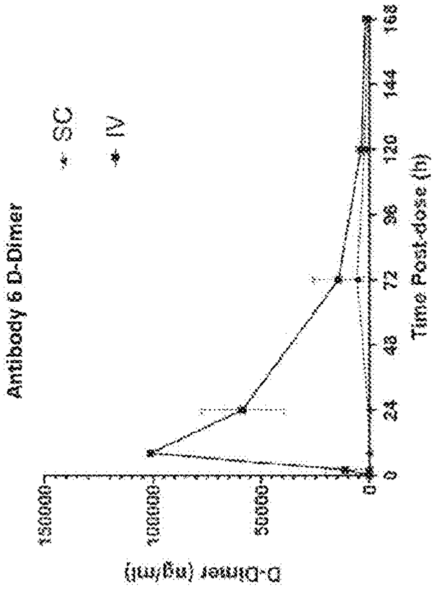
Figure 28F:
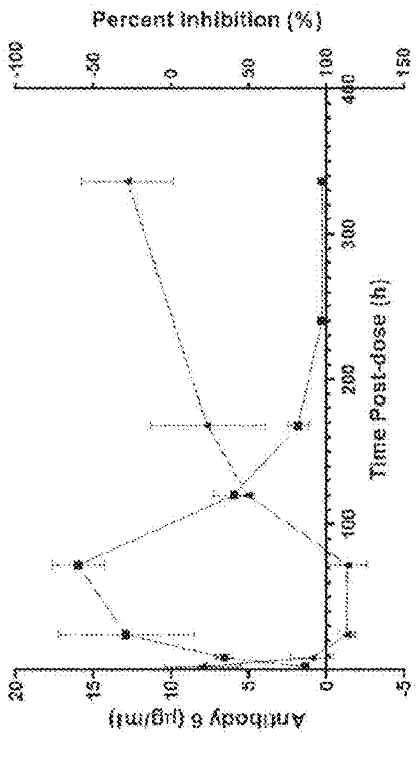
Figure 28I:
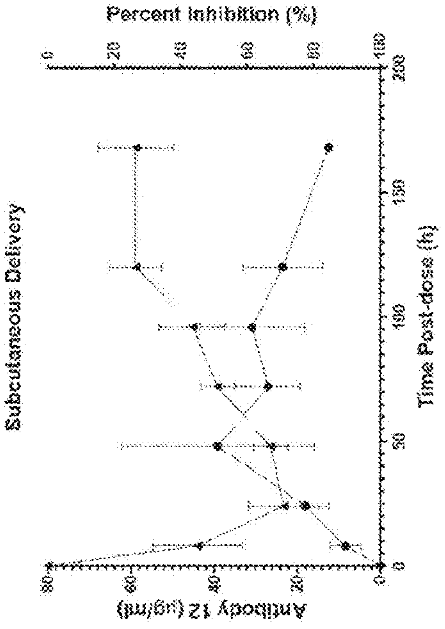
Figure 28J:
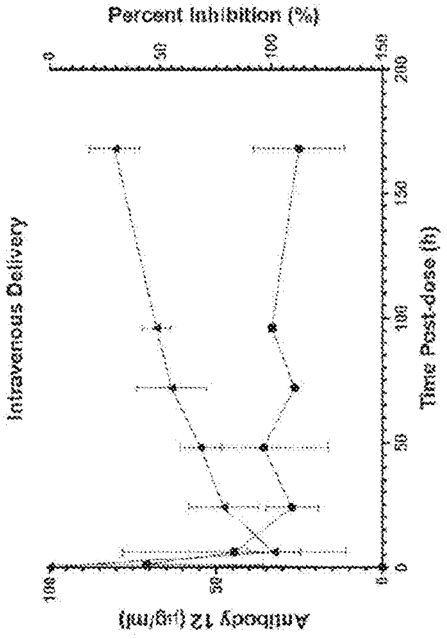
Figure 28K:
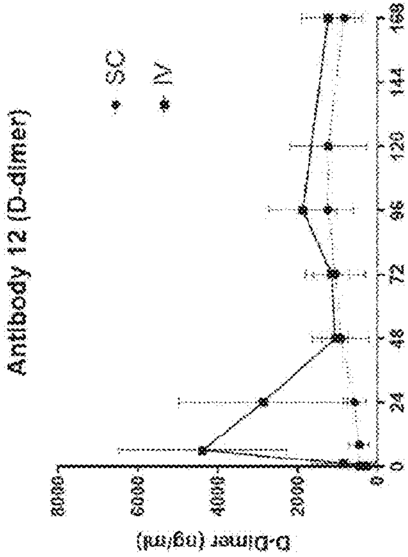
Figure 28M:
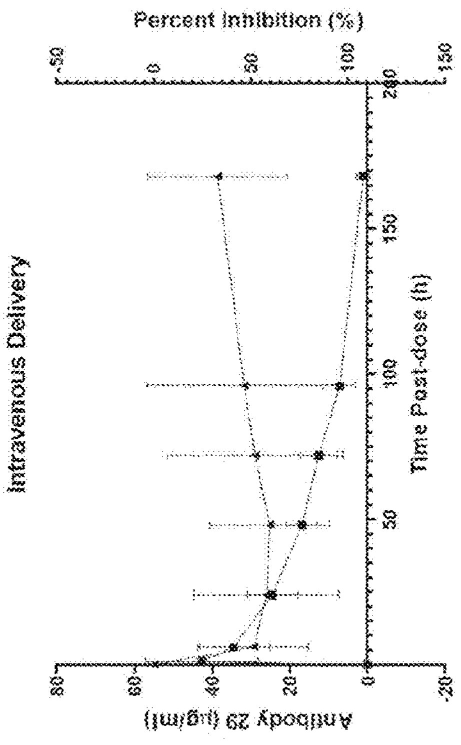
Figure 28L:
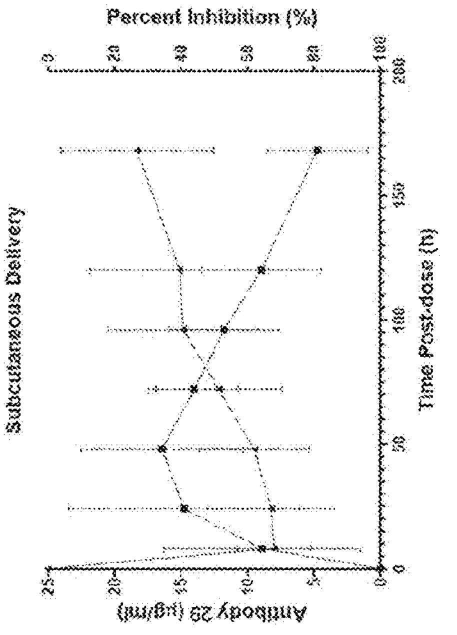
Figure 28N:
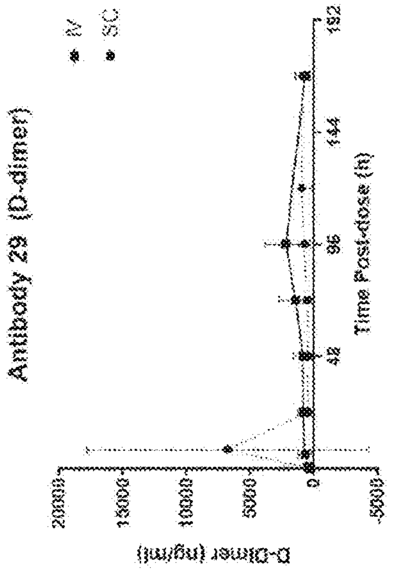
Figure 29:
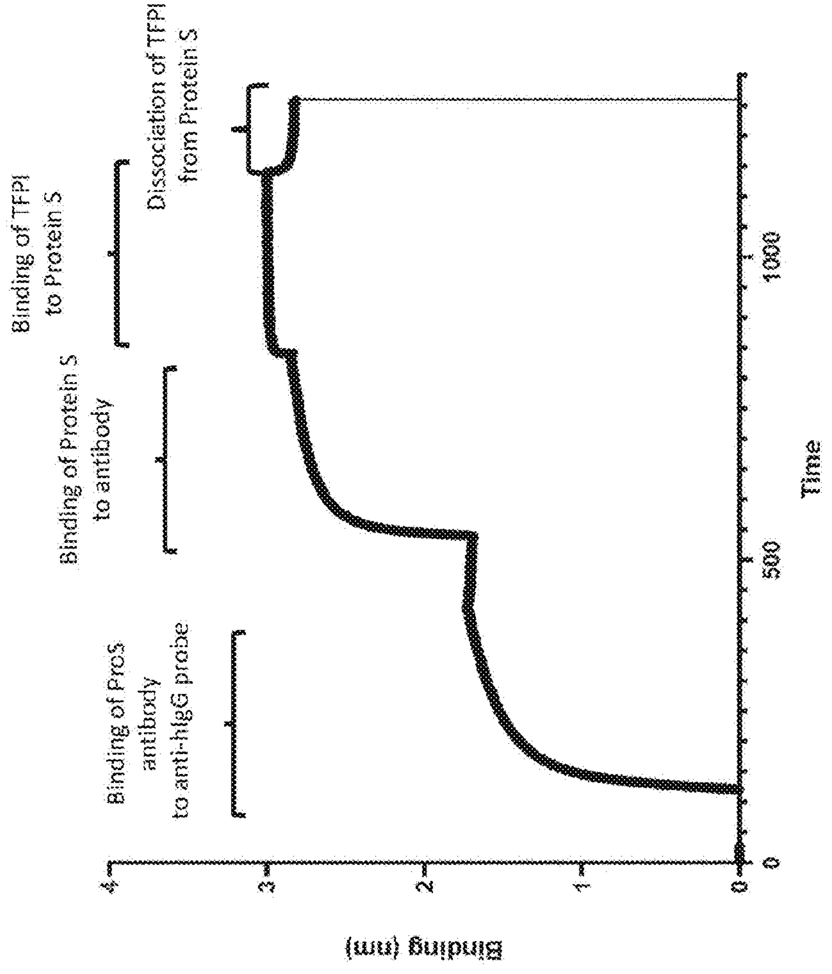
FIG. 29 depicts the effect of Antibody 2 on the ability of Protein S to bind TFPI.

FIGS. 28A-28N depict the results of APC cofactor assays, PK assays, and D-dimer assays for plasma samples collected after administration of Protein S antibodies into cynomolgus monkeys at 3 mg/kg subcutaneously and intravenously. The APC cofactor assay was used to measure the pharmacodynamic activity of the administered Protein S antibodies at the various times. In addition, FIGS. 28A-28N also show the levels of free antibody which was measured using an ELISA assay. And finally, elevated D-dimer, which was used as a biomarker of Protein S antibody induced coagulation activity, was observed in the monkeys and the data shown.

Specifically, FIGS. 28A-28B depict the levels of free antibody (left axis, filled circles) and percent inhibition in an APC cofactor assay (right axis, filled triangles) when Antibody 1 was administered to cynomolgus monkeys at 3 mg/kg subcutaneously and intravenously, respectively.

FIG. 28C depicts levels of D-dimer, as a marker of coagulation activity, measured over time in cynomolgus monkeys injected with Antibody 1, subcutaneously (SC) and intravenously (IV).

FIG. 28D depicts the levels of free antibody (left axis, filled squares) and percent inhibition in an APC cofactor assay (right axis, filled circles) when Antibody 3 was administered to cynomolgus monkeys at 3 mg/kg subcutaneously.

FIG. 28E depicts levels of D-dimer, as a marker of coagulation activity, measured over time in cynomolgus monkeys injected with Antibody 3.

FIGS. 28F-28G depict the levels of free antibody (left axis, filled squares) and percent inhibition in an APC cofactor assay (right axis, filled triangles) when Antibody 6 was administered to cynomolgus monkeys at 3 mg/kg subcutaneously and intravenously, respectively.

FIG. 28H depicts levels of D-dimer, as a marker of coagulation activity, measured over time in cynomolgus monkeys injected with Antibody 6.

FIGS. 28I-28J depict the levels of free antibody (left axis, filled circles) and percent inhibition in an APC cofactor assay (right axis, filled triangles) when Antibody 12 was administered to cynomolgus monkeys at 3 mg/kg subcutaneously and intravenously, respectively.

FIG. 28K depicts levels of D-dimer, as a marker of coagulation activity, measured over time in cynomolgus monkeys injected with Antibody 12.

FIGS. 28L-28M depict the levels of free antibody (left axis, filled squares) and percent inhibition in an APC cofactor assay (right axis, filled triangles) when Antibody 29 was administered to cynomolgus monkeys at 3 mg/kg subcutaneously and intravenously, respectively.

FIG. 28N depicts levels of D-dimer, as a marker of coagulation activity, measured over time in cynomolgus monkeys injected with Antibody 29.

Example 12

Effects of Protein S Antibodies on the Binding of Protein S to TFPI

The effect of the antibodies of the disclosure on the binding of Protein S to TFPI was measured.

Using the Octet System (Sartorius), an assay to measure the binding of TFPI to Protein S was developed. Briefly, the human Fc antibodies were immobilized onto anti-human Fc capture probes by placing the probes into 10 μg/ml antibody solution in 10 mg/ml bovine serum albumin, 20 mM Tris pH 7.0, 150 mM NaCl, and 4 mM calcium chloride. Then the bound antibodies were placed into a solution containing 10 μg/ml human Protein S followed by a 10 μg/ml solution containing human TFPI. Finally, the probe was placed into a buffer solution (wash) to observe the dissociation of TFPI from Protein S. The kinetics of association and dissociation of TFPI to Protein S were measured.

FIG. 31 depicts the binding of human TFPI to Protein S after the binding of Protein S to Antibody 2. These results demonstrate that Antibody 2 does not block the binding of TFPI to Protein S.

Example 13

Full-Length and Fab Fragments of Protein S Antibodies in APC Cofactor Assays

Figure 30B:
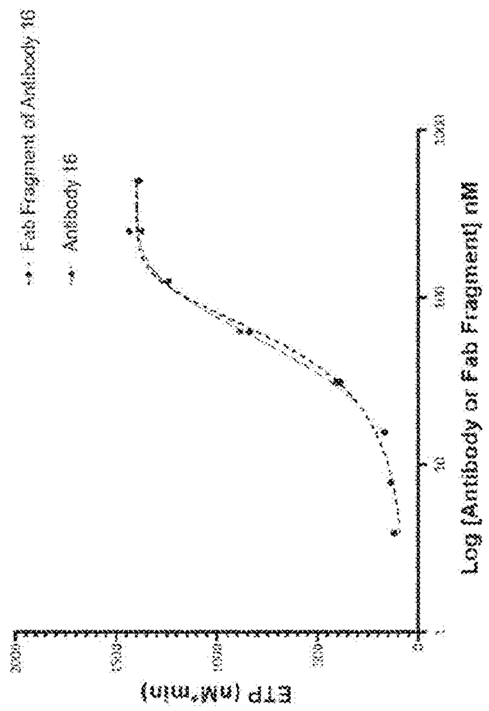
FIGS. 30A-30B depict similar dose-titration curves resulting from a full-length antibody or a Fab fragment of the same antibody in an APC cofactor assay.
Figure 30A:
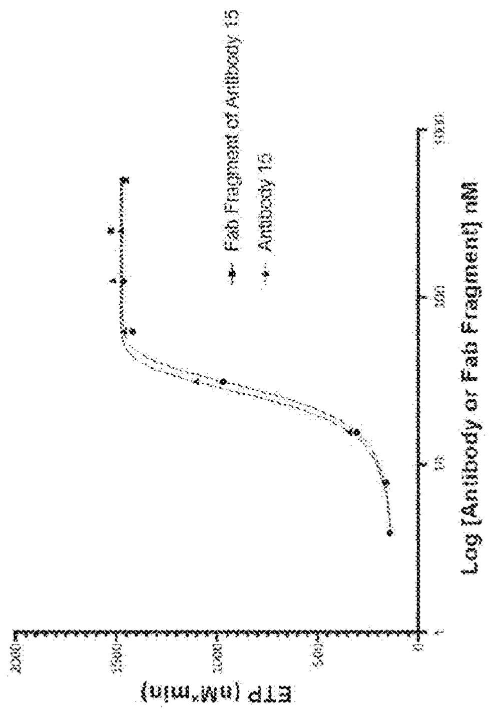

FIGS. 30A-30B depict similar dose-titration curves resulting from a full-length antibody or a Fab fragment of the same antibody in an APC cofactor assay. FIG. 30A shows the results using the full-length and Fab fragment of Antibody 15, and FIG. 30B shows the results using the full-length and Fab fragment of Antibody 16. These results demonstrate that both the full-length and the Fab fragments of the antibodies tested gave similar results in the APC cofactor assay.

The invention claimed is:

1. An antibody that binds Protein S, wherein the antibody comprises a heavy chain variable region (VH) and a light chain variable region (VL), wherein the VH and VL comprise a combination of six complementarity determining regions (CDRs), whose amino acid sequences comprise a CDR-L1 comprising the sequence of SEQ ID NO: 1, a CDR-L2 comprising an amino acid sequence of QDT, a CDR-L3 comprising the sequence of SEQ ID NO: 21, a CDR-H1 comprising the sequence of SEQ ID NO: 33, a CDR-H2 comprising the sequence of SEQ ID NO: 45, and a CDR-H3 comprising the sequence of SEQ ID NO: 57.

2. The antibody of claim 1, wherein the antibody binds to a thrombin-sensitive region of the Protein S.

3. The antibody of claim 1, wherein the antibody is capable of promoting generation of a marker associated with coagulation activity, wherein the marker of coagulation activity is one or more of the following: thrombin generation, D-dimer levels and fibrin generation.

4. The antibody of claim 1, wherein the antibody is a monoclonal antibody.

5. The antibody of claim 1, wherein the antibody is a full-length antibody.

6. The antibody of claim 1, wherein the antibody is an antibody fragment.

7. The antibody of claim 1, wherein the antibody is a humanized antibody.

8. The antibody of claim 1, wherein the antibody comprises a Fc domain.

9. The antibody of claim 8, wherein the Fc domain is human, wherein the human Fc domain is IgG1, IgG2, IgG3, or IgG4.

10. The antibody of claim 9, wherein the Fc domain of the antibody is human IgG4, optionally SEQ ID NO: 218, and comprises at least one amino acid substitution at a position selected from the group consisting of: 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 396, 428, 430, 433, 434, and 440, or comprises one or more of the substitutions selected from the group consisting of T250Q/M428L, M252Y/S254T/T256E, M428L/N434S, S267E/L328F, N325S/L328F, and H433K/N434F, wherein the position numbers of the amino acid residues are of the EU numbering scheme.

11. The Protein S antibody of claim 1, wherein the antibody comprises the light and heavy variable chain amino acid sequence of SEQ ID NOS: 69 and 70, respectively, or a light and heavy variable chain amino acid sequence with at least 80% sequence identity thereto.

12. A pharmaceutical composition comprising the antibody of claim 1, and optionally a pharmaceutically acceptable excipient.

13. A nucleic acid encoding for the antibody of claim 1.

14. A vector comprising the nucleic acid of claim 13.

15. An in vitro method of promoting the coagulation of blood, comprising contacting the antibody of claim 1 with a blood sample.

16. A method of prophylactically promoting the coagulation of blood in a subject in need thereof, comprising administering to the subject the pharmaceutical composition of claim 12, wherein the subject suffers from a bleeding disorder selected from the group consisting of hemophilia A, hemophilia B, von Willebrand disease (vWD) disease, menorrhagia, Factor I deficiency, Factor II deficiency, Factor VII deficiency, Factor XI deficiency, Factor VIII deficiency, Factor IX deficiency, trauma, and hereditary hemorrhagic telangiectasia.

17. A method of prophylactically promoting the generation of thrombin in a subject in need thereof, comprising administering to the subject the pharmaceutical composition of claim 12, wherein the subject suffers from a bleeding disorder selected from the group consisting of hemophilia A, hemophilia B, von Willebrand disease (vWD) disease, menorrhagia, Factor I deficiency, Factor II deficiency, Factor VII deficiency, Factor XI deficiency, Factor VIII deficiency, Factor IX deficiency, trauma, and hereditary hemorrhagic telangiectasia.

18. The method of claim 17, wherein the antibody restores or promotes the generation of thrombin.

19. A method of prophylactically treating a bleeding disorder in a subject in need thereof, comprising administering to the subject the pharmaceutical composition of claim 12, wherein the bleeding disorder is selected from the group consisting of hemophilia A, hemophilia B, von Willebrand disease (vWD) disease, menorrhagia, Factor I deficiency, Factor II deficiency, Factor VII deficiency, Factor XI deficiency, Factor VIII deficiency, Factor IX deficiency, trauma, and hereditary hemorrhagic telangiectasia.

20. The method of claim 19, wherein the bleeding disorder is a vWD subtype selected from the group consisting of vWD Type 1, vWD Type 2A, vWD Type 2B, vWD Type 2N, vWD Type 2M, vWD Type 3, and acquired vWD.

* * * * *